United States Patent
Bonfanti et al.

(10) Patent No.: US 7,449,463 B2
(45) Date of Patent: Nov. 11, 2008

(54) MORPHOLINYL CONTAINING BENZIMIDAZOLES AS INHIBITORS OF RESPIRATORY SYNCYTIAL VIRUS REPLICATION

(75) Inventors: Jean-François Bonfanti, Andé (FR); Koenraad Jozef Lodewijk Andries, Beerse (BE); Jérôme Michel Claude Fortin, Igoville (FR); Philippe Muller, Andé (FR); Frédéric Marc Maurice Doublet, Isneauville (FR); Christophe Meyer, Port St Ouen (FR); Rudy Edmond Willebrords, Merksplas (BE); Tom Valerius Josepha Gevers, Vosselaar (BE); Philip Maria Martha Bern Timmerman, Hasselt (BE)

(73) Assignee: Tibotec Pharmaceuticals Ltd., County Cork (IE)

( * ) Notice: Subject to any disclaimer, the term of this patent is extended or adjusted under 35 U.S.C. 154(b) by 284 days.

(21) Appl. No.: 10/563,691

(22) PCT Filed: Dec. 20, 2004

(86) PCT No.: PCT/EP2004/053620

§ 371 (c)(1), (2), (4) Date: Jan. 4, 2006

(87) PCT Pub. No.: WO2005/058871

PCT Pub. Date: Jun. 30, 2005

(65) Prior Publication Data

US 2007/0043022 A1    Feb. 22, 2007

Related U.S. Application Data

(60) Provisional application No. 60/567,182, filed on Apr. 30, 2004.

(30) Foreign Application Priority Data

Dec. 18, 2003  (EP) ................... 03104810
Oct. 26, 2004  (EP) ................... 04105312

(51) Int. Cl.
*A61K 31/535*   (2006.01)
*C07D 413/00*   (2006.01)

(52) U.S. Cl. .................... 514/237.8; 544/132

(58) Field of Classification Search .............. 514/237.8; 544/132
See application file for complete search history.

(56) References Cited

FOREIGN PATENT DOCUMENTS

| WO | WO 01/00611 A | 1/2001 |
| WO | WO 01/00612 A | 1/2001 |
| WO | WO 01/00615 A | 1/2001 |

OTHER PUBLICATIONS

Janssens F et al: "New Antihistamine N-Heterocyclic 4-Piperidinamines. 2. Synthesis and Antihistaminic Activity of 1-(4-Flourophenyl) Methyl-N-(4-Piperidinyl)-1H-Benzidazol-2-amines". Journal of Medicinal Chemistry, American Chemical Society. Washington, US, vol. 28, No. 12, Dec. 1985. pp. 1934-1943, XP000881979 ISSN: 0022-2623 example 8.

*Primary Examiner*—Zachary C Tucker
(74) *Attorney, Agent, or Firm*—Mary Appollina

(57) ABSTRACT

The present invention concerns morpholinyl containing benzimidazoles having inhibitory activity on the replication of the respiratory syncytial virus and having the formula (I)

a prodrug, N-oxide, addition salt, quaternary amine, metal complex or stereochemically isomeric form thereof wherein G is a direct bond or optionally substituted $C_{1-10}$alkanediyl; $R^1$ is $Ar^1$ or a monocyclic or bicyclic heterocycle Q is $R^7$, pyrrolidinyl substituted with $R^7$, piperidinyl substituted with $R^7$ or homopiperidinyl substituted with $R^7$; one of $R^{2a}$ and $R^{3a}$ is selected from halo, optionally mono- or polysubstituted $C_{1-6}$alkyl, optionally mono- or polysubstituted $C_{2-6}$alkenyl, nitro, hydroxy, $Ar^2$, $N(R^{4a}R^{4b})$, $N(R^{4a}R^{4b})$sulfonyl, $N(R^{4a}R^{4b})$carbonyl, $C_{1-6}$alkyloxy, $Ar^2$oxy, $Ar^2C_{1-6}$alkyloxy, carboxyl, $C_{1-6}$alkyloxycarbonyl, or —C(=Z)$Ar^2$; and the other one of $R^{2a}$ and $R^{3a}$ is hydrogen; in case $R^{2a}$ is different from hydrogen then $R^{2b}$ is hydrogen, $C_{1-6}$alkyl or halogen and $R^{3b}$ is hydrogen; in case $R^{3a}$ is different from hydrogen then $R^{3b}$ is hydrogen, $C_{1-6}$alkyl or halogen and $R^{2b}$ is hydrogen. It further concerns the preparation thereof and compositions comprising these compounds, as well as the use thereof as a medicine.

36 Claims, No Drawings

MORPHOLINYL CONTAINING BENZIMIDAZOLES AS INHIBITORS OF RESPIRATORY SYNCYTIAL VIRUS REPLICATION

This application is a National Stage application under 35 U.S.C. 371 of Application No. PCT/EP2004/053620 filed Dec. 20, 2004, which claims priority from European Patent Application No. EP03104810.1 filed Dec. 18, 2003, European Patent Application No. EP04105312.5 filed Oct. 26, 2004, and U.S. Provisional Application No. 60/567 182 filed Apr. 30, 2004, the contents of all of which are hereby incorporated by reference.

The present invention is concerned with morpholinyl containing benzimidazoles having antiviral activity, in particular, having an inhibitory activity on the replication of the respiratory syncytial virus (RSV). It further concerns the preparation thereof and compositions comprising these compounds.

Human RSV or Respiratory Syncytial Virus is a large RNA virus, member of the family of Paramyxoviridae, subfamily pneumoviridae together with bovine RSV virus. Human RSV is responsible for a spectrum of respiratory tract diseases in people of all ages throughout the world. It is the major cause of lower respiratory tract illness during infancy and childhood. Over half of all infants encounter RSV in their first year of life, and almost all within their first two years. The infection in young children can cause lung damage that persists for years and may contribute to chronic lung disease in later life (chronic wheezing, asthma). Older children and adults often suffer from a (bad) common cold upon RSV infection. In old age, susceptibility again increases, and RSV has been implicated in a number of outbreaks of pneumonia in the aged resulting in significant mortality.

Infection with a virus from a given subgroup does not protect against a subsequent infection with an RSV isolate from the same subgroup in the following winter season. Re-infection with RSV is thus common, despite the existence of only two subtypes, A and B.

Today only three drugs have been approved for use against RSV infection. A first one is ribavirin, a nucleoside analogue, provides an aerosol treatment for serious RSV infection in hospitalized children. The aerosol route of administration, the toxicity (risk of teratogenicity), the cost and the highly variable efficacy limit its use. The other two drugs, RespiGam® and palivizumab, polyclonal and monoclonal antibody immunostimulants, are intended to be used in a preventive way.

Other attempts to develop a safe and effective RSV vaccine have all met with failure thus far. Inactivated vaccines failed to protect against disease, and in fact in some cases enhanced disease during subsequent infection. Life attenuated vaccines have been tried with limited success. Clearly there is a need for an efficacious non-toxic and easy to administer drug against RSV replication.

Previously, benzimidazoles and imidazopyridines as inhibitors of RSV replication have been described in WO 01/00611, WO 01/00612 and WO 01/00615.

Several series of benzimidazolyl and imidazopyridinyl piperidines have been described in patents, patent applications and publications of janssen Pharmaceutica N.V. as compounds possessing antihistaminic properties. See for example EP-A-5 318, EP-A-99 139, EP-A-145 037, WO-92/01687, Janssens F. et al. in Journal of Medicinal Chemistry, Am. Chem. Soc., Vol. 28, no. 12, pp. 1934-1943 (1985).

The present invention concerns inhibitors of RSV replication, which can be represented by formula (I)

their prodrugs, N-oxides, addition salts, quaternary amines, metal complexes and stereochemically isomeric forms wherein G is a direct bond or $C_{1-10}$alkanediyl optionally substituted with one or more substituents individually selected from the group of substituents consisting of hydroxy, $C_{1-6}$alkyloxy, $Ar^1C_{1-6}$alkyloxy, $C_{1-6}$alkylthio, $Ar^1C_{1-6}$alkylthio, $HO(-CH_2-CH_2-O)_n-$, $C_{1-6}$alkyloxy($-CH_2-CH_2-O)_n-$ or $Ar^1C_{1-6}$alkyloxy($-CH_2-CH_2-O)_n-$;

$R^1$ is $Ar^1$ or a monocyclic or bicyclic heterocycle being selected from piperidinyl, piperazinyl, pyridyl, pyrazinyl, pyridazinyl, pyrimidinyl, furanyl, tetrahydrofuranyl, thienyl, pyrrolyl, thiazolyl, oxazolyl, imidazolyl, isothiazolyl, pyrazolyl, isoxazolyl, oxadiazolyl, quinolinyl, quinoxalinyl, benzofuranyl, benzothienyl, benzimidazolyl, benzoxazolyl, benzthiazolyl, pyridopyridyl, naphthiridinyl, 1H-imidazo[4,5-b]pyridinyl, 3H-imidazo[4,5-b]pyridinyl, imidazo[1,2-a]-pyridinyl, 2,3-dihydro-1,4-dioxino[2,3-b]pyridyl or a radical of formula -continued

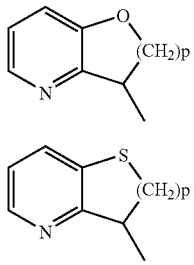
(c-7)

(c-8)

wherein each of said monocyclic or bicyclic heterocycles may optionally be substituted with 1 or where possible more, such as 2, 3, 4 or 5, substituents individually selected from the group of substituents consisting of halo, hydroxy, amino, cyano, carboxyl, $C_{1-6}$alkyl, $C_{1-6}$alkyloxy, $C_{1-6}$alkylthio, $C_{1-6}$alkyloxy$C_{1-6}$alkyl, $Ar^1$, $Ar^1C_{1-6}$alkyl, $Ar^1C_{1-6}$alkyloxy, hydroxy$C_{1-6}$alkyl, mono-or di($C_{1-6}$alkyl)amino, mono-or di($C_{1-6}$alkyl)amino$C_{1-6}$alkyl, polyhalo$C_{1-6}$alkyl, $C_{1-6}$alkylcarbonylamino, $C_{1-6}$alkyl-$SO_2$—$NR^{5c}$—, $Ar^1$—$SO_2$—$NR^{5c}$—, $C_{1-6}$alkyloxycarbonyl, —C(=O)—$NR^{5c}R^{5d}$, HO(—$CH_2$—$CH_2$—O)$_n$—, halo(—$CH_2$—$CH_2$—O)$_n$—, $C_{1-6}$allyloxy(—$CH_2$—$CH_2$—O)$_n$—, $Ar^1C_{1-6}$alkyloxy(—$CH_2$—$CH_2$—O)$_n$— and mono-or di($C_{1-6}$alkyl)amino(—$CH_2$—$CH_2$—O)$_n$—;

each n independently is 1, 2, 3 or 4;
each m independently is 1 or 2;
each p independently is 1 or 2;
each t independently is 0, 1 or 2;

Q is $R^7$, pyrrolidinyl substituted with $R^7$, piperidinyl substituted with $R^7$ or homo-piperidinyl substituted with $R^7$ wherein $R^7$ is $C_{1-6}$alkyl substituted with a heterocycle or $R^7$ is $C_{1-6}$alkyl substituted with both a radical —$OR^8$ and a heterocycle, wherein said heterocycle is selected from the group consisting of oxazolidine, thiazolidine, 1-oxo-thiazolidine, 1,1-dioxothiazolidine, morpholinyl, thiomorpholinyl, 1-oxo-thiomorpholinyl, 1,1-dioxothiomorpholinyl, hexahydrooxazepine, hexahydrothiazepine, 1-oxo-hexahydrothiazepine, 1,1-dioxo-hexahydrothiazepine; wherein each of said heterocycle may be optionally substituted with one or two substituents selected from the group consisting of $C_{1-6}$alkyl, hydroxy$C_{1-6}$alkyl, aminocarbonyl$C_{1-6}$alkyl, hydroxy, carboxyl, $C_{1-4}$alkyloxycarbonyl, aminocarbonyl, mono- or di($C_{1-4}$alkyl)aminocarbonyl, $C_{1-4}$alkylcarbonylamino, aminosulfonyl and mono- or di($C_{1-4}$alkyl)aminosulfonyl;

$R^8$ is hydrogen, $C_{1-6}$alkyl or $Ar^1C_{1-6}$alkyl;

one of $R^{2a}$ and $R^{3a}$ is selected from halo, optionally mono- or polysubstituted $C_{1-6}$alkyl, optionally mono- or polysubstituted $C_{2-6}$alkenyl, nitro, hydroxy, $Ar^2$, $N(R^{4a}R^{4b})$, $N(R^{4a}R^{4b})$sulfonyl, $N(R^{4a}R^{4b})$carbonyl, $C_{1-6}$alkyloxy, $Ar^2$oxy, $Ar^2C_{1-6}$alkyloxy, carboxyl, $C_{1-6}$alkyloxycarbonyl, or —C(=Z)$Ar^2$; and the other one of $R^{2a}$ and $R^{3a}$ is hydrogen;
wherein
=Z is =O, =CH—C(=O)—$NR^{5a}R^{5b}$, =$CH_2$, =CH—$C_{1-6}$alkyl, =N—OH or =N—O—$C_{1-6}$alkyl; and the optional substituents on $C_{1-6}$alkyl and $C_{2-6}$alkenyl can be the same or can be different relative to one another, and are each independently selected from the group of substituents consisting of hydroxy, cyano, halo, nitro, $N(R^{4a}R^{4b})$, $N(R^{4a}R^{4b})$sulfonyl, Het, $Ar^2$, $C_{1-6}$alkyloxy, $C_{1-6}$alkyl-S(=O)$_t$, $Ar^2$oxy, $Ar^2$—S(=O)$_t$, $Ar^2C_{1-6}$alkyloxy, $Ar^2C_{1-6}$alkyl-S(=O)$_t$, Hetoxy, Het-S(=O)$_t$, Het$C_{1-6}$alkyloxy, Het$C_{1-6}$alkyl-S(=O)$_t$, carboxyl, $C_{1-6}$alkyloxycarbonyl and —C(=Z)$Ar^2$;

in case $R^{2a}$ is different from hydrogen then $R^{2b}$ is hydrogen, $C_{1-6}$alkyl or halogen and $R^{3b}$ is hydrogen;
in case $R^{3a}$ is different from hydrogen then $R^{3b}$ is hydrogen, $C_{1-6}$alkyl or halogen and $R^{2b}$ is hydrogen;

$R^{4a}$ and $R^{4b}$ can be the same or can be different relative to one another, and are each independently selected from the group of substituents consisting of hydrogen, $C_{1-6}$alkyl, $Ar^2C_{1-6}$alkyl, $(Ar^2)$(hydroxy)$C_{1-6}$alkyl, Het-$C_{1-6}$alkyl, hydroxy$C_{1-6}$alkyl, mono- and di-($C_{1-6}$alkyloxy)$C_{1-6}$alkyl, (hydroxy$C_{1-6}$alkyl)oxy$C_{1-6}$alkyl, $Ar^1C_{1-6}$alkyloxy-$C_{1-6}$alkyl, dihydroxy$C_{1-6}$alkyl, ($C_{1-6}$alkyloxy)(hydroxy)$C_{1-6}$alkyl, ($Ar^1C_{1-6}$alkyloxy)(hydroxy)$C_{1-6}$alkyl, $Ar^1$oxy-$C_{1-6}$alkyl, ($Ar^1$oxy)(hydroxy)-$C_{1-6}$alkyl, amino$C_{1-6}$alkyl, mono- and di($C_{1-6}$alkyl)amino-$C_{1-6}$alkyl, carboxyl-$C_{1-6}$alkyl, $C_{1-6}$alkyloxycarbonyl$C_{1-6}$alkyl, aminocarbonyl$C_{1-6}$alkyl, mono- and di($C_{1-6}$alkyl)aminocarbonyl$C_{1-6}$alkyl, $C_{1-6}$alkylcarbonyl$C_{1-6}$alkyl, ($C_{1-4}$alkyloxy)$_2$-P(=O)—$C_{1-6}$alkyl, ($C_{1-4}$alkyloxy)$_2$P(=O)—O—$C_{1-6}$ alkyl, aminosulfonyl-$C_{1-6}$alkyl, mono- and di($C_{1-6}$ alkyl)aminosulfonyl-$C_{1-6}$alkyl, $C_{1-6}$alkylcarbonyl, $Ar^2$carbonyl, Het-carbonyl, $Ar^2C_{1-6}$alkylcarbonyl, Het-$C_{1-6}$alkylcarbonyl, $C_{1-6}$alkylsulfonyl, aminosulfonyl, mono- and di($C_{1-6}$alkyl)aminosulfonyl, $Ar^2$sulfonyl, $Ar^2C_{1-6}$alkylsulfonyl, $Ar^2$, Het, Het-sulfonyl, Het$C_{1-6}$ alkylsulfonyl;

$R^5$ is hydrogen or $C_{1-6}$alkyl;

$R^{5a}$ and $R^{5b}$ can be the same or can be different relative to one another, and are each independently hydrogen or $C_{1-6}$alkyl; or $R^{5a}$ and $R^{5b}$ taken together may form a bivalent radical of formula —$(CH_2)_s$— wherein s is 4 or 5;

$R^{5c}$ and $R^{5d}$ can be the same or can be different relative to one another, and are each independently hydrogen or $C_{1-6}$alkyl; or $R^{5c}$ and $R^{5d}$ taken together may form a bivalent radical of formula —$(CH_2)_s$— wherein s is 4 or 5;

$Ar^1$ is phenyl or phenyl substituted with 1 or more, such as 2, 3 or 4, substituents selected from halo, hydroxy, $C_{1-6}$alkyl, hydroxy$C_{1-6}$alkyl, polyhalo$C_{1-6}$alkyl, and $C_{1-6}$alkyloxy;

$Ar^2$ is phenyl, phenyl annelated with $C_{5-7}$cycloalkyl, or phenyl substituted with 1 or more, such as 2, 3, 4 or 5, substituents selected from halo, cyano, $C_{1-6}$alkyl, Het-$C_{1-6}$alkyl, $Ar^1$—$C_{1-6}$alkyl, cyano$C_{1-6}$alkyl, $C_{2-6}$alkenyl, cyano$C_{2-6}$alkenyl, $R^{6b}$—O—$C_{3-6}$alkenyl, $C_{2-6}$alkynyl, cyano$C_{2-6}$alkynyl, $R^{6b}$—O—$C_{3-6}$alkynyl, $Ar^1$, Het, $R^{6b}$—O—, $R^{6b}$—S—, $R^{6c}$—SO—, $R^{6c}$—$SO_2$—, $R^{6b}$—O—$C_{1-6}$alkyl-$SO_2$—, —$N(R^{6a}R^{6b})$, polyhalo$C_{1-6}$alkyl, polyhalo$C_{1-6}$alkyloxy, polyhalo$C_{1-6}$alkylthio, $R^{6c}$—C(=O)—, $R^{6b}$—O—C(=O)—, $N(R^{6a}R^{6b})$—C(=O)—, $R^{6b}$—O—$C_{1-10}$alkyl, $R^{6b}$—S—$C_{1-6}$alkyl, $R^{6c}$—S(=O)$_2$—$C_{1-6}$alkyl, $N(R^{6a}R^{6b})$—$C_{1-6}$alkyl, $R^{6c}$—C(=O)—$C_{1-6}$alkyl, $R^{6b}$—O—C(=O)—$C_{1-6}$alkyl, $N(R^{6a}R^{6b})$—C(=O)—$C_{1-6}$alkyl, $R^{6c}$—C(=O)—$NR^{6b}$—, $R^{6c}$—C(=O)—O—, $R^{6c}$—C(=O)—$NR^{6b}$—$C_{1-6}$alkyl, $R^{6c}$—C(=O)—O—$C_{1-6}$alkyl, $N(R^{6a}R^{6b})$—S(=O)$_2$—, $H_2N$—C(=NH)—;

$R^{6a}$ is hydrogen, $C_{1-6}$alkyl, $Ar^1$, $Ar^1C_{1-6}$alkyl, $C_{1-6}$alkylcarbonyl, $Ar^1$carbonyl, $Ar^1C_{1-6}$alkylcarbonyl, $C_{1-6}$alkylsulfonyl, $Ar^1$sulfonyl, $Ar^1C_{1-6}$alkylsulfonyl, $C_{1-6}$alkyloxy$C_{1-6}$alkyl, amino$C_{1-6}$alkyl, mono- or di($C_{1-6}$alkyl)amino$C_{1-6}$alkyl, hydroxy$C_{1-6}$alkyl, (carboxyl)-$C_{1-6}$alkyl, ($C_{1-6}$alkyloxycarbonyl)-$C_{1-6}$alkyl, aminocarbonyl$C_{1-6}$alkyl, mono- and di($C_{1-6}$alkyl)aminocarbonyl$C_{1-6}$alkyl, aminosulfonyl-$C_{1-6}$alkyl, mono- and di($C_{1-6}$alkyl)aminosulfonyl-$C_{1-6}$alkyl, Het, Het-$C_{1-6}$ alkyl, Het-carbonyl, Het-sulfonyl, Het-$C_{1-6}$alkyl-carbonyl;

$R^{6b}$ is hydrogen, $C_{1-6}$alkyl, $Ar^1$ or $Ar^1C_{1-6}$alkyl;

$R^{6c}$ is $C_{1-6}$alkyl, $Ar^1$ or $Ar^1C_{1-6}$alkyl;

Het is a heterocycle being selected from tetrahydrofuranyl, tetrahydrothienyl, pyrrolidinyl, pyrrolidinonyl, furanyl, thienyl, pyrrolyl, thiazolyl, oxazolyl, imidazolyl, isothiazolyl, pyrazolyl, isoxazolyl, oxadiazolyl, thiadiazolyl, piperidinyl, homopiperidinyl, piperazinyl, morpholinyl, pyridyl, pyrazinyl, pyridazinyl, pyrimidinyl, tetrahydroquinolinyl, quinolinyl, isoquinolinyl, benzodioxanyl, benzodioxolyl, indolinyl, indolyl, each of said heterocycle may optionally be substituted with oxo, amino, $Ar^1$, $C_{1-4}$alkyl, amino$C_{1-4}$alkyl, $Ar^1C_{1-4}$alkyl, mono- or di($C_{1-6}$alkyl)amino$C_{1-6}$alkyl, mono- or di($C_{1-6}$ alkyl)amino, (hydroxy$C_{1-6}$alkyl)amino, and optionally further with one or two $C_{1-4}$alkyl radicals.

The invention relates to the use of a compound of formula (I), or a prodrug, N-oxide, addition salt, quaternary amine, metal complex and stereochemically isomeric form thereof, for the manufacture of a medicament for inhibiting RSV replication. Or the invention relates to a method of inhibiting RSV replication in a warm-blooded animal said method comprising the administration of an effective amount of a compound of formula (I), or a prodrug, N-oxide, addition salt, quaternary amine, metal complex and stereochemically isomeric form thereof.

In a further aspect, this invention relates to novel compounds of formula (I) as well as methods for preparing these compounds.

The term 'prodrug' as used throughout this text means the pharmacologically acceptable derivatives, e.g. esters and amides, such that the resulting biotransformation product of the derivative is the active drug as defined in the compounds of formula (I). The reference by Goodman and Gilman (The Pharmacological Basis of Therapeutics, $8^{th}$ ed., McGraw-Hill, Int. Ed. 1992, "Biotransformation of Drugs", p. 13-15) describing prodrugs generally, is hereby incorporated. Prodrugs are characterized by a good aqueous solubility and bioavailability, and are readily metabolized into the active inhibitors in vivo.

The terms 'polysubstituted $C_{1-6}$alkyl' and 'polysubstituted $C_{2-6}$alkenyl' such as used in the definition of $R^{2a}$ and $R^{3a}$ meant to comprise $C_{1-6}$alkyl radicals having two or more substituents, for example two, three, four, five or six substituents, in particular two or three substituents, further in particular two substituents. The upper limit of the number of substituents is determined by the number of hydrogen atoms that can be replaced as well as by the general properties of the substituents such as their bulkiness, these properties allowing the skilled person to determine said upper limit.

The term '$C_{1-10}$alkanediyl optionally substituted with one or more substituents' as used in the definition of G is meant to comprise $C_{1-10}$alkanediyl radicals having no, one, two or more substituents, for example no, one, two, three, four, five or six substituents, in particular no, one, two or three substituents, further in particular no, one or two substituents. Also here, the upper limit of the number of substituents is determined by the factors mentioned above.

As used in the foregoing and hereinafter, 'polyhalo$C_{1-6}$ alkyl' as a group or part of a group, e.g. in polyhalo$C_{1-6}$ alkyloxy, is defined as mono- or polyhalo substituted $C_{1-6}$alkyl, in particular $C_{1-6}$alkyl substituted with up to one, two, three, four, five, six, or more halo atoms, such as methyl or ethyl with one or more fluoro atoms, for example, difluoromethyl, trifluoromethyl, trifluoroethyl. Also included are perfluoro $C_{1-6}$alkyl groups, which are $C_{1-6}$alkyl groups whereion all hydrogen atoms are replaced by fluoro atoms, e.g. pentafluoroethyl. In case more than one halogen atom is attached to an alkyl group within the definition of polyhalo$C_{1-4}$ alkyl, the halogen atoms may be the same or different.

Each of the monocyclic or bicyclic heterocycles in the definition of $R^1$ may optionally be substituted with 1 or where possible more substituents, such as 2, 3, 4 or 5, substituents. In particular, said heterocycles may optionally be substituted with up to 4, up to 3, up to 2 substituents, or up to 1 substituent.

Each $Ar^1$ or $Ar^2$ may be unsubstituted phenyl or phenyl substituted with 1 or more substituents, such as 5 or 4 substituents or, which is preferred, up to 3 substituents, or up to two substituents, or with one substituent.

A radical '$R^{6b}$—O—$C_{3-6}$alkenyl' or '$R^{6b}$—O—$C_{3-6}C_{3-6}$ alkynyl' such as mentioned among the substituents of $Ar^2$ in particular has the $R^{6b}$—O— group on a saturated carbon atom.

A hydroxy$C_{1-6}$alkyl group when substituted on an oxygen atom or a nitrogen atom preferably is a hydroxy$C_{2-6}$alkyl group wherein the hydroxy group and the oxygen or nitrogen are separated by at least two carbon atoms.

A dihydroxy$C_{1-6}$alkyl group as mentioned for example in the definition of $R^{4a}$ and $R^{4b}$, is a $C_{1-6}$alkyl group having two hydroxy substituents which in particular are substituted on different carbon atoms. The terms ($C_{1-6}$alkyloxy)(hydroxy)$C_{1-6}$alkyl, di($C_{1-6}$alkyl-oxy)$C_{1-6}$alkyl, ($Ar^1C_{1-6}$alkyloxy)(hydroxy)$C_{1-6}$alkyl refer to a $C_{1-6}$alkyl radical substitute with as well a $C_{1-6}$alkyloxy and a hydroxy group, with two $C_{1-6}$alkyloxy groups, and with a $Ar^1C_{1-6}$alkyloxy and a hydroxy group, respectively. Preferably in these radicals the substituents on the $C_{1-6}$alkyl group are on a carbon atom other than the carbon linked to the nitrogen atom to which $R^{4a}$ and/or $R^{4b}$ are linked.

As used herein $C_{1-3}$alkyl as a group or part of a group defines straight or branched chain saturated hydrocarbon radicals having from 1 to 3 carbon atoms such as methyl, ethyl, propyl, 1-methylethyl and the like; $C_{1-4}$alkyl as a group or part of a group defines straight or branched chain saturated hydrocarbon radicals having from 1 to 4 carbon atoms such as the group defined for $C_{1-3}$alkyl and butyl and the like; $C_{2-4}$alkyl as a group or part of a group defines straight or branched chain saturated hydrocarbon radicals having from 2 to 4 carbon atoms such as ethyl, propyl, 1-methylethyl, butyl and the like; $C_{1-6}$alkyl as a group or part of a group defines straight or branched chain saturated hydrocarbon radicals having from 1 to 6 carbon atoms such as the groups defined for $C_{1-4}$alkyl and pentyl, hexyl, 2-methylbutyl and the like; $C_{1-9}$alkyl as a group or part of a group defines straight or branched chain saturated hydrocarbon radicals having from 1 to 9 carbon atoms such as the groups defined for $C_{1-6}$alkyl and heptyl, octyl, nonyl, 2-methylhexyl, 2-methylheptyl and the like; $C_{1-10}$alkyl as a group or part of a group defines straight or branched chain saturated hydrocarbon radicals having from 1 to 10 carbon atoms such as the groups defined for $C_{1-9}$alkyl and decyl, 2-methylnonyl and the like.

The term '$C_{3-6}$alkenyl' used herein as a group or part of a group is meant to comprise straight or branched chain unsaturated hydrocarbon radicals having at least one double bond, or preferably having one double bond, and from 3 to 6 carbon atoms such as propenyl, buten-1-yl, buten-2-yl, penten-1-yl, penten-2-yl, hexen-1-yl, hexen-2-yl, hexen-3-yl, 2-methylbuten-1-yl, and the like. The term 'C$_{2-6}$alkenyl' used herein as a group or part of a group is meant to comprise —C$_{3-6}$alkenyl groups and ethylene. The term 'C$_{3-6}$alkynyl' defines straight or branched chain unsaturated hydrocarbon radicals having one triple bond and from 3 to 6 carbon atoms such as propenyl, butyn-1-yl, butyn-2-yl, pentyn-1-yl, pentyn-2-yl, hexyn-1-yl, hexyn-2-yl, hexyn-3-yl, 2-methylbutyn-1-yl, and the like. The term 'C$_{2-6}$alkynyl' used herein as a group or part of a group is meant to comprise C$_{3-6}$alkynyl groups and ethynyl.

C$_{3-7}$cycloalkyl is generic to cyclopropyl, cyclobutyl, cyclopentyl, cyclohexyl and cycloheptyl.

C$_{2-5}$alkanediyl defines bivalent straight and branched chain saturated hydrocarbon radicals having from 2 to 5 carbon atoms such as, for example, 1,2-ethanediyl, 1,3-propanediyl, 1,4-butanediyl, 1,2-propanediyl, 2,3-butanediyl, 1,5-pentanediyl and the like, C$_{1-4}$alkanediyl defines bivalent straight and branched chain saturated hydrocarbon radicals having from 1 to 4 carbon atoms such as, for example, methylene, 1,2-ethanediyl, 1,3-propanediyl, 1,4-butanediyl and the like; C$_{1-6}$alkanediyl is meant to include C$_{1-4}$alkanediyl and the higher homologues thereof having from 5 to 6 carbon atoms such as, for example, 1,5-pentanediyl, 1,6-hexanediyl and the like; C$_{1-10}$alkanediyl is meant to include C$_{1-6}$alkanediyl and the higher homologues thereof having from 7 to 10 carbon atoms such as, for example, 1,7-heptanediyl, 1,8-octanediyl, 1,9-nonanediyl, 1,10-decanediyl and the like.

As used herein the term 'R$^7$ is C$_{1-6}$alkyl substituted with both a radical —OR$^8$ and a heterocycle' refers to a C$_{1-6}$alkyl radical bearing two substituents, i.e. the group —OR$^8$ and a heterocycle and linked to the rest of the molecule through a carbon atom of the C$_{1-6}$alkyl moiety. Preferably the —OR$^8$ group is linked to a carbon atom of the C$_{1-6}$alkyl moiety that is not adjacent (not in α-position) to a heteroatom (such as a nitrogen atom). More preferably the radical R$^7$ being C$_{1-6}$alkyl substituted with both a radical —OR$^8$ and a heterocycle' is a radical that can be represented by the formula —CH$_2$—CH(OR$^8$)—CH$_2$—.

The heterocycle in R$^7$ preferably is linked to the group C$_{1-6}$alkyl via its nitrogen atom. The radicals hexahydrooxazepine, hexahydrothiazepine, 1-oxo-hexahydrothiazepine and 1,1-dioxo-hexahydrothiazepine preferably are 1,4-hexahydrooxazepine, 1,4-hexahydrothiazepine, 1-oxo-1,4-hexahydrothiazepine and 1,1-dioxo-1,4-hexahydrothiazepine.

As used herein before, the term (=O) forms a carbonyl moiety when attached to a carbon atom, a sulfoxide moiety when attached to a sulfur atom and a sulfonyl moiety when two of said terms are attached to a sulfur atom. The term (=N—OH) forms a hydroxyimine moiety when attached to a carbon atom.

The term halo is generic to fluoro, chloro, bromo and iodo. As used in the foregoing and hereinafter, polyhaloC$_{1-6}$alkyl as a group or part of a group is defined as mono- or polyhalosubstituted C$_{1-6}$alkyl, in particular methyl with one or more fluoro atoms, for example, difluoromethyl or trifluoromethyl. In case more than one halogen atom is attached to an alkyl group within the definition of polyhaloC$_{1-4}$alkyl, the halogen atoms may be the same or different.

It should be noted that the radical positions on any molecular moiety used in the definitions may be anywhere on such moiety as long as it is chemically stable.

Radicals used in the definitions of the variables include all possible isomers unless otherwise indicated. For instance pyridyl includes 2-pyridyl, 3-pyridyl and 4-pyridyl; pentyl includes 1-pentyl, 2-pentyl and 3-pentyl.

When any variable occurs more than one time in any constituent, each definition is independent.

Whenever used hereinafter, the term "compounds of formula (I)", or "the present compounds" or similar term is meant to include the compounds of general formula (I), their prodrugs, N-oxides, addition salts, quaternary amines, metal complexes and stereochemically isomeric forms. An interesting subgroup of the compounds of formula (I) or any subgroup thereof are the N-oxides, salts and all the stereoisomeric forms of the compounds of formula (I).

It will be appreciated that some of the compounds of formula (I) may contain one or more centers of chirality and exist as stereochemically isomeric forms.

The term "stereochemically isomeric forms" as used hereinbefore defines all the possible compounds made up of the same atoms bonded by the same sequence of bonds but having different three-dimensional structures which are not interchangeable, which the compounds of formula (I) may possess.

Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in a mixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers maybe separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of formula (I) can be obtained separately by conventional methods. Appropriate physical separation methods that may advantageously be employed are, for example, selective crystallization and chromatography, e.g. column chromatography.

For some of the compounds of formula (I), their prodrugs, N-oxides, salts, solvates, quaternary amines, or metal complexes and the intermediates used in the preparation thereof, the absolute stereochemical configuration was not experimentally determined. A person skilled in the art is able to determine the absolute configuration of such compounds using art-known methods such as, for example, X-ray diffraction.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

For therapeutic use, salts of the compounds of formula (I) are those wherein the counter-ion is pharmaceutically acceptable. However, salts of acids and bases, which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates, which the compounds of formula (I) as well as the salts thereof, are able to form. Such solvates are for example hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkyl halide, aryl halide or arylalkyl halide, e.g. methyliodide or benzyliodide. Other reactants with good leaving groups may also be used, such as alkyl trifluoromethane sulfonates, alkyl methane sulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compounds of formula (I) wherein one or several nitrogen atoms are oxidized to the so-called N-oxide.

It will be appreciated that the compounds of formula (I) may have metal binding, chelating, complexating properties and therefore may exist as metal complexes or metal chelates. Such metalated derivatives of the compounds of formula (I) are intended to be included within the scope of the present invention.

Some of the compounds of formula (I) may also exist in their tautomeric form. Such forms although not explicitly indicated in the above formula are intended to be included within the scope of the present invention.

One embodiment of the present invention concerns compounds of formula (I-a):

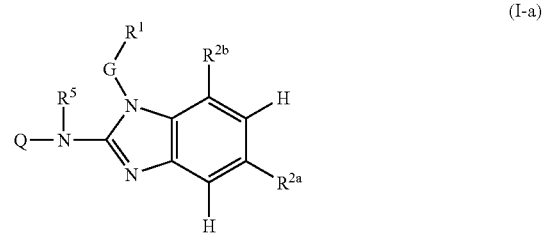

wherein Q, $R^5$, G, $R^1$, $R^{2a}$, $R^{2b}$ are as specified in the definitions of the compounds of formula (I) or any of the subgroups of compounds of formula (I) specified herein.

Another embodiment of the present invention concerns compounds of formula (I-b):

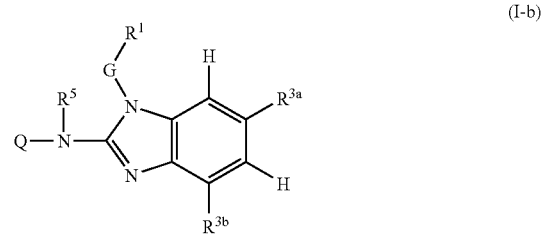

wherein Q, $R^5$, G, $R^1$, $R^{3a}$, $R^{3b}$ are as specified in the definitions of the compounds of formula (I) or any of the subgroups of compounds of formula (I) specified herein.

One particular embodiment of the present invention concerns compounds of formula (I-a-1):

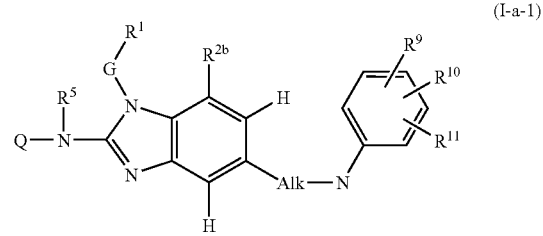

wherein Q, $R^5$, G, $R^1$, $R^{4a}$ and $R^{2b}$ are as specified in the definitions of the compounds of formula (I) or any of the subgroups of compounds of formula (I) specified herein; and Alk is $C_{1-6}$alkanediyl;

$R^9$, $R^{10}$, $R^{11}$ independently from one another have the same meanings as the substituents on $Ar^2$ as specified in the definitions of the compounds of formula (I) or of any of the subgroups thereof; and $R^{10}$ and/or $R^{11}$ may also be hydrogen.

Another particular embodiment of the present invention concerns compounds of formula (I-b-1):

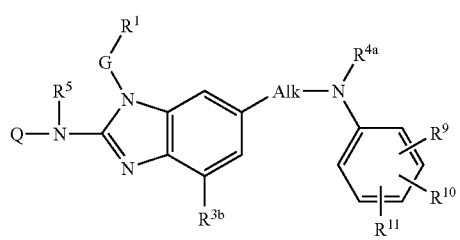
(I-b-1)

wherein Q, $R^5$, G, $R^1$, $R^{4a}$ and $R^{3b}$ are as specified in the definitions of the compounds of formula (I) or any of the subgroups of compounds of formula (I) specified herein; and Alk is $C_{1-6}$alkanediyl;

$R^9$, $R^{10}$, $R^{11}$ independently from one another have the same meanings as the substituents on $Ar^2$ as specified in the definitions of the compounds of formula (I) or of any of the subgroups thereof; and $R^{10}$ and/or $R^{11}$ may also be hydrogen.

Still other embodiments of the invention are groups of compounds which can be represented by formula:

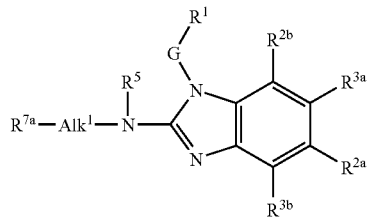
(I-c)

or by formula:

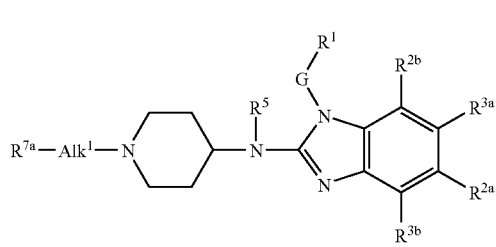
(I-d)

wherein in (I-c) or in (I-d) radicals $R^5$, G, $R^1$, $R^{2a}$, $R^{2b}$, $R^{3a}$, $R^{3b}$ are as specified in the definitions of the compounds of formula (I) or in any of the subgroups of compounds of formula (I) specified herein; and $Alk^1$ is $C_{1-6}$alkanediyl;

$R^{7a}$ is a heterocycle, the latter having the meanings of the heterocycle specified for radical $R^7$ in the definitions of the compounds of formula (I) or in any of the subgroups of compounds of formula (I) specified herein.

Interesting subgroups are those comprising compounds of formulae:

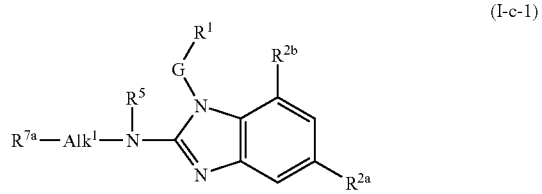
(I-c-1)

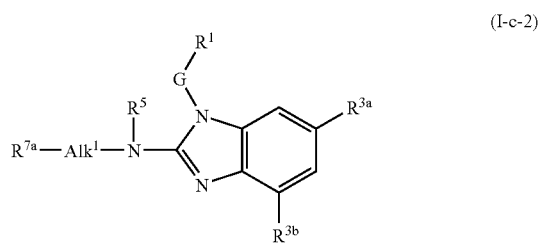
(I-c-2)

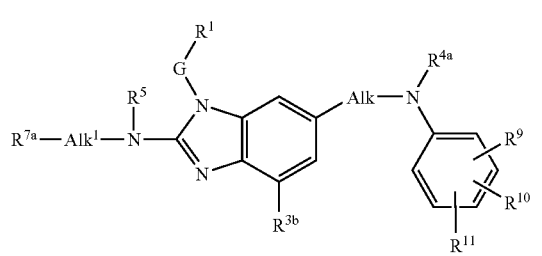
(I-c-3)

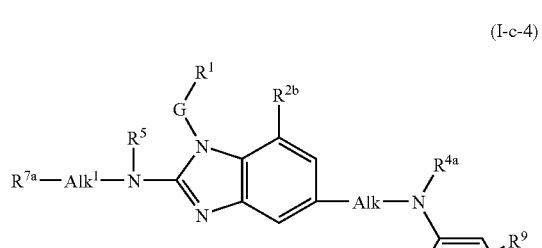
(I-c-4)

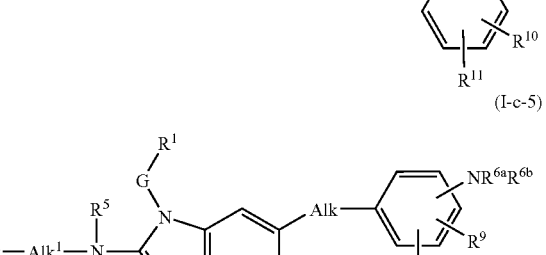
(I-c-5)

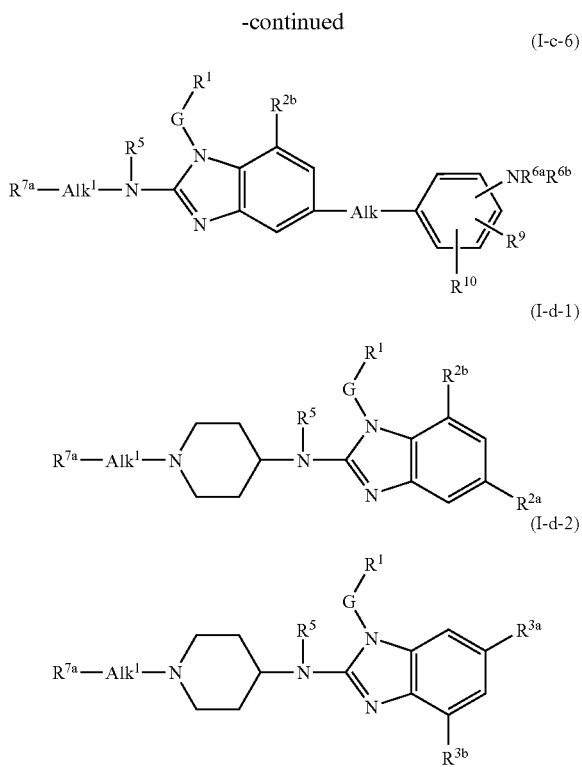

wherein in (I-c-1), (I-c-2), (I-c-3), (I-c-4), (I-c-5), (I-c-6), (I-d-1) or (I-d-2) the radicals $R^5$, G, $R^1$, $R^{2a}$, $R^{2b}$, $R^{3a}$, $R^{3b}$ are as specified in the definitions of the compounds of formula (I) or any of the subgroups of compounds of formula (I) specified herein; and the radicals Alk, $Alk^1$, $R^{7a}$, $R^9$, $R^{10}$, $R^{11}$ are as specified above or in any of the subgroups of compounds of formula (I) specified herein; and in (I-c-5) and (I-c-6) $R^{6a}$ and $R^{6b}$ are as specified in the definitions of the compounds of formula (I) or any of the subgroups of compounds of formula (I) specified herein.

Preferred subgroups are those subgroups of compounds of formula (I) wherein $R^{7a}$ is a heterocycle selected from the group consisting of oxazolidine, thiazolidine, morpholinyl, thiomorpholinyl, hexahydrooxazepine, hexahydrothiazepine; wherein each of said heterocyle may be optionally substituted with one or two substituents selected from the group consisting of $C_{1-6}$alkyl, hydroxy$C_{1-6}$alkyl, aminocarbonyl$C_{1-6}$alkyl, hydroxy, carboxyl, $C_{1-4}$alkyloxycarbonyl, aminocarbonyl, mono- or di($C_{1-4}$alkyl)aminocarbonyl, $C_{1-4}$alkylcarbonylamino, aminosulfonyl and mono- or di($C_{1-4}$ alkyl)aminosulfonyl; or preferably, wherein each of said heterocyle may be optionally substituted with one or two substituents selected from the group consisting of $C_{1-6}$alkyl, hydroxy$C_{1-6}$alkyl, aminocarbonyl$C_{1-6}$alkyl, carboxyl, $C_{1-4}$alkyloxy-carbonyl, aminocarbonyl, mono- or di($C_{1-4}$ alkyl)aminocarbonyl; or more preferably wherein each of said heterocyle may be optionally substituted with one or two substituents selected from the group consisting of $C_{1-6}$alkyl, hydroxy$C_{1-6}$alkyl, aminocarbonyl$C_{1-6}$alkyl.

More preferred subgroups are those subgroups of compounds of formula (I) wherein $R^{7a}$ is a heterocycle, wherein said heterocycle is oxazolidine, thiazolidine, morpholinyl, or thiomorpholinyl, wherein each of said heterocyle may be optionally substituted with one or two substituents selected from the group consisting of $C_{1-6}$alkyl, hydroxy-$C_{1-6}$alkyl, aminocarbonyl$C_{1-6}$alkyl.

Further preferred subgroups are those subgroups of compounds of formula (I) wherein $R^{7a}$ is a heterocycle, wherein said heterocycle is morpholinyl or thiomorpholinyl, wherein each of said heterocyle may be optionally substituted with one or two substituents selected from the group consisting of $C_{1-6}$alkyl, hydroxy$C_{1-6}$alkyl and aminocarbonyl-$C_{1-6}$alkyl.

Further preferred subgroups are those subgroups of compounds of formula (I) wherein $R^{7a}$ is a heterocycle, wherein said heterocycle is morpholinyl, which may be optionally substituted with one or two substituents selected from the group consisting of $C_{1-6}$alkyl, hydroxy$C_{1-6}$alkyl, aminocarbonyl-$C_{1-6}$alkyl.

Most preferred subgroups are those subgroups of compounds of formula (I) wherein $R^{7a}$ is morpholinyl.

Further preferred subgroups are those wherein Alk is ethylene or methylene, more preferably wherein Alk is methylene.

Further preferred subgroups are those wherein $Alk^1$ is $C_{1-4}$alkanediyl, more preferably wherein $Alk^1$ is $C_{2-3}$alkanediyl.

In (I-a-1), (I-b-1), (I-c-3) or (I-c-4) $R^{4a}$ preferably is hydrogen, hydoxy$C_{1-6}$alkyl, aminocarbonyl$C_{1-6}$alkyl.

In (I-a-1), (I-b-1), (I-c) (I-d), (I-c-1), (I-c-2), (I-c-3), (I-c-4), (I-c-5), (I-c-6), (I-d-1) or (I-d-2) the radicals
$R^9$, $R^{10}$, $R^{11}$ preferably and independently from one another are $C_{1-6}$alkyl or $R^{6b}$—O—$C_{1-6}$alkyl; and $R^{10}$ and/or $R^{11}$ may also be hydrogen; or
$R^9$, $R^{10}$ more preferably and independently from one another are $C_{1-6}$alkyl or $R^{6b}$—O—$C_{1-6}$alkyl; and $R^{11}$ is hydrogen; or
$R^9$, $R^{10}$ still more preferably are $C_{1-6}$alkyl and $R^{11}$ is hydrogen; or
$R^9$ is $C_{1-6}$alkyl, $R^{10}$ is $R^{6b}$—O—$C_{1-6}$alkyl and $R^{11}$ is hydrogen.

It is to be understood that the above defined subgroups of compounds of formulae (I-a), (I-b), etc. as well as any other subgroup defined herein are meant to also comprise any prodrugs, N-oxides, addition salts, quaternary amines, metal complexes and stereochemically isomeric forms of such compounds.

Particular subgroups of the compounds of formula (I) are those compounds of formula (I), or any subgroup of compounds of formula (I) specified herein, wherein G is $C_{1-10}$alkanediyl, more in particular wherein G is methylene.

Other particular subgroups of the compounds of formula (I) are those compounds of formula (I), or any subgroup of compounds of formula (I) specified herein, wherein
(a) $R^1$ is other than $Ar^1$; or wherein
(b) $R^1$ is $Ar^1$ or a monocyclic heterocycle, which is as specified in the definitions of the compounds of formula (I) or any of the subgroups thereof.

Further particular subgroups of the compounds of formula (I) are those compounds of formula (I), or any subgroup of compounds of formula (I) specified herein, wherein
(c) $R^1$ is pyridyl optionally substituted with 1 or 2 substituents independently selected from the group consisting of halo, hydroxy, amino, cyano, carboxyl, $C_{1-6}$alkyl, $C_{1-6}$alkyloxy, $C_{1-6}$alkylthio, $C_{1-6}$alkyloxy$C_{1-6}$alkyl, $Ar^1$, $Ar^1C_{1-6}$alkyl, $Ar^1C_{1-6}$alkyl-oxy, hydroxy$C_{1-6}$alkyl, mono-or di($C_{1-6}$alkyl)amino, mono-or di($C_{1-6}$alkyl)amino-$C_{1-6}$alkyl, polyhalo$C_{1-6}$alkyl, $C_{1-6}$alkylcarbonylamino, $C_{1-6}$alkyl-$SO_2$—$NR^{4a}$—, $Ar^1$—$SO_2$—$NR^{4a}$—, $C_{1-6}$alkyloxycarbonyl, —C(=O)—$NR^{4a}R^{4b}$, HO(—$CH_2$—$CH_2$—O)$_n$—, halo(—$CH_2$—$CH_2$—O)$_n$—, $C_{1-6}$alkyloxy(—$CH_2$—$CH_2$—O)$_n$—, $Ar^1C_{1-6}$alkyloxy(—$CH_2$—$CH_2$—O)$_n$— and mono-or di($C_{1-6}$alkyl)amino(—$CH_2$—$CH_2$—O)$_n$—; or more in particular (d) $R^1$ is pyridyl substituted with 1 or 2 substituents independently selected from the group consisting of hydroxy, $C_{1-6}$alkyl, halo, $C_{1-6}$alkyloxy, $Ar^1C_{1-6}$alkyloxy and ($C_{1-6}$alkyloxy)$C_{1-6}$alkyloxy; preferably wherein (e) $R^1$ is pyridyl substituted with 1 or 2 substituents independently selected from the group consisting of hydroxy, $C_{1-6}$alkyl, halo and $C_{1-6}$alkyloxy; or wherein (f) $R^1$ is pyridyl substituted with 1 or 2 substituents independently selected from the group consisting of hydroxy and $C_{1-6}$alkyl; more preferably wherein (g) $R^1$ is pyridyl substituted with hydroxy and $C_{1-6}$alkyl; or more preferably wherein (h) $R^1$ is pyridyl substituted with hydroxy and methyl; or wherein (i) $R^1$ is 3-hydroxy-6-methylpyrid-2-yl.

Further embodiments comprise those compounds of formula (I) or any of the subgroups of compounds of formula (I) wherein (j) $R^1$ is $Ar^1$, quinolinyl, benzimidazolyl, a radical of formula

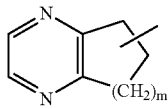

(c-4)

pyrazinyl, or pyridyl; or wherein (k) $R^1$ is $Ar^1$, quinolinyl, benzimidazolyl or a radical of formula (c-4) wherein m is 2, pyrazinyl, or pyridyl;

wherein each of the radicals in (j) and (k) may optionally be substituted with the substituents specified in the definition of the compounds of formula (I) and in particular pyridyl may be substituted as specified above in (a) to (i).

Further embodiments comprise those compounds of formula (I) or any of the subgroups of compounds of formula (I) wherein (l) $R^1$ is $Ar^1$, quinolinyl, benzimidazolyl or a radical of formula (c-4) wherein m is 2, pyrazinyl, or pyridyl, wherein each of these radicals may optionally be substituted with one, two or three radicals selected from the group consisting of halo, hydroxy, $C_{1-6}$alkyl, $C_{1-6}$alkyloxy, $Ar^1C_{1-6}$alkyloxy, ($C_{1-6}$alkyloxy)$C_{1-6}$alkyloxy; or more specifically wherein (m) $R^1$ is $Ar^1$, quinolinyl, benzimidazolyl or a radical of formula (c-4) wherein m is 2, pyrazinyl, or pyridyl, wherein each of these radicals may optionally be substituted with one, two or three radicals selected from the group consisting of halo, hydroxy, $C_{1-6}$alkyl, $C_{1-6}$alkyloxy, benzyloxy; or more specifically wherein (n) $R^1$ is phenyl optionally substituted with one, two or three radicals selected from the group consisting of halo, hydroxy, $C_{1-6}$alkyl, $C_{1-6}$alkyloxy; quinolinyl; a radical (c-4) wherein m is 2, optionally substituted with up to two radicals selected from $C_{1-6}$alkyl; benzimidazolyl optionally substituted with $C_{1-6}$alkyl; pyridyl optionally substituted with one or two radicals selected from hydroxy, halo, $C_{1-6}$alkyl, benzyloxy and $C_{1-6}$alkyloxy, pyrazinyl optionally substituted with up to three radicals selected from $C_{1-6}$alkyl; or pyridyl substituted or optionally substituted as specified above in (a)-(i); or wherein (o) $R^1$ is phenyl optionally substituted with one or two radicals selected from the group consisting of halo, hydroxy, $C_{1-6}$alkyl, $C_{1-6}$alkyloxy;

(p) $R^1$ is quinolinyl;

(q) $R^1$ is a radical (c-4) wherein m is 2, optionally substituted with up to two radicals selected from $C_{1-6}$alkyl;

(r) $R^1$ is benzimidazolyl optionally substituted with $C_{1-6}$alkyl; pyridyl optionally substituted with one or two radicals selected from hydroxy, halo, $C_{1-6}$alkyl, benzyloxy and $C_{1-6}$alkyloxy, (s) $R^1$ is pyrazinyl optionally substituted with up to three radicals selected from $C_{1-6}$alkyl.

Preferred subgroups of compounds of formula (I) or any of the subgroups of compounds of formula (I) are those wherein G is a direct bond or methylene and $R^1$ is as specified above in (a)-(s). Further preferred are the compounds of formula (I) or any of the subgroups specified herein wherein G is a direct bond and $R^1$ is a radical (c-4), in particular wherein m is 2, optionally substituted with up to two radicals selected from $C_{1-6}$alkyl. Further preferred are the compounds of formula (I) or any of the subgroups specified herein wherein or G is methylene and $R^1$ is as specified above in (a)-(s), but is other than a radical (c-4).

Further particular subgroups of the compounds of formula (I) are those compounds of formula (I), or any subgroup of compounds of formula (I) specified herein, wherein $R^5$ is hydrogen.

Other particular subgroups of the compounds of formula (I) are those compounds of formula (I), or any subgroup of compounds of formula (I) specified herein, wherein Q is $R^7$.

Interesting compounds are those compounds of formula (I) or of any of the subgroups specified herein, wherein Q is $R^7$ and the latter is $C_{1-6}$alkyl substituted with a heterocycle or $R^7$ is $C_{1-6}$alkyl substituted with both a radical —$OR^8$ and a heterocycle, wherein said heterocycle is selected from the group consisting of oxazolidine, thiazolidine, morpholinyl, thiomorpholinyl, hexahydrooxazepine, hexahydrothiazepine; wherein each of said heterocyle may be optionally substituted with one or two substituents selected from the group consisting of $C_{1-6}$alkyl, hydroxy$C_{1-6}$alkyl, aminocarbonyl$C_{1-6}$alkyl, hydroxy, carboxyl, $C_{1-4}$alkyloxycarbonyl, aminocarbonyl, mono- or di($C_{1-4}$alkyl)aminocarbonyl, $C_{1-4}$alkylcarbonylamino, aminosulfonyl and mono- or di($C_{1-4}$ alkyl)aminosulfonyl; or preferably, wherein each of said heterocyle may be optionally substituted with one or two substituents selected from the group consisting of $C_{1-6}$alkyl, hydroxy$C_{1-6}$alkyl, aminocarbonyl$C_{1-6}$alkyl, carboxyl, $C_{1-4}$alkyloxycarbonyl, aminocarbonyl, mono- or di($C_{1-4}$ alkyl)aminocarbonyl; or more preferably wherein each of said heterocyle may be optionally substituted with one or two substituents selected from the group consisting of $C_{1-6}$alkyl, hydroxy$C_{1-6}$alkyl, aminocarbonyl$C_{1-6}$alkyl.

An interesting subgroup of compounds are those compounds of formula (I) or of any of the subgroups specified herein, wherein Q is $R^7$ and the latter is $C_{1-6}$alkyl substituted with a heterocycle or $R^7$ is $C_{1-6}$alkyl substituted with both a radical —$OR^8$ and a heterocycle, wherein said heterocycle is oxazolidine, thiazolidine, morpholinyl, or thiomorpholinyl, wherein each of said heterocyle may be optionally substituted with one or two substituents selected from the group consisting of $C_{1-6}$alkyl, hydroxy-$C_{1-6}$alkyl, aminocarbonyl$C_{1-6}$ alkyl.

A further interesting subgroup of compounds are those compounds of formula (I) or of any of the subgroups specified herein, wherein Q is $R^7$ and the latter is $C_{1-6}$alkyl substituted with a heterocycle or $R^7$ is $C_{1-6}$alkyl substituted with both a radical —$OR^8$ and a heterocycle, wherein said heterocycle is morpholinyl or thiomorpholinyl, wherein each of said heterocyle may be optionally substituted with one or two substituents selected from the group consisting of $C_{1-6}$alkyl, hydroxy$C_{1-6}$alkyl and aminocarbonyl-$C_{1-6}$alkyl.

Still a further interesting subgroup of compounds are those compounds of formula (I) or of any of the subgroups specified herein, wherein Q is $R^7$ and the latter is $C_{1-6}$alkyl substituted with morpholinyl, which may be optionally substituted with one or two substituents selected from the group consisting of $C_{1-6}$alkyl, hydroxy$C_{1-6}$alkyl, aminocarbonyl-$C_{1-6}$alkyl, or preferably wherein Q is $R^7$ and the latter is $C_{1-6}$alkyl substituted with morpholinyl.

Other particular subgroups of the compounds of formula (I) are those compounds of formula (I), or any subgroup of compounds of formula (I) specified herein, wherein Q is pyrrolidinyl substituted with $R^7$, piperidinyl substituted with $R^7$ or homopiperidinyl substituted with $R^7$; in particular wherein Q is piperidinyl substituted with $R^7$.

Still other particular subgroups of the compounds of formula (I) are those compounds of formula (I), or any subgroup of compounds of formula (I) specified herein, wherein Q is pyrrolidinyl substituted with $R^7$, piperidinyl substituted with $R^7$ or homopiperidinyl substituted with $R^7$; in particular wherein Q is piperidinyl substituted with $R^7$; wherein (a) each $R^7$ is $C_{1-6}$alkyl substituted with a heterocycle or $R^7$ is $C_{1-6}$alkyl substituted with both a radical —$OR^8$ and a heterocycle, wherein said heterocycle is oxazolidine, thiazolidine, morpholinyl, thiomorpholinyl, hexahydrooxazepine, or hexahydrothiazepine; wherein each of said heterocyle may be optionally substituted with one or two substituents selected from the group consisting of $C_{1-6}$alkyl, hydroxyl$C_{1-6}$alkyl, aminocarbonyl$C_{1-6}$alkyl, hydroxy, carboxyl, $C_{1-4}$alkyloxycarbonyl, aminocarbonyl, mono and di($C_{1-4}$alkyl)aminocarbonyl, $C_{1-4}$alkylcarbonylamino, aminosulfonyl and mono- or di($C_{1-4}$alkyl)aminosulfonyl; or preferably, wherein each of said heterocyle may be optionally substituted with one or two substituents selected from the group consisting of $C_{1-6}$alkyl, hydroxyl-$C_{1-6}$alkyl, aminocarbonyl$C_{1-6}$alkyl, carboxyl, $C_{1-4}$alkyloxycarbonyl, amino-carbonyl, mono and di($C_{1-4}$alkyl)aminocarbonyl; or more preferably wherein each of said heterocyle may be optionally substituted with one or two substituents selected from the group consisting of $C_{1-6}$alkyl; or (b) wherein each $R^7$ is $C_{1-6}$alkyl substituted with a heterocycle or $R^7$ is $C_{1-6}$alkyl substituted with both a radical —$OR^8$ and a heterocycle, wherein said heterocycle is oxazolidine, thiazolidine, morpholinyl, or thiomorpholinyl, wherein each of said heterocyle may be optionally substituted with one or two substituents selected from the group consisting of $C_{1-6}$alkyl, hydroxy-$C_{1-6}$alkyl and aminocarbonyl-$C_{1-6}$alkyl; or (c) wherein each $R^7$ is $C_{1-6}$alkyl substituted with a heterocycle or $R^7$ is $C_{1-6}$alkyl substituted with both a radical —$OR^8$ and a heterocycle, wherein said heterocycle is morpholinyl or thiomorpholinyl, wherein each of said heterocyle may be optionally substituted with one or two substituents selected from the group consisting of $C_{1-6}$alkyl, hydroxy$C_{1-6}$alkyl and aminocarbonyl$C_{1-6}$alkyl; or (d) wherein each $R^7$ is $C_{1-6}$alkyl substituted with morpholinyl, which may be optionally substituted with one or two substituents selected from the group consisting of $C_{1-6}$alkyl, hydroxy$C_{1-6}$alkyl, aminocarbonyl-$C_{1-6}$alkyl; or preferably (e) wherein Q is $R^7$ and the latter is $C_{1-6}$alkyl substituted with morpholinyl.

Of particular interest are the compounds of formula (I) or any of the subgroups specified herein wherein $R^8$ is hydrogen.

Other subgroups of the compounds of formula (I) are those compounds of formula (I), or any subgroup of compounds of formula (I) specified herein, wherein (a) $R^{4a}$ and $R^{4b}$ are each independently selected from hydrogen, $C_{1-6}$alkyl, $Ar^2C_{1-6}$alkyl, $(Ar^2)$(hydroxy)$C_{1-6}$alkyl, Het-$C_{1-6}$alkyl, hydroxy$C_{1-6}$alkyl, mono- and di-($C_{1-6}$alkyloxy)$C_{1-6}$alkyl, (hydroxy$C_{1-6}$alkyl)oxy$C_{1-6}$alkyl, $Ar^1C_{1-6}$alkyloxy-$C_{1-6}$alkyl, dihydroxy$C_{1-6}$alkyl, ($C_{1-6}$alkyloxy)(hydroxy)$C_{1-6}$alkyl, ($Ar^1C_{1-6}$alkyloxy)(hydroxy)$C_{1-6}$alkyl, $Ar^1$oxy$C_{1-6}$alkyl, ($Ar^1$oxy)(hydroxy)-$C_{1-6}$alkyl, amino$C_{1-6}$alkyl, mono- and di($C_{1-6}$alkyl)amino-$C_{1-6}$alkyl, carboxyl$C_{1-6}$alkyl, $C_{1-6}$alkyloxycarbonyl-$C_{1-6}$alkyl, aminocarbonyl$C_{1-6}$alkyl, mono- and di($C_{1-6}$alkyl)aminocarbonyl-$C_{1-6}$alkyl, $C_{1-6}$alkylcarbonyl$C_{1-6}$alkyl, ($C_{1-4}$alkyloxy)$_2$P(=O)—$C_{1-6}$alkyl, ($C_{1-4}$alkyloxy)$_2$P(=O)—O—$C_{1-6}$alkyl, aminosulfonyl-$C_{1-6}$alkyl, mono- and di($C_{1-6}$alkyl)aminosulfonyl-$C_{1-6}$alkyl, $C_{1-6}$alkylcarbonyl, $Ar^2$carbonyl, Het-carbonyl, $Ar^2C_{1-6}$alkylcarbonyl, Het-$C_{1-6}$alkylcarbonyl, $Ar^2$ and Het; or wherein (b) $R^{4a}$ and $R^{4b}$ are each independently selected from hydrogen, $C_{1-6}$alkyl, $Ar^2C_{1-6}$alkyl, $(Ar^2)$(hydroxy)$C_{1-6}$alkyl, Het-$C_{1-6}$alkyl, hydroxy$C_{1-6}$alkyl, mono- and di-($C_{1-6}$alkyloxy)$C_{1-6}$alkyl, (hydroxy$C_{1-6}$alkyl)oxy$C_{1-6}$alkyl, $Ar^1C_{1-6}$alkyloxy-$C_{1-6}$alkyl, dihydroxy$C_{1-6}$alkyl, ($C_{1-6}$alkyloxy)(hydroxy)$C_{1-6}$alkyl, ($Ar^1C_{1-6}$alkyloxy)(hydroxy)$C_{1-6}$alkyl, $Ar^1$oxy-$C_{1-6}$alkyl, ($Ar^1$oxy)(hydroxy)-$C_{1-6}$alkyl, amino$C_{1-6}$alkyl, mono- and di($C_{1-6}$alkyl)amino-$C_{1-6}$alkyl, carboxyl-$C_{1-6}$alkyl, $C_{1-6}$alkyloxycarbonyl$C_{1-6}$alkyl, aminocarbonyl$C_{1-6}$alkyl, mono- and di($C_{1-6}$alkyl)aminocarbonyl$C_{1-6}$alkyl, $C_{1-6}$alkylcarbonyl$C_{1-6}$alkyl, ($C_{1-4}$alkyloxy)$_2$-P(=O)—$C_{1-6}$alkyl, ($C_{1-4}$alkyloxy)$_2$P(=O)—O—$C_{1-6}$alkyl, aminosulfonyl-$C_{1-6}$alkyl, mono- and di($C_{1-6}$alkyl)aminosulfonyl-$C_{1-6}$alkyl, $Ar^2$ and Het; or wherein (c) $R^{4a}$ and $R^{4b}$ are each independently selected from hydrogen, $C_{1-6}$alkyl, $Ar^2C_{1-6}$alkyl, $(Ar^2)$(hydroxy)$C_{1-6}$alkyl, Het-$C_{1-6}$alkyl, hydroxy$C_{1-6}$alkyl, ($C_{1-6}$alkyloxy)$C_{1-6}$alkyl, (hydroxy$C_{1-6}$alkyl)oxy$C_{1-6}$alkyl, $Ar^1C_{1-6}$alkyloxy-$C_{1-6}$alkyl, $Ar^1$oxy-$C_{1-6}$alkyl, ($Ar^1$oxy)(hydroxy)-$C_{1-6}$alkyl, amino$C_{1-6}$alkyl, mono- and di($C_{1-6}$alkyl)amino-$C_{1-6}$alkyl, carboxyl$C_{1-6}$alkyl, $C_{1-6}$alkyloxycarbonyl-$C_{1-6}$alkyl, aminocarbonyl$C_{1-6}$alkyl, mono- and di($C_{1-6}$alkyl)aminocarbonyl-$C_{1-6}$alkyl, ($C_{1-4}$alkyloxy)$_2$P(=O)—$C_{1-6}$alkyl, ($C_{1-4}$alkyloxy)$_2$P(=O)—O—$C_{1-6}$alkyl, aminosulfonyl-$C_{1-6}$alkyl, mono- and di($C_{1-6}$alkyl)aminosulfonyl-$C_{1-6}$alkyl and $Ar^1$; or wherein (d) $R^{4a}$ and $R^{4b}$ are each independently selected from hydrogen, $C_{1-6}$alkyl, $(Ar^2)$(hydroxy)$C_{1-6}$alkyl, Het-$C_{1-6}$alkyl, hydroxy$C_{1-6}$alkyl, ($C_{1-6}$alkyloxy)$C_{1-6}$alkyl, (hydroxy$C_{1-6}$alkyl)oxy$C_{1-6}$alkyl, $Ar^1C_{1-6}$alkyloxy-$C_{1-6}$alkyl, $Ar^1$oxy$C_{1-6}$alkyl, ($Ar^1$oxy)(hydroxy)-$C_{1-6}$alkyl, amino$C_{1-6}$alkyl, mono- and di($C_{1-6}$alkyl)amino-$C_{1-6}$alkyl, carboxyl$C_{1-6}$alkyl, aminocarbonyl$C_{1-6}$alkyl, mono- and di($C_{1-6}$alkyl)-aminocarbonyl$C_{1-6}$alkyl, ($C_{1-4}$alkyloxy)$_2$P(=O)—$C_{1-6}$alkyl, ($C_{1-4}$alkyloxy)$_2$-P(=O)—O—$C_{1-6}$alkyl, aminosulfonyl-$C_{1-6}$alkyl, mono- and di($C_{1-6}$alkyl)amino-sulfonyl-$C_{1-6}$alkyl and $Ar^1$.

Interesting subgroups of the compounds of formula (I) are those compounds of formula (I), or any subgroup of compounds of formula (I) specified herein, wherein (e) $R^{4a}$ and $R^{4b}$ are each independently selected from hydrogen, morpholinyl-$C_{1-6}$alkyl, hydroxy$C_{1-6}$alkyl, ($C_{1-6}$alkyloxy)$C_{1-6}$alkyl, amino$C_{1-6}$alkyl, mono- and di($C_{1-6}$alkyl)amino-$C_{1-6}$alkyl, carboxyl$C_{1-6}$alkyl, aminocarbonyl$C_{1-6}$alkyl, mono- and di($C_{1-6}$-alkyl)aminocarbonyl$C_{1-6}$alkyl, aminosulfonyl-$C_{1-6}$alkyl, mono- and di($C_{1-6}$alkyl)aminosulfonyl-$C_{1-6}$alkyl and $Ar^1$; or wherein (f) $R^{4a}$ and $R^{4b}$ are each independently selected from hydrogen, hydroxy$C_{1-6}$alkyl, ($C_{1-6}$alkyloxy)$C_{1-6}$alkyl, amino$C_{1-6}$alkyl, mono- and di($C_{1-6}$alkyl)amino$C_{1-6}$alkyl, carboxyl$C_{1-6}$alkyl, aminocarbonyl$C_{1-6}$alkyl, mono- and di($C_{1-6}$alkyl)amino-carbonyl-$C_{1-6}$alkyl; or wherein (g) $R^{4a}$ and $R^{4b}$ are each independently selected from hydrogen, hydroxy$C_{1-6}$alkyl, aminocarbonyl$C_{1-6}$alkyl, mono- and di($C_{1-6}$alkyl)aminocarbonyl$C_{1-6}$alkyl; or wherein (h) $R^{4a}$ and $R^{4b}$ are each independently selected from hydrogen, hydroxy$C_{1-6}$alkyl and aminocarbonyl$C_{1-6}$alkyl.

Other interesting subgroups of the compounds of formula (I) are those compounds of formula (I), or any subgroup of compounds of formula (I) specified herein, wherein $R^{4a}$ is hydrogen and $R^{4b}$ is as specified above in the restricted definitions (a) to (h).

Other subgroups of the compounds of formula (I) are those compounds of formula (I), or any subgroup of compounds of formula (I) specified herein, wherein (a) $Ar^2$ is phenyl, phenyl annelated with $C_{5-7}$cycloalkyl, or phenyl substituted with 1, 2, or 3 substituents selected from halo, cyano, $C_{1-6}$alkyl, Het-$C_{1-6}$alkyl, $Ar^1$—$C_{1-6}$alkyl, cyano$C_{1-6}$alkyl, $C_{2-6}$alkenyl, cyano$C_{2-6}$alkenyl, $R^{6b}$—O—$C_{3-6}$alkenyl, $C_{2-6}$alkynyl, cyano$C_{2-6}$alkynyl, $R^{6b}$—O—$C_{3-6}$alkynyl, $Ar^1$, Het, $R^{6b}$—O—, $R^{6b}$—S—, $R^{6c}$—SO—, $R^{6c}$—SO$_2$—, $R^{6b}$—O—$C_{1-6}$alkyl-SO$_2$—, —N($R^{6a}R^{6b}$), CF$_3$, CF$_3$-oxy, CF$_3$-thio, $R^{6c}$—C(=O)—, $R^{6b}$—O—C(=O)—, N($R^{6a}R^{6b}$)—C(=O)—, $R^{6b}$—O—$C_{1-6}$alkyl, $R^{6b}$—S—$C_{1-6}$alkyl, $R^{6c}$—S(=O)$_2$—$C_{1-6}$alkyl, N($R^{6a}R^{6b}$)—$C_{1-6}$alkyl, $R^{6c}$—C(=O)—$C_{1-6}$alkyl, $R^{6b}$—O—C(=O)—$C_{1-6}$alkyl, N($R^{6a}R^{6b}$)—C(=O)—$C_{1-6}$alkyl, $R^{6c}$—C(=O)—NR$^{6b}$, $R^{6c}$—C(=O)—O—, $R^{6c}$—C(=O)—NR$^{6b}$—$C_{1-6}$alkyl, $R^{6c}$—C(=O)—O—$C_{1-6}$alkyl, N($R^{6a}R^{6b}$)—S(=O)$_2$—, H$_2$N—C(=NH)—;

(b) $Ar^2$ is phenyl, phenyl annelated with $C_{5-7}$cycloalkyl, or phenyl substituted with 1, 2, or 3 substituents, or with 1 or 2 substituents, selected from halo, cyano, $C_{1-6}$alkyl, Het-$C_{1-6}$alkyl, $Ar^1$—$C_{1-6}$alkyl, cyano$C_{1-6}$alkyl, $C_{2-6}$alkenyl, cyano-$C_{2-6}$alkenyl, $R^{6b}$—O—$C_{3-6}$alkenyl, $C_{2-6}$alkynyl, cyano$C_{2-6}$alkynyl, $R^{6b}$—O—$C_{3-6}$alkynyl, $Ar^1$, Het, $R^{6b}$—O—, $R^{6b}$—S—, $R^{6c}$—SO—, $R^{6c}$—SO$_2$—, $R^{6b}$—O—$C_{1-6}$alkyl-SO$_2$—, —N($R^{6a}R^{6b}$), CF$_3$, $R^{6c}$—C(=O)—, $R^{6b}$—O—C(=O)—, N($R^{6a}R^{6b}$)—C(=O)—, $R^{6b}$—O—$C_{1-6}$alkyl, $R^{6b}$—S—$C_{1-6}$alkyl, $R^{6c}$—S(=O)$_2$—$C_{1-6}$alkyl, N($R^{6a}R^{6b}$)—$C_{1-6}$alkyl, $R^{6c}$—C(=O)—$C_{1-6}$alkyl, $R^{6b}$—O—C(=O)—$C_{1-6}$alkyl, N($R^{6a}R^{6b}$)—C(=O)—$C_{1-6}$alkyl, $R^{6c}$—C(=O)—NR$^{6b}$, H$_2$N—C(=NH)—;

(c) $Ar^2$ is phenyl, phenyl annelated with $C_{5-7}$cycloalkyl, or phenyl substituted with 1, 2, or 3, or with 1 or 2, substituents selected from halo, cyano, $C_{1-6}$alkyl, Het-$C_{1-6}$alkyl, $Ar^1$—$C_{1-6}$alkyl, cyano$C_{1-6}$alkyl, $C_{2-6}$alkenyl, cyano$C_{2-6}$alkenyl, $R^{6b}$—O—$C_{3-6}$alkenyl, $C_{2-6}$alkynyl, cyano$C_{2-6}$alkynyl, $R^{6b}$—O—$C_{3-6}$alkynyl, Het, $R^{6b}$—O—, $R^{6c}$—S—, $R^{6c}$—SO$_2$—, —N($R^{6a}R^{6b}$), CF$_3$, $R^{6b}$—O—C(=O)—, N($R^{6a}R^{6b}$)—C(=O)—, $R^{6b}$—O—$C_{1-6}$alkyl, $R^{6b}$—S—$C_{1-6}$alkyl, $R^{6c}$—S(=O)$_2$—$C_{1-6}$alkyl, N($R^{6a}R^{6b}$)—$C_{1-6}$alkyl, $R^{6c}$—C(=O)—

$C_{1-6}$alkyl, $R^{6b}$—O—C(=O)—$C_{1-6}$alkyl, N($R^{6a}R^{6b}$)—C(=O)—$C_{1-6}$alkyl, $R^{6c}$—C(=O)—NR$^{6b}$—;

(d) $Ar^2$ is phenyl, phenyl annelated with $C_{5-7}$cycloalkyl, or phenyl substituted with 1, 2, or 3, or with 1 or 2, substituents selected from $C_{1-6}$alkyl, Het-$C_{1-6}$alkyl, $Ar^1$—$C_{1-6}$alkyl, cyano$C_{1-6}$alkyl, $C_{2-6}$alkenyl, cyano$C_{2-6}$alkenyl, $R^{6b}$—O—$C_{3-6}$alkenyl, $C_{2-6}$alkynyl, cyano$C_{2-6}$alkynyl, $R^{6b}$—O—$C_{3-6}$alkynyl, $R^{6b}$—O—$C_{1-6}$alkyl, $R^{6b}$—S—$C_{1-6}$alkyl, $R^{6c}$—S(=O)$_2$—$C_{1-6}$alkyl, N($R^{6a}R^{6b}$)—$C_{1-6}$alkyl, $R^{6b}$—O—C(=O)—$C_{1-6}$alkyl, N($R^{6a}R^{6b}$)—C(=O)—$C_{1-6}$alkyl;

(e) $Ar^2$ is phenyl, or phenyl substituted with 1, 2, or 3 substituents, or with 1 or 2 substituents, selected from $C_{1-6}$alkyl, Het-$C_{1-6}$alkyl, $Ar^1$—$C_{1-6}$alkyl, cyano$C_{1-6}$alkyl, $C_{2-6}$alkenyl, cyano$C_{2-6}$alkenyl, hydroxy-$C_{3-6}$alkenyl, $C_{2-6}$alkynyl, cyano$C_{2-6}$alkynyl, hydroxy-$C_{3-6}$alkynyl, $R^{6b}$—O—$C_{1-6}$alkyl, amino-S(=O)$_2$—$C_{1-6}$alkyl, N($R^{6a}R^{6b}$)—$C_{1-6}$alkyl, $R^{6b}$—O—C(=O)—$C_{1-6}$alkyl, amino-C(=O)—$C_{1-6}$alkyl, mono- and di-$C_{1-6}$alkyl amino-C(=O)—$C_{1-6}$alkyl;

(f) $Ar^2$ is phenyl, or phenyl substituted with 1, 2, or 3 substituents or with 1 or 2 substituents selected from $C_{1-6}$alkyl, Het-$C_{1-6}$alkyl, $Ar^1$—$C_{1-6}$alkyl, cyano$C_{1-6}$alkyl, $C_{2-6}$alkenyl, cyano$C_{2-6}$alkenyl, $C_{2-6}$alkynyl, cyano$C_{2-6}$alkynyl, $R^{6b}$—O—$C_{1-6}$alkyl, amino-S(=O)$_2$—$C_{1-6}$alkyl, $R^{6b}$—O—C(=O)—$C_{1-6}$alkyl, amino-C(=O)—$C_{1-6}$alkyl, mono- and di-$C_{1-6}$alkylamino-C(=O)—$C_{1-6}$alkyl;

(g) $Ar^2$ is phenyl, or phenyl substituted with 1, 2, or 3 substituents or with 1 or 2 substituents selected from $C_{1-6}$alkyl, $R^{6b}$—O—$C_{1-6}$alkyl and amino-C(=O)—$C_{1-6}$ alkyl; or selected from $C_{1-6}$alkyl, hydroxy-$C_{1-6}$alkyl and amino-C(=O)—$C_{1-6}$alkyl.

The limitations in the substitutions on $Ar^2$ as specified under (a)-(g) above preferably apply to any $Ar^2$ being part of a radical $R^{2a}$ or $R^{3a}$ being $C_{1-6}$alkyl substituted with a radical —NR$^{4a}R^{4b}$ wherein $R^{4a}$ and/or $R^{4b}$ is or are a radical $Ar^2$.

Other subgroups of the compounds of formula (I) are those compounds of formula (I), or any subgroup of compounds of formula (I) specified herein, wherein (h) $Ar^2$ is phenyl substituted with $C_{1-6}$alkyl, Het-$C_{1-6}$alkyl, $Ar^1$—$C_{1-6}$alkyl, cyano$C_{1-6}$alkyl, $C_{2-6}$alkenyl, cyano$C_{2-6}$ alkenyl, $C_{2-6}$alkynyl, cyano$C_{2-6}$alkynyl, $R^{6b}$—O—$C_{1-6}$alkyl, amino-S(=O)$_2$—$C_{1-6}$alkyl, $R^{6b}$—O—C(=O)—$C_{1-6}$alkyl, amino-C(=O)—$C_{1-6}$alkyl, mono- and di-$C_{1-6}$alkylamino-C(=O)—$C_{1-6}$alkyl; and optionally further substituted with one or with two of the substituents of $Ar^2$ mentioned above in restrictions (a) to (g); or (i) $Ar^2$ is phenyl substituted with $R^{6b}$—O—$C_{1-6}$alkyl, amino-C(=O)—$C_{1-6}$alkyl; or phenyl substituted with hydroxy-$C_{1-6}$alkyl, amino-C(=O)—$C_{1-6}$alkyl; and optionally further substituted with one or with two of the substituents on $Ar^2$ mentioned above in restrictions (a) to (g).

The limitations in the substitutions on $Ar^2$ as specified under (h)-(i) above preferably apply to any $Ar^2$ being part of a radical $R^{2a}$ or $R^{3a}$ being $C_{1-6}$alkyl substituted with a radical $Ar^2$.

Further subgroups are compounds of formula (I) or of any of the subgroups of compounds of formula (I) wherein:

(a) $R^{6a}$ in particular is hydrogen, $C_{1-6}$alkyl, $Ar^1$, $Ar^1C_{1-6}$alkyl, $C_{1-6}$alkylcarbonyl, $Ar^1$carbonyl, $Ar^1C_{1-6}$alkylcarbonyl, $C_{1-6}$alkyloxy$C_{1-6}$alkyl, amino$C_{1-6}$alkyl, mono- or di($C_{1-6}$alkyl)amino$C_{1-6}$alkyl, hydroxy$C_{1-6}$alkyl, (carboxyl)-$C_{1-6}$alkyl, ($C_{1-6}$alkyl-oxycarbonyl)-$C_{1-6}$alkyl, aminocarbonyl$C_{1-6}$alkyl, mono- and di($C_{1-6}$alkyl)amino-carbonyl$C_{1-6}$alkyl, aminosulfonyl-$C_{1-6}$alkyl, mono- and di($C_{1-6}$alkyl)aminosulfonyl-$C_{1-6}$alkyl, Het, Het-$C_{1-6}$alkyl, Het-carbonyl, Het-$C_{1-6}$alkyl-carbonyl;

(b) $R^{6a}$ more in particular is hydrogen, $C_{1-6}$alkyl, $Ar^1$, $Ar^1C_{1-6}$alkyl, $C_{1-6}$alkyloxy-$C_{1-6}$alkyl, amino$C_{1-6}$alkyl, mono- or di($C_{1-6}$alkyl)amino$C_{1-6}$alkyl, hydroxy$C_{1-6}$alkyl, (carboxyl)-$C_{1-6}$alkyl, ($C_{1-6}$alkyloxycarbonyl)-$C_{1-6}$alkyl, aminocarbonyl$C_{1-6}$alkyl, mono- and di($C_{1-6}$alkyl)aminocarbonyl$C_{1-6}$alkyl, aminosulfonyl-$C_{1-6}$alkyl, mono- and di($C_{1-6}$alkyl)aminosulfonyl-$C_{1-6}$alkyl, Het, Het-$C_{1-6}$alkyl;

(c) $R^{6a}$ further in particular is hydrogen, $C_{1-6}$alkyl, $Ar^1C_{1-6}$alkyl, $C_{1-6}$alkyloxy$C_{1-6}$alkyl, amino$C_{1-6}$alkyl, mono- or di($C_{1-6}$alkyl)amino$C_{1-6}$alkyl, hydroxy$C_{1-6}$alkyl, (carboxyl)-$C_{1-6}$alkyl, ($C_{1-6}$alkyloxycarbonyl)-$C_{1-6}$alkyl, aminocarbonyl$C_{1-6}$alkyl, mono- and di($C_{1-6}$alkyl)aminocarbonyl$C_{1-6}$alkyl, aminosulfonyl-$C_{1-6}$alkyl, mono- and di($C_{1-6}$alkyl)aminosulfonyl-$C_{1-6}$alkyl, Het-$C_{1-6}$alkyl;

(d) $R^{6a}$ further in particular is hydrogen, $C_{1-6}$alkyl, $Ar^1C_{1-6}$alkyl, amino$C_{1-6}$alkyl, hydroxy$C_{1-6}$alkyl, (carboxyl)-$C_{1-6}$alkyl, aminocarbonyl$C_{1-6}$alkyl, aminosulfonyl-$C_{1-6}$alkyl, morpholinyl-$C_{1-6}$alkyl; (e) $R^{6a}$ further in particular is hydrogen, hydroxy$C_{1-6}$alkyl, aminocarbonyl$C_{1-6}$alkyl, aminosulfonyl-$C_{1-6}$alkyl; or wherein (e) $R^{6a}$ is hydrogen, $C_{1-6}$alkyl, $Ar^1$ or $Ar^1C_{1-6}$alkyl; or $R^{6a}$ is hydrogen or $C_{1-6}$alkyl; or $R^{6a}$ is hydrogen.

Further subgroups are compounds of formula (I) or of any of the subgroups of compounds of formula (I) wherein:

(f) $R^{6b}$ preferably is hydrogen or $C_{1-6}$alkyl; or more preferably is hydrogen;

(g) $R^{6b}$ preferably is $C_{1-6}$alkyl.

In the group of compounds of formula (I) or in any of the subgroups of compounds of formula (I):

(a) $Ar^1$ preferably is phenyl or phenyl substituted with up to 3 substituents, or with up to 2 substituents, or with one substituent, selected from halo, hydroxy, $C_{1-6}$alkyl, hydroxy$C_{1-6}$alkyl, trifluormethyl, and $C_{1-6}$alkyloxy;

(b) $Ar^1$ more preferably is phenyl or phenyl substituted with up to 3 substituents, or with up to 2 substituents, or with one substituent, selected from halo, hydroxy, $C_{1-6}$alkyl and $C_{1-6}$alkyloxy;

(c) $Ar^1$ more preferably is phenyl or phenyl substituted with up to 3 substituents, or with up to 2 substituents, or with one substituent, selected from halo and $C_{1-6}$alkyl.

Other subgroups of the compounds of formula (I) are those compounds of formula (I), or any subgroup of compounds of formula (I) specified herein, wherein (a) Het is tetrahydrofuranyl, furanyl, thienyl, thiazolyl, oxazolyl, imidazolyl, isothiazolyl, pyrazolyl, isoxazolyl, piperidinyl, homopiperidinyl, piperazinyl, morpholinyl, pyridyl, pyrazinyl, pyrimidinyl, tetrahydroquinolinyl, quinolinyl, isoquinolinyl, benzodioxanyl, benzodioxolyl, indolinyl, indolyl, which may optionally be substituted with oxo, amino, $Ar^1$, $C_{1-4}$alkyl, amino$C_{1-4}$ alkyl, $Ar^1C_{1-4}$alkyl, mono- or di($C_{1-6}$alkyl)amino$C_{1-6}$ alkyl, mono- or di($C_{1-6}$alkyl)amino, (hydroxy$C_{1-6}$ alkyl)amino, and optionally further with one or two $C_{1-4}$alkyl radicals; or (b) Het is tetrahydrofuranyl, furanyl, thienyl, thiazolyl, oxazolyl, imidazolyl, pyrazolyl, isoxazolyl, piperidinyl, homopiperidinyl, piperazinyl, morpholinyl, pyridyl, pyrazinyl, pyrimidinyl, tetrahydroquinolinyl, quinolinyl, isoquinolinyl, benzodioxanyl, benzodioxolyl, indolinyl, indolyl, which may optionally be substituted with oxo, amino, $Ar^1$, $C_{1-4}$alkyl, amino$C_{1-4}$alkyl, and optionally further with one or two $C_{1-4}$alkyl radicals; or (c) Het is furanyl, thienyl, pyrazolyl isoxazolyl, morpholinyl, pyrimidinyl, quinolinyl, indolinyl, which may optionally be substituted with one or two $C_{1-4}$alkyl radicals.

(d) Het is morpholinyl, which may optionally be substituted with one or two $C_{1-4}$alkyl radicals; or (d) Het is morpholinyl.

A particular embodiment of the present invention concerns compounds of formula (I) wherein Q, G, $R^1$ and $R^5$ are as specified above in the definition of formula (I) or as in any of the subgroups of compounds of formula (I) specified herein; and wherein (a) one of $R^{2a}$ and $R^{3a}$ is selected from —N($R^{4a}R^{4b}$), ($R^{4a}R^{4b}$)N—CO—, $C_{1-6}$alkyl substituted with one or two substituents selected from hydroxy, cyano, $Ar^2$, Het or —N($R^{4a}R^{4b}$) and $C_{2-6}$alkenyl substituted with cyano or $Ar^2$; and the other one of $R^{2a}$ and $R^{3a}$ is hydrogen; or (b) one of $R^{2a}$ and $R^{3a}$ is selected from —N($R^{4a}R^{4b}$); ($R^{4a}R^{4b}$)N—CO—; $C_{1-6}$alkyl optionally substituted with hydroxy, cyano, $Ar^2$, Het or —N($R^{4a}R^{4b}$); $C_{1-6}$alkyl substituted with hydroxy and $Ar^2$; and $C_{2-6}$alkenyl substituted with cyano or $Ar^2$; and the other one of $R^{2a}$ and $R^{3a}$ is hydrogen; or (c) one of $R^{2a}$ and $R^{3a}$ is selected from ($R^{4a}R^{4b}$)N—CO—; $C_{1-6}$alkyl optionally substituted with hydroxy, $Ar^2$, Het or —N($R^{4a}R^{4b}$); and $C_{2-6}$alkenyl substituted with $Ar^2$; and the other one of $R^{2a}$ and $R^{3a}$ is hydrogen; and in case $R^{2a}$ is different from hydrogen then $R^{2b}$ is hydrogen, $C_{1-6}$alkyl or halogen and $R^{3b}$ is hydrogen;

in case $R^{3a}$ is different from hydrogen then $R^{3b}$ is hydrogen, $C_{1-6}$alkyl or halogen and $R^{2b}$ is hydrogen;

$Ar^2$, Het, $R^{4a}$ and $R^{4b}$ are as in the definitions of the compounds of formula (I) or as in any subgroup specified herein.

Another particular embodiment of the present invention concerns compounds of formula (I) wherein Q, G, $R^1$ and $R^5$ are as specified above in the definition of formula (I) or as in any of the subgroups of compounds of formula (I) specified herein; and (d) one of $R^{2a}$ and $R^{3a}$ is selected from ($R^{4a}R^{4b}$)N—CO—; $C_{1-6}$alkyl optionally substituted with hydroxy, $Ar^2$, Het or —N($R^{4a}R^{4b}$); and $C_{2-6}$alkenyl substituted with $Ar^1$; and the other one of $R^{2a}$ and $R^{3a}$ is hydrogen; or (e) one of $R^{2a}$ and $R^{3a}$ is selected from ($R^{4a}$)HN—CO—; $C_{1-6}$alkyl optionally substituted with hydroxy, $Ar^2$, Het, —NH($R^{4a}$) or —N($R^{4a}$) $Ar^2$; and $C_{2-6}$alkenyl substituted with $Ar^1$; and the other one of $R^{2a}$ and $R^{3a}$ is hydrogen; or (f) one of $R^{2a}$ and $R^{3a}$ is $C_{1-6}$alkyl optionally substituted with hydroxy, $Ar^2$, Het, —NH($R^{4a}$) or —N($R^{4a}$) $Ar^2$; and the other one of $R^{2a}$ and $R^{3a}$ is hydrogen; or (g) one of $R^{2a}$ and $R^{3a}$ is $C_{1-6}$alkyl optionally substituted with hydroxy, $Ar^2$, —NH($R^{4a}$) or —N($R^{4a}$) $Ar^2$; and the other one of $R^{2a}$ and $R^{3a}$ is hydrogen;

(h) one of $R^{2a}$ and $R^{3a}$ is $C_{1-6}$alkyl optionally substituted with —NH($R^{4a}$) or —N($R^{4a}$)$Ar^2$; and the other one of $R^{2a}$ and $R^{3a}$ is hydrogen;

(i) one of $R^{2a}$ and $R^{3a}$ is $C_{1-6}$alkyl optionally substituted with —NH($R^{4a}$); and the other one of $R^{2a}$ and $R^{3a}$ is hydrogen;

(j) one of $R^{2a}$ and $R^{3a}$ is $C_{1-6}$alkyl optionally substituted with —N($R^{4a}$) $Ar^2$; and the other one of $R^{2a}$ and $R^{3a}$ is hydrogen;

in case $R^{2a}$ is different from hydrogen then $R^{2b}$ is hydrogen or $C_{1-6}$alkyl and $R^{3b}$ is hydrogen;

in case $R^{3a}$ is different from hydrogen then $R^{3b}$ is hydrogen or $C_{1-6}$alkyl and $R^{2b}$ is hydrogen;

$Ar^2$, Het, $R^{4a}$ and $R^{4b}$ are as in the definitions of the compounds of formula (I) or as in any subgroup specified herein.

Another particular embodiment of the present invention concerns compounds of formula (I) wherein Q, G, $R^1$ and $R^5$ are as specified above in the definition of formula (I) or as in any of the subgroups of compounds of formula (I) specified herein; wherein $R^{2a}$ and $R^{3a}$ are as defined in (a)-(j) above and $R^{2b}$ and $R^{3b}$ are both hydrogen.

Another embodiment of the present invention concerns compounds of formula (I) wherein Q, G, $R^1$ and $R^5$ are as specified above in the definition of formula (I) or as in any of the subgroups of compounds of formula (I) specified herein; wherein (k) one of $R^{2a}$ and $R^{3a}$ is $C_{1-6}$alkyl; and the other one of $R^{2a}$ and $R^{3a}$ is hydrogen; in case $R^{2a}$ is different from hydrogen then $R^{2b}$ is $C_{1-6}$alkyl and $R^{3b}$ is hydrogen; in case $R^{3a}$ is different from hydrogen then $R^{3b}$ is $C_{1-6}$alkyl and $R^{2b}$ is hydrogen.

Still another embodiment of the present invention concerns compounds of formula (I) wherein Q, G, $R^1$ and $R^5$ are as specified above in the definition of formula (I) or as in any of the subgroups of compounds of formula (I) specified herein; wherein one of $R^{2a}$ and $R^{3a}$ is selected from $C_{1-6}$alkyl substituted with —N($R^{4a}R^{4b}$), wherein $R^{4b}$ is hydrogen;

and the other one of $R^{2a}$ and $R^{3a}$ is hydrogen; and in case $R^{2a}$ is different from hydrogen then $R^{2b}$ is hydrogen and $R^{3b}$ is hydrogen;

in case $R^{3a}$ is different from hydrogen then $R^{3b}$ is hydrogen and $R^{2b}$ is hydrogen.

Still another embodiment of the present invention concerns compounds of formula (I) wherein Q, G, $R^1$ and $R^5$ are as specified above or as in any of the subgroups of compounds specified herein; and one of $R^{2a}$ and $R^{3a}$ is selected from $C_{1-6}$alkyl substituted with —N($R^{4a}R^{4b}$); and the other one of $R^{2a}$ and $R^{3a}$ is hydrogen; and in case $R^{2a}$ is different from hydrogen then $R^{2b}$ is hydrogen and $R^{3b}$ is hydrogen;

in case $R^{3a}$ is different from hydrogen then $R^{3b}$ is hydrogen and $R^{2b}$ is hydrogen; and further wherein $R^{4a}$ is $Ar^2$ and $R^{4b}$ is $C_{1-6}$alkyl, $Ar^2C_{1-6}$alkyl, $C_{1-6}$alkyloxy$C_{1-6}$alkyl, hydroxy$C_{1-6}$alkyloxy$C_{1-6}$alkyl, $Ar^1C_{1-6}$alkyloxy$C_{1-6}$alkyl, ($C_{1-6}$alkyloxy)(hydroxy)$C_{1-6}$alkyl, ($Ar^1C_{1-6}$alkyloxy)(hydroxy)$C_{1-6}$alkyl, amino$C_{1-6}$alkyl, mono- and di($C_{1-6}$alkyl)amino$C_{1-6}$alkyl, hydroxy-$C_{1-6}$alkyl, aminocarbonyl$C_{1-6}$alkyl, mono- and di($C_{1-6}$alkyl)aminocarbonyl$C_{1-6}$alkyl, $C_{1-4}$alkyloxycarbonyl$C_{1-6}$alkyl, hydroxycarbonyl$C_{1-6}$alkyl, Het or Het-$C_{1-6}$alkyl.

Preferred compounds are those compounds listed in tables 1 through 13, more in particular the compound numbers 1 to 128, 131 to 153, 161 to 164, 171 to 182, 185, and 192 to 293.

Most preferred are:

compound 3 in Table 1, exemplified in example 11, the name of which is 2-[6-{[2-(3-hydroxy-propyl)-5-methyl-phenylamino]-methyl}-2-(3-morpholin-4-yl-propylamino)-benzimidazol-1-ylmethyl]-6-methyl-pyridin-3-ol, compound 58, in Table 2, exemplified in example 14, the name of which is 2-[6-{[(3,5-dimethyl-phenyl)-(2-hydroxy-ethyl)-amino]-methyl}-2-(3-morpholin-4-yl-propylamino)-benzimidazol-1-ylmethyl]-6-methyl-pyridin-3-ol, compound 59, in Table 2 the name of which is 2, 2-[6-{[(3,5-dimethyl-phenyl)-(3-aminocarbonyl-propyl)-amino]-methyl}-2-(3-morpholin-4-yl-propylamino)-benzimidazol-1-ylmethyl]-6-methyl-pyridin-3-ol as well as the prodrugs, N-oxides, addition salts, quaternary amines and metal complexes thereof, in particular said three compounds and the acid-addition salts thereof.

The compounds of formula (I) or any of the subgroups thereof can be prepared as in the following reaction schemes.

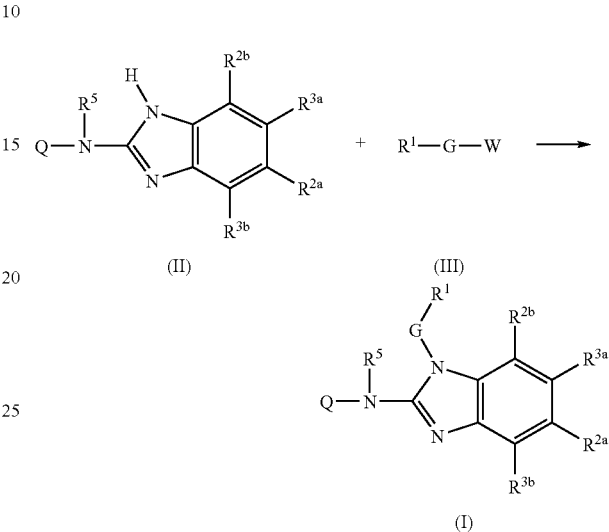

In this scheme Q, G, $R^1$, $R^{2a}$, $R^{2b}$, $R^{3a}$, $R^{3b}$, $R^5$ have the meanings defined above for the compounds of formula (I) or of any of the subgroups thereof. W is an appropriate leaving group, preferably it is chloro or bromo. The reaction of this scheme is typically conducted in a suitable solvent such as an ether, e.g. THF, a halogenated hydrocarbon, e.g. dichloromethane, $CHCl_3$, toluene, a polar aprotic solvent such as DMF, DMSO, DMA and the like. A base may be added to pick up the acid that is liberated during the reaction. If desired, certain catalysts such as iodide salts (e.g. KI) maybe added.

Compounds of formula (I) may be converted into each other following art-known functional group transformation reactions, comprising those described hereinafter.

Compounds of formula (I) wherein $R^{2a}$ or $R^{3a}$ is $C_{1-6}$alkoxycarbonyl or $C_{1-6}$alkyl substituted with $C_{1-6}$alkoxycarbonyl can be reduced, e.g. with $LiAlH_4$, to the corresponding compounds wherein $R^{2a}$ or $R^{3a}$ is hydroxy $C_{1-6}$alkyl. The latter group can be oxidized to an aldehyde group, e.g. with $MnO_2$, which can further be derivatized with amines, e.g. with a reductive amination process, to the corresponding $C_{1-6}$alkylamines or derivatized amines. Alternatively the compounds of formula (I) wherein $R^{2a}$ or $R^{3a}$ is hydroxy$C_{1-6}$alkyl can be converted to the corresponding halo$C_{1-6}$alkyl compounds, e.g. by treatment with a suitable halogenating agent such as $SOCl_2$ or $POCl_3$, which compounds subsequently are reacted with an amine or amine derivative.

These reactions can be represented in the following reaction schemes wherein a compound (I-1-a) or (I-1-b) is reduced to obtain a compound (I-2-a) or (I-2-b) and subsequently the alcohol group in (I-2-a) or (I-2-b) is oxidized with a mild oxidant to obtain an intermediate (I-3-a) or (I-3-b) and subsequently (I-3-a) or (I-3-b) are alkylated to obtain (I-4-a) or (I-4-b), which is further alkylated to obtain (I-5-a) or (I-5-b), wherein $R^{12}$ is $C_{1-6}$alkyl wherein is $R^{4a}$ and $R^{4b}$ are as defined in this specification and claims but are other than hydrogen:

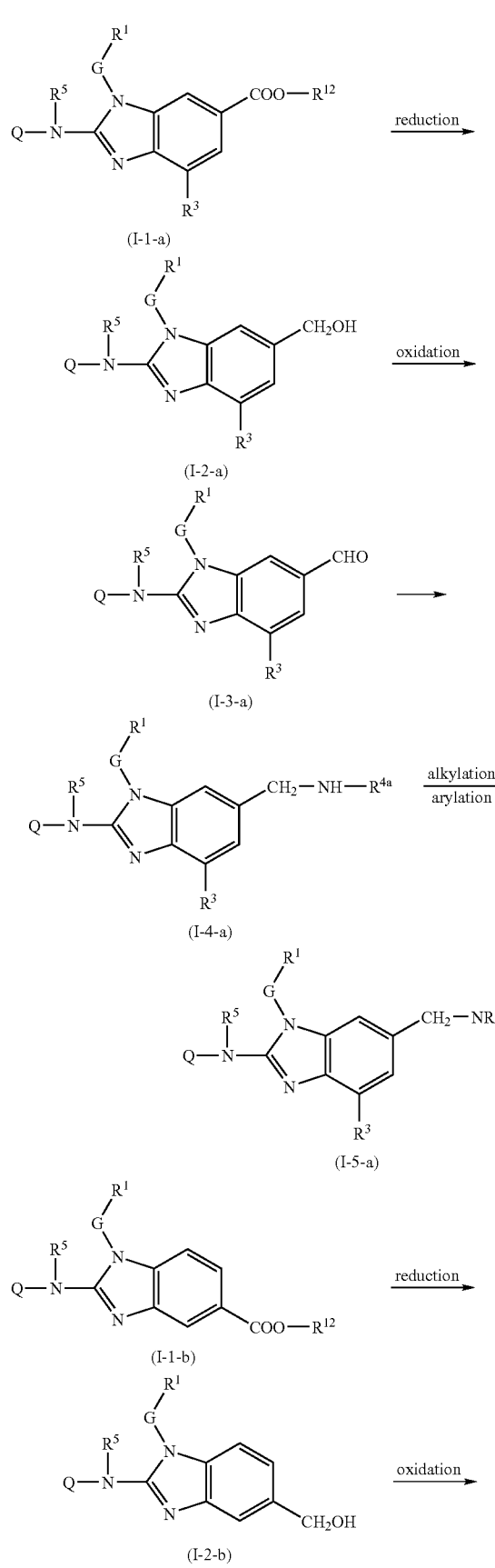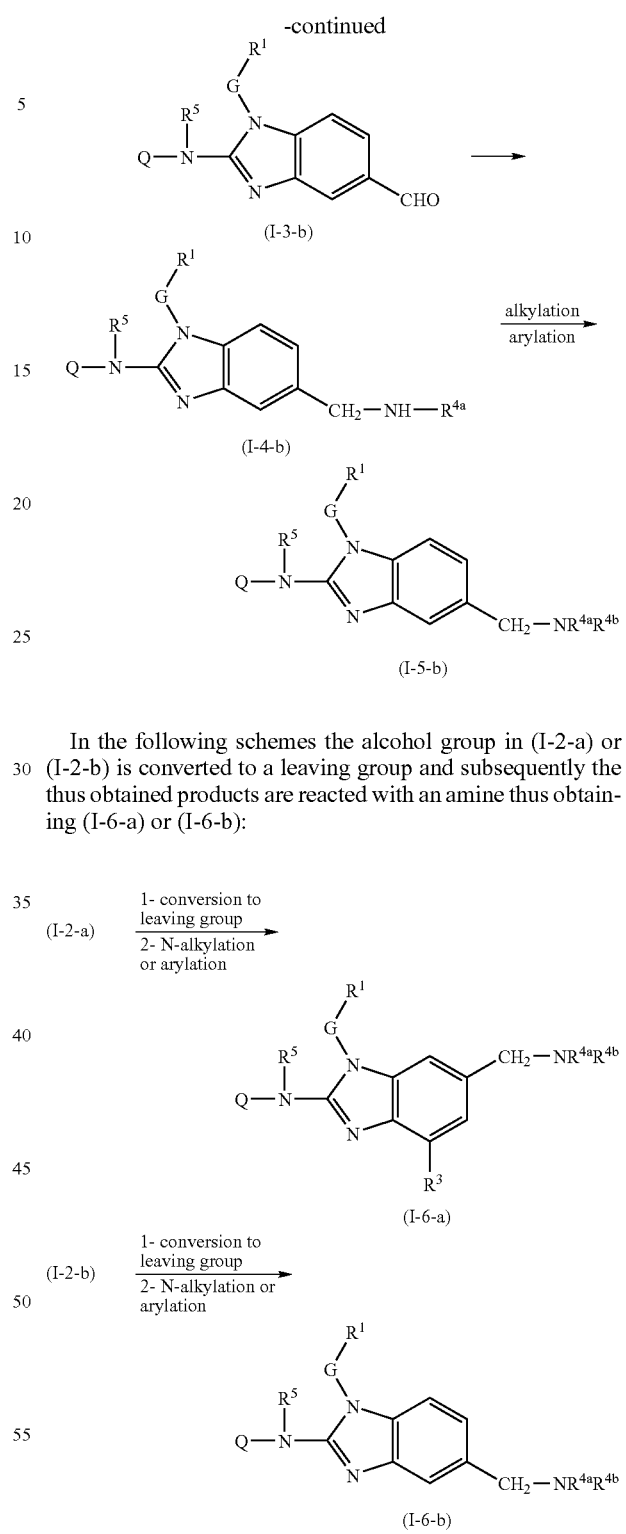

In the following schemes the alcohol group in (I-2-a) or (I-2-b) is converted to a leaving group and subsequently the thus obtained products are reacted with an amine thus obtaining (I-6-a) or (I-6-b):

Compounds of formula (I) wherein $R^{2a}$ or $R^{3a}$ is an aldehyde can be converted to the corresponding compounds wherein $R^{2a}$ or $R^{3a}$ is $C_{2-6}$alkenyl or substituted $C_{2-6}$alkenyl by a Wittig reaction or a Wittig-Horner reaction. In the former instance a Wittig type reagent is used, such as a triphenylphosphoniumylide in a suitable reaction-inert solvent such as an ether, staring from triphenylphosphine and a halo derivative. The Wittig-Horner reaction is performed using a phosphonate, such as e.g. a reagent of formula di($C_{1-6}$alkyloxy)-P(=O)—$CH_2$—$CH_2$—CN in the presence of a base, preferably a strong base, in an aprotic organic solvent. Compounds wherein $R^{2a}$ or $R^{3a}$ is $C_{2-6}$alkenyl or substituted $C_{2-6}$alkenyl can be reduced to the corresponding saturated alkyls, e.g. with hydrogen in the presence of a suitable catalyst such as Raney Ni.

These reactions can be represented in the following reaction schemes wherein an intermediate (I-3-a) or (I-3-b) is converted to a compound (I-7-a) or (I-7-b) using a Wittig or Wittig-Horner procedure; the double bond in (I-7-a) or (I-7-b) is selectively reduced thus obtaining compounds (I-8-a) or (I-8-b); the cyano group in (I-9-a) or (I-9-b) is reduced to a methylene-amine group thus obtaining compounds (I-10-a) or (I-10-b); the latter are mono- or dialkylated the latter thus obtaining compounds (I-11-a) or (I-11-b); or (I-12-a) or (I-12-b), wherein $Alk^1$ is $C_{4-6}$alkanediyl, $R^{2a-1}$ is any of the substituents on alkenyl as defined in this specification and claims, and preferably wherein $R^{2a-1}$ is $Ar^2$ or CN:

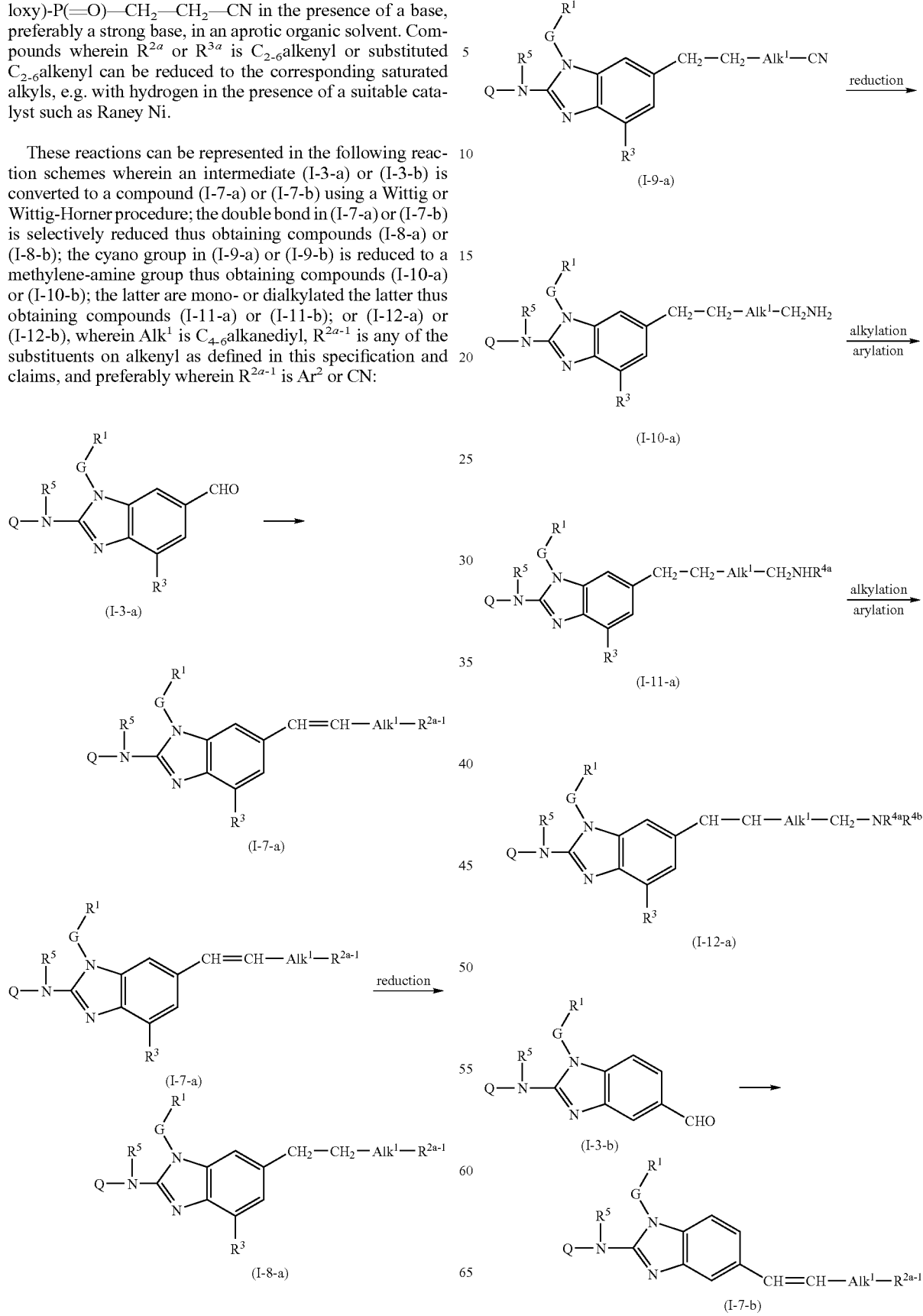

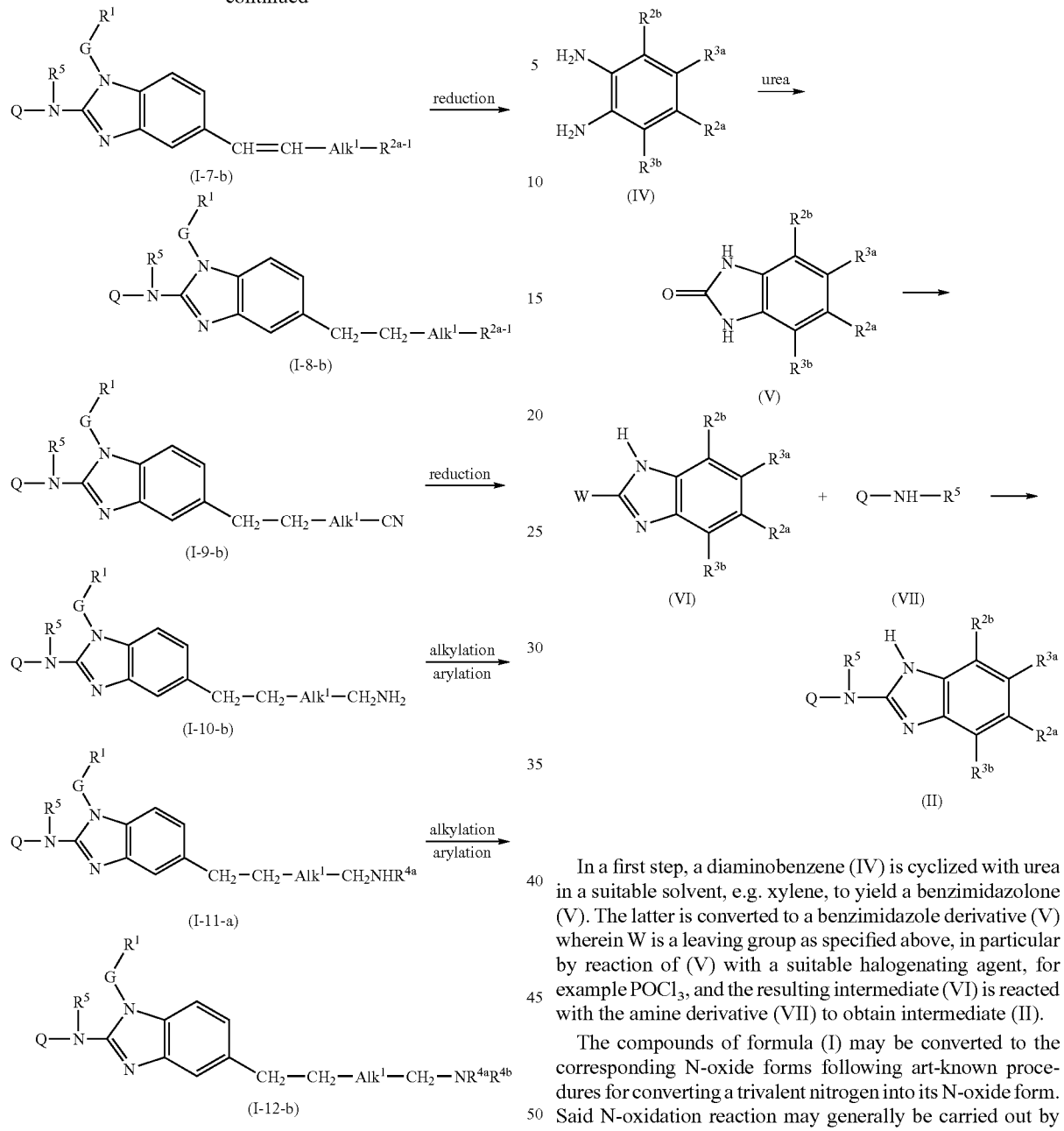

Compounds of formula (I) wherein $R^{2a}$ or $R^{3a}$ is an aldehyde can also be derivatized with a Grignard type of reaction to introduce aryl or alkyl groups.

Nitro groups can be reduced to amino groups, which subsequently may be alkylated to mono- or dialkylamino groups, or acylated to arylcarbonylamino or alkylcarbonyl-amino and the like groups. Cyano groups may be reduced to aminomethylene groups, which similarly may be derivatized.

A number of the intermediates used to prepare the compounds of formula (I) are known compounds or are analogs of known compounds which can be prepared following modifications of art-known methodologies readily accessible to the skilled person. A number of preparations of intermediates are given hereafter in somewhat more detail.

In a first step, a diaminobenzene (IV) is cyclized with urea in a suitable solvent, e.g. xylene, to yield a benzimidazolone (V). The latter is converted to a benzimidazole derivative (V) wherein W is a leaving group as specified above, in particular by reaction of (V) with a suitable halogenating agent, for example $POCl_3$, and the resulting intermediate (VI) is reacted with the amine derivative (VII) to obtain intermediate (II).

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g., counter-current distribution, liquid chromatography and the like.

The compounds of formula (I) as prepared in the hereinabove described processes are generally racemic mixtures of enantiomers which can be separated from one another following art-known resolution procedures. The racemic compounds of formula (I) which are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure staring materials.

In a further aspect, the present invention concerns a pharmaceutical composition comprising a therapeutically effective amount of a compound of formula (I) as specified herein, or a compound of any of the subgroups of compounds of formula (I) as specified herein, and a pharmaceutically acceptable carrier. A therapeutically effective amount in this context is an amount sufficient to prophylaxictically act against, to stabilize or to reduce viral infection, and in particular RSV viral infection, in infected subjects or subjects being at risk of being infected. In still a further aspect, this invention relates to a process of preparing a pharmaceutical composition as specified herein, which comprises intimately mixing a pharmaceutically acceptable carrier with a therapeutically effective amount of a compound of formula (I), as specified herein, or of a compound of any of the subgroups of compounds of formula (I) as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

The compounds of the present invention may also be administered via oral inhalation or insufflation by means of methods and formulations employed in the art for administration via this way. Thus, in general the compounds of the present invention may be administered to the lungs in the form of a solution, a suspension or a dry powder, a solution being preferred. Any system developed for the delivery of solutions, suspensions or dry powders via oral inhalation or insufflation are suitable for the administration of the present compounds.

Thus, the present invention also provides a pharmaceutical composition adapted for administration by inhalation or insufflation through the mouth comprising a compound of formula (I) and a pharmaceutically acceptable carrier. Preferably, the compounds of the present invention are administered via inhalation of a solution in nebulized or aerosolized doses.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula (I) show antiviral properties. Viral infections treatable using the compounds and methods of the present invention include those infections brought on by ortho- and paramyxoviruses and in particular by human and bovine respiratory syncytial virus (RSV). A number of the compounds of this invention moreover are active against mutated strains of RSV. Additionally, many of the compounds of this invention show a favorable pharmacokinetic profile and have attractive properties in terms of bioavailabilty, including an acceptable half-life, AUC and peak values and lacking unfavourable phenomena such as insufficient quick onset and tissue retention.

The in vitro antiviral activity against RSV of the present compounds was tested in a test as described in the experimental part of the description, and may also be demonstrated in a virus yield reduction assay. The in vivo antiviral activity against RSV of the present compounds may be demonstrated in a test model using cotton rats as described in Wyde et al. (Antiviral Research (1998), 38, 31-42).

Due to their antiviral properties, particularly their anti-RSV properties, the compounds of formula (I) or any subgroup thereof, their prodrugs, N-oxides, addition salts, quaternary amines, metal complexes and stereochemically isomeric forms, are useful in the treatment of individuals experiencing a viral infection, particularly a RSV infection, and for the prophylaxis of these infections. In general, the compounds of the present invention may be useful in the treatment of warm-blooded animals infected with viruses, in particular the respiratory syncytial virus.

The compounds of the present invention or any subgroup thereof may therefore be used as medicines. Said use as a medicine or method of treatment comprises the systemic administration to viral infected subjects or to subjects susceptible to viral infections of an amount effective to combat the conditions associated with the viral infection, in particular the RSV infection.

The present invention also relates to the use of the present compounds or any subgroup thereof in the manufacture of a medicament for the treatment or the prevention of viral infections, particularly RSV infection.

The present invention furthermore relates to a method of treating a warm-blooded animal infected by a virus, or being at risk of infection by a virus, in particular by RSV, said method comprising the administration of an anti-virally effective amount of a compound of formula (I), as specified herein, or of a compound of any of the subgroups of compounds of formula (I), as specified herein.

In general it is contemplated that an antivirally effective daily amount would be from 0.01 mg/kg to 500 mg/kg body weight, more preferably from 0.1 mg/kg to 50 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be thing, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

Also, the combination of another antiviral agent and a compound of formula (I) can be used as a medicine. Thus, the present invention also relates to a product containing (a) a compound of formula (I), and (b) another antiviral compound, as a combined preparation for simultaneous, separate or sequential use in antiviral treatment. The different drugs may be combined in a single preparation together with pharmaceutically acceptable carriers. For instance, the compounds of the present invention may be combined with interferon-beta or tumor necrosis factor-alpha in order to treat or prevent RSV infections.

EXAMPLES

The following examples are intended to illustrate the present invention and not to limit it thereto.

The terms 'compound 58, compound 143, etc. used in these examples refers to the same compounds in the tables.

The compounds were analyzed by LC/MS using the following equipment:

LCT: electrospray ionisation in positive mode, scanning mode from 100 to 900 amu; Xterra MS C18 (Waters, Milford, Mass.) 5 µm, 3.9×150 mm); flow rate 1 ml/min. Two mobile phases (mobile phase A: 85% 6.5 mM ammonium acetate+15% acetonitrile; mobile phase B: 20% 6.5 mM ammonium acetate+80% acetonitrile) were employed to run a gradient from 100% A for 3 min to 100% B in 5 min., 100% B for 6 min to 100% A in 3 min, and equilibrate again with 100% A for 3 min).

ZQ: electrospray ionisation in both positive and negative (pulsed) mode scanning from 100 to 1000 amu; Xterra RP C18 (Waters, Milford, Mass.) 5 µm, 3.9×150 mm); flow rate 1 ml/min. Two mobile phases (mobile phase A: 85% 6.5 mM ammonium acetate+15% acetonitrile; mobile phase B: 20% 6.5 mM ammonium acetate+80% acetonitrile) were employed to run a gradient condition from 100% A for 3 min to 100% B in 5 min., 100% B for 6 min to 100% A in 3 min, and equilibrate again with 100% A for 3 min).

Example 1

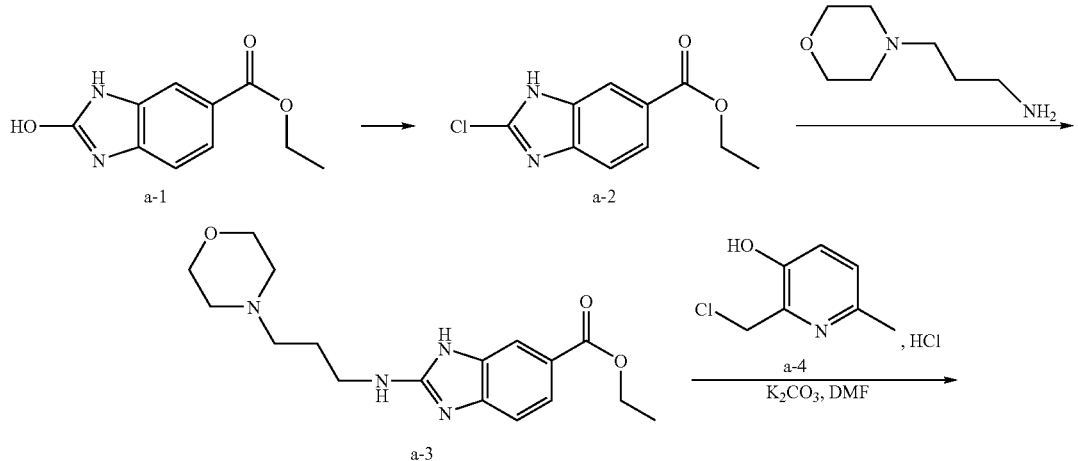

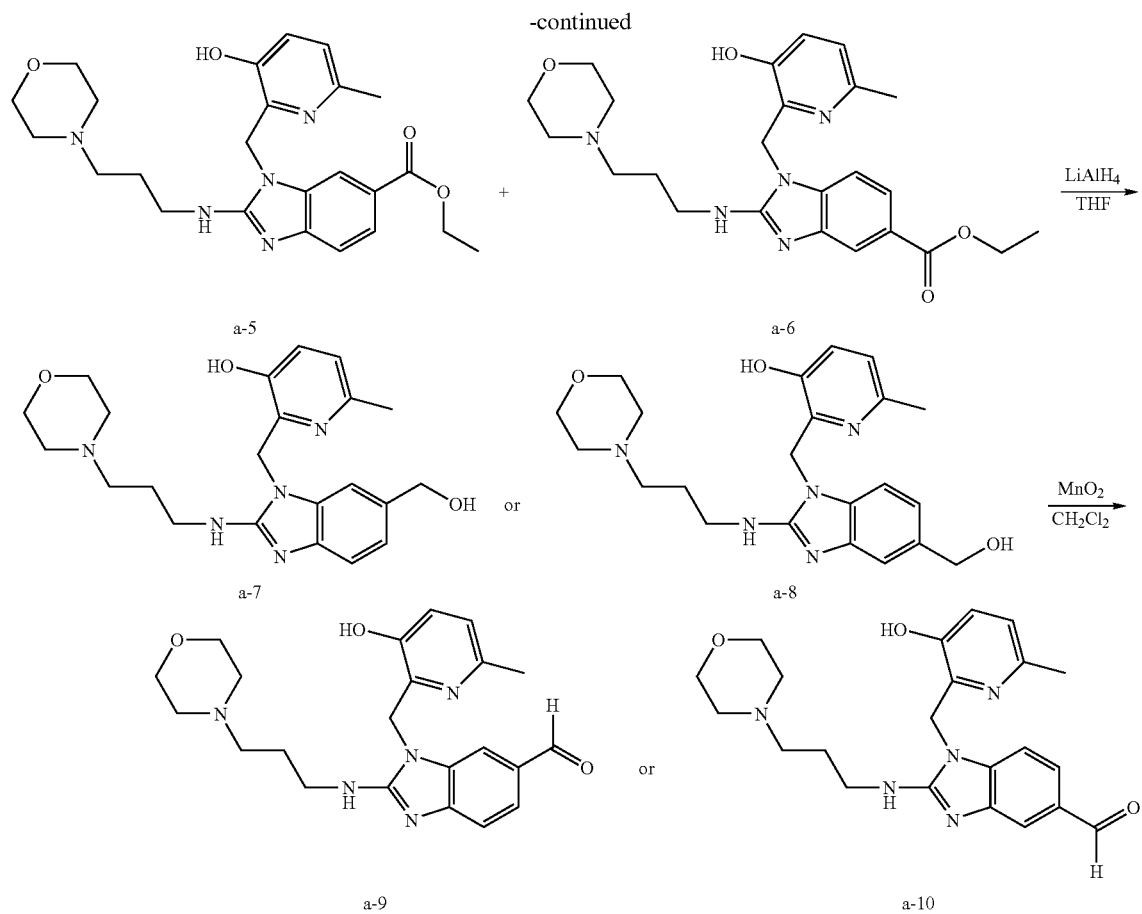

A mixture of 3,4-diamino benzoic acid ethyl ester (0.166 mol) and urea (0.199 mol) in xylene (300 ml) was stirred under reflux for 12 hours. The reaction was cooled down to room temperature. The precipitate was filtered off, rinsed with xylene and diisopropylether, and then dried, yielding 32 g of intermediate a-1 (93%, melting point: >260° C.).

A mixture of a-1 (0.073 mol) in $POCl_3$ (150 ml) was stirred at 100° C. HCl conc. (around 1.5 ml) was added drop wise very carefully until the dissolution of a-1. The mixture was stirred at 120° C. for 6 hours. The solvent was evaporated until dryness. The residue was takenup in $H_2O$/ice, basified with $K_2CO_3$ (powder) and extracted with ethylacetate+10% methanol. The organic layer was separated, dried (over $MgSO_4$), filtered and the solvent was evaporated until dryness, yielding 13.5 g of intermediate a-2 (83%, melting point: 178° C.).

A mixture of a-2 (0.0356 mol) and N-propylamino-morpholine (0.0427 mol) was stirred at 120° C. for 4 hours, and then taken up in $CH_2Cl_2/CH_3OH$. The organic layer was washed with a 10% solution of $K_2CO_3$ in water, dried (over $MgSO_4$), filtered and the solvent was evaporated until dryness. The residue (11.9 g) was purified by column chromatography over silica gel (eluent $CH_2Cl_2/CH_3OH/NH_4OH$ 94/6/0.2; 15-40 μm). The pure fractions were collected and the solvent was evaporated, yielding 6 g of intermediate a-3 (47%).

A mixture of a-3 (0.018 mol), a-4 (0.027 mol) and $K_2CO_3$ (0.054 mol) in $CH_3CN$ (100 ml) and dimethylformamide (10 ml) was stirred at 80° C. for 12 hours. The solvent was evaporated until dryness. The residue was taken up in $CH_2Cl_2/H_2O$. The organic layer was separated, dried (over $MgSO_4$), filtered and the solvent was evaporated until dryness. The residue was crystallized from 2-propanone. The precipitate was filtered, washed with $H_2O$ and dried, yielding 2.8 g of intermediate a-6 (34%, melting point: 176° C.). The mother layer was evaporated until dryness and purified by chromatography over silica gel (eluent: $CH_2Cl_2/CH_3OH/NH_4OH$ 93/7/0.7; 15-40 μm). The pure fractions were collected and the solvent was evaporated. The residue was crystallized from $CH_3CN$/diisopropylether, yielding 1.6 g of intermediate a-5 (20%, melting point: 184° C.).

A mixture of a-5 (0.0035 mol) in tetrahydrofuran (60 ml) was cooled down to 5° C. under $N_2$ flow. $LiAlH_4$ (0.0105 mol) was added portion wise. The mixture was stirred at 5° C. for 1 hour, and then sired at room temperature for 2 hours. A minimum of $H_2O$ was added. $CH_2Cl_2$ was added. The organic layer was separated, dried (over $MgSO_4$), filtered and the solvent was evaporated until dryness. The residue was crystallized from 2-propanone/diisopropylether. The precipitate was filtered off and dried, yielding 1.2 g of intermediate a-7 (83%). Part of this fraction (0.1 g) was crystallized from 2-propanone/$CH_3CN$/diisopropylether. The precipitate was filtered off and dried, yielding 0.074 g (melting point: 192° C.). Intermediate a-8 (melting point: 134° C.) was prepared in an analogous way.

A mixture of a-7 (0.0024 mol) and $MnO_2$ (2 g) in $CH_2Cl_2$ (50 ml) was stirred at room temperature for 12 hours, and then filtered over celite. Celite was washed with $H_2O$. The solvent of the filtrate was evaporated until dryness, yielding 0.9 g of intermediate a-9 (90%, melting point: 206° C.). Intermediate a-10 was prepared in an analogous way.

Example 2

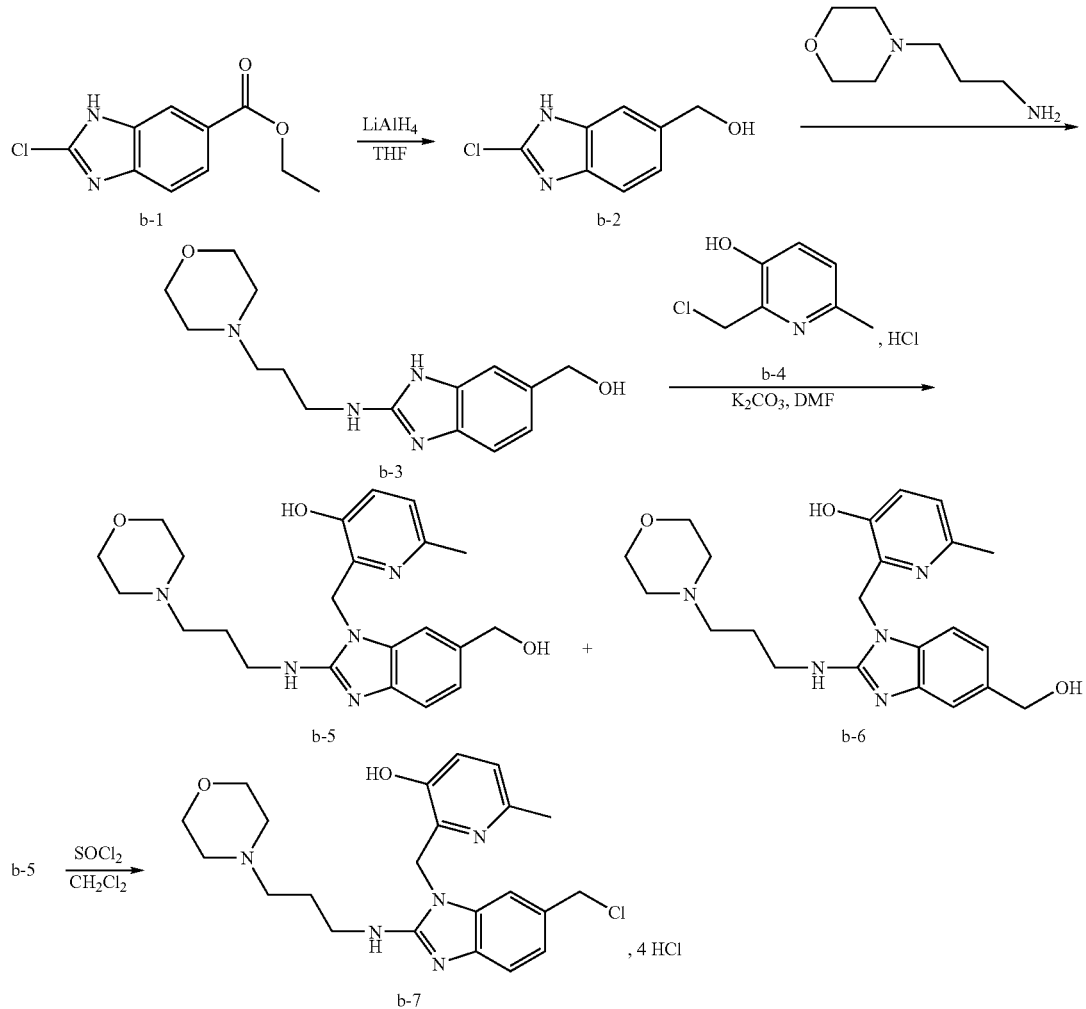

Scheme B

LiAlH$_4$ (0.146 mol) was added portion wise to a solution of tetrahydrofuran (200 ml) at 5° C. under N$_2$ flow. A solution of b-1 (0.073 mol) in tetrahydrofuran (200 ml) was then added drop wise. The mixture was stirred at 5° C. for 3 hours. A minimum of H$_2$O was then added, followed by a solution of CH$_2$Cl$_2$/CH$_3$OH (90/10). The resulting mixture was dried (over MgSO$_4$), filtered and the solvent was evaporated until dryness, yielding 12.6 g of intermediate b-2 (95%, melting point: 179° C.).

A mixture of b-2 (0.069 mol) and N-propylamino-morpholine (0.207 mol) was stirred at 125° C. for 4 hours, and then taken up in CH$_2$Cl$_2$/CH$_3$OH. The organic layer was washed with a 10% solution of K$_2$CO$_3$ in water, dried (over MgSO$_4$), filtered and the solvent was evaporated until dryness. The residue (37 g) was purified by column chromatography over silica gel (eluent: CH$_2$Cl$_2$/CH$_3$OH/NH$_4$OH 90/10/0.5; 20-45 μm). The pure fractions were collected and the solvent was evaporated, yielding 16.5 g of intermediate b-3 (82%).

A mixture of b-3 (0.0396 mol), b-4 (0.0475 mol) and K$_2$CO$_3$ (0.1188 mol) in dimethylformamide (110 ml) was stirred at room temperature for 12 hours. The reaction was poured into ice/water. The aqueous layer was saturated with K$_2$CO$_3$ (powder) and extracted with a solution of CH$_2$Cl$_2$/CH$_3$OH (95/5). The residue was purified by chromatography over silica gel (eluent CH$_2$Cl$_2$/CH$_3$OH/NH$_4$OH 90/10/1; 20-45 μm). The pure fractions were collected and the solvent was evaporated, yielding 5.4 g of intermediate b-5 (33%, melting point: 192° C.) and 5 g of intermediate b-6 (31%, melting point: 134° C.).

SOCl$_2$ (0.81 ml) was added drop wise to a mixture of b-5 (0.0006 mol) in CH$_2$Cl$_2$ (10 ml) at 5° C. The mixture was stirred at 5° C. for 2 hours, then brought to room temperature and stirred for 12 hours. The solvent was evaporated until dryness, yielding 0.42 g of intermediate b-7 (100%).

Example 3

Scheme C

TiCl₃ (15% in H₂O) (0.026 mol) was added drop wise at 0° C. to a solution of c-1 (3-(4-Methyl-2-nitro-phenyl)-prop-2-en-1-ol, 0.0026 mol) in tetrahydrofuran (30 ml). The mixture was stirred at 0° C. for 30 minutes, then at room temperature for 12 hours, poured into H₂O and basified slowly at 0° C. with K₂CO₃. EtOAc was added. The mixture was filtered over celite. Celite was washed with EtOAc. The filtrate was decanted. The organic layer was washed with H₂O, dried (over MgSO₄), filtered, and the solvent was evaporated. The residue (0.4 g) was purified by column chromatography over silica gel (eluent: CH₂Cl₂/CH₃OH/NH₄OH 97/3/0.1). The pure fractions were collected and the solvent was evaporated Yield: 0.1 g of intermediate c-2 (3-(2-Amino-4-methyl-phenyl)-prop-2-en-1-ol, 24%).

Example 4

Scheme D

A mixture of d-1 (4-Methyl-2-nitro-phenol, 0.00653 mol), 2-bromo-ethanol (0.00653 mol) and K₂CO₃ (0.0131 mol) in CH₃CN (15 ml) was stirred under reflux for 6 hours and then cooled down to room temperature. The solution was concentrated. The residue was taken up in CH₂Cl₂ and washed with H₂O. The organic layer was separated, dried (over MgSO₄), filtered and concentrated. Yield: 1.3 g of intermediate d-2 (2-(4-Methyl-2-nitro-phenoxy)-ethanol, 1000%). The compound was used directly in the next reaction step.

A mixture of d-2 (2-(4-Methyl-2-nitro-phenoxy)-ethanol, 0.0066 mol) and Raney Nickel (1.3 g) in CH₃OH (30 ml) was hydrogenated under a 3 bar pressure at room temperature for 2 hours. The solution was filtered through a pad of celite. The pad was rinsed with CH₃OH and the filtrate was concentrated. The residue was taken up in CH₂Cl₂. The precipitate was filtered off and dried. Yield: 0.41 g of intermediate d-3 (2-(2-Amino-4-methyl-phenoxy)-ethanol, 37%, melting point: 135° C.).

Example 5

Scheme E

A mixture of e-1 (3-(4-Methyl-2-nitro-phenyl)-acrylic acid ethyl ester, 0.0063 mol) in a solution of NH₃/CH₃OH 7N (20 ml) was stirred at 80° C. for 24 hours, then cooled to room temperature and evaporated. The residue was taken up in CH₂Cl₂. The precipitate was filtered off and dried. Yield: 0.78 g of e-2 (3-(4-Methyl-2-nitro-phenyl)-acrylamide, 60%, melting point: 208° C.).

A mixture of e-2 (3-(4-Methyl-2-nitro-phenyl)-acrylamide, 0.0037 mol) and Raney Nickel (0.7 g) in CH₃OH (30 ml) was hydrogenated at room temperature for 2 hours, and then filtered over celite. Celite was washed with CH₃OH. The filtrate was evaporated. Yield: 0.7 g of e-3 (3-(2-Amino-4-methyl-phenyl)-propionamide, 100%).

Example 6

Scheme F

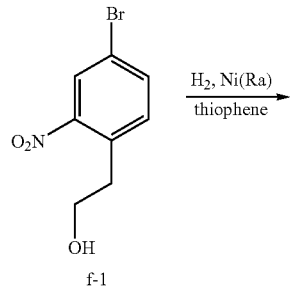

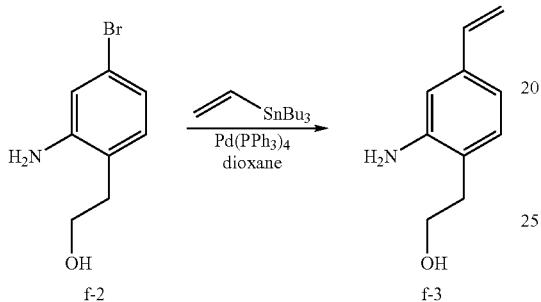

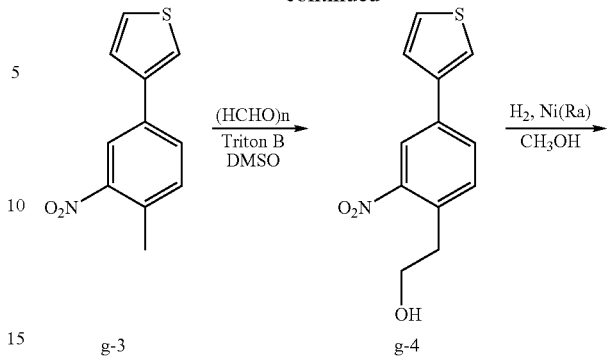

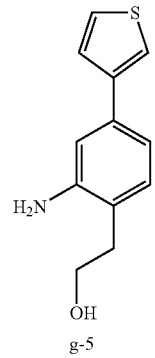

A mixture of f-1 (2-(4-Bromo-2-nitro-phenyl)-ethanol, 0.002 mol) and Raney Nickel (0.002 mol) in CH$_3$OH (20 ml) and thiophene (0.5 ml) was hydrogenated at room temperature for 1 hour under a 3 bar pressure, then filtered over celite. Celite was washed with CH$_3$OH. The filtrate was evaporated. Yield: 0.4 g of f-2 (2-(2-Amino-4-bromo-phenyl)-ethanol, 91%).

Tributyl-vinyl-stannane (0.0092 mol) was added drop wise at room temperature to a mixture of f-2 (2-(2-Amino-4-bromo-phenyl)-ethanol, 0.0046 mol) and Pd(PPh$_3$)$_4$ (0.0004 mol) in dioxane (20 ml) under N$_2$ flow. The mixture was stirred at 80° C. for 12 hours, poured into H$_2$O and extracted with Ethylacetate. The organic layer was separated, dried (over MgSO$_4$), filtered and the solvent was evaporated. The residue (3.4 g) was purified by column chromatography over silica gel (eluent: CH$_2$Cl$_2$/CH$_3$OH/NH$_4$OH 96/4/0.1; 15-40 μm). The pure fractions were collected and the solvent was evaporated. Yield: 0.21 g of f-3 (2-(2-Amino-4-vinyl-phenyl)-ethanol, 28%).

Example 7

Scheme G

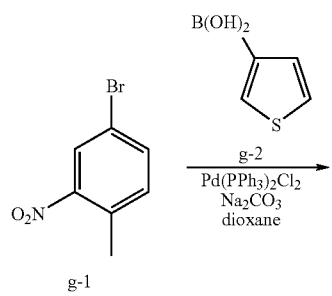

A mixture of g-1 (4-Bromo-1-methyl-2-nitro-benzene, 0.0104 mol), g-2 (3-thiopheneboronic acid, 0.0156 mol), Na$_2$CO$_3$ 2M in H$_2$O (30 ml) and Pd(PPh$_3$)$_2$Cl$_2$ (0.00104 mol) in dioxane (30 ml) was stirred under reflux for 2 hours. The reaction was cooled down to room temperature and ethylacetate was added. The organic layer was separated, washed with a saturated solution of NaCl, dried (over MgSO$_4$), filtered and the solvent was evaporated. Yield: 3.7 g of g-3 (3-(4-Methyl-3-nitro-phenyl)-thiophene, 100%). The crude compound was used directly in the next reaction step.

A mature of g-3 (3-(4-Methyl-3-nitro-phenyl)-thiophene, 0.00502 mol), paraformaldehyde (0.002 mol) and Triton B 40% in H$_2$O (0.11 ml) in DMSO (1.1 ml) was stirred at 90° C. for 3 hours. The crude solution was purified by column chromatography over silica gel (eluent: CH$_2$Cl$_2$). Yield: 0.44 g of g-4 (2-(2-Nitro-4-thiophen-3-yl-phenyl)-ethanol, 35%).

A mixture of g-4 (2-(2-Nitro-4-thiophen-3-yl-phenyl)-ethanol, 0.00176 mol) and Raney Nickel (0.4 g) in CH$_3$OH (40 ml) was hydrogenated at room temperature for 2 hours under a 3 bar pressure, then filtered over celite. Celite was washed with CH$_3$OH. The filtrate was evaporated. Yield: 0.37 g of g-5 (2-(2-Amino-4-thiophen-3-yl-phenyl)-ethanol, 96%).

Example 8

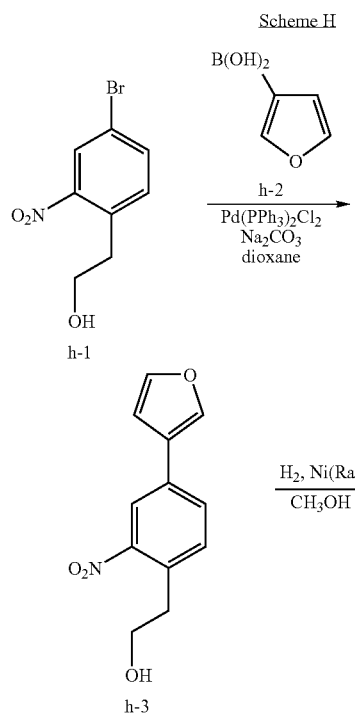

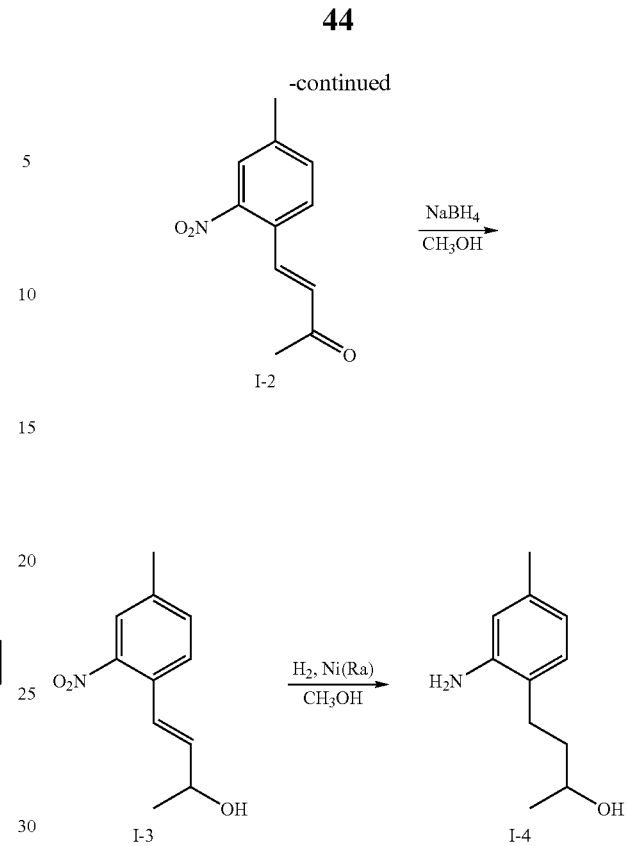

A mixture of h-1 (2-(4-Bromo-2-nitro-phenyl)-ethanol, 0.00205 mol), h-2 (furan-3-boronic acid, 0.00307 mol), Na$_2$CO$_3$ 2M in H$_2$O (7.5 ml) and Pd(PPh$_3$)$_2$Cl$_2$ (0.000205 mol) in dioxane (7.5 ml) was stirred under reflux for 3 hours. The reaction was cooled down to room temperature and ethylacetate was added. The organic layer was separated, washed with a saturated solution of NaCl, dried (over MgSO$_4$), filtered and the solvent was evaporated. The residue was purified by column chromatography over silica gel (eluent: CH$_2$Cl$_2$). Yield: 0.8 g of h-3 (2-(4-Furan-3-yl-2-nitro-phenyl)-ethanol, 73%).

A mixture of h-3 (2-(4-Furan-3-yl-2-nitro-phenyl)-ethanol, 0.0015 mol) and Raney Nickel (0.3 g) in CH$_3$OH (30 ml) was hydrogenated at room temperature for 2 hours under a 3 bar pressure, then filtered over celite. Celite was washed with CH$_3$OH. The filtrate was evaporated. The residue was purified by column chromatography over silica gel (eluent: CH$_2$Cl$_2$/CH$_3$OH/NH$_4$OH 98/2/0.2; 10 μm). Yield: 0.09 g of h-4 (2-(2-Amino-4-furan-3-yl-phenyl)-ethanol, 30%).

Example 9

Scheme I

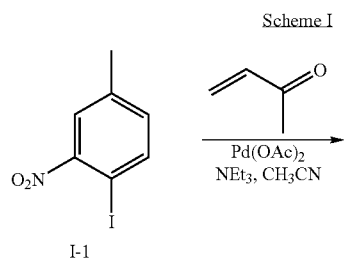

A mixture of i-1 (1-Iodo-4-methyl-2-nitro-benzene, 0.0038 mol), methyl-vinylketone (0.0076 mol), Et$_3$N (0.0076 mol) and Pd(OAc)$_2$ (0.00019 mol) in CH$_3$CN (6 ml) were stirred in a microwave oven (100° C., 100 W) for 5 min. The reaction was then filtered through a pad of celite and the filtrate was concentrated. The residue was purified by column chromatography over silica gel (eluent: CH$_2$Cl$_2$/Cyclohexane 70/30). Yield: 0.65 g of i-2 (4-(4-Methyl-2-nitro-phenyl)-but-3-en-2-one, 78%, melting point: 58° C.).

NaBH$_4$ (0.00633 mol) was added drop wise to a solution of i-2 (4-(4-Methyl-2-nitro-phenyl)-but-3-en-2-one, 0.00316 mol) in CH$_3$OH (10 ml) at 0° C. The reaction was stirred at 0° C. for 1 hour and then poured on ice. The aqueous layer was extracted with ethylacetate. The organic layer was separated, dried (over MgSO$_4$), filtered and the solvent was evaporated. Yield: 0.65 g of i-3 (4-(4-Methyl-2-nitro-phenyl)-but-3-en-2-ol, 1000%). The crude compound was used directly in the next reaction step.

A mixture of i-3 (4-(4-Methyl-2-nitro-phenyl)-but-3-en-2-ol, 0.00316 mol) and Raney Nickel (0.6 g) in CH$_3$OH (20 ml) was hydrogenated at room temperature for 2 hours under a 3 bar pressure, then filtered over celite. Celite was washed with CH$_3$OH. The filtrate was evaporated. Yield: 0.5 g of i-4 (4-(2-Amino-4-methyl-phenyl)-butan-2-ol, 88%).

Example 10

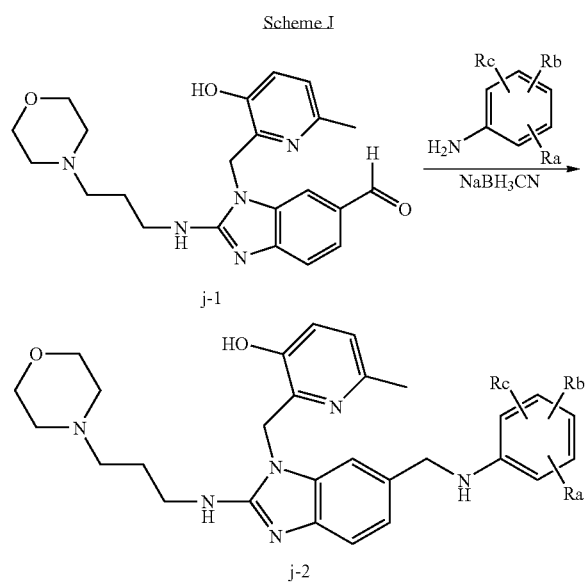

CH$_3$CO$_2$H (0.2 ml) was added at room temperature to a mixture of j-1 (0.0004 mol), 3,5-dimethyl-aniline (0.0005 mol) and NaBH$_3$CN (0.0005 mol) in CH$_3$CN (25 ml). The mixture was stirred at room temperature for 30 minutes. CH$_3$CO$_2$H (0.2 ml) was added. The mixture was stirred at room temperature for 12 hours. The solvent was evaporated until dryness. The residue was taken up in CH$_2$Cl$_2$. The organic layer was washed with a 10% solution of K$_2$CO$_3$ in water, dried (over MgSO$_4$), filtered and the solvent was evaporated until dryness. The residue (0.24 g) was purified by column chromatography over silica gel (eluent: CH$_2$Cl$_2$/CH$_3$OH/NH$_4$OH 90/10/0.2; 10 μm). The pure fractions were collected and the solvent was evaporated. The residue (0.15 g, 60%) was crystallized from 2-propanone/CH$_3$CN/diisopropylether. The precipitate was filtered off and dried, yielding 0.121 g of 2-[6-[(3,5-dimethyl-phenylamino)-methyl]-2-(3-morpholin-4-yl-propylamino)-benzoimidazol-1-ylmethyl]-6-methyl-pyridin-3-ol (example of j-2, compound 23, 48%, melting point: 199° C.).

Example 11

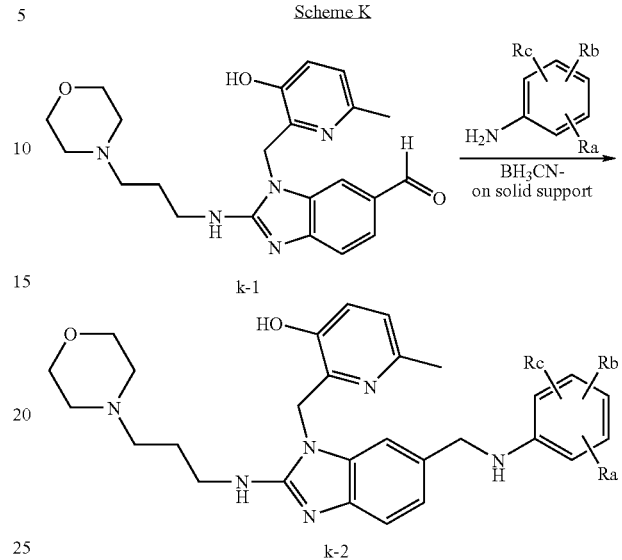

CH$_3$CO$_2$H (0.2 ml) was added at room temperature to a mixture of k-1 (0.0004 mol), 3-(2-amino-4-methyl-phenyl)-propan-1-ol (0.0005 mol) and BH$_3$CN— on solid support (0.0007 mol) in CH$_3$OH (20 ml). The mixture was stirred at room temperature for 12 hours. The solid support was filtered off, rinsed with CH$_3$OH and the filtrate was concentrated. The residue was taken up in a 10% solution of K$_2$CO$_3$ in water and extracted with CH$_2$Cl$_2$/CH$_3$OH (95/5). The organic layer was separated, dried (over MgSO$_4$), filtered and the solvent was evaporated until dryness. The residue was purified by colony chromatography over silica gel (eluent: CH$_2$Cl$_2$/CH$_3$OH/NH$_4$OH 92/8/1; 10 μm). The pure fractions were collected and the solvent was evaporated. The residue was crystallized from 2-propanone/diisopropylether. The precipitate was filtered off and dried, yielding 0.223 g of 2-[6-{[2-(3-Hydroxypropyl)-5-methyl-phenylamino]-methyl}-2-(3-morpholin-4-yl-propylamino)-benzoimidazol-1-ylmethyl]-6-methyl-pyridin-3-ol (example of k-2, compound 3, 82%, melting point: 208° C.).

Example 12

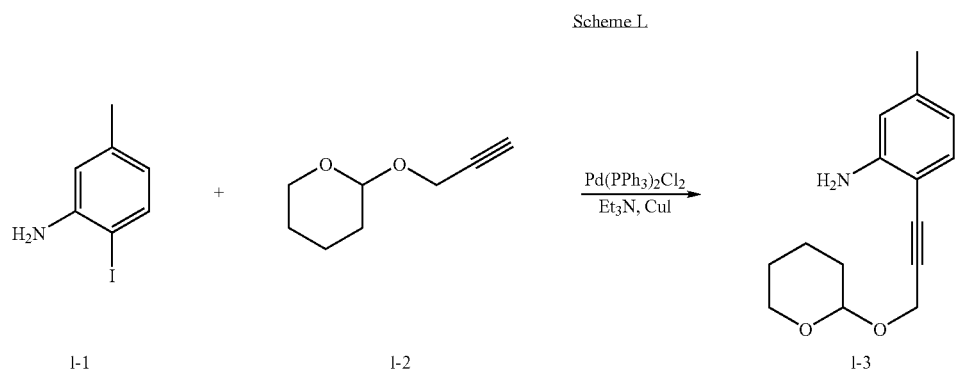

-continued

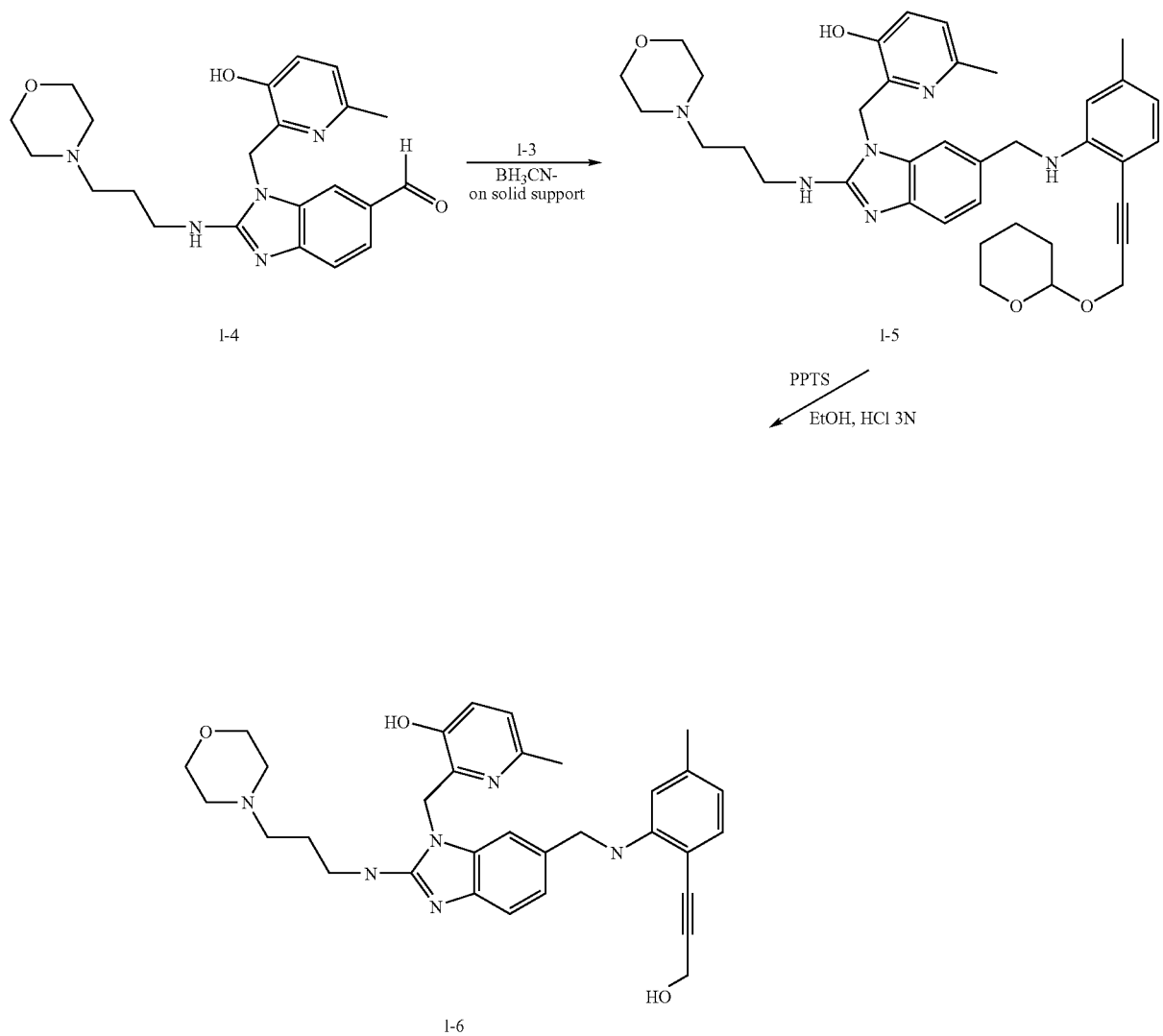

1-2 (0.0103 mol) was added drop wise to a mixture of 1-1 (0.0051 mol), Pd(PPh₃)₂Cl₂ (0.0005 mol) and CuI (0.0005 mol) in Et₃N (15 ml) under N₂ flow. The mixture was stirred at room temperature for 4 hours, poured into H₂O and extracted with EtOAc. The organic layer was washed with H₂O, dried (over MgSO₄), filtered and the solvent was evaporated. The residue (2.1 g) was purified by column chromatography over silica gel (eluent: CH₂Cl₂/cyclohexane 70/30). The pure fractions were collected and the solvent was evaporated. Yield: 1 g of intermediate 1-3 (79%).

CH₃CO₂H (5 drops) then BH₃CN— on solid support (0.0009 mol) were added at room temperature to a mixture of 1-4 (0.0004 mol) and 1-3 (0.0007 mol) in CH₃OH (3 ml). The mixture was stirred at room temperature for 48 hours, then filtered and washed with CH₂Cl₂/CH₃OH. The filtrate was evaporated. Yield: 0.4 g of intermediate 1-5 (100%). This product was used directly in the next reaction step.

A mixture of 1-5 (0.0004 mol) and pyridinium p-toluene sulfonate (0.00004 mol) in EtOH (15 ml) was stirred at 60° C. for 12 hours. HCl 3N (5 drops) was added. The mixture was stirred at 60° C. for 3 hours, then cooled to room temperature and evaporated. The residue was taken up in CH₂Cl₂/CH₃OH. The organic layer was washed with K₂CO₃ 10%, dried (over MgSO₄), filtered and the solvent was evaporated. The residue (0.33 g) was purified by column chromatography over silica gel (eluent: CH₂Cl₂/CH₃OH/NH₄OH 94/6/0.5). The pure fractions were collected and the solvent was evaporated. The residue was crystallized from diethyl ether. The precipitate was filtered off and dried Yield: 0.016 g of 2-[6-{[2-(3-Hydroxy-prop-1-ynyl)-5-methyl-phenylamino]-methyl}-2-(3-morpholin-4-yl-propylamino)-benzoimidazol-1-ylmethyl]-6-methyl-pyridin-3-ol (1-6, compound 34, 6%, melting point: 225° C.).

Example 13

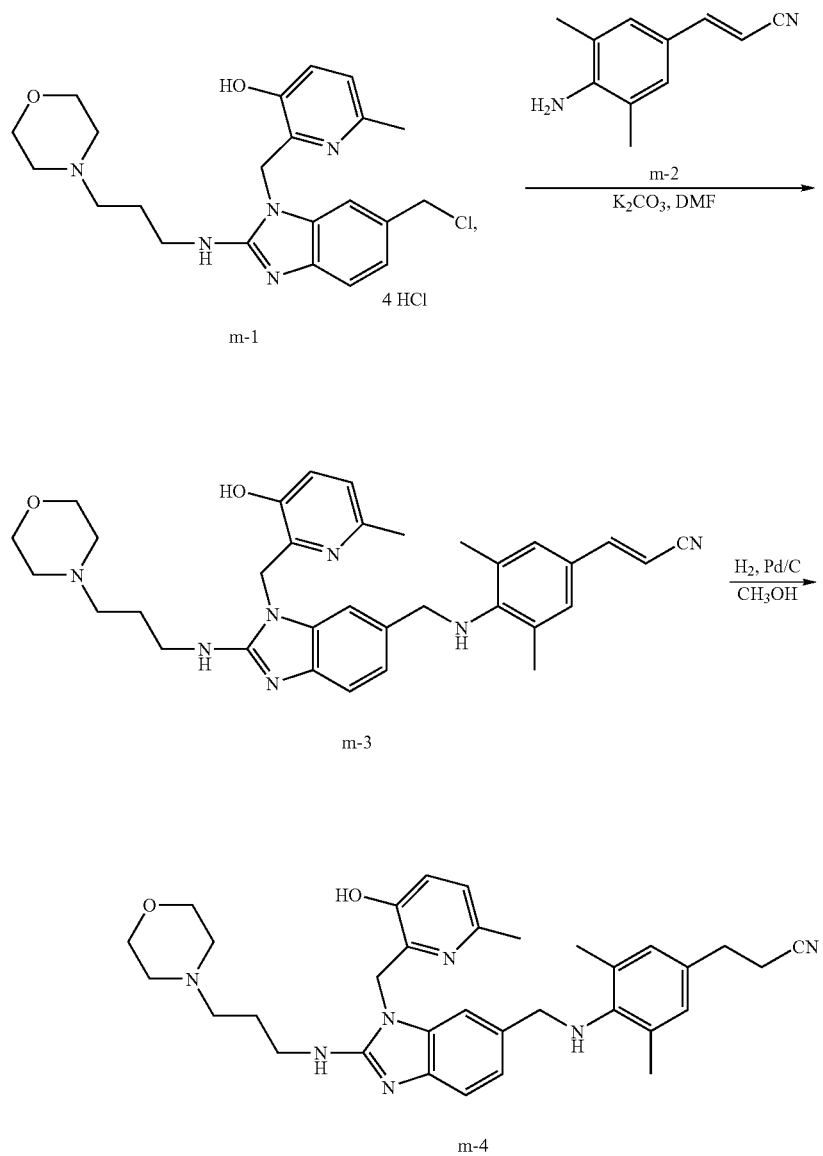

A mixture of m-1 (0.000347 mol), m-2 (0.00041 mol) and K$_2$CO$_3$ (0.00173 mol) in dimethylformamide (10 ml) was stirred at 80° C. for 3 hours. The reaction was cooled down to room temperature and was poured into a 10% solution of K$_2$CO$_3$ in water. The solution was saturated with K$_2$CO$_3$ (powder) and extracted with CH$_2$Cl$_2$/CH$_3$OH (95/5). The organic layer was separated, dried (over MgSO$_4$), filtered and the solvent was evaporated until dryness. The residue (0.15 g) was purified by column chromatography over silica gel (eluent: CH$_2$Cl$_2$/CH$_3$OH/NH$_4$OH 95/5/0.5; 10 μm). The pure fractions were collected and the solvent was evaporated, yielding 0.03 g of intermediate m-3 (15%, mixture E/Z (89/11)).

A mixture of m-3 (0.000106 mol) and Pd/C 10% (0.020 g) in CH$_3$OH (15 ml) and tetrahydrofuran (15 ml) was hydrogenated at room temperature for 6 hours under a 3 bar pressure. The reaction was filtered over celite. The celite was rinsed and the filtrate was evaporated until dryness. The residue (0.06 g) was purified by column chromatography over silica gel (eluent: CH$_2$Cl$_2$/CH$_3$OH/NH$_4$OH 93/7/0.5; 10 μm). The pure fractions were collected and the solvent was evaporated. The residue (0.028 g) was crystallized from 2-propanone/diisopropylether, yielding 0.021 g of 3-(4-{[3-(3-hydroxy-6-methyl-pyridin-2-ylmethyl)-2-(3-morpholin-4-yl-propylamino)-3H-benzoimidazol-5-ylmethyl]-amino}-3,5-dimethyl-phenyl)-propionitrile (m-4, compound 49, 35%, melting point: 114° C.).

The isomers substituted in position 5 on the benzimidazole moiety were synthesized analogous to the procedures described in schemes J and K, starting from intermediate a-10.

Example 14

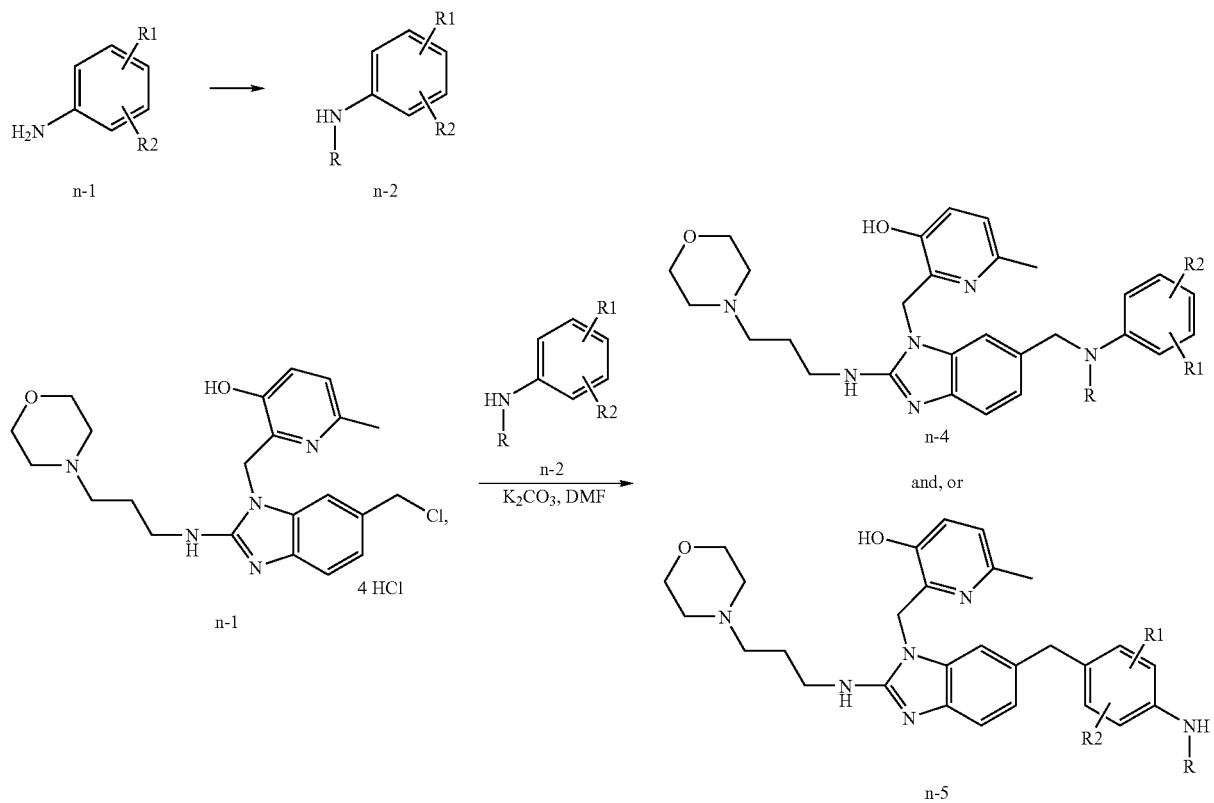

Scheme N (a) Synthesis of Anilines n-2:

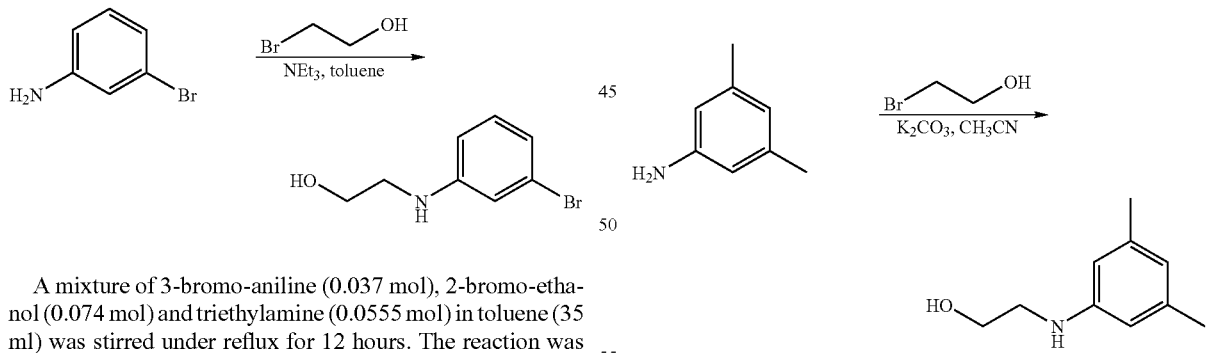

A mixture of 3-bromo-aniline (0.037 mol), 2-bromo-ethanol (0.074 mol) and triethylamine (0.0555 mol) in toluene (35 ml) was stirred under reflux for 12 hours. The reaction was cooled down to room temperature and the precipitate was filtered off. The solvent of the filtrate was evaporated until dryness. The residue (22 g) was purified by column chromatography over silica gel (eluent: $CH_2Cl_2/CH_3OH/NH_4OH$ 98/2/0.1; 20-45 μm). The pure fractions were collected and the solvent was evaporated, yielding 4.8 g of 2-(3-bromo-phenylamino)-ethanol (60%).

5-(3,5-dimethyl-phenylamino)-pentanoic acid ethyl ester and 3-(3-bromo-phenylmino)-propionic acid ethyl ester and 4-m-tolylamino-butane-1-sulfonic acid amide and phosphoric acid 2-(3,5-dimethyl-phenylamino)-ethyl ester diethyl ester and [2-(3,5-dimethyl-phenylamino)-ethyl]-phosphonic acid diethyl ester and 4-m-tolylamino-butane-1-sulfonic acid methylamide were prepared analogously.

A mixture of 3,5-dimethyl-aniline (0.04 mol), 2-bromo-ethanol (0.033 mol) and $K_2CO_3$ (0.033 mol) in $CH_3CN$ (50 ml) was stirred at 80° C. for 12 hours. The reaction was cooled down to room temperature and the solvent was evaporated. The residue was taken up in $CH_2Cl_2/CH_3OH$ (95/5) and washed with a saturated solution of $K_2CO_3$ in water. The organic layer was separated, dried (over $MgSO_4$), filtered and the solvent was evaporated until dryness. The residue was purified by column chromatography over silica gel (eluent: $CH_2Cl_2/CH_3OH/NH_4OH$ 98/2/0.1; 20-45 μm). The pure fractions were collected and the solvent was evaporated, yielding 1.9 g of 2-(3,5-dimethyl-phenylamino)-ethanol (29%).

3-(3,5-dimethyl-phenylamino)-propionic acid ethyl ester and 4-(3,5-dimethyl-phenylamino)-butyric acid ethyl ester and (3,5-dimethyl-phenyl)-(2-morpholin-4-yl-ethyl)-amine and [2-(3,5-dimethyl-phenylamino)-ethyl]-carbamic acid tert-butyl ester were prepared analogously.

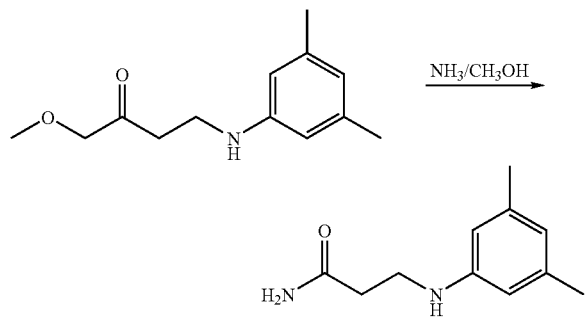

3-(3,5-dimethyl-phenylamino)-propionic acid ethyl ester (0.0026 mol) in a 7N solution of NH$_3$ in CH$_3$OH was stirred at 80° C. in a sealed vessel. The reaction was cooled down to room temperature and the solvent was evaporated until dryness, yielding 0.5 g of 3-(3,5-dimethyl-phenylamino)-propionamide (100%).

4-(3,5-dimethyl-phenylamino-butyramide and 4-m-tolylamino-butyramide and 3-m-tolylamino-propionamide and 3-(3-bromo-phenylamino)-propionamide were prepared analogously.

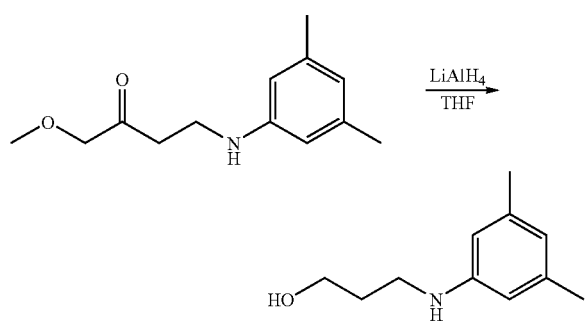

3-(3,5-dimethyl-phenylamino)-propionic acid ethyl ester (0.00226 mol) in tetrahydrofuran (5 ml) was added drop wise to a slurry of LiAlH$_4$ (0.0034 mol) in tetrahydrofuran (10 ml) at 5° C. under N$_2$ flow. The mixture was stirred at 5° C. for 1 hour. A minimum of water and CH$_2$Cl$_2$/CH$_3$OH (95/5) were added. The solution was dried (over MgSO$_4$), filtered and the solvent was evaporated until dryness, yielding 0.35 g of 3-(3,5-dimethyl-phenylamino-propan-1-ol (86%). 5-(3,5-dimethyl-phenylamino)-pentan-1-ol was prepared analogously.

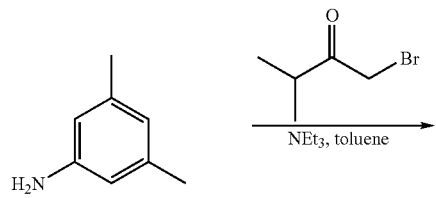

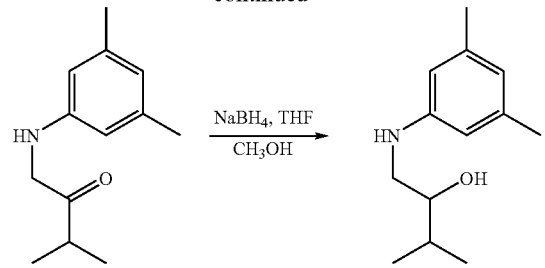

A mixture of 3,5-Dimethyl-phenylamine (0.0289 mol), 1-Bromo-3-methyl-butan-2-one (0.0347 mol) and NEt$_3$ (0.0433 mol) in toluene (80 ml) was stirred at 120° C. for 24 hours. The precipitate was filtered. The filtrate was evaporated until dryness. The residue (6.3 g) was purified by column chromatography over silica gel (Cyclohexane/AcOEt 95/5; 15-40 μm). The pure fractions were collected and the solvent was evaporated. Yield: 0.789 g of 1-(3,5-Dimethyl-phenylamino)-3-methyl-butan-2-one (13%).

NaBH$_4$ (0.0046 mol) was added portion wise at 5° C. to a solution of 1-(3,5-Dimethyl-phenylamino)-3-methyl-butan-2-one, 0.0038 mol) in tetrahydrofuran (10 ml) and CH$_3$OH (10 ml). The mixture was stirred at room temperature for 6 hours, poured into K$_2$CO$_3$ 10% and extracted with CH$_2$Cl$_2$. The organic layer was separated, dried (over MgSO$_4$), filtered and the solvent was evaporated. The residue was purified by column chromatography over silica gel (eluent: CH$_2$Cl$_2$/CH$_3$OH/NH$_4$OH 99/1/0.1; 20 μm). The pure fractions were collected and the solvent was evaporated. Yield: 0.25 g of 1-(3,5-Dimethyl-phenylamino)-3-methyl-butan-2-ol (52%, melting point: 65° C.).

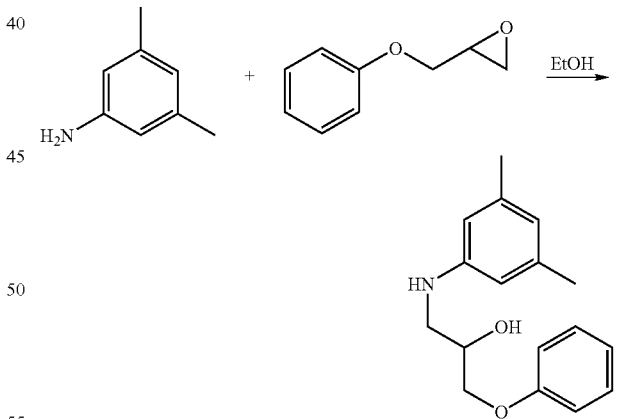

A mixture of 3,5-Dimethyl-phenylamine (0.0422 mol) and 2-phenoxymethyl-oxirane (0.0422 mol) in EtOH (50 ml) was stirred at 80° C. for 12 hours, and then cooled to room temperature. The precipitate was filtered, washed with H$_2$O and dried. The mother layer was evaporated until dryness. The residue was purified by column chromatography over silica gel (eluent: CH$_2$Cl$_2$; 10 μm). Two fractions were collected and the solvent was evaporated Yield: 0.4 g of intermediate 1-(3,5-Dimethyl-phenylamino)-3-phenoxy-propan-2-ol (4%, melting point: 65° C.).

(b) Synthesis of Final Compounds n-4 and n-5:

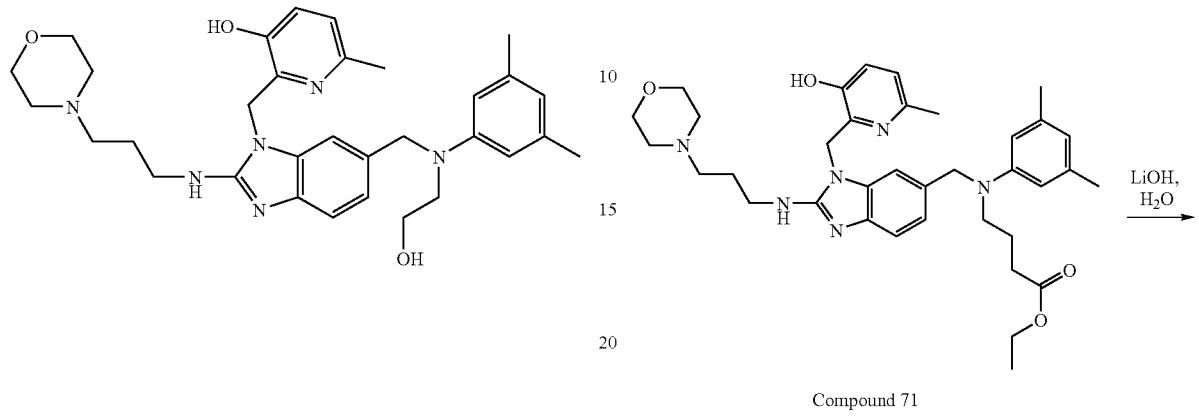

Compound 58

Compound 71

Compound 143

Compound 62

A mixture of n-3 (0.000695 mol), 2-(3,5-dimethyl-phenylamino)-ethanol (0.0009 mol) and $K_2CO_3$ (0.0035 mol) in dimethylformamide (40 ml) was stirred at 80° C. for 4 hours. $H_2O$ was added. The solution was saturated with $K_2CO_3$ (powder) and extracted with $CH_2Cl_2/CH_3OH$ (95/5). The organic layer was separated, dried (over $MgSO_4$), filtered and the solvent was evaporated. The residue (0.5 g) was purified by column chromatography over silica gel (eluent: $CH_2Cl_2/CH_3OH/NH_4OH$ 93/7/0.5; 15-40 μm). The pure fractions were collected and the solvent was evaporated, yielding 0.120 g of fraction 1 (31%) and 0.045 g of fraction 2 (12%). Fraction 1 was crystallized from $CH_3CN$/diisopropylether. The precipitate was filtered, rinsed with diisopropylether and dried, yielding 0.1 g of 2-[6-{[(3,5-ethyl-phenyl)-(2-hydroxy-ethyl)-amino]-methyl}-2-(3-morpholin-4-yl-propylamino)-benzoimidazol-1-ylmethyl]-6-methyl-pyridin-3-ol (Compound 58, example of compound n-4; 26%, melting point: 180° C.). Fraction 2 was crystallized from 2-propanone/diisopropylether. The precipitate was filtered, rinsed with diisopropylether and dried, yielding 0.016 g of 2-[6-[4-(2-hydroxy-ethylamino)-2,6-dimethylbenzyl]-2-(3-morpholin-4-yl-propylamino)-benzoimidazol-1-ylmethyl]-6-methyl-pyridin-3-ol (Compound 143, example of compound n-5, 4%, melting point: 162° C.).

A mixture of 4-{(3,5-dimethyl-phenyl)-[3-(3-hydroxy-6-methyl-pyridin-2-ylmethyl)-2-(3-morpholin-4-yl-propylamino)-3H-benzoimidazol-5-ylmethyl]-amino}-butyric acid ethyl ester (Compound 71), prepared as described for compounds n-4, (0.000175 mol) and $LiOH/H_2O$ (0.00035 mol) in tetrahydrofuran (8 ml) and $H_2O$ (8 ml) was stirred at room temperature for 12 hours. The tetrahydrofuran was evaporated and a 1N solution of NaOH in water was added. The solution was extracted with $CH_2Cl_2/CH_3OH$ (95/5). The organic layer was separated, dried (over $MgSO_4$), filtered and the solvent was evaporated. The residue was taken up in $H_2O$. The precipitate was filtered off and dried, yielding 0.059 g of 4-{(3,5-dimethyl-phenyl)-[3-(3-hydroxy-6-methyl-pyridin-2-ylmethyl)-2-(3-morpholin-4-yl-propylamino)-3H-benzoimidazol-5-ylmethyl]-amino}-butyric acid (Compound 62, 56%, melting point: 121° C.).

Example 15

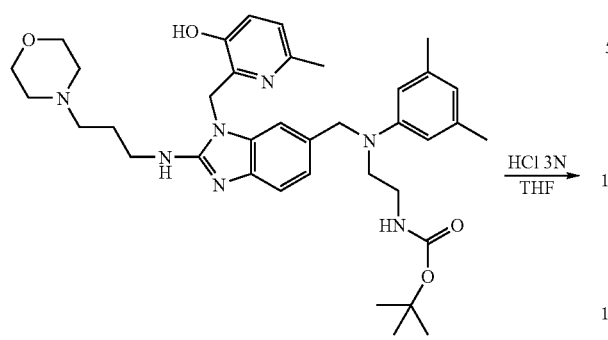

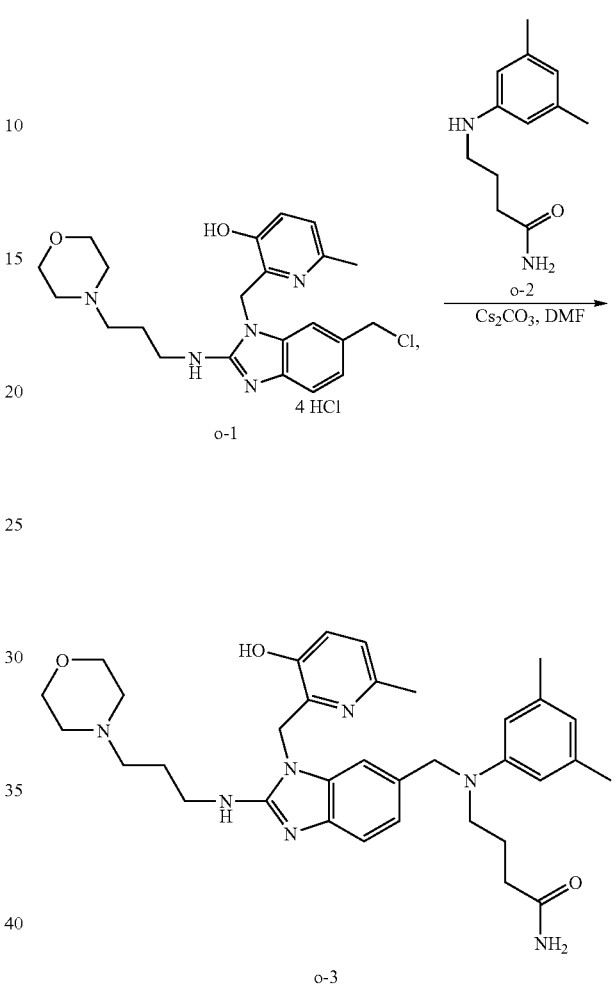

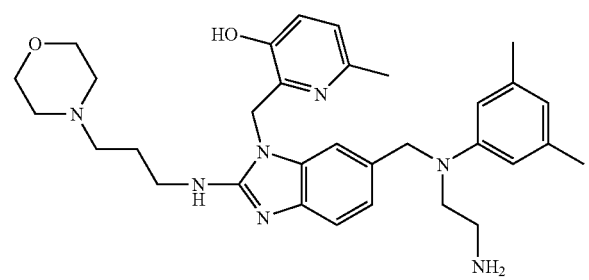

Compound 66

A mixture of (2-{(3,5-dimethyl-phenyl)-[3-(3-hydroxy-6-methyl-pyridin-2-ylmethyl)-2-(3-morpholin-4-yl-propylamino)-3H-benzoimidazol-5-ylmethyl]-amino}-ethyl)-carbamic acid tert-butyl ester, prepared as described for compounds n-4, (0.00012 mol) in a 3N solution of HCl in water (10 ml) and tetrahydrofuran (10 ml) was stirred at room temperature for 12 hours. The precipitate was filtered off and taken up in a 10% solution of $K_2CO_3$ in water. The solution was saturated with $K_2CO_3$ (powder) and extracted with $CH_2Cl_2/CH_3OH$ (95/5). The organic layer was separated, dried (over $MgSO_4$), filtered and the solvent was evaporated until dryness. The residue (0.07 g) was purified by column chromatography over silica gel (eluent: $CH_2Cl_2/CH_3OH/NH_4OH$ 92/8/1; 10 µm). The pure fractions were collected and the solvent was evaporated. The residue was crystallized from $CH_3CN/CH_3OH$/diisopropylether, yielding 0.03 g of 2-[6-{[(2-amino-ethyl)-(3,5-dimethyl-phenyl)-amino]-methyl}-2-(3-morpholin-4-yl-propylamino)-benzoimidazol-1-ylmethyl]-6-methyl-pyridin-3-ol (Compound 66, 44%, melting point: 196° C.).

A mixture of o-1 (0.0125 mol), o-2 (0.0145 mol) and $Cs_2CO_3$ (0.0605 mol) in dimethylformamide (300 ml) was stirred at 80° C. for 4 hours, poured into ice water and extracted with $CH_2Cl_2$. The organic layer was separated, dried (over $MgSO_4$), filtered and the solvent was evaporated. The residue (11.3 g) was purified by column chromatography over silica gel (eluent: $CH_2Cl_2/CH_3OH/NH_4OH$ 93/7/0.5; 15-40 µm). The pure fictions were collected and the solvent was evaporated. Yield: 2.6 g (35%). This fraction was crystallized from 2-propanone/$CH_3OH$/Diisopropylether. The precipitate was filtered off and dried. Yield: 2.17 g of 4-{(3,5-Dimethyl-phenyl)-[3-(3-hydroxy-6-methyl-pyridin-2-ylmethyl)-2-(3-morpholin-4-yl-propylamino)-3H-benzoimidazol-5-ylmethyl]-amino}-butyramide (o-3, compound 59, 29%, melting point: 170° C.).

Example 16

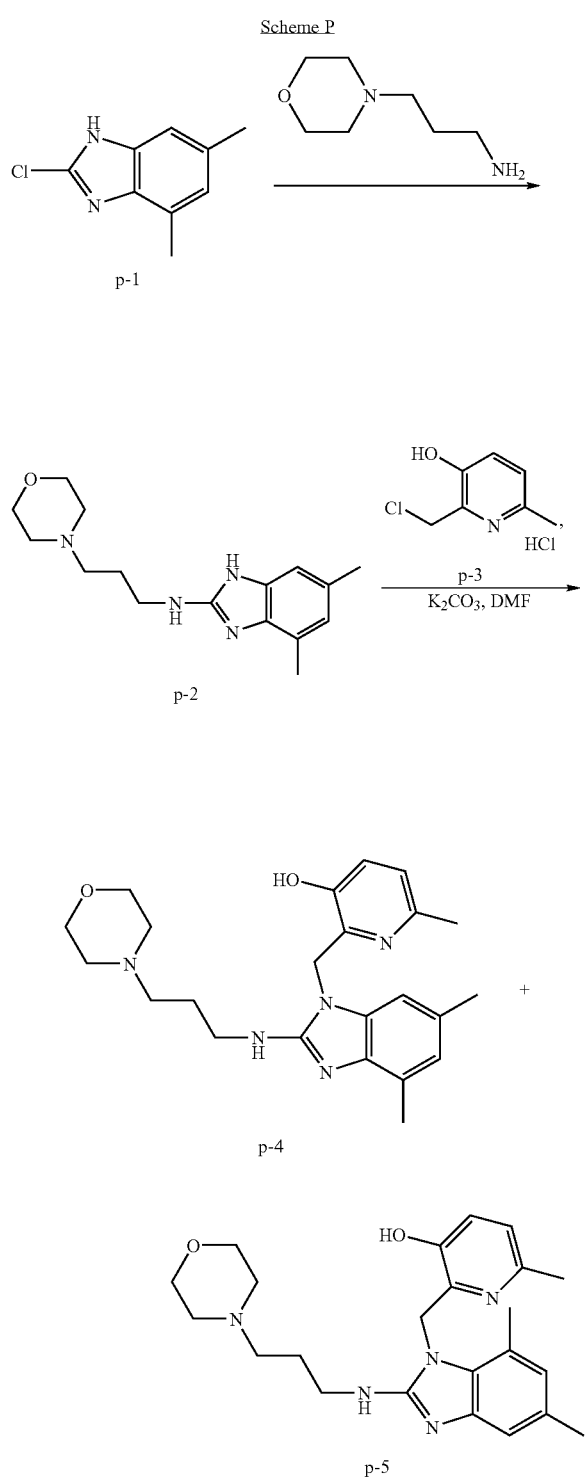

A mixture of p-1 (0.0011 mol) and N-(propylamino)-morpholine (0.0044 mol) was stirred at 130° C. for 4 hours, then brought to room temperature, taken up in H₂O and extracted with CH₂Cl₂. The organic layer was separated, dried (over MgSO₄), filtered and the solvent was evaporated. The residue (0.328 g) was purified by column chromatography over silica gel (eluent CH₂Cl₂/CH₃OH/triethylamine 99/1/0.1 to 90/10/1; 10 µm). The pure fractions were collected and the solvent was evaporated, yielding 0.216 g of intermediate p-2 (68%).

A mixture of p-2 (0.0007 mol), p-3 (0.0008 mol) and K₂CO₃ (0.003 mol) in dimethylformamide (6 ml) was stirred at 70° C. for 12 hours, then brought to room temperature, taken up in H₂O and extracted with CH₂Cl₂. The organic layer was separated, dried (over MgSO₄), filtered and the solvent was evaporated. The residue (0.5 g) was purified by column chromatography over silica gel (eluent: CH₂Cl₂/CH₃OH/NH₄OH 93/710.5 then toluene/iPrOH/NH₄OH 80/20/1; 10 µm). Two fractions were collected and the solvent was evaporated, yielding 0.13 g of fraction 1 and 0.036 g of fraction 2. Fraction 1 was taken up in diisopropylether. The precipitate was filtered off and dried, yielding 0.1 g of 2-[4,6-dimethyl-2-(3-morpholin-4-yl-propylamino)-benzoimidazol-1-yl-methyl]-6-methyl-pyridin-3-ol (p-4, compound 154, 33%, melting point: 228° C.). Fraction 2 was taken up in diisopropylether. The precipitate was filtered off and dried, yielding 0.03 g of 2-[5,7-dimethyl-2-(3-morpholin-4-yl-propylamino)-benzoimidazol-1-ylmethyl]-6-methyl-pyridin-3-ol (p-5, compound 156, 10%, melting point: 234° C.).

Example 17

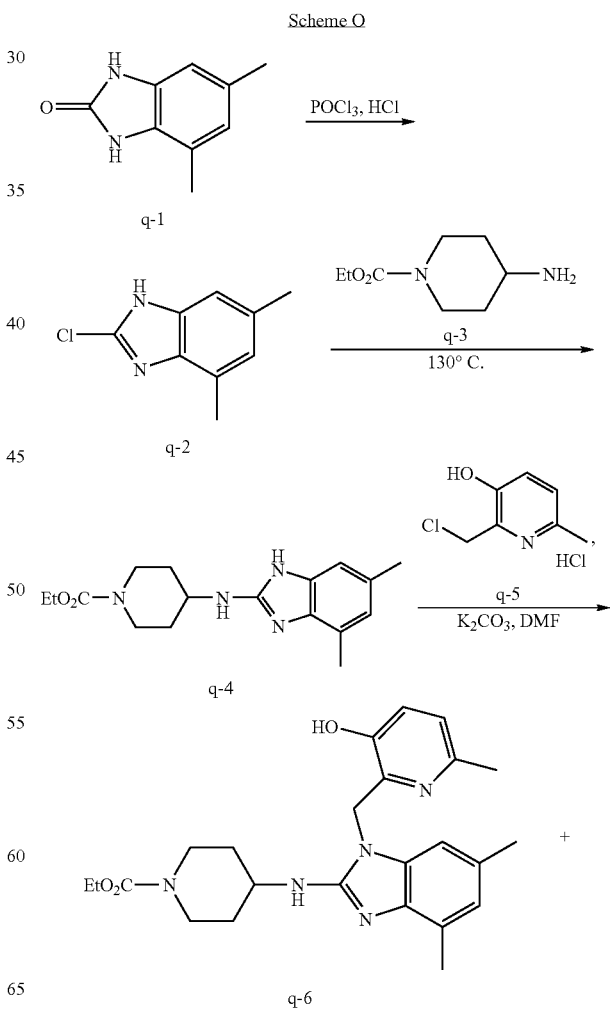

-continued

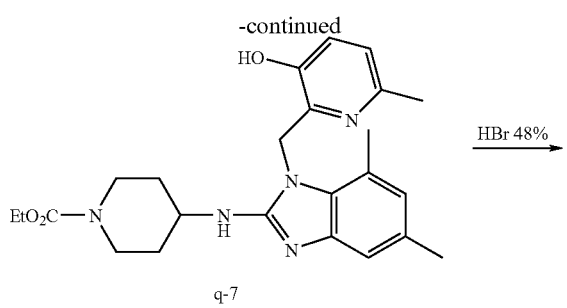
q-7

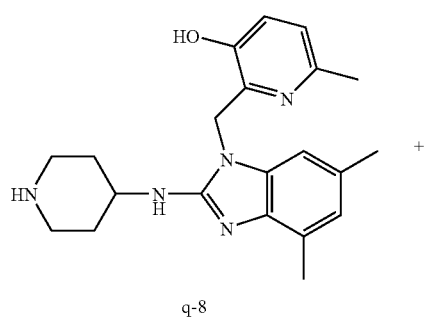
q-8

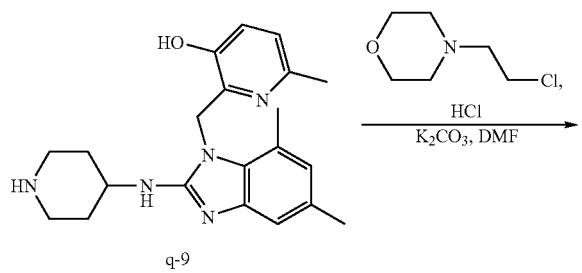
q-9

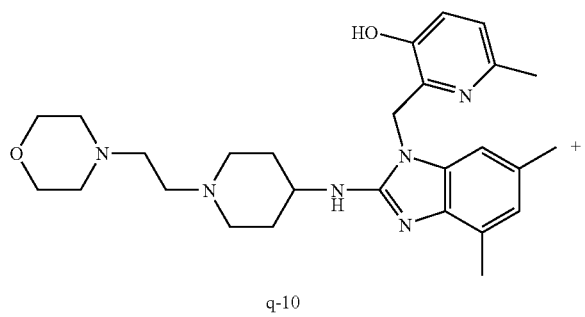
q-10

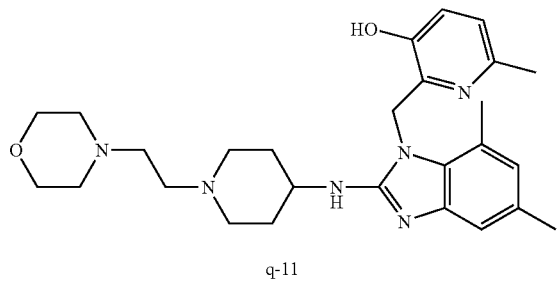
q-11

The mixture of q-1 (0.06 mol) and POCl$_3$ (100 ml) was heated at 100° C. and HCl 12N (2.5 ml) was added drop wise very carefully. The reaction was then stirred during 12 hours at 120° C. and allowed to cool down to room temperature. The solvent was evaporated under reduced pressure and a 10% solution of potassium carbonate in water was added to the residue. The resulting precipitate was filtered off; rinsed with water and dried, yielding 10 g of q-2 (93%, melting point: 152° C.).

q-2 (0.022 mol) and q-3 (0.088 mol) were stirred at 130° C. during 12 hours. The reaction was then allowed to cool down to room temperature, the residue was taken up in acetone and the precipitate was filtered off. The acetone solution was concentrated under reduced pressure. The residue was purified by column chromatography over silica gel (eluent: CH$_2$Cl$_2$/MeOH/NH$_4$OH 95/5/0.1). The pure fractions were collected and the solvent was evaporated, yielding 5 g of q-4 (72%).

A mixture of q-4 (0.0158 mol), q-5 (0.019 mol) and potassium carbonate (0.0553 mol) in dimethylformamide (100 ml) was stirred at 70° C. for 24 hours. The solvent was evaporated until dryness. The residue was taken up in CH$_2$Cl$_2$/CH$_3$OH (90/10). The organic layer was washed with a 10% solution of K$_2$CO$_3$ in water, dried (over MgSO$_4$), filtered and the solvent was evaporated under reduced pressure. The residue was taken up in 2-propanone. The precipitate was filtered off, washed with H$_2$O and dried, yielding 5 g of q-6 and q-7 (50/50 mixture, 73%).

A mixture of q-6 and q-7 (0.0103 mol) in a 48% solution of HBr in water (50 ml) was stirred at 60° C. during 12 hours. The solvent was evaporated until dryness. The residue was taken up in CH$_2$Cl$_2$/CH$_3$OH (90/10). 10% solution of K$_2$CO$_3$ in water was added. The aqueous layer was saturated with K$_2$CO$_3$ (powder). The organic layer was separated, dried (over MgSO$_4$), filtered, and the solvent was evaporated until dryness, yielding 3.7 g of q-8 and q-9 (100%). This product was used directly in the next reaction step.

A mixture of q-8 (0.0006 mol), q-9 (0.0006 mol), N-(2-chloro-ethyl)-morpholine, HCl (0.0016 mol) and K$_2$CO$_3$ (0.0048 mol) in dimethylformamide (30 ml) was stirred at room temperature for 48 hours. The solvent was evaporated until dryness. The residue was taken up in CH$_2$Cl$_2$. The mixture was filtered. The filtrate was evaporated until dryness. The residue (1.2 g) was purified by column chromatography over silica gel (eluent: CH$_2$Cl$_2$/CH$_3$OH/NH$_4$OH 90/10/0.5; 10 μm). Two fractions were collected and the solvent was evaporated, yielding 0.023 g of fraction 1 (4%) and 0.12 g of fraction 2 (18%). Fraction 1 was crystallized from CH$_3$OH/CH$_3$CN/diisopropylether. The precipitate was filtered off and dried, yielding 0.02 g of 2-[5,7-dimethyl-2-(2-morpholin-4-ylethyl-piperidin-4-ylamino)-benzoindazol-1-ylmethyl]-6-methyl-pyridin-3-ol (q-10, compound 162, 3%, melting point: 226° C.). Fraction 2 was crystallized from CH$_3$OH/CH$_3$CN/diisopropylether. The precipitate was filtered off and dried, yielding 0.1 g of 2-[4,6-dimethyl-2-(2-morpholin-4-ylethyl-piperidin-4-ylamino)-benzoimidazol-1-ylmethyl]-6-methyl-pyridin-3-ol (q-11, compound 170, 15%, melting point: 237° C.).

Example 18

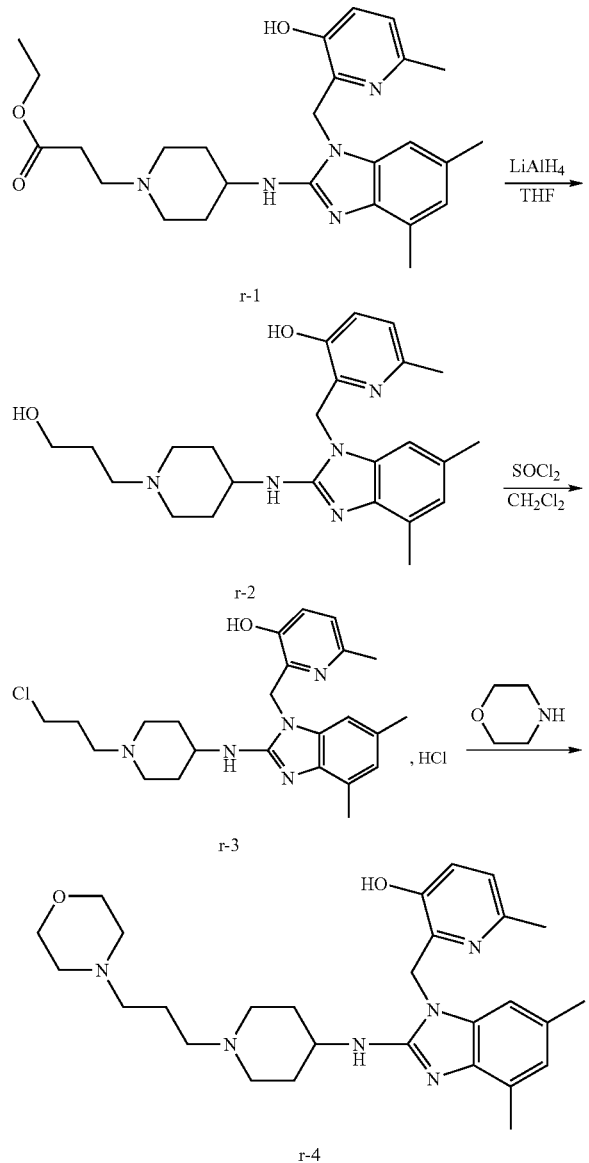

LiAlH$_4$ (0.0002 mol) was added at 5° C. to a mixture of 3-{4-[1-(3-hydroxy-6-methyl-pyridin-2-ylmethyl)-4,6-dimethyl-1H-benzoimidazol-2-ylamino]-piperidin-1-yl}-propionic acid ethyl ester (r-1; 0.00009 mol; melting point: 172° C.) in tetrahydrofuran (10 ml) under N$_2$ flow. The mixture was stirred at 5° C. for 1 hour, then at room temperature for 3 hours. A minimum of H$_2$O and ethylacetate were added. The organic layer was separated, dried (over MgSO$_4$), filtered and the solvent was evaporated until dryness. The residue was crystallized from 2-propanone/CH$_3$CN/diisopropylether. The precipitate was filtered off and dried, yielding 0.026 g of 2-{2-[1-(3-hydroxy-propyl)-piperidin-4-ylamino]-4,6-dimethyl-benzoimidazol-1-ylmethyl}-6-methyl-pyridin-3-ol (r-2; 68%, melting point: 209° C.).

A mixture of r-2 (0.0001 mol) and CH$_2$Cl$_2$ (15 ml) was cooled in a bath of ice. SOCl$_2$ (0.0005 mol) was added drop wise. The mixture was stirred at 5° C. for 1 hour, then at room temperature for 12 hours. SOCl$_2$ (0.0005 mol) was added. The mixture was stirred at room temperature for 4 hours. The solvent was evaporated until dryness, yielding 0.06 g of intermediate r-3 (HCl, 100%). This product was used directly in the next reaction step.

A mixture of r-3 (0.0001 mol), morpholine (0.0003 mol) and K$_2$CO$_3$ (0.0011 mol) in CH$_3$CN (15 ml) was stirred at 70° C. for 6 hours. The solvent was evaporated until dryness. The residue was taken up in CH$_2$Cl$_2$/H$_2$O. The organic layer was separated, dried (over MgSO$_4$), filtered and the solvent was evaporated until dryness. The residue (0.06 g) was purified by column chromatography over silica gel (eluent: CH$_2$Cl$_2$/CH$_3$OH/NH$_4$OH 88/11/1; 5 μm). The pure fractions were collected and the solvent was evaporated, yielding 0.016 g of 2-[4,6-dimethyl-2-(2-morpholin-4-ylpropyl-piperidin-4-ylamino)-benzoimidazol-1-ylmethyl]-6-methyl-pyridin-3-ol (r-4, compound 161, 18%, melting point: 223° C.).

Example 19

Scheme S

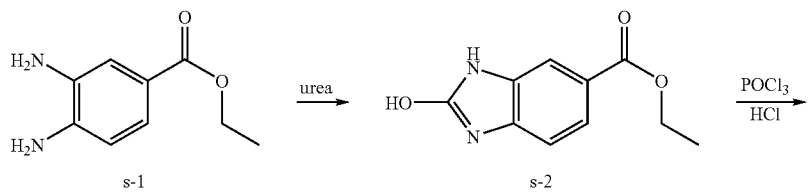

-continued
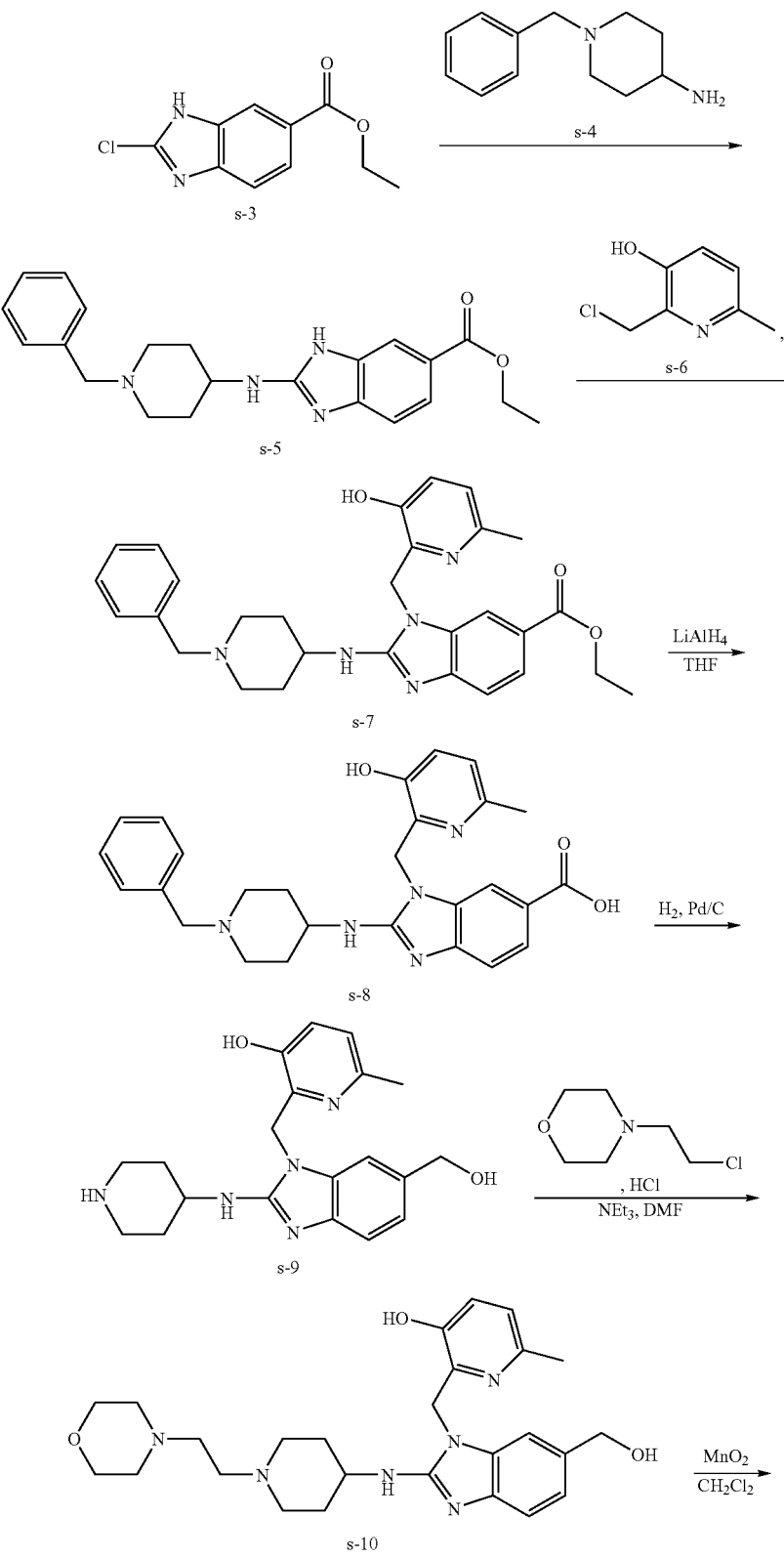

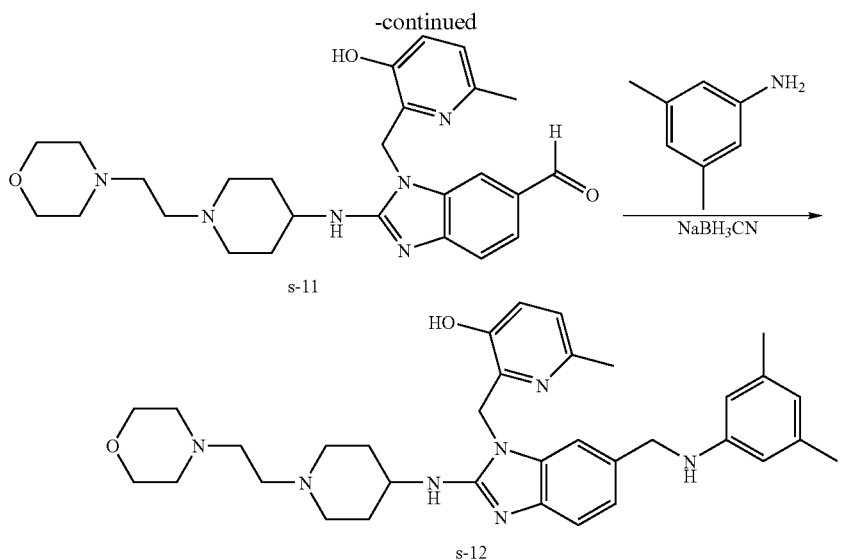

A mixture of s-1 (0.166 mol) and urea (0.199 mol) in xylene (300 ml) was stirred under reflux for 12 hours. The reaction was cooled down to room temperature. The precipitate was filtered off, rinsed with xylene and diisopropylether, and then dried, yielding 32 g of intermediate s-2 (93%, melting point: >260° C.).

A mixture of s-2 (0.073 mol) in $POCl_3$ (150 ml) was stirred at 100° C. HCl conc. (around 1.5 ml) was added drop wise very carefully until the dissolution of s-2. The mixture was stirred at 120° C. for 6 hours. The solvent was evaporated until dryness. The residue was taken-up in $H_2O$/ice, basified with $K_2CO_3$ (powder) and extracted with ethylacetate+10% methanol. The organic layer was separated, dried (over $MgSO_4$), filtered and the solvent was evaporated until dryness, yielding 13.5 g of intermediate s-3 (83%, melting point: 178° C.).

A mixture of s-3 (0.051 mol) and s-4 (0.056 mol) was stirred at 160° C. for 2 hours. The residue was taken-up in $CH_2Cl_2/H_2O$ and basified with a 10% solution of $K_2CO_3$ in water. The organic layer was separated, dried (over $MgSO_4$), filtered and the solvent was evaporated until dryness. The residue was purified by column chromatography over silica gel (eluent: $CH_2Cl_2$/methanol/$NH_4OH$ 95/5/0.5). The pure fractions were collected and the solvent was evaporated, yielding 15.3 g of intermediate s-5 (79%).

A mixture of s-5 (0.0396 mol), s-6 (0.059 mol) and $K_2CO_3$ (0.1584 mol) in $CH_3CN$ (180 ml) was stirred and refluxed for 12 hours. The solvent was evaporated until dryness. The residue was taken up in $CH_2Cl_2$. The organic layer was washed with $H_2O$, dried (over $MgSO_4$), filtered and the solvent was evaporated until dryness. The residue (20 g) was purified by column chromatography over silica gel (eluent: Toluene/2-propanol/$NH_4OH$ 85/15/1; 20-45 μm). Two fractions were collected and the solvent was evaporated, yielding 5.3 g of fraction 1 (27%) and 6.3 g of fraction 2 (32%). Fraction 1 was crystallized twice in 2-propanone/$CH_3CN$/diisopropylether. The precipitate was filtered off and dried, yielding 4.9 g of intermediate s-7 (25%, melting point: 179° C.).

$LiAlH_4$ (0.009 mol) was added portion wise to a mixture of s-7 (0.003 mol) in tetrahydrofuran (60 ml) at 5° C. under $N_2$ flow. The reaction was stirred at 5° C. for 1 hour and then at room temperature for 12 hours. Ethylacetate and $H_2O$ were added carefully and the aqueous layer was saturated with $K_2CO_3$ (powder). The organic layer was separated, dried (over $MgSO_4$) and then filtered over celite. The filtrate was evaporated until dryness, yielding 1.3 g of intermediate s-8 (97%). The crude product was used directly in the next reaction step.

A mixture of s-8 (0.0028 mol) and Pd/C 10% (2.5 g) in $CH_3OH$ (40 ml) was hydrogenated at 40° C. for 12 hours under an 8 bar pressure, then filtered over celite. Celite was washed with a solution of $CH_3OH$/tetrahydrofuran (50/50). The filtrate was evaporated until dryness, yielding 1.8 g of intermediate s-9 (95%, melting point: 260° C.).

A mixture of s-9 (0.0027 mol), N-(2-chloro-ethyl)-morpholine, HCl (0.0032 mol) and triethylamine (0.0067 mol) in dimethylformamide (40 ml) was stirred at 50° C. for 48 hours, poured into ice water and extracted 3 times with $CH_2Cl_2$. The organic layer was separated, dried (over $MgSO_4$), filtered and the solvent was evaporated until dryness. The residue was purified by column chromatography over silica gel (eluent: $CH_2Cl_2/CH_3OH/NH_4OH$; 85/14/1; 35-70 μm). The pure fractions were collected and the solvent was evaporated. The residue was taken up in 2-propanone/diisopropylether. The precipitate was filtered off and dried, yielding 0.8 g of intermediate s-10 (compound 168, 61%, melting point: 147° C.).

A mixture of s-10 (0.0014 mol) and $MnO_2$ (1.6 g) in $CH_2Cl_2$ (50 ml) was stirred at room temperature for 12 hours, and then filtered over celite. The solvent of the filtrate was evaporated until dryness. The residue was crystallized from 2-propanone/diisopropylether. The precipitate was filtered off and dried, yielding 0.47 g of intermediate s-11 (67%, melting point: 136° C.).

$CH_3CO_2H$ (0.3 ml) was added at room temperature to a mixture of s-11 (0.0005 mol), 3,5-dimethyl-aniline (0.0006 mol) and $NaBH_3CN$ (0.0006 mol) in $CH_3CN$ (30 ml). The mixture was stirred at room temperature for 30 minutes. $CH_3CO_2H$ (0.3 ml) was added. The mixture was stirred at room temperature for 6 hours. The solvent was evaporated until dryness. The residue was taken up in $CH_2Cl_2$. The organic layer was washed with a 10% solution of $K_2CO_3$ in water, dried (over $MgSO_4$), filtered and the solvent was evaporated until dryness. The residue (0.26 g) was purified by column chromatography over silica gel (eluent: CH$_2$Cl$_2$/CH$_3$OH/NH$_4$OH 90/10/1; 5 μm). The pure fractions were collected and the solvent was evaporated. The residue (0.12 g, 36%) was crystallized from CH$_3$CN/diisopropylether. The precipitate was filtered off and dried, yielding 0.07 g of 2-{6-[(3,5-dimethyl-phenylamino)-methyl]-2-[2-(2-morpholin-4-yl-ethyl)-piperidin-4-ylamino]-benzoimidazol-1-ylmethyl}-6-methyl-pyridin-3-ol (s-12, compound 163, 21%, melting point: 150° C.).

Example 20 the solvent was evaporated until dryness. The residue was crystallized from CH$_3$OH. The precipitate was filtered off and dried, yielding 0.13 g of 6-methyl-2-{2-[2-(2-morpholin-4-yl-ethyl)-piperidin-4-ylamino]-6-styryl-benzoimidazol-1-ylmethyl}-pyridin-3-ol (t-2; compound 169, 37%, melting point: 224° C.).

A mixture of t-2 (0.0002 mol) and Pd/C 10% (0.035 g) in CH$_3$OH (5 ml) and tetrahydrofuran (5 ml) was hydrogenated

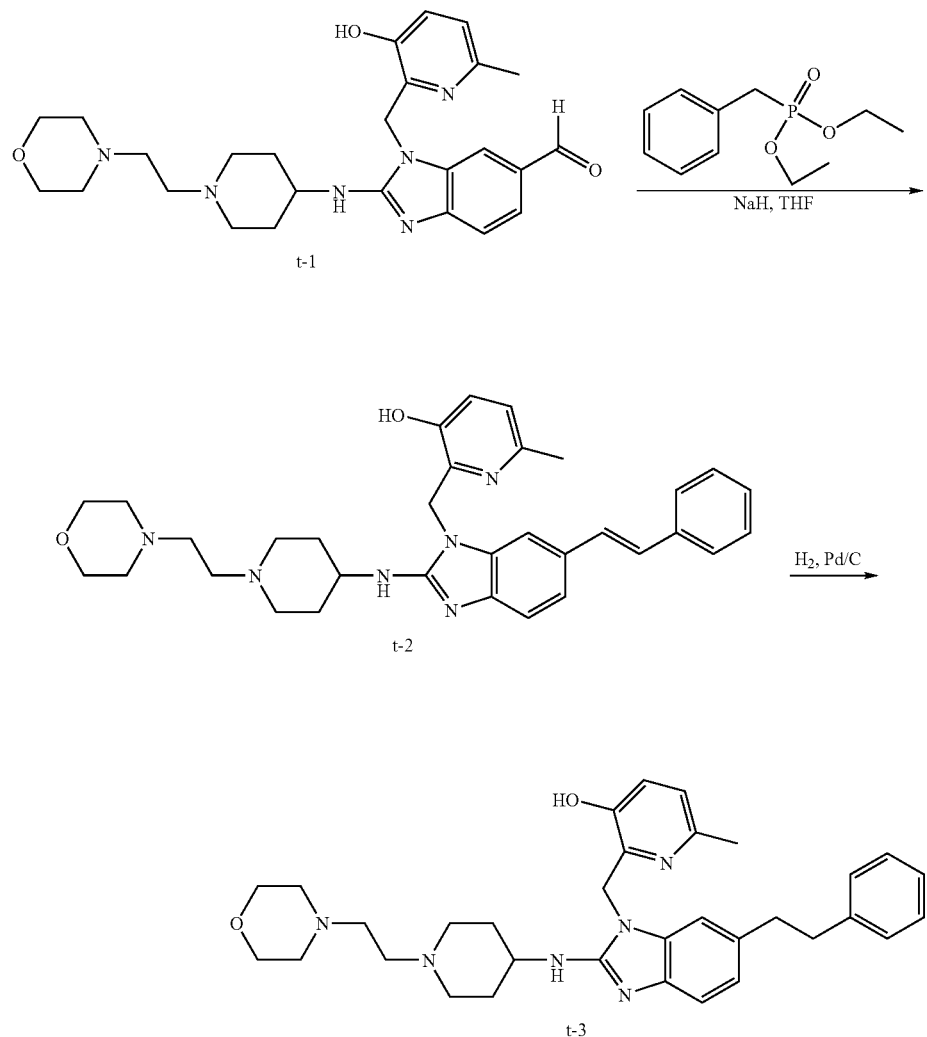

Benzyl-diethylphosphonate (0.0019 mol) was added to a mixture of NaH (0.0037 mol) in tetrahydrofuran (15 ml) at 5° C. under N$_2$ flow. The mixture was stirred at 5° C. for 30 minutes. A solution of t-1 (0.0006 mol) in tetrahydrofuran (10 ml) was added drop wise. The mixture was stirred at 5° C. for 1 hour, then at room temperature for 12 hours. H$_2$O was added. The mixture was extracted with ethylacetate. The organic layer was separated, dried (over MgSO$_4$), filtered and at room temperature for 6 hours under a 8 bar pressure, and then filtered over celite. Celite was washed with H$_2$O. The filtrate was evaporated until dryness. The residue was taken up in 2-propanone. The precipitate was filtered, washed with H$_2$O and dried, yielding 0.08 g of 6-methyl-2-{2-[2-(2-morpholin-4-yl-ethyl)-piperidin-4-ylamino]-6-phenethyl-benzoimidazol-1-ylmethyl}-pyridin-3-ol (t-3, compound 165, 72%, melting point: 159° C.).

Example 21
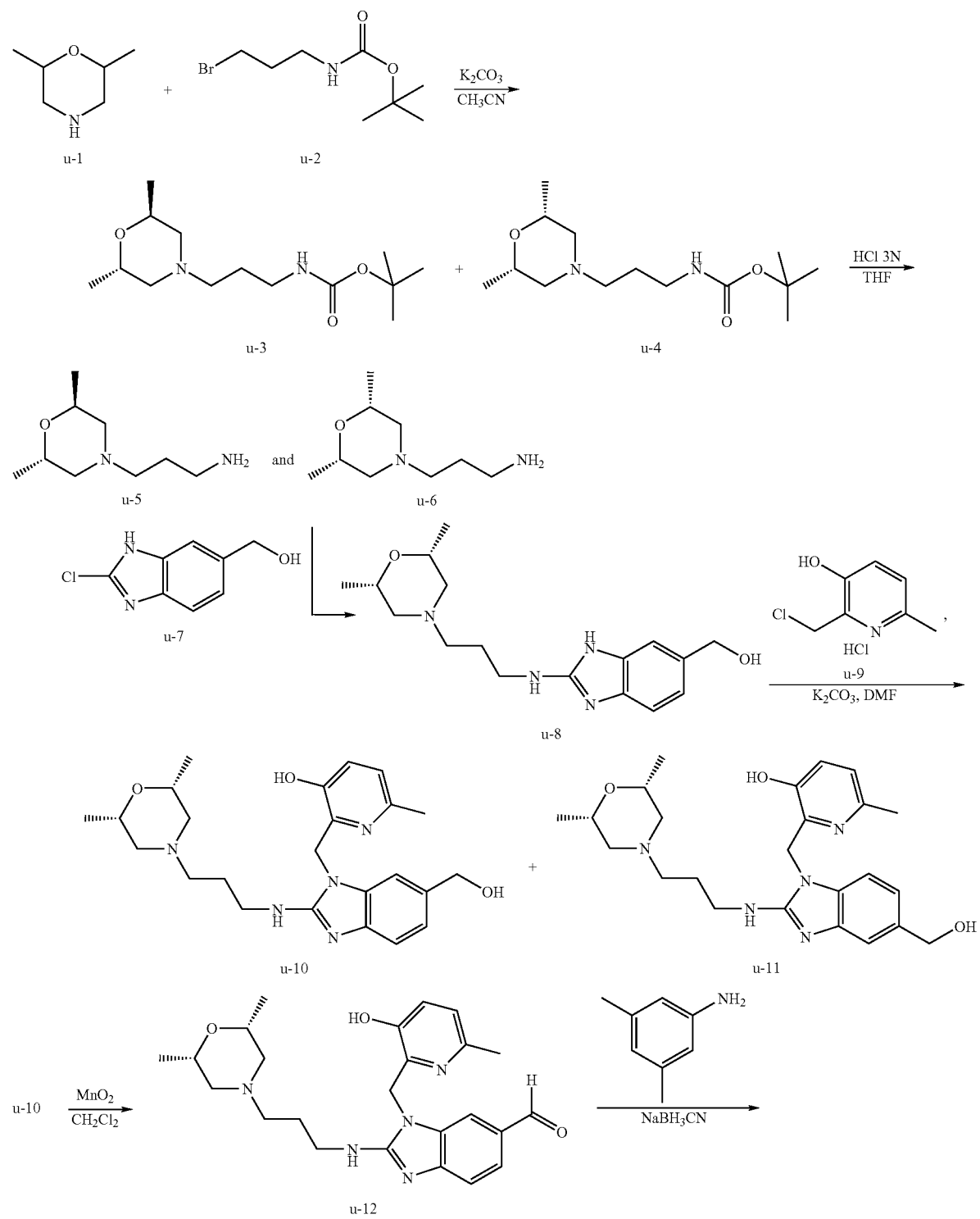

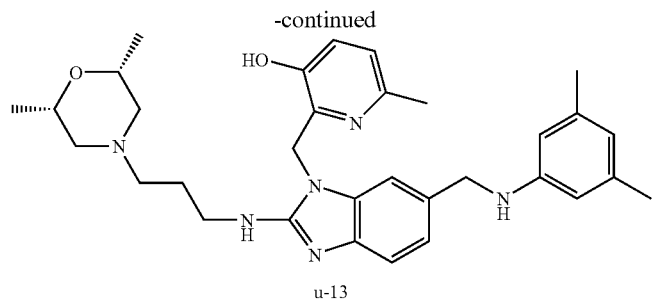

u-13

A mixture of u-1 (mixture cis+trans) (0.0379 mol), u-2 (0.0416 mol) and K₂CO₃ (0.1136 mol) was stirred at 80° C. for 12 hours. H₂O was added. The mixture was extracted with CH₂Cl₂. The organic layer was separated, dried (over MgSO₄), filtered and the solvent was evaporated. The residue (10 g) was purified by column chromatography over silica gel (eluent: CH₂Cl₂/CH₃OH/NH₄OH 97/3/0.1, 35-70 μm). Two fractions were collected and the solvent was evaporated, yielding 3 g of intermediate u-3 (trans) (29%) and 7.3 g of intermediate u-4 (cis) (71%).

A mixture of u-4 (0.0279 mol) in a 3N solution of HCl in water (50 ml) and tetrahydrofuran (50 ml) was stirred at room temperature for 12 hours. K₂CO₃ (powder) was added. CH₂Cl₂ was added. The aqueous layer was saturated with K₂CO₃ powder). The mixture was extracted with CH₂Cl₂. The organic layer was separated, dried (over MgSO₄), filtered and the solvent was evaporated, yielding 4.39 g of intermediate u-6 (93%). Analogously, u-5 was prepared.

A mixture of u-7 (0.0085 mol) and u-6 (0.0255 mol) was stirred at 120° C. for 4 hours. A 10% solution of K₂CO₃ in water was added. The aqueous layer was saturated with K₂CO₃ (powder). The mixture was extracted with CH₂Cl₂. The organic layer was separated, dried (over MgSO₄), filtered and the solvent was evaporated. The residue (4.1 g) was purified by column chromatography over silica gel (eluent: CH₂Cl₂/CH₃OH/NH₄OH 90/10/1; 15-40 μm). The pure fractions were collected and the solvent was evaporated, yielding 1.6 g of intermediate u-8 (59%).

A mixture of u-8 (0.0048 mol), u-9 (0.0058 mol) and K₂CO₃ (0.0145 mol) in dimethylformamide (30 ml) was stirred at room temperature for 24 hours, poured into H₂O, saturated with K₂CO₃ (powder) and extracted with CH₂Cl₂/CH₃OH. The organic layer was separated, dried (over MgSO₄), filtered and the solvent was evaporated until dryness. The residue (3.3 g) was purified by column chromatography over silica gel (eluent: CH₂Cl₂/CH₃OH/NH₄OH 90/10/0.5; 15-40 μm). Two fractions were collected and the solvent was evaporated, yielding 0.55 g of intermediate u-10 (26%) and 0.36 g of intermediate u-11 (17%). A small fraction of intermediate u-10 was crystallized from 2-propanone/CH₃CN/diisopropylether. The precipitate was filtered off and dried, yielding 0.04 g (compound 175, melting point: 199° C.). A small fraction of intermediate u-11 was crystallized from 2-propanone/CH₃CN/diisopropylether. The precipitate was filtered off and dried, yielding 0.04 g (compound 187, melting point: 227° C.).

A mixture of u-10 (0.0011 mol) and MnO₂ (1 g) in CH₂Cl₂ (50 ml) and CH₃OH (3 ml) was stirred at room temperature for 12 hours, and then filtered over celite. Celite was washed with H₂O. The filtrate was evaporated until dryness, yielding 0.5 g of intermediate u-12 (100%). The crude product was used directly in the next reaction step.

CH₃CO₂H (0.25 ml) was added to a mixture of u-12 (0.0005 mol), 3,5-dimethyl-aniline (0.0006 mol) and NaBH₃CN (0.0006 mol) in CH₂Cl₂ (30 ml). The mixture was stirred at room temperature for 12 hours. A 10% solution of K₂CO₃ in water was added. The mixture was saturated with K₂CO₃ (powder). The organic layer was separated, dried (over MgSO₄), filtered and the solvent was evaporated until dryness. The residue was purified by column chromatography over silica gel (eluent: CH₂Cl₂/CH₃OH/NH₄OH 95/5/0.1; 35-70 μm). The pure fractions were collected and the solvent was evaporated. The residue (0.25 g, 80%) was crystallized from 2-propanone/CH₃CN/diisopropylether. The precipitate was filtered off and dried, yielding 0.183 g of 2-{2-[3-(2,6-dimethyl-morpholin-4-yl)-propylamino]-6-[(3,5-dimethyl-phenylamino)-methyl]-benzoimidazol-1-ylmethyl}-6-methyl-pyridin-3-ol (u-13, compound 172, 59%, melting point: 192° C.).

Example 22

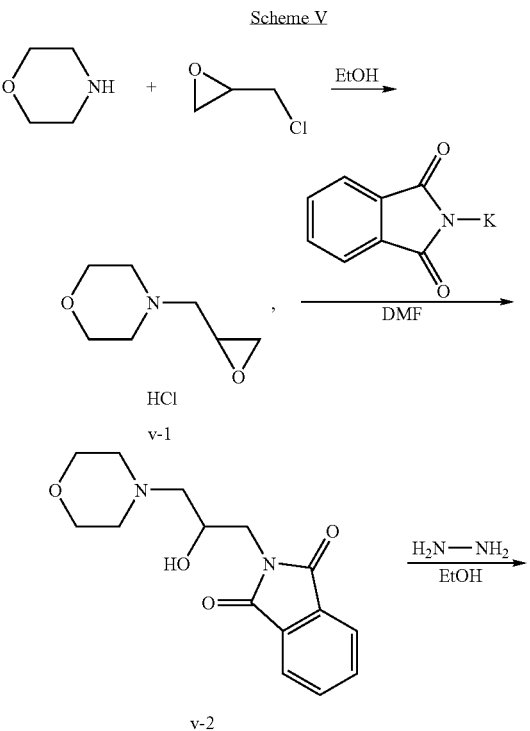

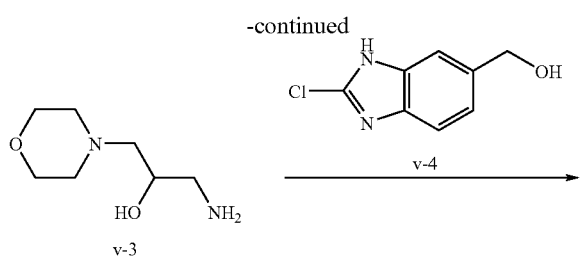

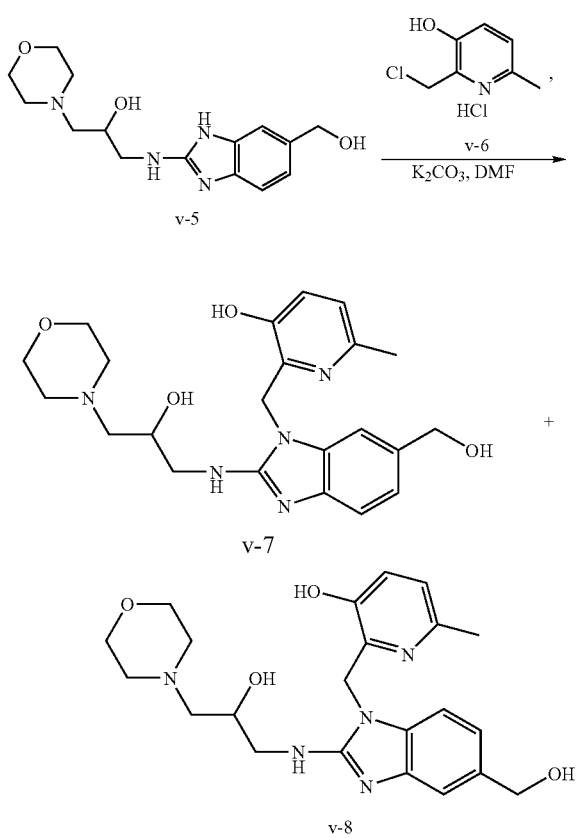

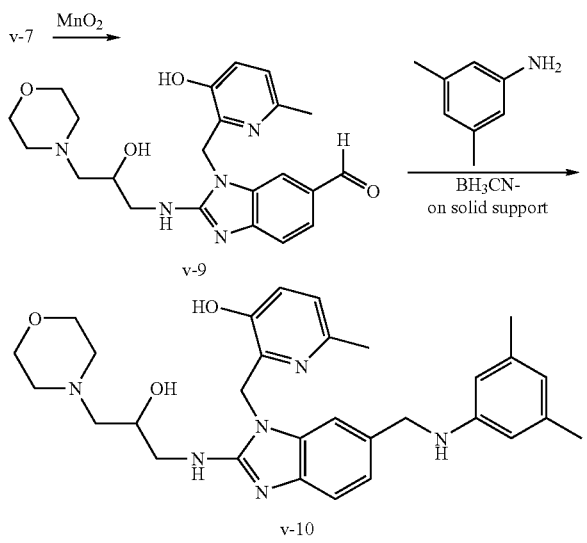

A mixture of morpholine (0.0116 mol), epichlorohydrin (0.0116 mol) in ethanol (30 ml) was stirred at room temperature for 24 hours. The solvent was evaporated until dryness, yielding 2.08 g of intermediate v-1 (100%). The crude product was used directly in the next reaction step.

A mixture of v-1 (0.0116 mol), potassium phthalimide (0.01276 mol) in dimethylformamide (25 ml) was stirred under reflux for 4 hours. The solvent was evaporated. The residue was taken up in $CH_2Cl_2$ and washed with $H_2O$. The organic layer was separated, dried (over $MgSO_4$), filtered and the solvent was evaporated until dryness, yielding 3.4 g of intermediate v-2 (100%). The crude product was used directly in the next reaction step.

A mixture of v-2 (0.116 mol) and hydrazine (15 ml) in ethanol (350 ml) was stirred at 80° C. for 1 hour. The reaction was cooled down to room temperature. The precipitate was filtered off and rinsed with ethanol and $CH_2Cl_2$. A 10% solution of $K_2CO_3$ in water was added. The aqueous layer was saturated with $K_2CO_3$ (powder) and extracted with $CH_2Cl_2$/$CH_3OH$ (95/5). The organic layer was separated, dried (over $MgSO_4$), filtered and the solvent was evaporated until dryness, yielding 14.8 g of intermediate v-3 (80%). The crude product was used directly in the next reaction step.

Intermediate v-5 was prepared in an analogous way to the procedure described for intermediate u-8. Intermediates v-7 (2 g; 31%; melting point: 184° C.) and v-8 (2.1 g; 33%, melting point: 208° C.) were prepared in an analogous way to the procedure described for preparing u-10 and u-11. Intermediate v-9 (0.77 g; 77%; melting point: 152° C.) was prepared in an analogous way to the procedure described for intermediate u-12.

$CH_3CO_2H$ (0.2 ml) was added at room temperature to a mixture of v-9 (0.00047 mol), 3,5-dimethyl-aniline (0.00056 mol) and $BH_3CN$— on solid support (0.000705 mol) in $CH_3OH$ (10 ml). The mixture was sired at room temperature for 18 hours. The solid support was filtered off, rinsed with $CH_3OH$ and the filtrate was concentrated. The residue was taken up with a 10% solution of $K_2CO_3$ in water. The aqueous layer was saturated with $K_2CO_3$ (powder) and extracted with $CH_2Cl_2$/$CH_3OH$ (95/5). The organic layer was separated, dried (over $MgSO_4$), filtered and the solvent was evaporated until dryness. The residue was purified by column chromatography over silica gel (eluent: $CH_2Cl_2$/$CH_3OH$/$NH_4OH$ 95/5/0.1; 35-70 μm). The pure fractions were collected and the solvent was evaporated. The residue (0.2 g) was crystallized from 2-propanone/diisopropylether. The precipitate was filtered off and dried, yielding 0.154 g of 2-[6-[(3,5-dimethyl-phenylamino)-methyl]-2-(2-hydroxy-3-morpholin-4-yl-propyl-amino)-benzoimidazol-1-ylmethyl]-6-methyl-pyridin-3-ol (v-10; compound 171, 62%, melting point: 198° C.).

Example 23
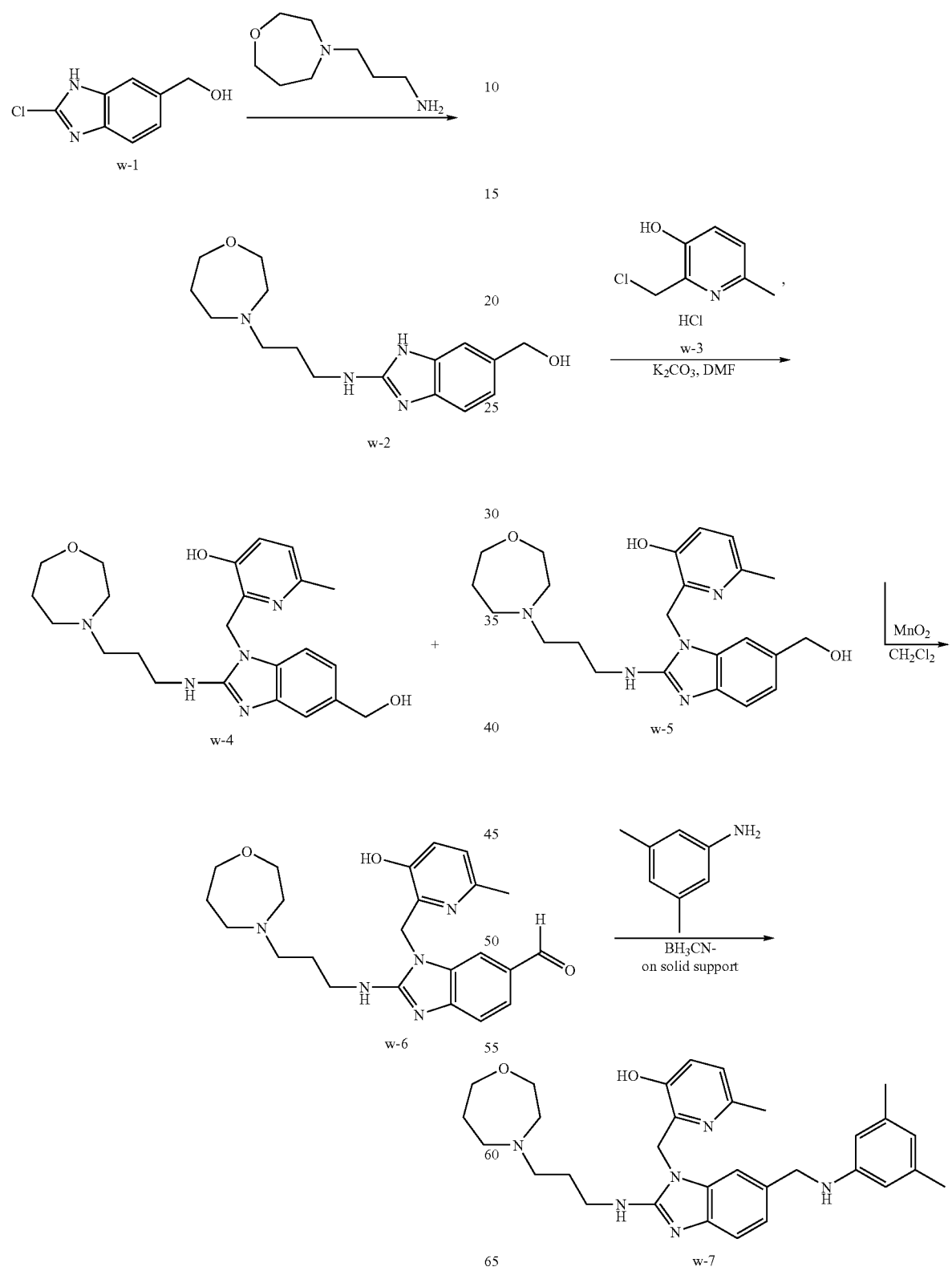

Intermediate w-2 was prepared in an analogous way to the procedure described for intermediate u-8. Intermediates w-4 (0.28 g; 28%) and w-5 (0.025 g; 26%) were prepared in an analogous way to the procedure described for intermediate u-10 and u-11. Intermediate w-6 (0.020 g; 80%) was prepared in an analogous way to the procedure described for intermediate u-12.

2-[5-[(3,5-Dimethyl-phenylamino)-methyl]-2-(3-[1,4]ox-azepan-4-yl-propylamino)-benzoimidazol-1-ylmethyl]-6-methyl-pyridin-3-ol (w-7, compound 174, 0.007 g; 28%) was prepared in an analogous way to the procedure described for compound v-10.

Example 24

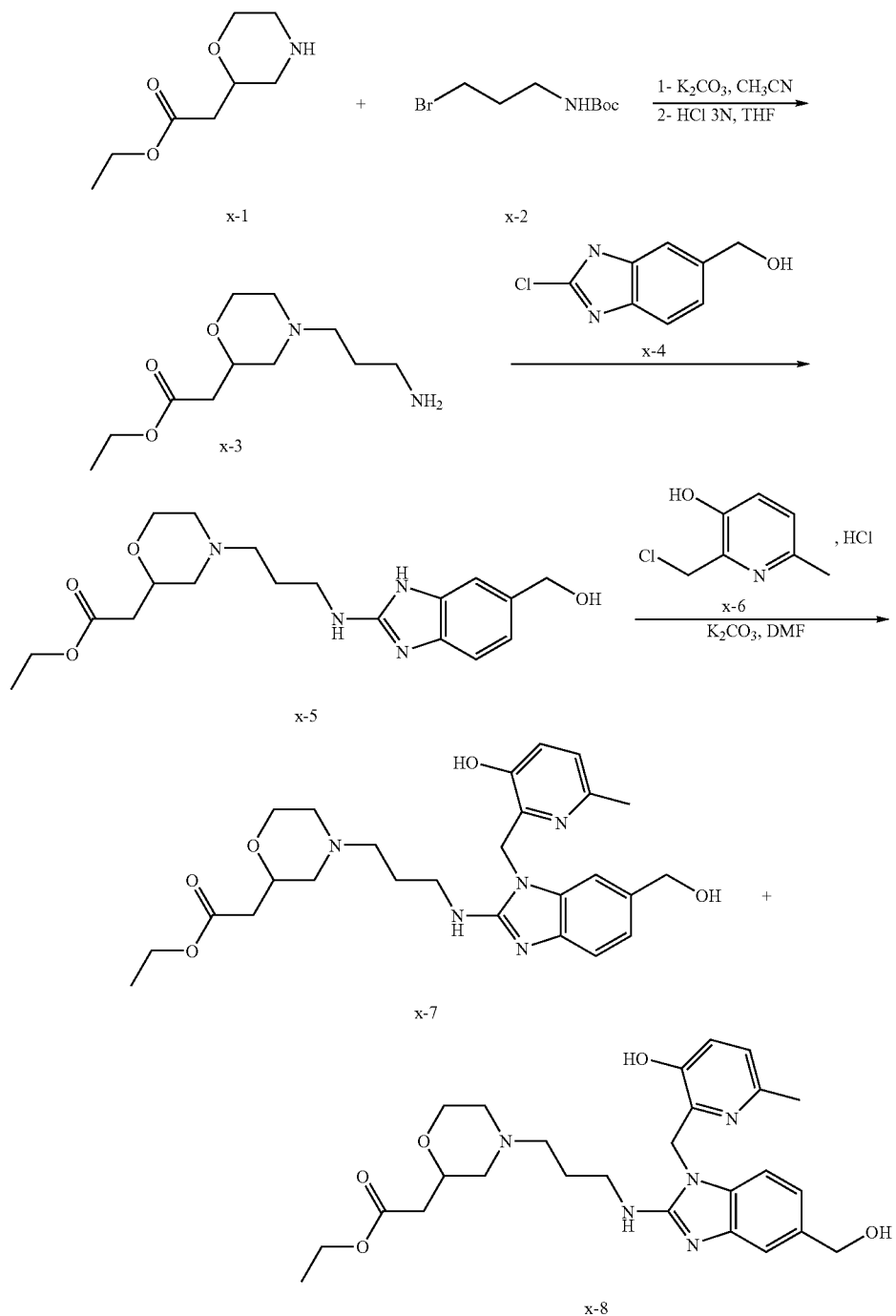

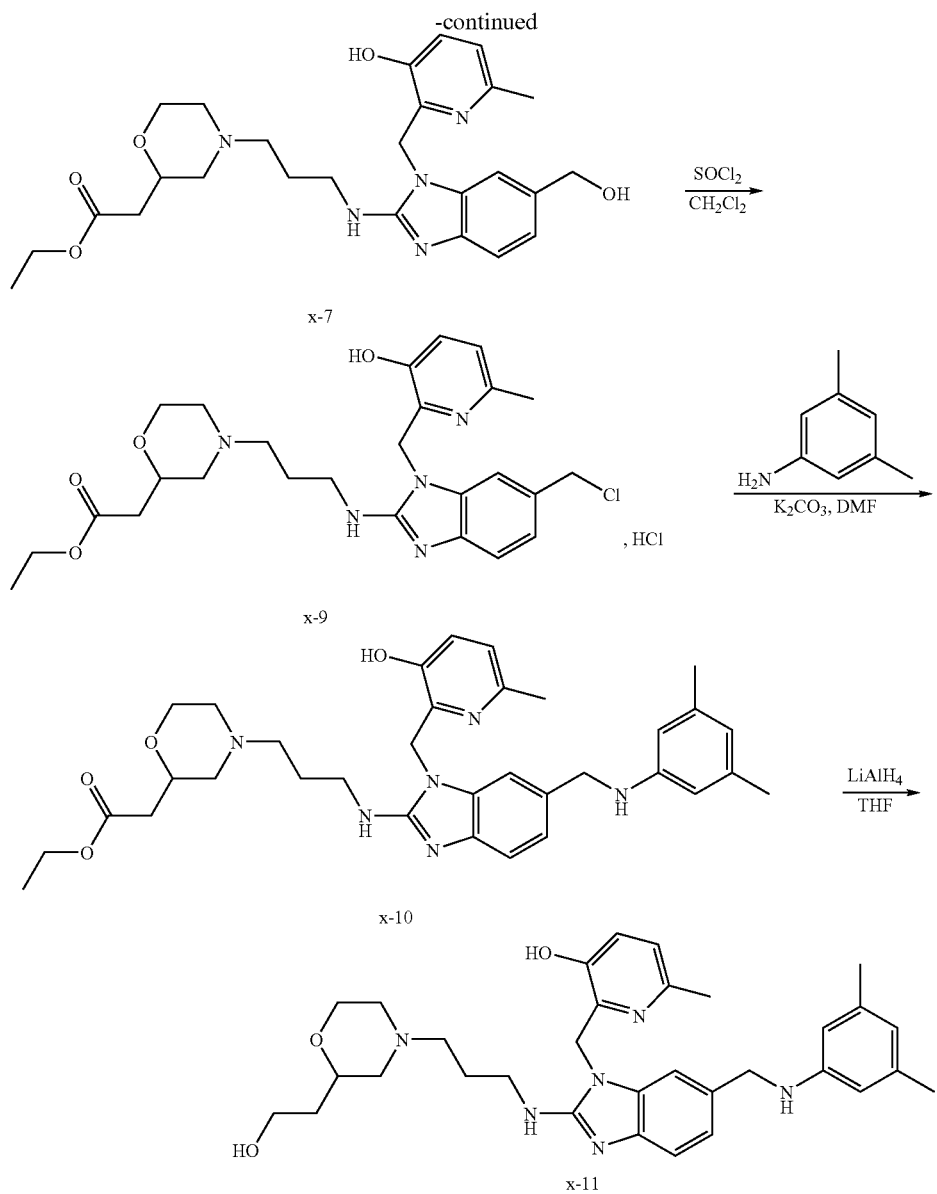

A mixture of x-1 (0.0635 mol), x-2 (0.0635 mol) and K₂CO₃ (0.19 mol) in CH₃CN (110 ml) was stirred at 80° C. for 12 hours, then cooled to room temperature, poured on ice and extracted with CH₂Cl₂. The organic layer was separated, dried (over MgSO₄), filtered, and the solvent was evaporated until dryness. Yield: 20.2 g (96%). HCl 3N (200 ml) and tetrahydrofuran (200 ml) were then added and the reaction was stirred at room temperature for 12 hours. K₂CO₃ was added. CH₂Cl₂ was added. The organic layer was separated, dried (over MgSO₄), filtered and the solvent was evaporated until dryness. Yield: 8.4 g of intermediate x-3 (60%).

A mixture of x-4 (0.0173 mol) and x-3 (0.026 mol) was stirred at 125° C. for 4 hours, and then taken up in CH₂Cl₂/CH₃OH. The organic layer was washed with saturated K₂CO₃ solution, dried (over MgSO₄), filtered and the solvent was evaporated until dryness. The residue (9 g) was purified by column chromatography over silica gel (eluent: CH₂Cl₂/CH₃OH/NH₄OH 90/10/0.5; 20-45 μm). Two fractions were collected and the solvent was evaporated. Yield: 0.7 g of intermediate x-5 (10%).

A mixture of x-5 (0.0018 mol), x-6 (0.0022 mol) and K₂CO₃ (0.0056 mol) in dimethylformamide (20 ml) was sired at room temperature for 12 hours, poured on ice, saturated with K₂CO₃ and extracted with CH₂Cl₂. The organic layer was separated, dried (over MgSO₄), filtered and the solvent was evaporated until dryness. The residue (1.4 g) was purified by column chromatography over silica gel (eluent: CH₂Cl₂/CH₃OH/NH₄OH 93/7/0.5; 5-40 μm). Two fractions were collected and the solvent was evaporated. Yield: 0.29 g of intermediate x-7 (31%) and 0.2 g of intermediate x-8 (22%).

SOCl₂ (0.0015 mol) was added at 5° C. to a mixture of x-7 (0.0003 mol) in CH₂Cl₂ (20 ml). The mixture was stirred at 5° C. for 2 hours, and then stirred at room temperature for 12 hours. The solvent was evaporated until dryness. The residue was taken up in Diisopropylether. The precipitate was filtered off and dried. Yield: 0.198 g of intermediate x-9 (HCl salt, 100%).

A mixture of x-9 (0.0003 mol), 3,5-dimethylaniline (0.0003 mol) and K₂CO₃ (0.0015 mol) in dimethylformamide (20 ml) was stirred at 80° C. for 4 hours, poured into ice water, saturated with K₂CO₃ and extracted with CH₂Cl₂/CH₃OH. The organic layer was separated, dried (over MgSO₄), filtered and the solvent was evaporated until dryness. The residue (0.17 g) was purified by column chromatography over silica gel (eluent: CH₂Cl₂/CH₃OH/NH₄OH 93/7/0.5; 10 µm). The pure fractions were collected and the solvent was evaporated. Yield: 0.023 g of intermediate x-10 (13%).

LiAlH₄ (0.00008 mol) was added at 5° C. to a mixture of x-10 (0.00004 mol) in tetrahydrofuran (10 ml). The mixture was stirred at 5° C. for 2 hours, poured into H₂O. CH₂Cl₂ was added. The organic layer was separated, dried (over MgSO₄), filtered and the solvent was evaporated. The residue (0.023 g) was purified by column chromatography over silica gel (eluent CH₂Cl₂/CH₃OH/NH₄OH 92/8/0.5; 10 µm). The pure fractions were collected and the solvent was evaporated. Yield: 0.009 g of 2-(6-[(3,5-Dimethyl-phenylamino)-methyl]-2-{3-[2-(2-hydroxy-ethyl)-morpholin-4-yl]-propylamino}-benzoimidazol-1-ylmethyl)-6-methyl-pyridin-3-ol (x-11, compound 181, 41%).

Example 25

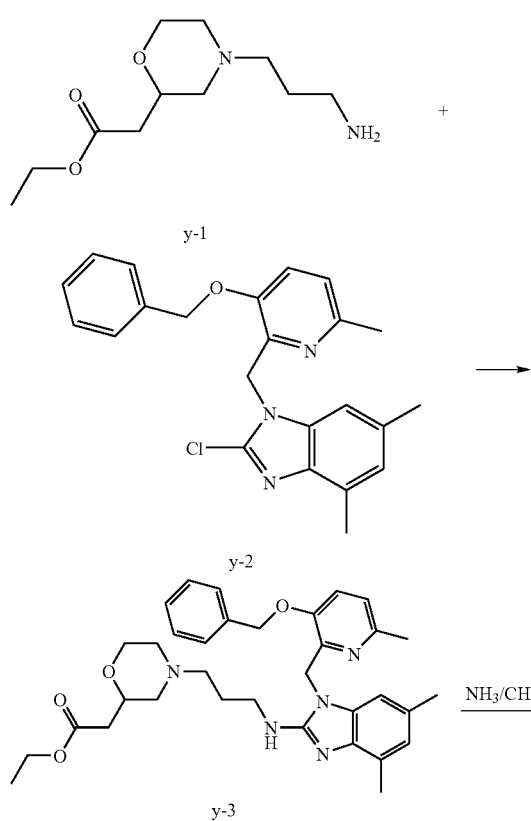

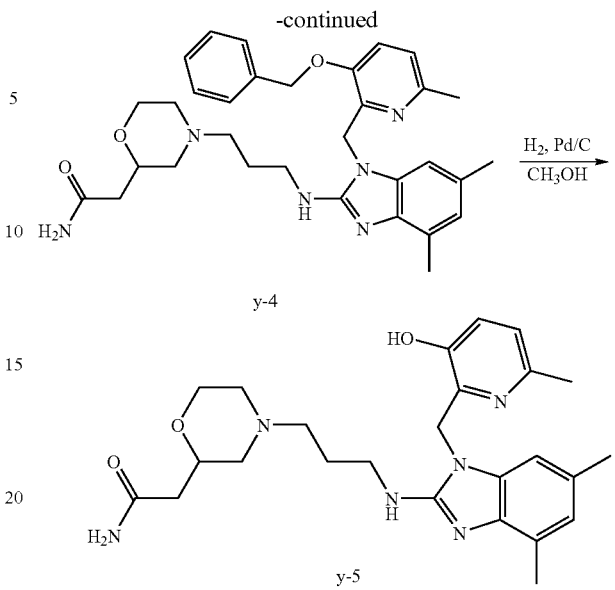

A mixture of y-2 (0.0012 mol) and y-1 (0.0073 mol) was stirred at 160° C. for 2 hours, and then taken up in CH₂Cl₂/CH₃OH. The organic layer was washed with K₂CO₃ 10%, dried (over MgSO₄), filtered and the solvent was evaporated until dryness. The residue (1.5 g) was purified by column chromatography over silica gel (eluent: CH₂Cl₂/CH₃OH/NH₄OH 96/4/0.2; 15-40 µm). The pure fractions were collected and the solvent was evaporated. Yield: 0.08 g of intermediate y-3 (11%).

A solution of y-3 (0.0001 mol) in NH₃/CH₃OH 7N (15 ml) was stirred at 80° C. in a sealed vessel for 24 hours. The solvent was evaporated until dryness. Yield: 0.075 g of intermediate y-4 (100%). The crude compound was used directly in the next reaction step.

A mixture of y-4 (0.0001 mol) and Pd/C (0.03 g) in CH₃OH (30 ml) was hydrogenated at room temperature for 2 hours under a 3 bar pressure, then filtered over celite. Celite was washed with H₂O. The filtrate was evaporated until dryness. The residue was crystallized from 2-propanone/Diisopropylether. The precipitate was filtered off and dried. Yield: 0.034 g of 2-(4-{3-[1-(3-Hydroxy-6-methyl-pyridin-2-ylmethyl)-4,6-dimethyl-1H-benzoimidazol-2-ylamino]-propyl}-morpholin-2-yl)-acetamide (y-5, compound 191, 55%, melting point: 148° C.).

Example 26

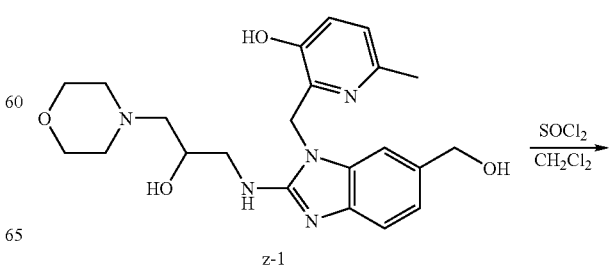

85

-continued

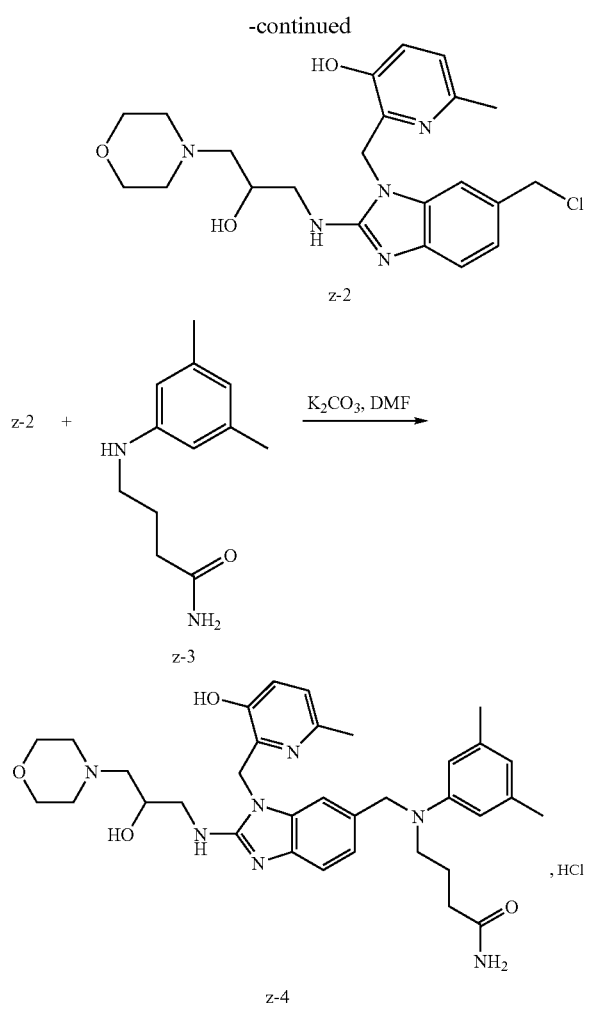

SOCl$_2$ (0.0035 mol) was added drop wise at 5° C. to a mixture of z-1 (0.0007 mol) in CH$_2$Cl$_2$ (30 ml). The mixture was stirred at 5° C. for 2 hours, and then stirred at room temperature for 12 hours. The solvent was evaporated until dryness. The residue was taken up in Diisopropylether. The precipitate was filtered, washed with H$_2$O and dried. Yield: 0.415 g of intermediate z-2 (4 HCl, 100%).

A mixture of z-2 (0.0014 mol), z-3 (0.0016 mol) and K$_2$CO$_3$ (0.007 mol) in dimethylformamide (80 ml) was sired at 80° C. for 4 hours, poured into ice water, saturated with K$_2$CO$_3$ and extracted with CH$_2$Cl$_2$. The organic layer was separated, dried (over MgSO$_4$), filtered and the solvent was evaporated until dryness. The residue (1 g) was purified by column chromatography over silica gel (eluent: CH$_2$Cl$_2$/CH$_3$OH/NH$_4$OH 93/7/1; 10 μm). The pure fractions were collected and the solvent was evaporated. Yield: 0.22 g of the free base (26%). This fraction was dissolved in 2-propanone/diisopropylether/HCl 7N and converted into the hydrochloric acid salt. The precipitate was filtered off and dried. Yield: 0.25 g of 4-{(3,5-Dimethyl-phenyl)-[3-(3-hydroxy-6-methyl-pyridin-2-ylmethyl)-2-(2-hydroxy-3-morpholin-4-yl-propylamino)-3H-benzoimidazol-5-ylmethyl]-amino}-butyramide, HCl salt (z-4, compound 178, 4 HCl, 24%, melting point: 164° C.).

86

Example 27

Scheme AA

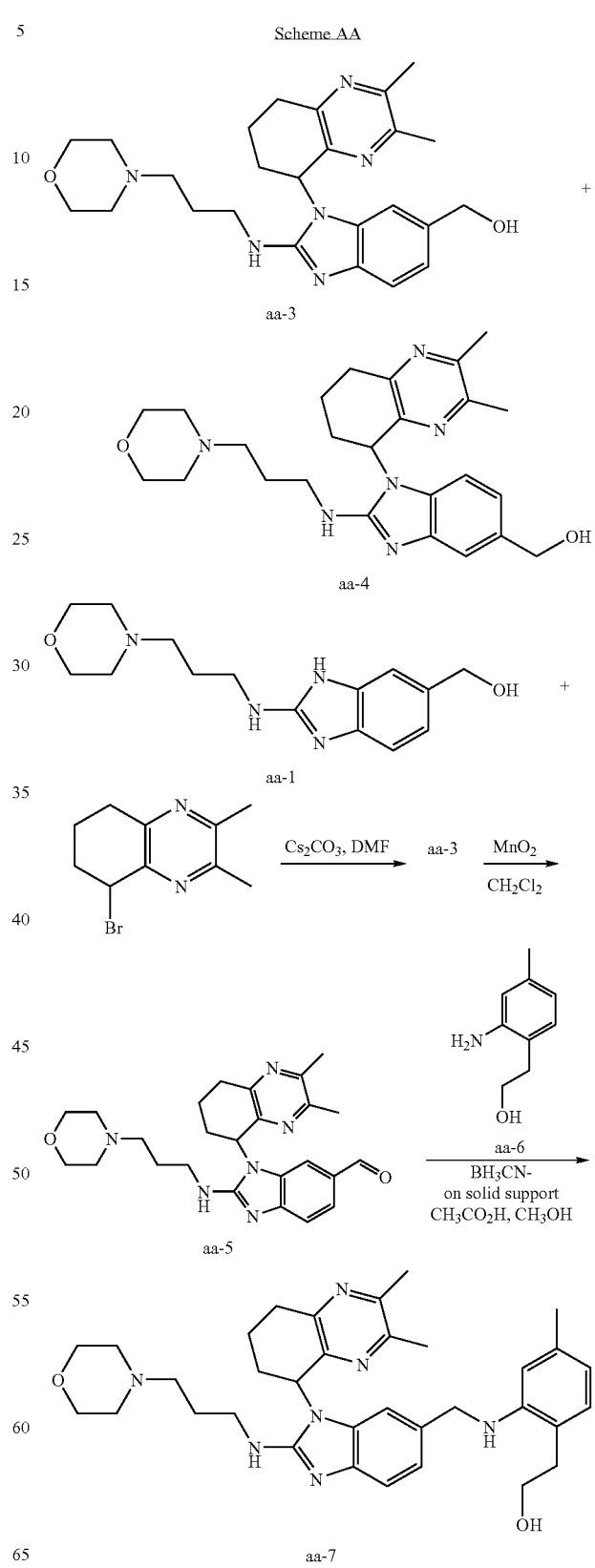

A mixture of aa-1 (0.0104 mol), aa-2 (0.0114 mol) and Cs$_2$CO$_3$ (0.0034 mol) in dimethylformamide (40 ml) was stirred at room temperature for 12 hours, poured on ice, saturated with K$_2$CO$_3$ and extracted with CH$_2$Cl$_2$. The organic layer was separated, dried (over MgSO$_4$), filtered and the solvent was evaporated until dryness. The residue (8.6 g) was purified by column chromatography over silica gel (eluent: CH$_2$Cl$_2$/CH$_3$OH/NH$_4$OH 94/6/0.5). Two fractions were collected and the solvent was evaporated. Yield F1 and F2. F1 was crystallized from CH$_3$OH/2-propanone/diisopropylether. The precipitate was filtered and dried. Yield: 0.75 g of intermediate aa-3 (compound 311, 16%, melting point: 160° C.). F2 was crystallized from few CH$_3$OH/2-propanone/diisopropylether. The precipitate was filtered, washed with diisopropylether and dried. Yield: 0.4 g of intermediate aa-4 (compound 336, 9%, melting point: 202° C.).

A mixture of aa-3 (0.0005 mol) and MnO$_2$ (2.5 g) in CH$_2$Cl$_2$ (50 ml) and CH$_3$OH (few quantity) was stirred at room temperature for 3 hours, and then filtered over celite. Celite was washed with CH$_2$Cl$_2$. The filtrate was evaporated until dryness. Yield: 0.21 g of intermediate aa-5 (84%).

A mixture of aa-5 (0.0004 mol), aa-6 (0.0005 mol) and BH$_3$CN— on solid support (0.0007 mol) in CH$_3$OH (15 ml) and CH$_3$CO$_2$H (1.5 ml) was stirred at room temperature for 24 hours, and then filtered. The filtrate was evaporated until dryness. The residue (0.25 g) was purified by column chromatography over silica gel (eluent: CH$_2$Cl$_2$/CH$_3$OH/NH$_4$OH 95/5/0.5; 5 μm). The pure fractions were collected and the solvent was evaporated. The residue was crystallized from 2-propanone. The precipitate was filtered off and dried. Yield: 0.068 g of 2-(2-{[3-(2,3-Dimethyl-5,6,7,8-tetrahydroquinoxalin-5-yl)-2-(3-morpholin-4-yl-propylamino)-3H-benzoimidazol-5-ylmethyl]-amino}-4-methyl-phenyl)-ethanol (aa-7, compound 193, 25%, melting point: 162° C.).

Example 28

Scheme AB

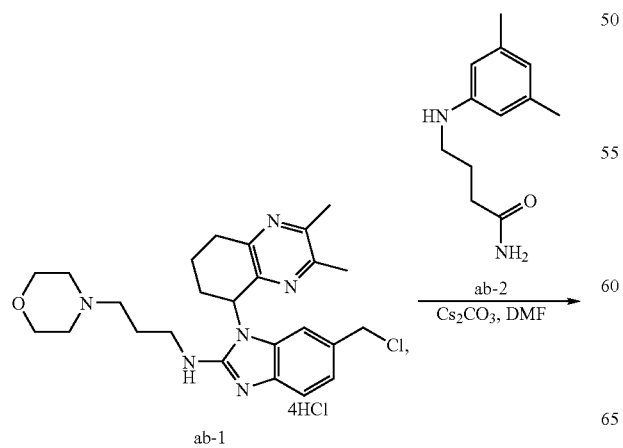

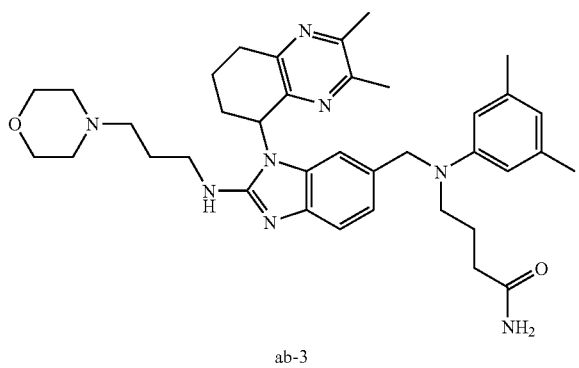

SOCl$_2$ (0.0016 mol) was added drop wise at 5° C. to a solution of aa-3 (0.0003 mol) in CH$_2$Cl$_2$ (0.0016 mol). The mixture was stirred at 5° C. for 2 hours, and then stirred at room temperature for 12 hours. The solvent was evaporated until dryness. The residue was taken up in diisopropylether. The precipitate was filtered off and dried. Yield: 0.16 g of intermediate ab-1 (4 HCl, 78%).

A mixture of ab-1 (0.0003 mol), ab-2 (0.0003 mol) and Cs$_2$CO$_3$ (0.0016 mol) in dimethylformamide (25 ml) was stirred at 80° C. for 3 hours, poured on ice, saturated with K$_2$CO$_3$ and extracted with CH$_2$Cl$_2$. The organic layer was separated, dried (over MgSO$_4$), filtered and the solvent was evaporated until dryness. The residue (0.45 g) was purified by column chromatography over silica gel (eluent: CH$_2$Cl$_2$/CH$_3$OH/NH$_4$OH 89/10/1; 10 μm). The pure fractions were collected and the solvent was evaporated. The residue (0.07 g) was crystallized from 2-propanone/diisopropylether. The precipitate was filtered, washed with H$_2$O and dried. Yield: 0.07 g of 4-{(3,5-Dimethyl-phenyl)-[3-(2,3-dimethyl-5,6,7,8-tetrahydro-quinoxalin-5-yl)-2-(3-morpholin-4-yl-propylamino)-3H-benzoimidazol-5-ylmethyl]-amino}-butyramide (ab-3, compound 213, 17%, melting point: 109° C.).

Example 29

Scheme AC

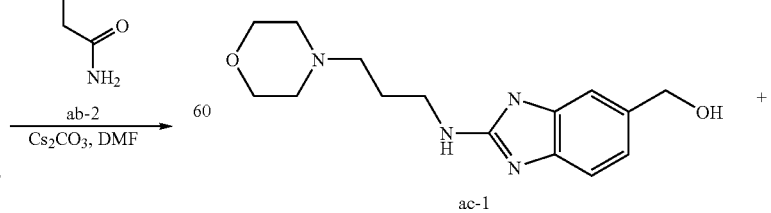

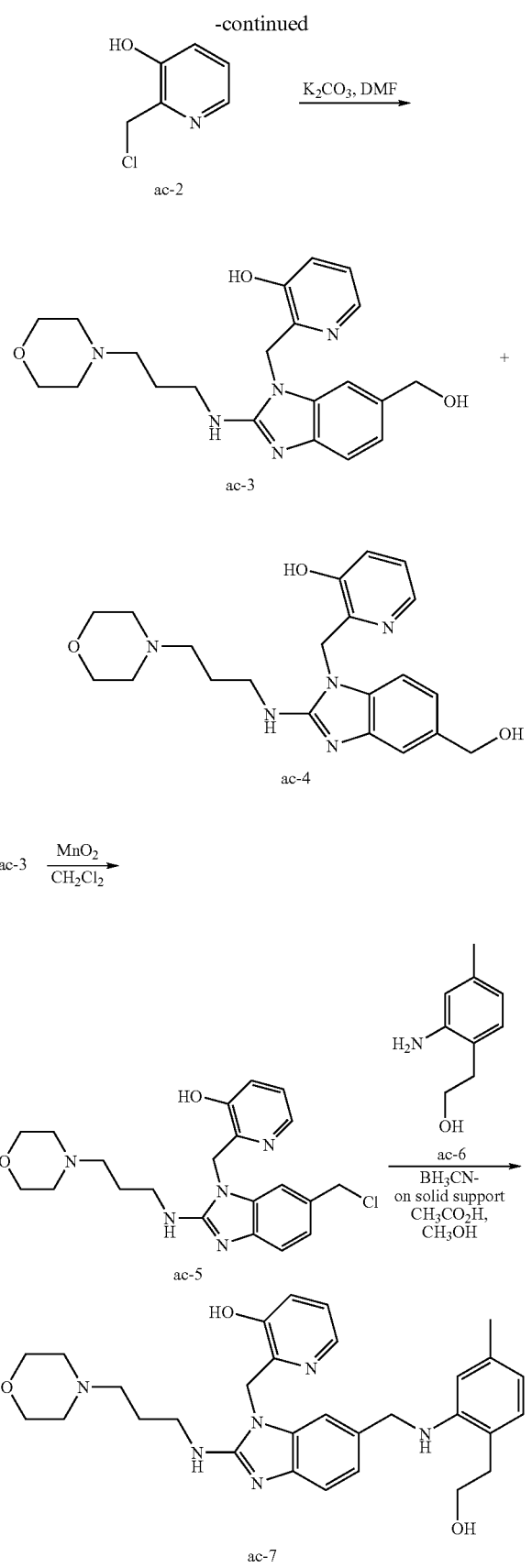
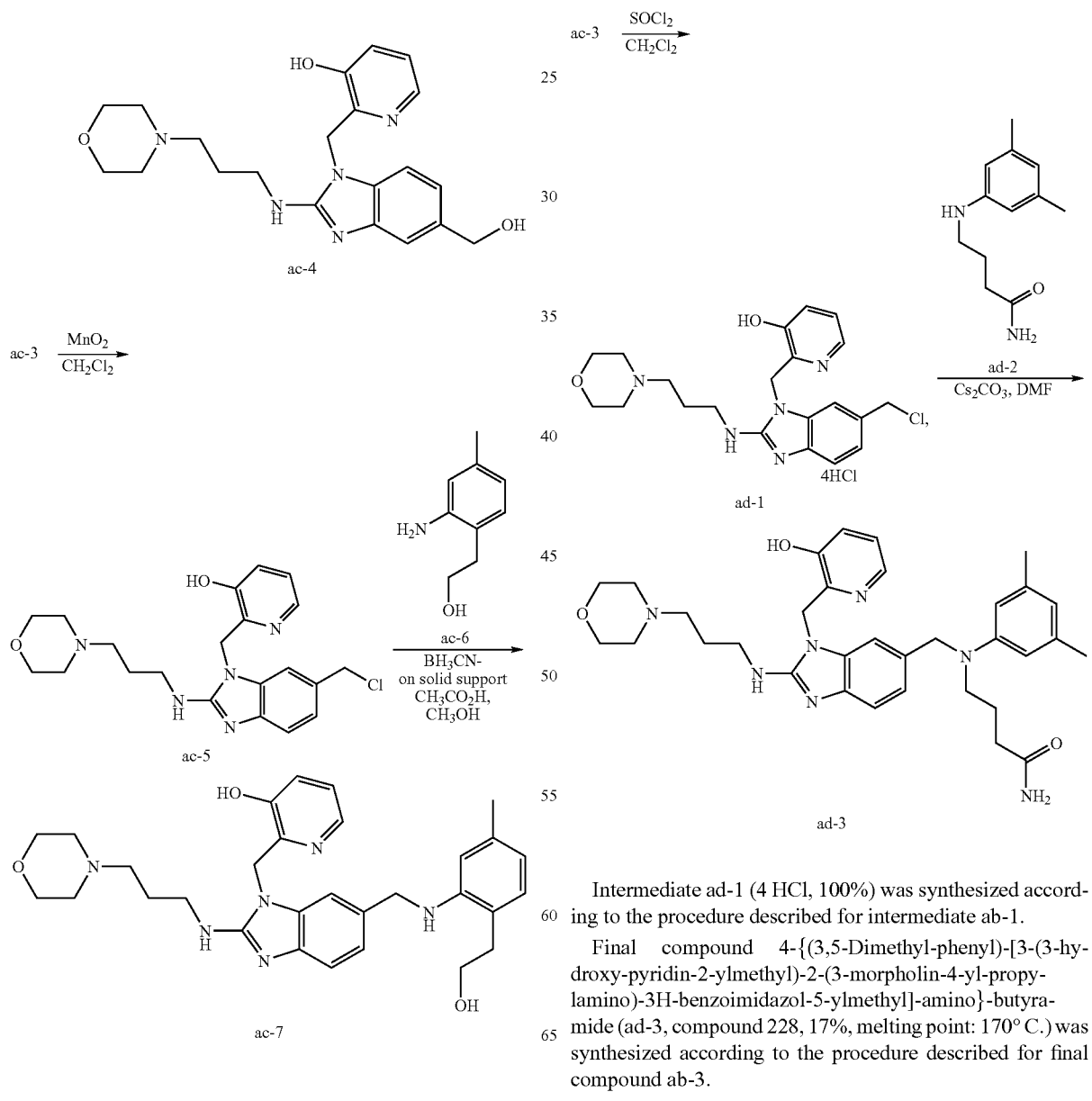

Intermediates ac-3 (compound 327, 24%, melting point: 254° C.) and ac-4 (compound 359, 17%, melting point: 242° C.) were synthesized according to the procedure described for intermediates aa-3 and aa-4 but using $K_2CO_3$ instead of $Cs_2CO_3$.

Intermediate ac-5 (80%, melting point: 208° C.) was synthesized according to the procedure described for intermediate aa-5.

Final compound 2-[6-{[2-(2-Hydroxy-ethyl)-5-methyl-phenylamino]-methyl}-2-(3-morpholin-4-yl-propylamino)-benzoimidazol-1-ylmethyl]-pyridin-3-ol (ac-7, compound 192, 81%, melting point: 192° C.) was synthesized according to the procedure described for final compound aa-7.

Example 30

Scheme AD

Intermediate ad-1 (4 HCl, 100%) was synthesized according to the procedure described for intermediate ab-1.

Final compound 4-{(3,5-Dimethyl-phenyl)-[3-(3-hydroxy-pyridin-2-ylmethyl)-2-(3-morpholin-4-yl-propylamino)-3H-benzoimidazol-5-ylmethyl]-amino}-butyramide (ad-3, compound 228, 17%, melting point: 170° C.) was synthesized according to the procedure described for final compound ab-3.

Example 31

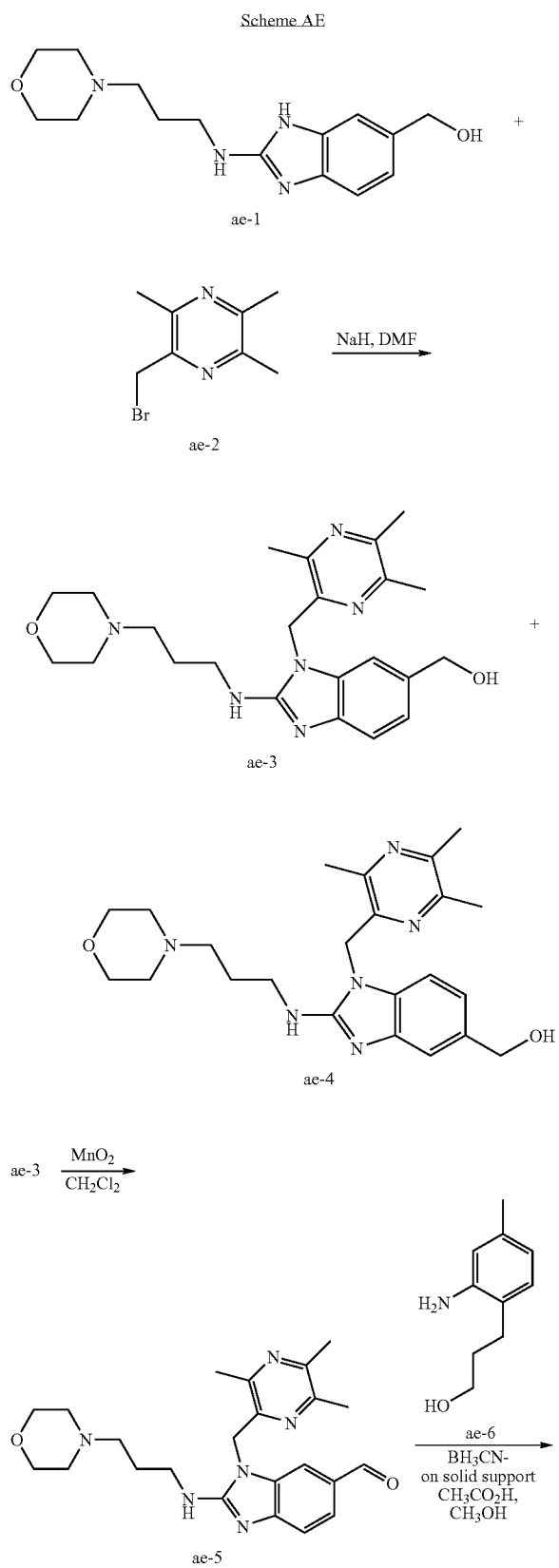

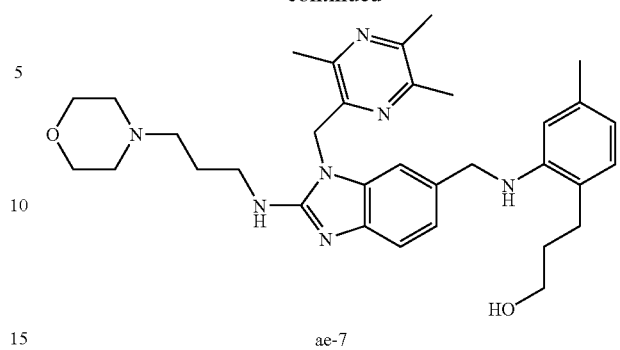

A solution of ae-2 (0.0246 mol) in dimethylformamide (30 ml) was added to a mixture of ae-1 (0.0205 mol) and NaH (0.0226 mol) in dimethylformamide (70 ml). The mixture was stirred at 50° C. for 48 hours. The solvent was evaporated until dryness. H$_2$O was added. The mixture was extracted three times with CH$_2$Cl$_2$. The organic layer was separated, dried (over MgSO$_4$), filtered and the solvent was evaporated until dryness. The residue (11 g) was purified by column chromatography over silica gel (eluent: CH$_2$Cl$_2$/CH$_3$OH/NH$_4$OH 95/5/0.5 to 93/7/0.5; 15-40 µm). Two fractions were collected and the solvent was evaporated. Yield: 3.6 g of intermediate ae-3 (41%) and 2.3 g of intermediate ae-4 (26%).

Intermediate ae-5 (62%, melting point: 130° C.) was synthesized according to the procedure described for intermediate aa-5.

Final compound 3-(4-Methyl-2-{[2-(3-morpholin-4-yl-propylamino)-3-(3,5,6-trimethyl-pyrazin-2-ylmethyl)-3H-benzoimidazol-5-ylmethyl]-amino}-phenyl)-propan-1-ol (ae-7, compound 255, 41%, melting point: 120° C.) was synthesized according to the procedure described for final compound aa-7.

Example 32

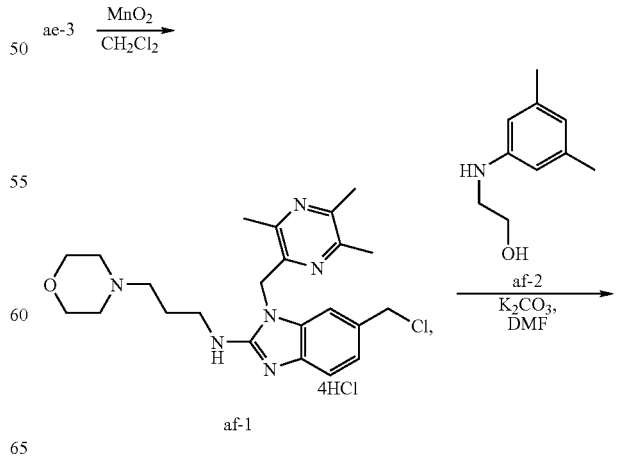

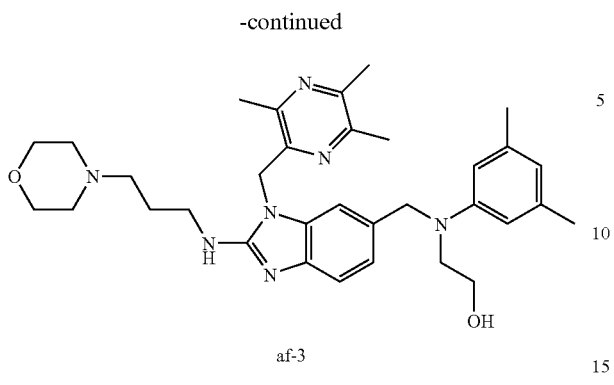

af-3

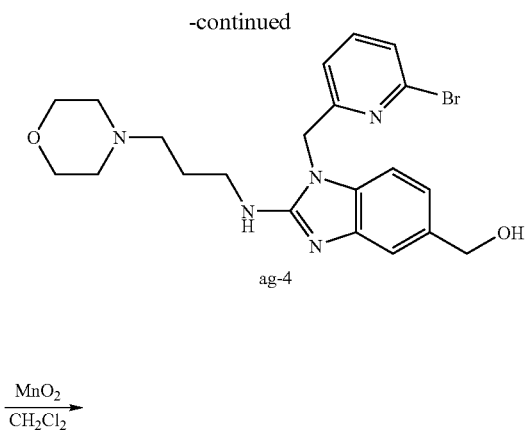

ag-4

Intermediate af-1 (4 HCl, 100%) was synthesized according to the procedure described for intermediate ab-1.

Final compound 2-{(3,5-Dimethyl-phenyl)-[2-(3-morpholin-4-yl-propylamino)-3-(3,5,6-trimethyl-pyrazin-2-yl-methyl)-3H-benzoimidazol-5-ylmethyl]-amino}-ethanol (af-3, compound 233, 24%, melting point: 140° C.) was synthesized according to the procedure described for final compound ab-3 but using $K_2CO_3$ instead of $Cs_2CO_3$.

Example 33

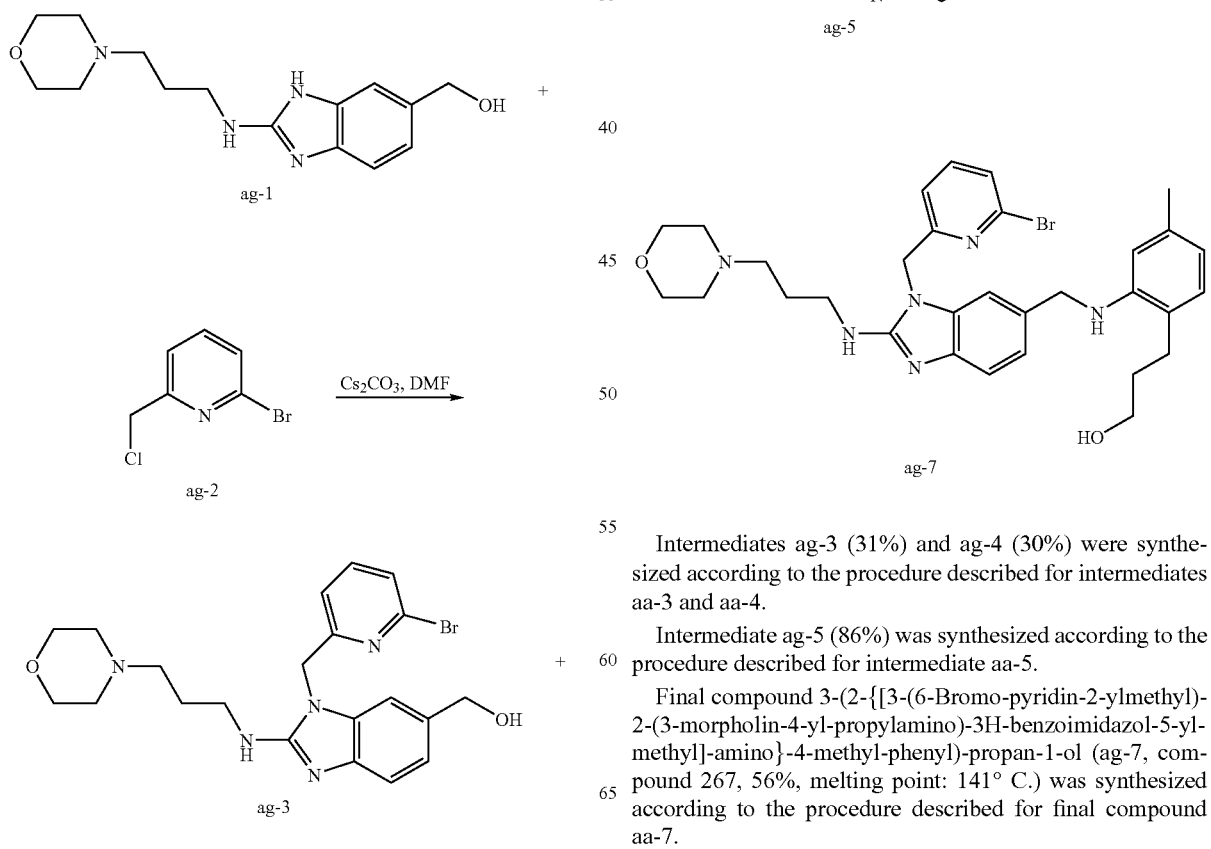

Intermediates ag-3 (31%) and ag-4 (30%) were synthesized according to the procedure described for intermediates aa-3 and aa-4.

Intermediate ag-5 (86%) was synthesized according to the procedure described for intermediate aa-5.

Final compound 3-(2-{[3-(6-Bromo-pyridin-2-ylmethyl)-2-(3-morpholin-4-yl-propylamino)-3H-benzoimidazol-5-yl-methyl]-amino}-4-methyl-phenyl)-propan-1-ol (ag-7, compound 267, 56%, melting point: 141° C.) was synthesized according to the procedure described for final compound aa-7.

Example 34

Scheme AH

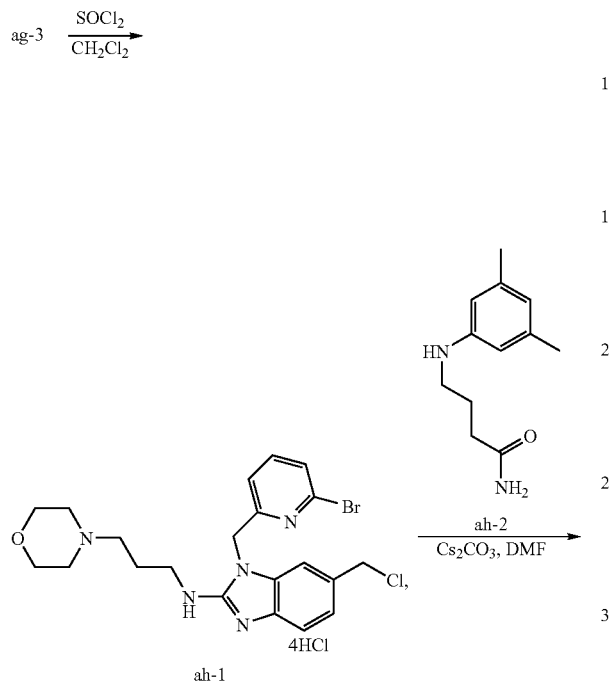

Intermediate ah-1 (4 HCl, 89%) was synthesized according to the procedure described for intermediate ab-1.

Final compound 4-[[3-(6-Bromo-pyridin-2-ylmethyl)-2-(3-morpholin-4-yl-propyl-amino)-3H-benzoimidazol-5-yl-methyl]-(3,5-dimethyl-phenyl)-amino]-butyramide (ah-3, compound 261, 18%, melting point: 82° C.) was synthesized according to the procedure described for final compound ab-3.

Example 35

Scheme AI

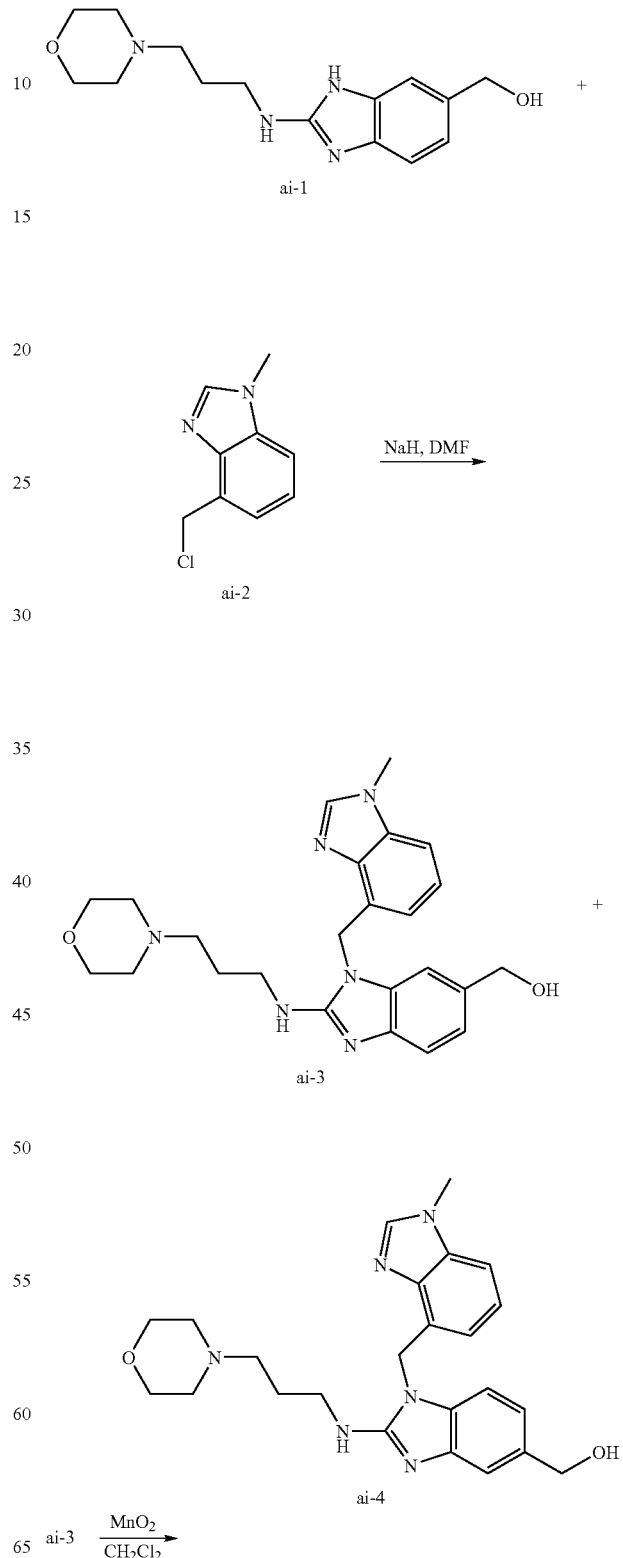

Example 36

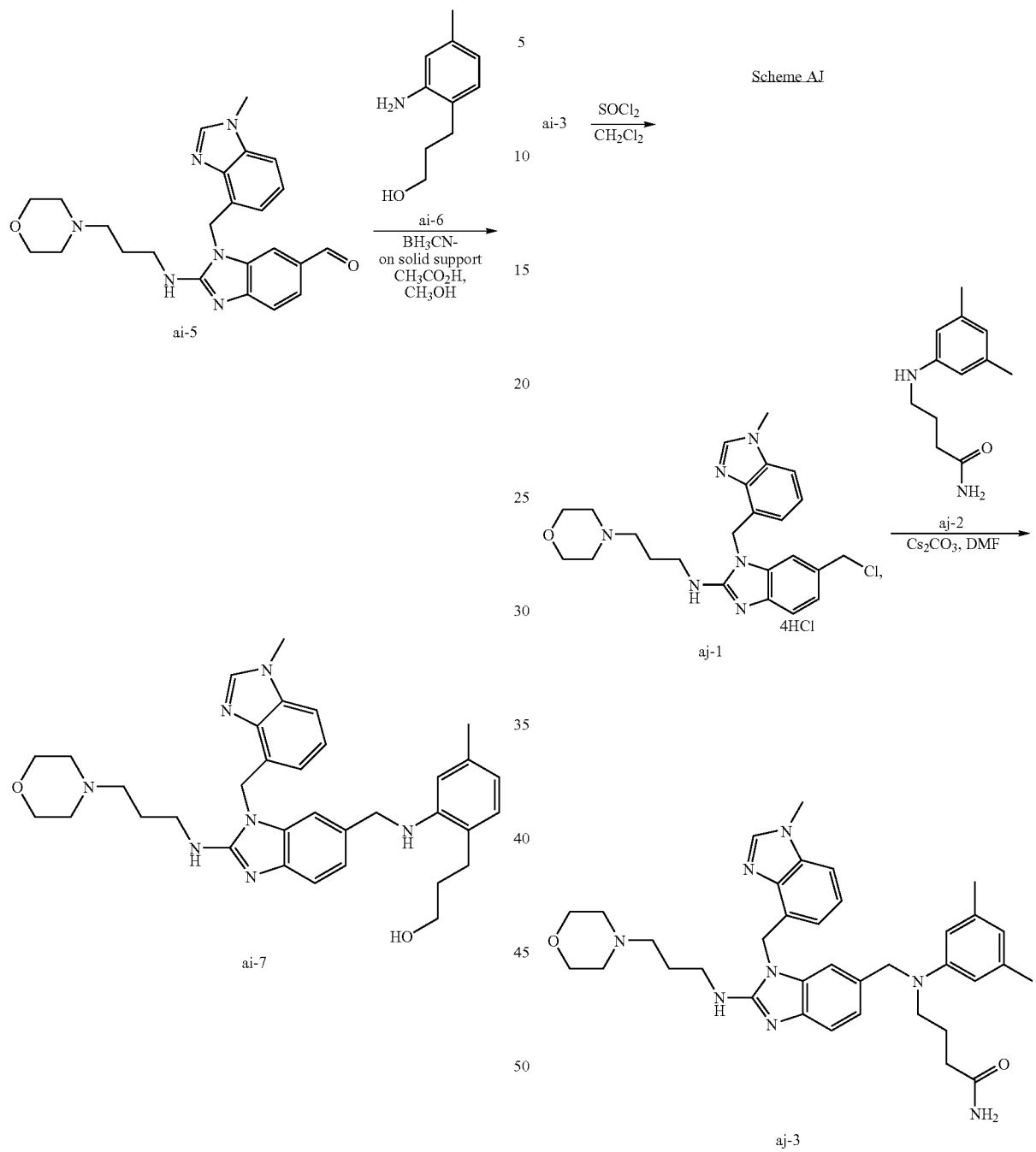

Intermediates ai-3 (compound 325, 19%, melting point: 167° C.) and ai-4 (compound 358, 9%, melting point: 173° C.) were synthesized according to the procedure described for intermediates ae-3 and ae-4.

Intermediate ai-5 (100%) was synthesized according to the procedure described for intermediate aa-5.

Final compound 3-(4-Methyl-2-{[3-(1-methyl-1H-benzoimidazol-4-ylmethyl)-2-(3-morpholin-4-yl-propylamino)-3H-benzoimidazol-5-ylmethyl]-amino}-phenyl)-propan-1-ol (ai-7, compound 218, 70%, melting point: 198° C.) was synthesized according to the procedure described for final compound aa-7.

Intermediate aj-1 (4 HCl, 100%) was synthesized according to the procedure described for intermediate ab-4.

Final compound 4-{(3,5-Dimethyl-phenyl)-[3-(1-methyl-1H-benzoimidazol-4-ylmethyl)-2-(3-morpholin-4-yl-propylamino)-3H-benzoimidazol-5-ylmethyl]-amino}-butyramide (aj-3, compound 230, 21%, melting point: 206° C.) was synthesized according to the procedure described for final compound ab-3.

Example 37

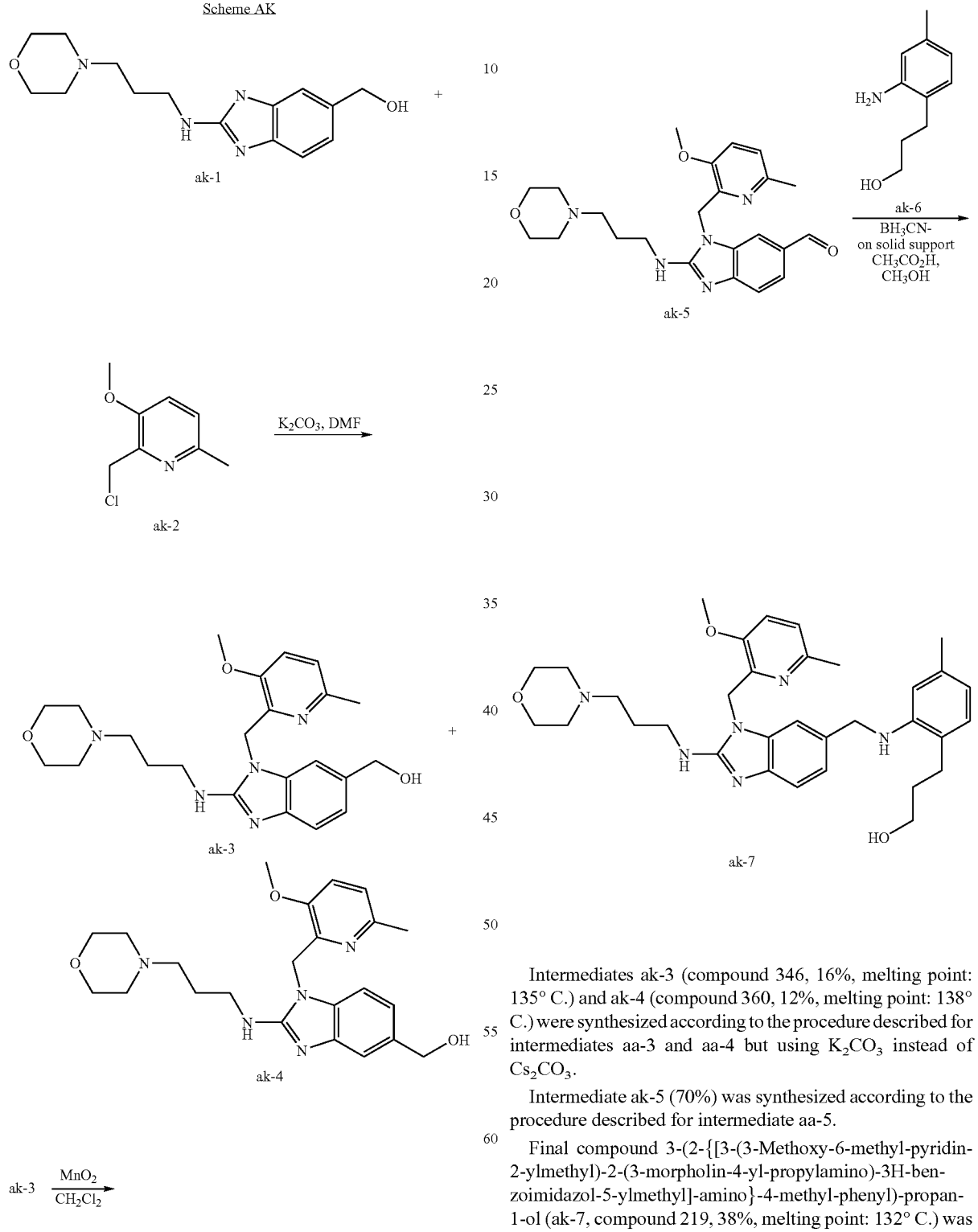

Intermediates ak-3 (compound 346, 16%, melting point: 135° C.) and ak-4 (compound 360, 12%, melting point: 138° C.) were synthesized according to the procedure described for intermediates aa-3 and aa-4 but using $K_2CO_3$ instead of $Cs_2CO_3$.

Intermediate ak-5 (70%) was synthesized according to the procedure described for intermediate aa-5.

Final compound 3-(2-{[3-(3-Methoxy-6-methyl-pyridin-2-ylmethyl)-2-(3-morpholin-4-yl-propylamino)-3H-benzoimidazol-5-ylmethyl]-amino}-4-methyl-phenyl)-propan-1-ol (ak-7, compound 219, 38%, melting point: 132° C.) was synthesized according to the procedure described for final compound aa-7.

Example 38

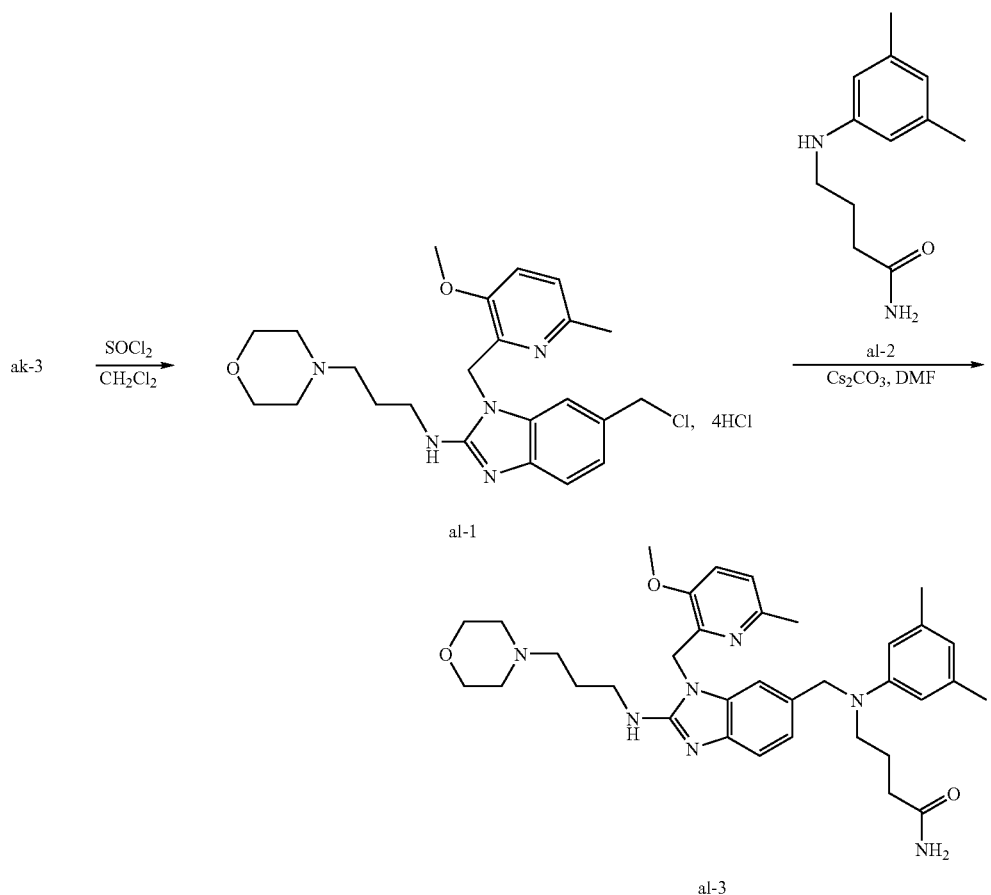

Intermediate al-1 (4 HCl, 100%) was synthesized according to the procedure described for intermediate ab-1.

Final compound-{(3,5-Dimethyl-phenyl)-[3-(3-methoxy-6-methyl-pyridin-2-ylmethyl)-2-(3-morpholin-4-yl-propylamino)-3H-benzoimidazol-5-ylmethyl]-amino}-butyramide (al-3, compound 210, 16%, melting point: 130° C.) was synthesized according to the procedure described for final compound ab-3.

Example 39

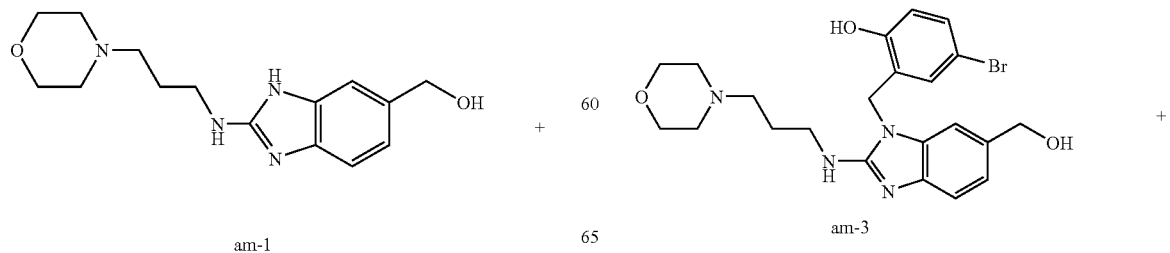

-continued

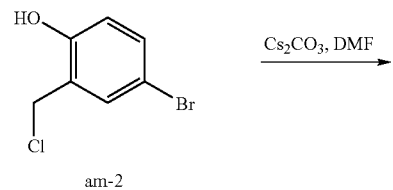

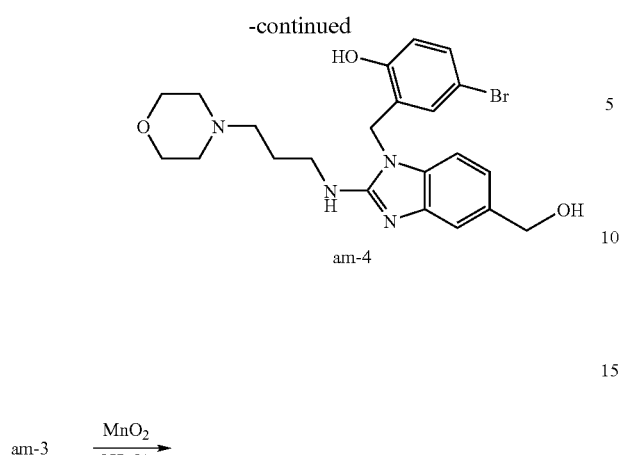

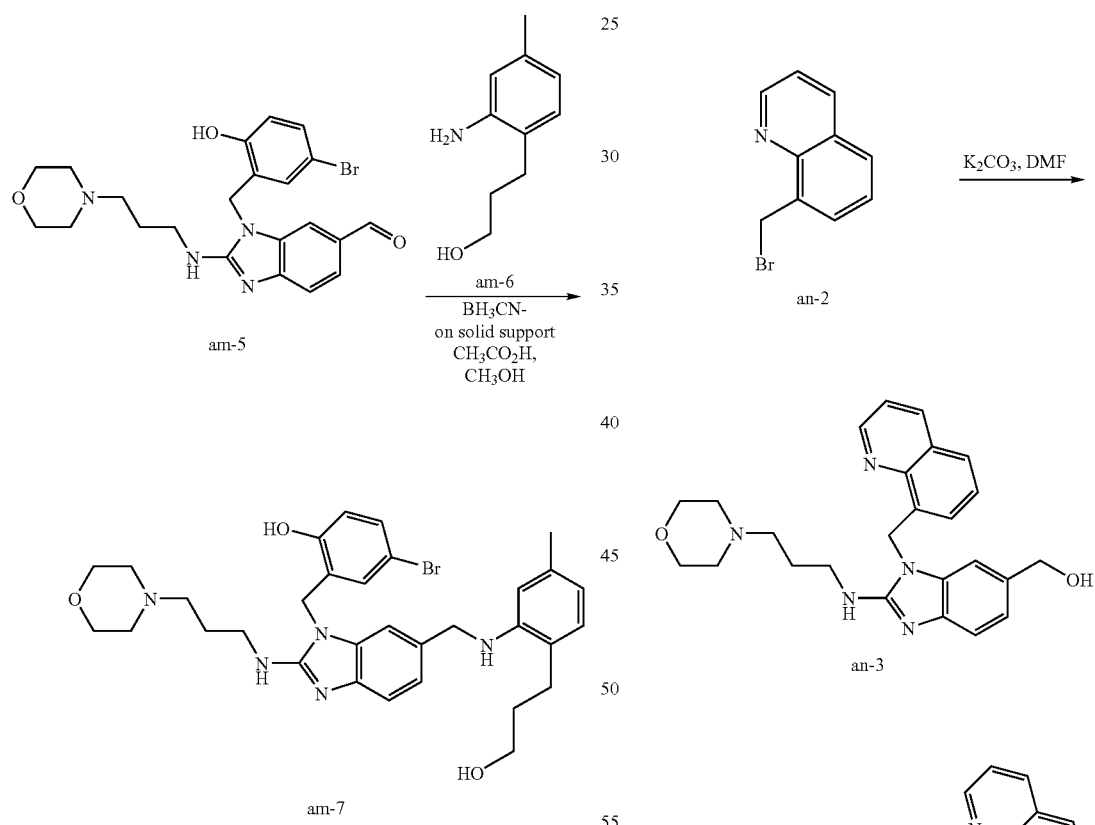

Intermediates am-3 (compound 308, 8%, melting point: 230° C.) and am-4 (compound 322, 12%, melting point: 235° C.) were synthesized according to the procedure described for intermediates aa-3 and aa-4.

Intermediate am-5 (46%) was synthesized according to the procedure described for intermediate aa-5.

Final compound 4-Bromo-2-[6-{[2-(3-hydroxy-propyl)-5-methyl-phenylamino]-methyl}-2-(3-morpholin-4-yl-propylamino)-benzoimidazol-1-ylmethyl]-phenol (am-7, compound 201, 42%, melting point: 134° C.) was synthesized according to the procedure described for final compound aa-7.

Example 40

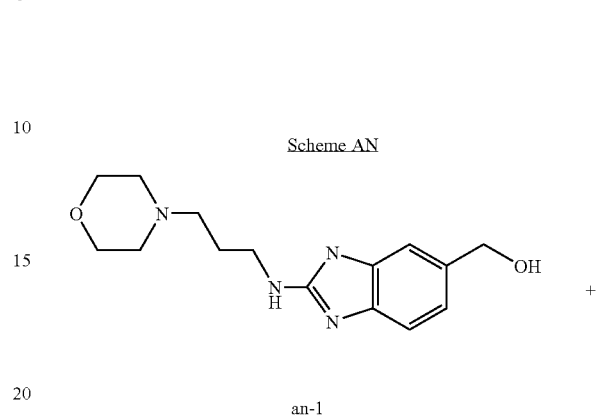

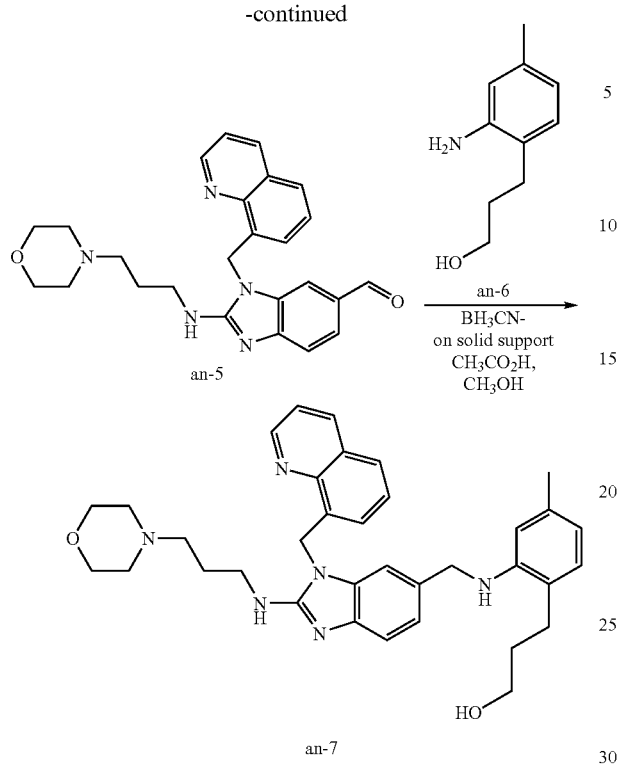

Intermediates an-3 (22%, melting point: 198° C.) and an-4 (19%, melting point: 200° C.) were synthesized according to the procedure described for intermediates aa-3 and aa-4 but using $K_2CO_3$ instead of $Cs_2CO_3$.

Intermediate an-5 (82%, melting point 148° C.) was synthesized according to the procedure described for intermediate aa-5.

Final compound 3-(4-Methyl-2-{[2-(3-morpholin-4-yl-propylamino)-3-quinolin-8-ylmethyl-3H-benzoimidazol-5-ylmethyl]-amino}-phenyl)-propan-1-ol (an-7, compound 234, 50%, melting point: 165° C.) was synthesized according to the procedure described for final compound aa-7.

Example 41

Scheme AO

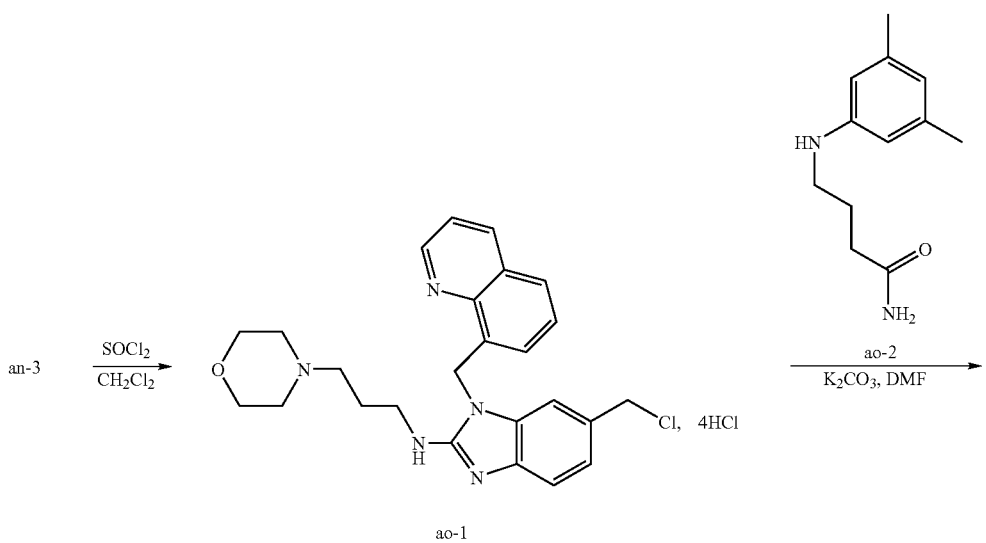

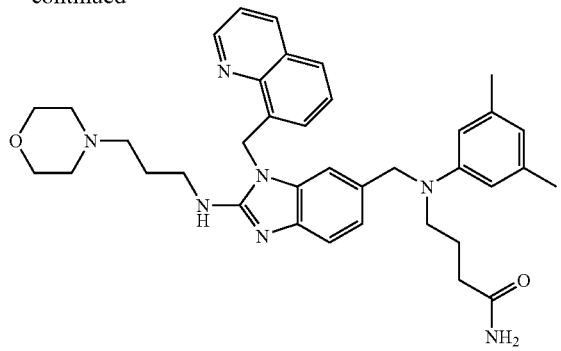

ao-3

Intermediate ao-1 (4 HCl, 100%) was synthesized according to the procedure described for intermediate ab-1.

Final compound 4-{(3,5-Dimethyl-phenyl)-[2-(3-morpholin-4-yl-propylamino)-3-quinolin-8-ylmethyl-3H-benzoimidazol-5-ylmethyl]-amino}-butyramide (ao-3, compound 223, 16%, melting point: 154° C.) was synthesized according to the procedure described for final compound ab-3 but using $K_2CO_3$ instead of $Cs_2CO_3$.

The following tables list compounds that were prepared according to any one of the above examples.

TABLE 1

| Comp. No. | R²a | R³a | Activity | Mass (MH+) | Melting point/salt | Synthesis scheme |
|---|---|---|---|---|---|---|
| 1 | H | (3-ethylamino-4-(2-hydroxyethyl)-benzonitrile group) | 10 | 556 | 205° C. | K |
| 2 | H | (4-bromo-2-ethylamino-phenyl with 3-hydroxypropyl group) | 10 | 623 | 210° C. | K |

TABLE 1-continued

[Structure shown: benzimidazole with morpholinopropyl-NH at 2-position, N1-CH2-(3-hydroxy-6-methylpyridin-2-yl), with R²a and R³a substituents on benzimidazole]

| Comp. No. | R²a | R³a | Activity | Mass (MH+) | Melting point/salt | Synthesis scheme |
|---|---|---|---|---|---|---|
| 3 | H | 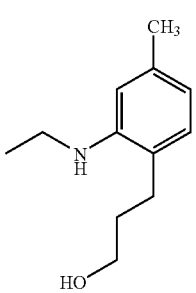 2-(ethylamino)-4-methyl-phenyl with 3-hydroxypropyl | 9.9 | 559 | 208° C. | K |
| 4 | H | 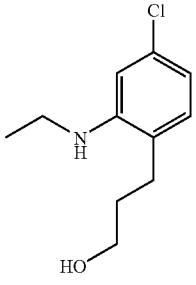 4-chloro-2-(ethylamino)phenyl with 3-hydroxypropyl | 9.9 | 579 | 205° C. | K |
| 5 | H | 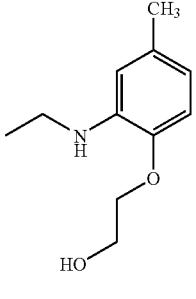 2-(ethylamino)-4-methylphenyl with 2-hydroxyethoxy | 9.8 | 561 | | K |
| 6 | H | 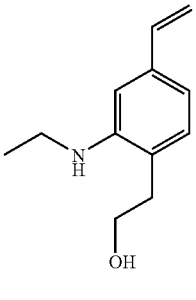 2-(ethylamino)-4-vinylphenyl with 2-hydroxyethyl | >9.6 | 557 | 202° C. | K |

TABLE 1-continued
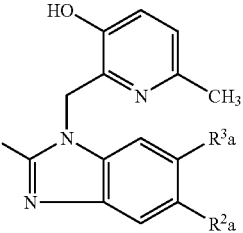
| Comp. No. | R²a | R³a | Activity | Mass (MH+) | Melting point/salt | Synthesis scheme |
|---|---|---|---|---|---|---|
| 7 | H | 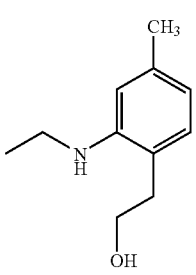 | 9.6 | 545 | 199° C. | K |
| 8 | H | 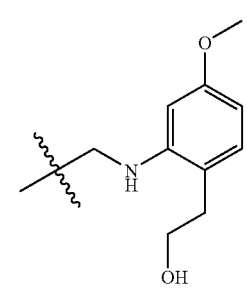 | 9.6 | 555 | 178° C. | K |
| 9 | H | 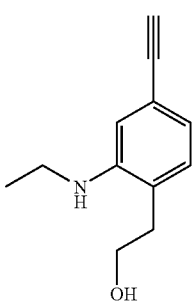 | 9.6 | 561 | | K |
| 10 | H |  | 9.6 | 555 | | K |

TABLE 1-continued

| Comp. No. | R²a | R³a | Activity | Mass (MH+) | Melting point/salt | Synthesis scheme |
|---|---|---|---|---|---|---|
| 11 | H | (4-Br, 2-NHEt, 1-CH₂CH₂OH phenyl) | 9.6 | 609 | | K |
| 12 | H | (4-Me, 2-NHCH₂-, 1-SO₂CH₂CH₂OH phenyl) | 9.6 | 609 | 170° C. | K |
| 13 | H | (4-CF₃, 2-NHEt, 1-CH₂CH₂CH₂OH phenyl) | 9.5 | 613 | 232° C. | K |
| 14 | H | (4-OMe, 2-NHCH₂-, 1-CH₂CH₂CH₂OH phenyl) | 9.4 | 575 | 185° C. | K |

TABLE 1-continued

| Comp. No. | R²a | R³a | Activity | Mass (MH+) | Melting point/salt | Synthesis scheme |
|---|---|---|---|---|---|---|
| 15 | H | | 9.3 | 573 | 161° C. | K |
| 16 | H | | 9.3 | 572 | 190° C. | K |
| 17 | H | | 9.3 | 573 | | K |
| 18 | H | | 9.6 | 549 | | K |

TABLE 1-continued
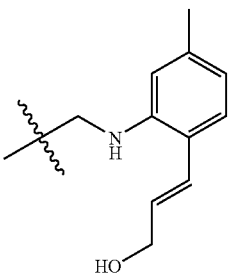
| Comp. No. | R²a | R³a | Activity | Mass (MH+) | Melting point/salt | Synthesis scheme |
|---|---|---|---|---|---|---|
| 19 | H | 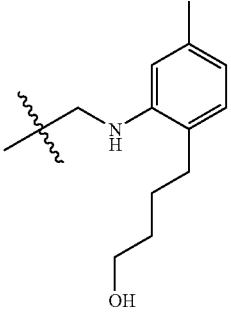 | 9.3 | 557 | 185° C. | K |
| 20 | H | 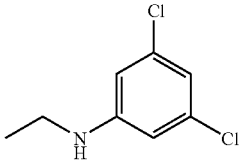 | 9.2 | 573 | 189° C. | K |
| 21 | H | 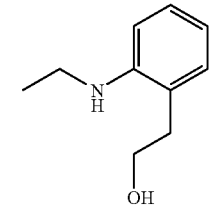 | 9.1 | 539 | 206° C. | J |
| 22 | H | 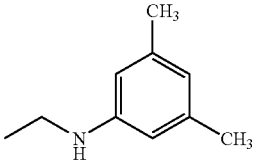 | 9.1 | 531 | 140° C. | K |
| 23 | H |  | 9 | 515 | 199° C. | J |

TABLE 1-continued
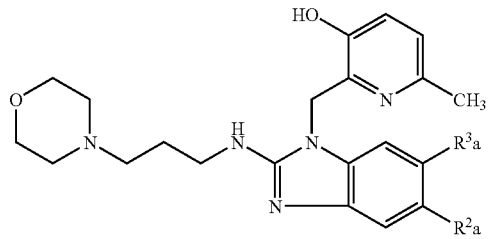
| Comp. No. | R²a | R³a | Activity | Mass (MH+) | Melting point/salt | Synthesis scheme |
|---|---|---|---|---|---|---|
| 24 | H | ![3-CF3, 2-NHEt phenyl with CH2CH2C(O)NH2] | | 626 | 185° C. | K |
| 25 | H | ![2-NHEt, 6-CH3 phenyl with CH2CH2OH] | 8.9 | 545 | 208° C. | K |
| 26 | H | ![3-Br, NHEt phenyl] | 8.7 | 565 | 205° C. | K |
| 27 | H | ![2-NHEt phenyl with CN] | 8.7 | 512 | 217° C. | K |
| 28 | H | ![3-CH3, NHEt phenyl] | 8.6 | 501 | 195° C. | K |
| 29 | H | ![2-NHEt phenyl with CH2OH] | 8.6 | 517 | 130° C. | K |

TABLE 1-continued

| Comp. No. | R²a | R³a | Activity | Mass (MH+) | Melting point/salt | Synthesis scheme |
|---|---|---|---|---|---|---|
| 30 | H | (3-ethynyl-N-ethylanilino) | 8.6 | 511 | 186° C. | J |
| 31 | H | (3-chloro-N-ethylanilino) | 8.6 | 522 | 212° C. | J |
| 32 | H | (2-ethylamino-5-methyl-benzyl alcohol) | 8.6 | 531 | 131° C. | K |
| 33 | H | (2-ethylamino-phenyl propanamide) | 8.6 | 558 | 164° C. | K |
| 34 | H | (substituted aniline with propargyl alcohol) | 8.6 | 555 | 225° C. | L |
| 35 | H | (3-fluoro-N-ethylanilino) | 8.5 | 505 | 210° C. | J |

TABLE 1-continued
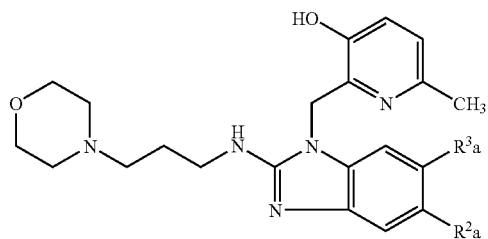
| Comp. No. | R²a | R³a | Activity | Mass (MH+) | Melting point/salt | Synthesis scheme |
|---|---|---|---|---|---|---|
| 36 | H | | 8.5 | 571 | 163° C. | K |
| 37 | H | | 8.5 | 566 | >260° C. | K |
| 38 | H | | 8.5 | 530 | 175° C. | K |
| 39 | H | | 8.5 | 560 | | K |
| 40 | H | | 8.4 | 515 | 209° C. | K |
| 41 | H | | 8.3 | 515 | 210° C. | K |

TABLE 1-continued
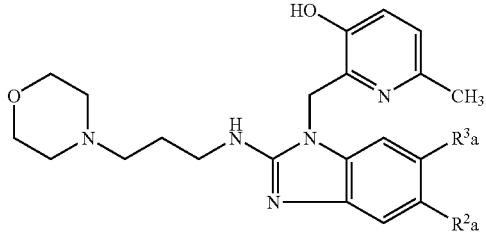
| Comp. No. | R²a | R³a | Activity | Mass (MH+) | Melting point/salt | Synthesis scheme |
|---|---|---|---|---|---|---|
| 42 | H | 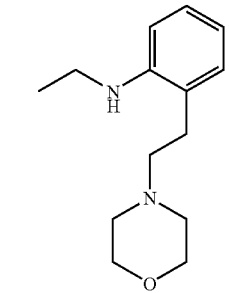 | 8.3 | 600 | 132° C. | K |
| 43 | H | 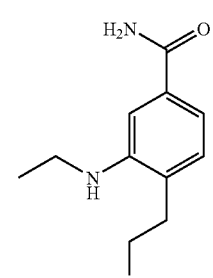 | 8.2 | 531 | 231° C. | K |
| 44 | H | 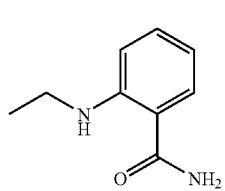 | 8.1 | 574 | | K |
| 45 | H | 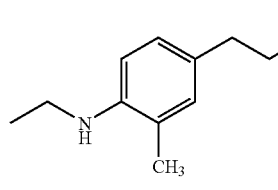 | 7.9 | 530 | 145° C. | K |
| 46 | H | 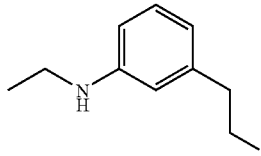 | 7.9 | 552 | 150° C. | K |
| 47 | H |  | 7.9 | 531 | 158° C. | K |

TABLE 1-continued

[Core structure: 1-[(3-hydroxy-6-methylpyridin-2-yl)methyl]-2-[(3-morpholinopropyl)amino]-benzimidazole with R²a and R³a substituents on the benzimidazole ring]

| Comp. No. | R²a | R³a | Activity | Mass (MH+) | Melting point/salt | Synthesis scheme |
|---|---|---|---|---|---|---|
| 48 | H | —CH₂—NH—(2-(2-hydroxyethyl)-5-methanesulfonyl-phenyl) | 7.7 | 609 | | K |
| 49 | H | 3,5-dimethyl-4-(ethylamino)phenyl-CH₂CH₂CN | 7.4 | 568 | 114° C. | M |
| 50 | H | —CH₂—NH—(2-iodo-5-methyl-phenyl) | 7.3 | 627 | 225° C. | K |
| 51 | ethylamino-3,5-dimethylphenyl | H | 7.2 | 515 | 176° C. | J |
| 52 | H | —CH₂—OH | 7.2 | 412 | 192° C. | A |
| 53 | —CH₂—OH | H | 5.6 | 412 | 134° C. | A |
| 54 | H | 3-ethylamino-4-(2-hydroxyethyl)-5-(thiophen-3-yl)phenyl |  | 613 | 194° C. | K |

TABLE 1-continued
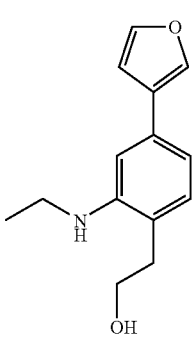
| Comp. No. | R²a | R³a | Activity | Mass (MH+) | Melting point/salt | Synthesis scheme |
|---|---|---|---|---|---|---|
| 55 | H | 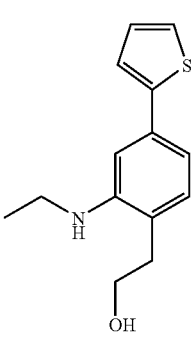 | | 597 | 228° C. | K |
| 56 | H | 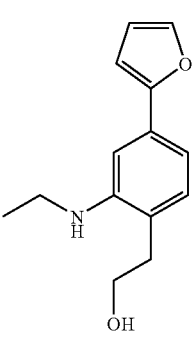 | | 613 | 220° C. | K |
| 57 | H |  | | 597 | 230° C. | K |

TABLE 2 compounds prepared according to synthesis scheme N or O

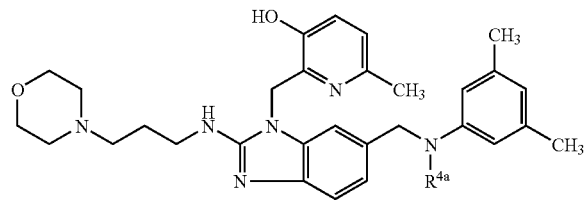

| Comp. No. | R⁴ᵃ | Activity | Mass (MH+) | Melting point/ salt |
|---|---|---|---|---|
| 58 | —(CH₂)₂—OH | 9.4 | 559 | 180° C. |
| 59 | pentanamide | 9.6 | 600 | 170° C. |
| 60 | butanamide | 9.5 | 586 | 138° C. |
| 61 | —(CH₂)₄—OH | 9.5 | 587 | 170° C. |
| 62 | pentanoic acid | 9.4 | 601 | 121° C. |
| 63 | —(CH₂)₃—OH | 9.3 | 573 | 137° C. |
| 64 | —(CH₂)₅—OH | 9.3 | 601 | 120° C. |
| 65 | propyl-morpholine | 9 | 628 | 169° C. |
| 66 | —(CH₂)₂—NH₂ | 8.9 | 558 | 196° C. |
| 67 | propyl diethyl phosphate | 8.8 | 695 | 152° C. |
| 68 | butyl-morpholine | 8.7 | 642 | 169° C. |
| 69 | —(CH₂)₂—COOH | 8.7 | 587 | 128° C. |
| 70 | propyl diethyl phosphonate | 8.6 | 679 | 175° C. |
| 71 | ethyl butanoate | 8.6 | 629 | 130° C. |

TABLE 2-continued compounds prepared according to synthesis scheme N or O

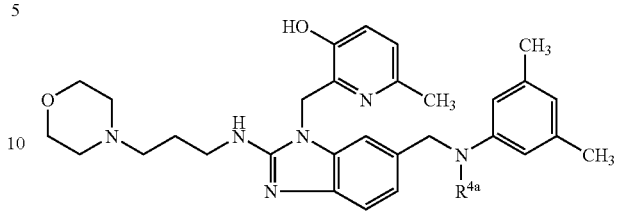

| Comp. No. | R⁴ᵃ | Activity | Mass (MH+) | Melting point/ salt |
|---|---|---|---|---|
| 72 | ethyl pentanoate | 8.5 | 615 | 136° C. |
| 73 | butanesulfonamide | 9.6 | 636 | 136° C. |
| 74 | pentanesulfonamide | 9.5 | 650 | 105° C. |
| 75 | hexanamide | 9.5 | 614 | 190° C. |
| 76 | N-methyl butanesulfonamide | 9.4 | 650 | 120° C. |
| 77 | N-methyl pentanamide | 9.4 | 614 | 150° C. |
| 78 | hydroxy-isopropyl | 9.2 | 601 | 205° C. |
| 79 | propyl-O-ethyl-OH | 9.1 | 603 | 152° C. |
| 80 | hydroxy-phenoxy-butyl | 9.1 | 665 | 120° C. |
| 81 | ethyl-imidazole | 8.9 | 595 | 135° C. |
| 82 | —(CH₂)₂—OCH₃ | 8.6 | 573 | 215° C. |

TABLE 2-continued compounds prepared according to synthesis scheme N or O

| Comp. No. | R⁴ᵃ | Activity | Mass (MH+) | Melting point/salt |
|---|---|---|---|---|
| 83 | (OH, benzyl, ethyl group) | 8.6 | 649 | 168° C./HCl |
| 84 | (OH, tert-butyl group) | 8.5 | 615 | 230° C. |

TABLE 3 compounds prepared according to synthesis scheme N or O

| Comp No. | R⁴ᵃ | Rᵃ | Activity | Mass (MH+) | Melting point/salt |
|---|---|---|---|---|---|
| 85 | —(CH₂)₂—OH | 3-Br | 9.3 | 609 | 210° C. |
| 86 | —(CH₂)₂—OH | 5-CH₃ | 9.3 | 545 | 205° C. |
| 87 | (butyramide) | 3-CH₃ | 9.2 | 586 | 139° C. |
| 88 | —(CH₂)₂—OH | 4-CN | 9.1 | 556 | 195° C. |
| 89 | (propanamide) | 3-CH₃ | 9 | 572 | 128° C. |
| 90 | (butyramide) | 5-Br | 9 | 650 | 180° C. |
| 91 | (butanesulfonamide) | 5-CH₃ | 8.9 | 636 | 140° C. |
| 92 | —(CH₂)₄—OH | 3-CH₃ | 8.8 | 573 | 169° C. |
| 93 | —(CH₂)₃—OH | 3-CH₃ | 8.7 | 559 | 109° C. |
| 94 | (propyl morpholine) | 3-CH₃ | 8.6 | 614 | 153° C. |

TABLE 3-continued compounds prepared according to synthesis scheme N or O

| Comp No. | R$^{4a}$ | R$^a$ | Activity | Mass (MH+) | Melting point/salt |
|---|---|---|---|---|---|
| 95 | —(CH$_2$)$_3$—OH | 5-Br | 8.6 | 623 | 120° C. |
| 96 | CH$_3$CH$_2$CH$_2$CH$_2$—C(=O)—NH$_2$ | 4-CN | 8.6 | 597 | 170° C. |
| 97 | —(CH$_2$)$_2$—OH | H | 8.5 | 531 | 190° C. |
| 98 | CH$_3$CH$_2$CH$_2$—S(=O)$_2$—NH—CH$_3$ | 5-CH$_3$ | 8.5 | 636 | 125° C. |
| 99 | —(CH$_2$)$_2$—OH | 3-[—C≡CH] | 8.5 | 555 | 186° C. |
| 100 | —(CH$_2$)$_2$—N(CH$_3$)$_2$ | 3-CH$_3$ | 8.4 | 572 | 172° C. |
| 101 | CH$_3$CH$_2$—C(=O)—NH$_2$ | 2-[—(CH$_2$)$_2$—OH] | 8.3 | 588 | 175° C. |
| 102 | CH$_3$CH$_2$CH$_2$—C(=O)—O—CH$_3$ | 3-CH$_3$ | 8.3 | 601 | 150° C. |
| 103 | propyl-morpholine | 6-[—(CH$_2$)$_2$—OH] | 8.2 | 644 | 146° C. |
| 104 | CH$_3$CH$_2$CH$_2$—C(=O)—NH$_2$ | 3-[—(CH$_2$)$_2$—OH] | 8.2 | 602 | 124° C. |
| 105 | —(CH$_2$)$_2$—OH | 4-[—C(=O)—NH$_2$] | 8.2 | 574 | 130° C. |
| 106 | phenyl | 4-OH | 8.1 | 579 | 175° C. |
| 107 | —(CH$_2$)$_2$—OH | 6-[—(CH$_2$)$_2$—OH] | 8.1 | 575 | 165° C. |
| 108 | H | 6-[—CH$_2$—NH$_2$] | 8 | 516 | 116° C. |
| 109 | phenyl | 3-OH | 7.9 | 579 | 135° C. |
| 110 | —(CH$_2$)$_2$—OH | 6-CH$_3$ | 7.8 | 545 | 165° C. |
| 111 | —(CH$_2$)$_2$—OH | 2-[—C(=O)—NH$_2$] | 7.6 | 574 | 145° C. |
| 112 | CH$_3$CH$_2$CH$_2$—S(=O)$_2$—NH$_2$ | 5-[—C≡CH] | 9.5 | 632 | 142° C. |

TABLE 3-continued
compounds prepared according to synthesis scheme N or O
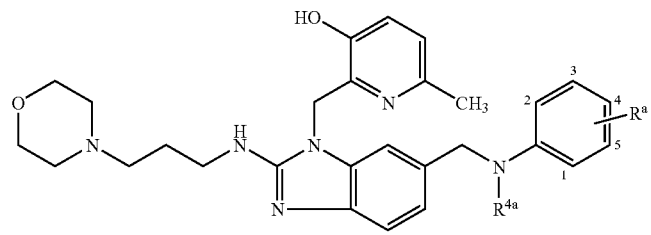
| Comp No. | R^4a | R^a | Activity | Mass (MH+) | Melting point/salt |
|---|---|---|---|---|---|
| 113 | ~~~C(=O)NH₂ (propyl-C(O)NH₂) | 5-Br | 9.3 | 636 | 140° C. |
| 114 | ~~~~C(=O)NH₂ (butyl-C(O)NH₂) | 5-[—C≡CH] | 9.3 | 596 | 162° C. |
| 115 | ~~~C(=O)NH₂ | 5-[—C≡CH] | 9.3 | 582 | 147° C. |
| 116 | ~~~C(=O)OH | 5-[—C≡CH] | 8.7 | 597 | 134° C. |
| 117 | ~~~~OH | 5-Br | 8.6 | 637 | 160° C. |
| 118 | ~~~C(=O)NH₂ | 4-CN | 8.6 | 583 | 195° C. |
| 119 | ~~~OH | 4-CN | 8.6 | 570 | 115° C. |
| 120 | ~~OH | 4-[S(=O)₂NH₂] | 8.5 | 610 | 135° C. |
| 121 | ~~OH | 5-F | 8.3 | 549 | 195° C. |
| 122 | CH₃ | 6-[—(CH₂)₂—OH] | 7.5 | 555 | 175° C. |

TABLE 4 compounds prepared according to synthesis scheme N or O

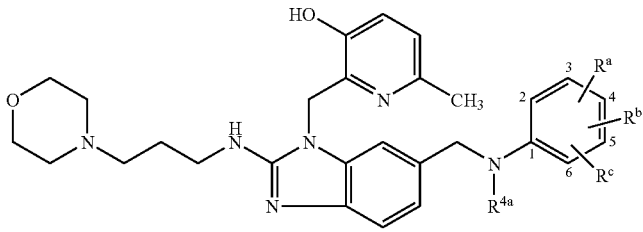

| Comp. No. | R4a | Ra | Rb | Rc | Activity | Mass (MH+) | Melting point/salt |
|---|---|---|---|---|---|---|---|
| 123 | ~~~C(O)NH2 | 3-Cl | H | 5-Cl | 9.6 | 640 | 185° C. |
| 124 | ~~~OH | 3-Cl | H | 5-Cl | 9.3 | 627 | 202° C. |
| 125 | ~~C(O)NH2 | 3-CH$_3$ | H | 6-CH$_3$ | 7.9 | 586 | 165° C. |
| 126 | ~~~C(O)NH2 | 2-CH$_3$ | H | 5-CH(CH$_3$)$_2$ | 7.8 | 628 | 170° C./HCl |
| 127 | ~~~C(O)NH2 | 2-CH$_3$ | 3-CH$_3$ | 5-CH$_3$ | 7.6 | 614 | 116° C. |
| 128 | ~~OH | 3-CH$_3$ | H | 6-CH$_3$ | 7.6 | 559 | 172° C. |
| 129 | ~~OH | 2-CH$_3$ | H | 5-CH(CH$_3$)$_2$ | 6.9 | 587 | 143° C. |
| 130 | ~~OH | 2-CH$_3$ | 3-CH$_3$ | 5-CH$_3$ | 6.9 | 573 | 199° C. |

TABLE 5 compounds prepared according to synthesis scheme N or O

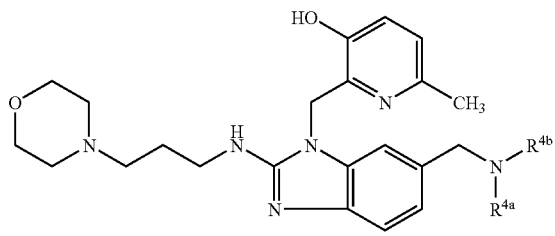

| Comp. No. | R4a | R4b | Activity | Mass (MH+) | Melting point/salt |
|---|---|---|---|---|---|
| 131 | ~~~C(O)NH2 | 3-methylquinoline | 9.3 | 623 | 168° C. |

TABLE 5-continued compounds prepared according to synthesis scheme N or O

[Structure: morpholine-propyl-NH connected to benzimidazole with N-CH2-(3-hydroxy-6-methylpyridin-2-yl) and CH2-N(R4a)(R4b) substituent]

| Comp. No. | R4a | R4b | Activity | Mass (MH+) | Melting point/salt |
|---|---|---|---|---|---|
| 132 | propyl-OH | 3-quinolinyl | 8.2 | 582 | 175° C. |
| 133 | butyl-C(O)NH2 | 2-methylpyrimidin-yl | 8.1 | 574 | 215° C. |
| 134 | propyl-OH | 2-methylpyrimidin-yl | 7.9 | 533 | 150° C. |
| 135 | butyl-C(O)NH2 | 1-ethyl-pyrazol-5-yl | 7.8 | 590 | 129° C. |
| 136 | propyl-OH | 1-ethyl-pyrazol-5-yl | 7.5 | 549 | 105° C. |
| 137 | butyl-C(O)NH2 | 3-methylpyridin-yl | 7.3 | 573 | 185° C. |
| 138 | propyl-OH | 5-methylisoxazol-3-yl | 7.3 | 536 | 230° C. |

TABLE 6 compounds prepared according to synthesis scheme N

| Comp. No. | R$^{6a}$ | R$^a$ | R$^b$ | Activity | Mass (MH+) | Melting point/salt |
|---|---|---|---|---|---|---|
| 139 | ethyl pentanoate | 2-CH$_3$ | 6-CH$_3$ | 7.6 | 629 | 164° C. |
| 140 | propyl-OH | 3-CH$_3$ | H | 8.1 | 545 | 190° C. |
| 141 | propyl-OH | 3-OCH$_3$ | H | 8.1 | 561 | 170° C. |
| 142 | pentyl-OH | 6-CH$_3$ | H | 8.1 | 573 | |
| 143 | propyl-OH | 2-CH$_3$ | 6-CH$_3$ | 8 | 559 | 162° C. |
| 144 | propyl-morpholine | 2-CH$_3$ | 6-CH$_3$ | 7.9 | 628 | 158° C. |
| 145 | CH(CH$_3$)CH$_2$N(CH$_3$)$_2$ | 2-CH$_3$ | 6-CH$_3$ | 7.9 | 586 | 140° C. |
| 146 | propyl-OH | 3-[OC(O)OCH$_2$CH$_3$] | H | 7.9 | 603 | 150° C. |
| 147 | butyl-OH | 2-CH$_3$ | 6-CH$_3$ | 7.8 | 587 | 156° C./ HCl |
| 148 | butyl-SO$_2$NH$_2$ | 2-CH$_3$ | 6-CH$_3$ | 8.4 | 636 | 171° C./ HCl |
| 149 | CH(CH$_3$)CH(Et)CH$_2$OH | 2-CH$_3$ | 6-CH$_3$ | 7.9 | 187° C. | 187° C./ HCl |

TABLE 6-continued compounds prepared according to synthesis scheme N

| Comp. No. | R6a | Rᵃ | Rᵇ | Activity | Mass (MH+) | Melting point/salt |
|---|---|---|---|---|---|---|
| 150 | (propanamide, -CH2CH2C(O)NH2) | 3-CH3 | 6-CH3 | 7.9 | 586 | 175° C. |
| 151 | (propanol, -CH2CH2CH2OH) | 3-CH3 | 6-CH3 | 7.7 | 559 | 210° C. |

Compound prepared according to scheme N:

| Comp. No. | Activity | Mass (MH+) | Melting point/salt |
|---|---|---|---|
| 152 | 8.1 | 549 | 168° C. |

Compound prepared according to scheme N:

| Comp. No. | Activity | Mass (MH+) | Melting point/salt |
|---|---|---|---|
| 153 | 7.3 | 527 | 212° C. |

TABLE 7 compounds prepared according to synthesis scheme P

| Comp. No. | R3b | R2a | R3a | R2b | Activity | Mass (MH+) | Melting point/salt |
|---|---|---|---|---|---|---|---|
| 154 | —CH3 | H | —CH3 | H | 6.9 | 410 | 228° C. |
| 155 | H | H | H | H | 6.8 | 382 | 203° C. |
| 156 | H | —CH3 | H | —CH3 | 4.9 | 410 | 234° C. |

TABLE 8
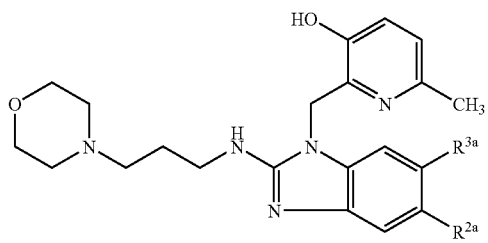
| Comp. No. | R²ᵃ | R³ᵃ | Activity | Mass (MH+) | Melting point/salt |
|---|---|---|---|---|---|
| 157 | H | 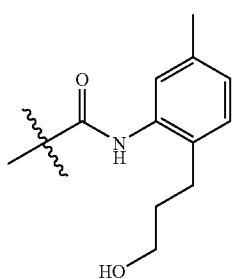 | 6.3 | 576 | 186° C. |
| 158 | 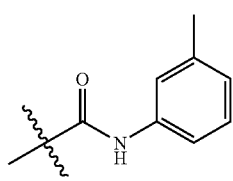 | H | <4 | 515 | 170° C. |
| 159 | H | 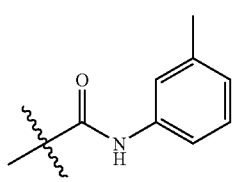 | 4.7 | 515 | 168° C. |
| 160 | H | 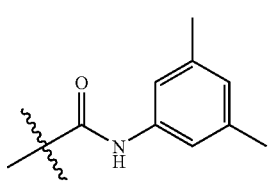 | <5 | 529 | 172° C. |

TABLE 9

[Structure: Core scaffold with morpholine-N-(CH2)n-piperidine-NH-benzimidazole substituted with R2a, R2b, R3a, R3b, with N-CH2-(3-hydroxy-6-methylpyridin-2-yl) group]

| Comp. No. | n | R3b | R2a | R3a | R2b | Activity | Mass (MH+) | Melting point/salt | Synthesis scheme |
|---|---|---|---|---|---|---|---|---|---|
| 161 | 3 | —CH₃ | H | —CH₃ | H | 8.6 | 493 | 223° C. | R |
| 162 | 2 | —CH₃ | H | —CH₃ | H | 7.9 | 479 | 226° C. | Q |
| 163 | 2 | H | H | N-ethyl-3,5-dimethylanilino | H | 7.9 | 584 | 150° C. | S |
| 164 | 2 | H | H | N-ethyl-3-methylanilino | H | 7.5 | 570 | 130° C. | S |
| 165 | 2 | H | H | n-propylphenyl | H | 6.9 | 555 | 159° C. | T |
| 166 | 2 | —CH₃ | H | H | H | 6.8 | 465 | 238° C. | Q |
| 167 | 2 | H | (E)-styryl | H | H | 6.7 | 553 | 225° C. | T |
| 168 | 2 | H | H | —CH₂—OH | H | 6.5 | 481 | 147° C. | S |
| 169 | 2 | H | H | (E)-styryl | H | 6.2 | 553 | 224° C. | T |
| 170 | 2 | H | —CH₃ | H | —CH₃ | 6.1 | 479 | 237° C. | Q |

TABLE 10
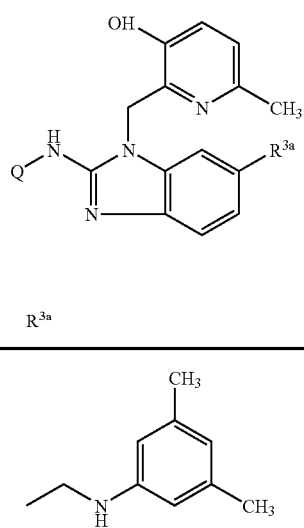
| Comp. No. | Q | R³ᵃ | Activity | Mass (MH+) | Melting point/salt | Synthesis scheme |
|---|---|---|---|---|---|---|
| 171 | 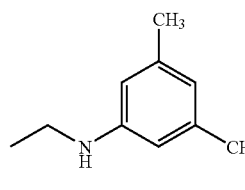 | 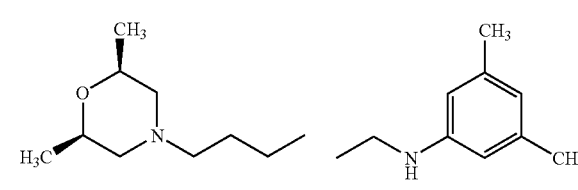 | 8.6 | 531 | 198° C. | V |
| 172 | 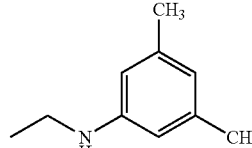 | 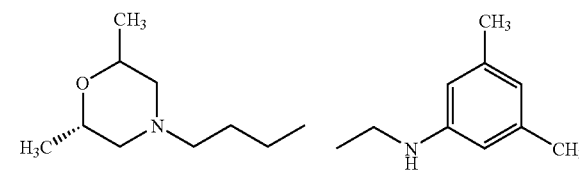 | 7.8 | 543 | 192° C. | U |
| 173 | 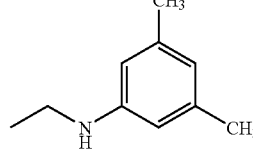 | 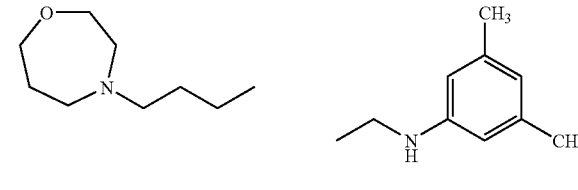 | 7.7 | 543 | 169° C. | U |
| 174 | 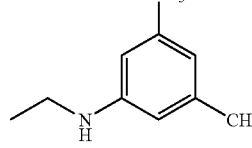 | 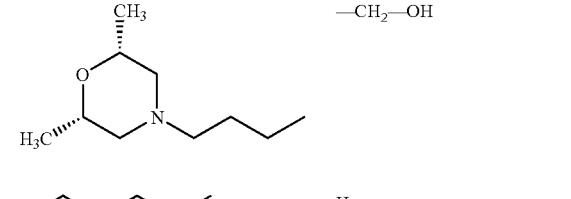 | 8.6 | 529 | — | W |
| 175 |  | —CH₂—OH | 6.2 | 440 | 199° C. | U |
| 176 | 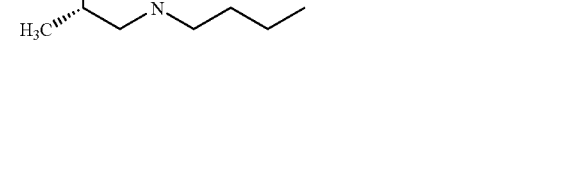 | H | 5.7 | 410 | 205° C. | P |
| 177 |  | —CH₂—OH | 5.7 | 440 | 202° C. | U |

TABLE 10-continued
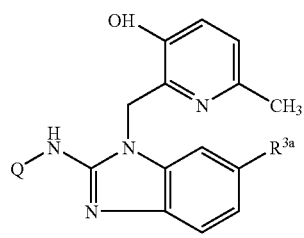
| Comp. No. | Q | R³ᵃ | Activity | Mass (MH+) | Melting point/salt | Synthesis scheme |
|---|---|---|---|---|---|---|
| 178 | 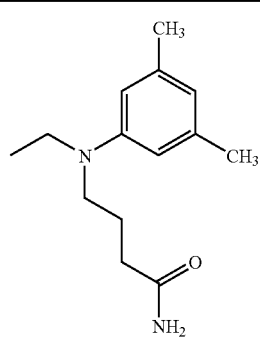 | 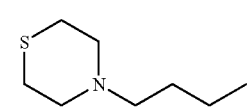 | 9.6 | 750 | 164° C./ HCl | Z |
| 179 | 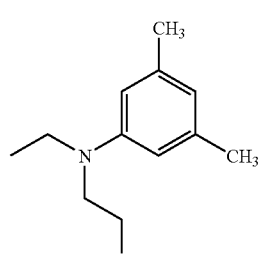 | 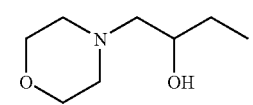 | 9.6 | 561 | 210° C. | N |
| 180 | 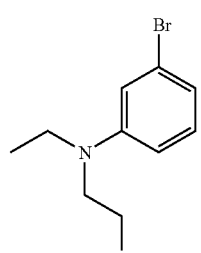 | 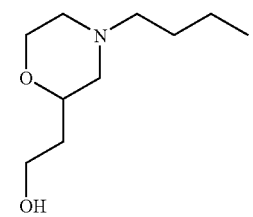 | 9.3 | 625 | 156° C./ HCl | Z |
| 181 | 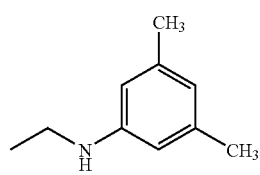 | 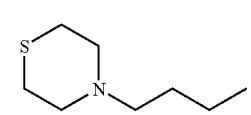 | 8.2 | 559 | — | X |
| 182 |  | —CH₂—OH | 7.1 | 428 | 212° C. | A |

TABLE 11

| Comp. No. | Q | R²ᵃ | Activity | Mass (MH+) | Melting point/salt | Synthesis scheme |
|---|---|---|---|---|---|---|
| 183 | (1,4-oxazepane-N-butyl) | 3,5-dimethyl-N-ethylaniline | 6.7 | 529 | 198° C. | W |
| 184 | (2,6-dimethylmorpholine-N-butyl) | 3,5-dimethyl-N-ethylaniline | 6.3 | 543 | 209° C. | U |
| 185 | (2,6-dimethylmorpholine-N-butyl) | 3,5-dimethyl-N-ethylaniline | 7.7 | 543 | 169° C. | U |
| 186 | (2,6-dimethylmorpholine-N-butyl) | —CH₂—OH | 4.9 | 440 | 212 | U |
| 187 | (2,6-dimethylmorpholine-N-butyl) | —CH₂—OH | <4 | 440 | 227° C. | U |
| 188 | (2-(2-hydroxyethyl)morpholine-N-butyl) | —CH₂—OH | <4 | 456 | 210° C. | X |
| 189 | (thiomorpholine-N-butyl) | —CH₂—OH | <4 | 428 | 165° C. | A |

TABLE 12
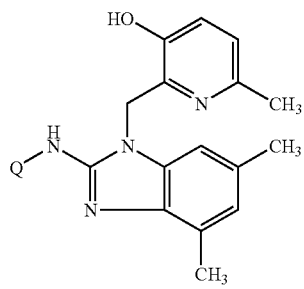
| Comp. No. | Q | Activity | Mass (MH+) | Melting point/salt | Synthesis scheme |
|---|---|---|---|---|---|
| 190 | (morpholine with butyl-CH2CH2OH chain) | 6.9 | 454 | 168° C. | Y |
| 191 | (morpholine with butyl-CH2C(O)NH2 chain) | 6.8 | 467 | 148° C. | Y |
TABLE 13
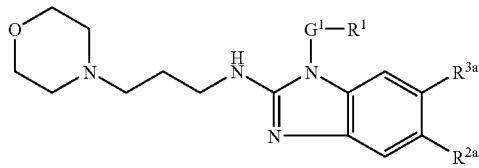
| Comp. No. | G¹—R¹ | $R^{2a}$ | $R^{3a}$ | Activity | Mass (MH+) | Melting point/salt | Synthesis scheme |
|---|---|---|---|---|---|---|---|
| 192 | HO-pyridine-ethyl | H | methyl-phenyl-NH- with CH2CH2OH | 9.3 | 531 | 192° C. | AC |
| 193 | tetrahydroquinoxaline-dimethyl | H | methyl-phenyl-NH- with CH2CH2OH | 9.3 | 584 | 162° C. | AA |

TABLE 13-continued

| Comp. No. | G¹—R¹ | R²ᵃ | R³ᵃ | Activity | Mass (MH+) | Melting point/salt | Synthesis scheme |
|---|---|---|---|---|---|---|---|
| 194 | tetrahydroquinoxaline-methyl | H | 2-(ethylamino)phenyl-propan-1-ol | 9.3 | 584 | — | AA |
| 195 | tetrahydroquinoxaline-methyl | H | 2-(amino)-3-methylphenyl-ethan-1-ol | 9.3 | 584 | — | AA |
| 196 | tetrahydroquinoxaline-methyl | H | 2-amino-5-methyl-benzyl alcohol | 9.3 | 570 | — | AA |
| 197 | tetrahydroquinoxaline-methyl | H | 2,5-dimethylaniline | 9.3 | 554 | 198° C. | AA |
| 198 | tetrahydroquinoxaline-methyl | H | 2-amino-5-methylbenzyl alcohol | 9.3 | 570 | — | AA |
| 199 | tetrahydroquinoxaline-methyl | H | 2-(ethylamino)benzamide | 9.3 | 569 | — | AA |

TABLE 13-continued

| Comp. No. | G¹—R¹ | R²ᵃ | R³ᵃ | Activity | Mass (MH+) | Melting point/salt | Synthesis scheme |
|---|---|---|---|---|---|---|---|
| 200 | (5,6,7,8-tetrahydroquinoxaline-2,3-dimethyl) | H | 2-(ethylamino)phenyl-CH₂CH₂C(O)NH₂ | 9.3 | 597 | 153° C. | AA |
| 201 | 4-bromo-2-ethylphenol | H | N-methyl-[2-(3-hydroxypropyl)-4-methylphenyl]amino | 9.3 | 622 | 134° C. | AM |
| 202 | 3-hydroxy-2-ethylpyridine | H | 3-(ethylamino)-4-(2-hydroxyethyl)benzonitrile | 9.3 | 542 | 208° C. | AC |
| 203 | 4-bromo-2-ethylphenol | H | 3-(ethylamino)-4-(2-hydroxyethyl)benzonitrile | 9.3 | 619 | 212° C. | AM |
| 204 | (5,6,7,8-tetrahydroquinoxaline-2,3-dimethyl) | H | 2-(ethylamino)phenyl-CH₂OH | 9.2 | 556 | — | AA |

TABLE 13-continued

| Comp. No. | G¹—R¹ | R²ª | R³ª | Activity | Mass (MH+) | Melting point/salt | Synthesis scheme |
|---|---|---|---|---|---|---|---|
| 205 | tetrahydroquinoxaline-methyl | H | 4-(ethylamino)benzamide | 9.2 | 569 | — | AA |
| 206 | 3-hydroxy-2-ethylpyridine | H | 4-ethynyl-2-(ethylamino)phenethyl alcohol | 9.2 | 541 | 211° C. | AC |
| 207 | tetrahydroquinoxaline-methyl | H | substituted aminophenyl propanol | 9.1 | 598 | 130° C. | AA |
| 208 | tetrahydroquinoxaline-methyl | H | 3,5-dimethylanilino-methyl | 9.1 | 554 | — | AA |
| 209 | tetrahydroquinoxaline-methyl | H | 4-(ethylamino)benzenesulfonamide | 9.1 | 605 | 165° C. | AA |
| 210 | 3-oxy-2-methyl-6-methylpyridine | H | N-(3,5-dimethylphenyl)-N-(butanamide) | 9 | 614 | 130° C. | AL |

TABLE 13-continued
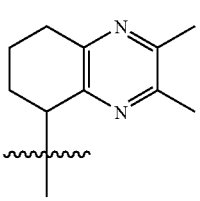
| Comp. No. | G¹—R¹ | R²ᵃ | R³ᵃ | Activity | Mass (MH+) | Melting point/salt | Synthesis scheme |
|---|---|---|---|---|---|---|---|
| 211 | 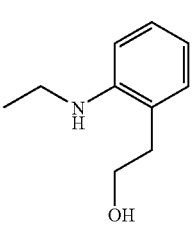 | H | 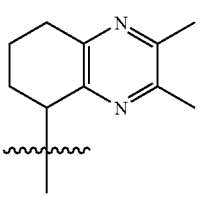 | 9 | 570 | 205° C. | AA |
| 212 | 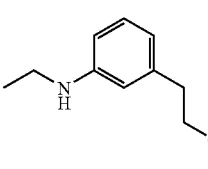 | H | 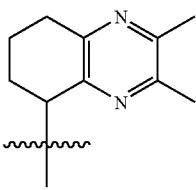 | 9 | 570 | — | AA |
| 213 | 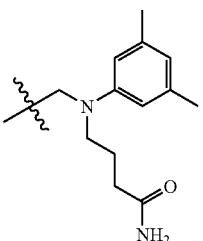 | H | 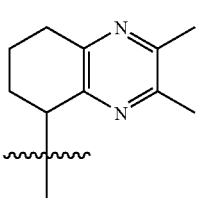 | 8.8 | 639 | 109° C. | AB |
| 214 | 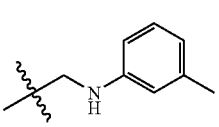 | H | 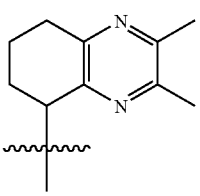 | 8.8 | 540 | — | AA |
| 215 | 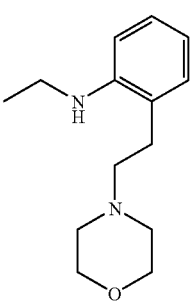 | H |  | 8.7 | 639 | — | AA |

TABLE 13-continued

| Comp. No. | G¹—R¹ | R²ᵃ | R³ᵃ | Activity | Mass (MH+) | Melting point/salt | Synthesis scheme |
|---|---|---|---|---|---|---|---|
| 216 | HO-pyridine-ethyl | H | CF₃-phenyl-NHEt-propanol | 8.7 | 599 | 216° C. | AC |
| 217 | HO-phenyl-Br-ethyl | H | CF₃-phenyl-NHEt-propanol | 8.7 | 676 | 149° C. | AM |
| 218 | N-methylbenzimidazole-CH₂ | H | methyl-phenyl-NH-CH-propanol | 8.6 | 582 | 198° C. | AI |
| 219 | methoxy-methylpyridine-CH₂ | H | methyl-phenyl-NH-CH-propanol | 8.6 | 573 | 132° C. | AK |
| 220 | methoxy-methylpyridine-CH₂ | H | methyl-phenyl-NH-CH-ethanol | 8.6 | 559 | — | AK |

TABLE 13-continued

| Comp. No. | G¹—R¹ | R²ᵃ | R³ᵃ | Activity | Mass (MH+) | Melting point/salt | Synthesis scheme |
|---|---|---|---|---|---|---|---|
| 221 | 2,3-dimethyl-5,6,7,8-tetrahydroquinoxalin-5-yl-methyl | H | N-ethyl-3-bromoanilino | 8.6 | 604 | — | AA |
| 222 | 2,3-dimethyl-5,6,7,8-tetrahydroquinoxalin-5-yl-methyl | H | N-ethyl-4-(3-hydroxypropyl)-5-trifluoromethylanilino | 8.6 | 652 | 147° C. | AA |
| 223 | 8-ethylquinolin-5-yl | H | N-(3,5-dimethylphenyl)-N-(3-carbamoylpropyl)amino-methyl | 8.5 | 620 | 154° C. | AO |
| 224 | (1-methylbenzimidazol-4-yl)methyl | H | N-ethyl-2-(3-hydroxypropyl)anilino | 8.5 | 568 | — | AI |
| 225 | 2,3-dimethyl-5,6,7,8-tetrahydroquinoxalin-5-yl-methyl | H | N-ethyl-3,5-dichloroanilino | 8.5 | 594 | — | AA |
| 226 | 2,3-dimethyl-5,6,7,8-tetrahydroquinoxalin-5-yl-methyl | H | N-ethyl-3-ethynylanilino | 8.5 | 550 | — | AA |

TABLE 13-continued
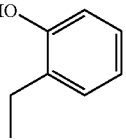
| Comp. No. | G¹—R¹ | R²ᵃ | R³ᵃ | Activity | Mass (MH+) | Melting point/salt | Synthesis scheme |
|---|---|---|---|---|---|---|---|
| 227 | 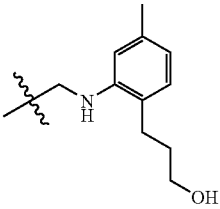 | H | 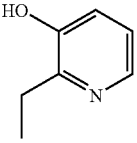 | 8.5 | 544 | 203° C. | AM |
| 228 | 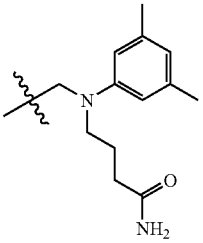 | H | 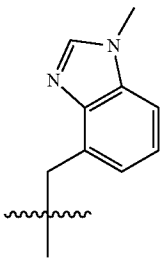 | 8.4 | 568 | 170° C. | AC |
| 229 | 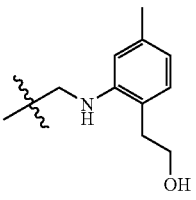 | H | 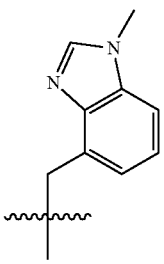 | 8.4 | 568 | 193° C. | AI |
| 230 | 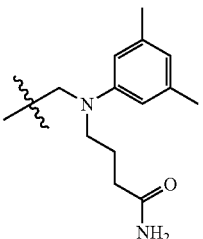 | H | 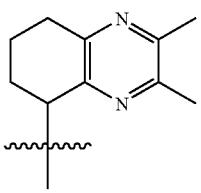 | 8.4 | 623 | 206° C. | AJ |
| 231 | 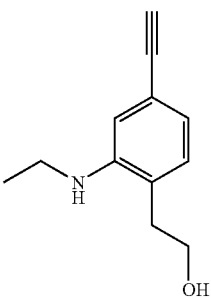 | H | | 8.4 | 594 | 220° C. | AA |

TABLE 13-continued

| Comp. No. | G¹—R¹ | R²ᵃ | R³ᵃ | Activity | Mass (MH+) | Melting point/salt | Synthesis scheme |
|---|---|---|---|---|---|---|---|
| 232 | 1-methylbenzimidazol-4-ylmethyl | H | 4-bromo-2-(ethylamino)-phenyl with propanol | 8.4 | 646 | 138° C. | AI |
| 233 | (3,5,6-trimethylpyrazin-2-yl)methyl | H | N-(3,5-dimethylphenyl)-N-(2-hydroxyethyl)aminomethyl | 8.3 | 572 | 140° C. | AF |
| 234 | 8-ethylquinolinyl | H | 5-methyl-2-(ethylamino)phenyl with propanol, aminomethyl linker | 8.3 | 579 | 165° C. | AW |
| 235 | 8-ethylquinolinyl | H | 4-ethynyl-2-(ethylamino)phenyl with ethanol | 8.3 | 575 | 182° C. | AW |
| 236 | 1-methylbenzimidazol-4-ylmethyl | H | 4-ethynyl-2-(ethylamino)phenyl with ethanol | 8.1 | 578 | 187° C. | AI |

TABLE 13-continued

| Comp. No. | G¹—R¹ | R²ᵃ | R³ᵃ | Activity | Mass (MH+) | Melting point/salt | Synthesis scheme |
|---|---|---|---|---|---|---|---|
| 237 | 1-methylbenzimidazol-4-ylmethyl | H | 2-(ethylamino)phenyl-ethanol | 7.9 | 554 | — | AI |
| 238 | 1-methylbenzimidazol-4-ylmethyl | H | 2-(ethylamino)phenyl-propanamide | 7.9 | 581 | — | AI |
| 239 | (6-methyl-3-methoxypyridin-2-yl)methyl | H | 2-(ethylamino)phenyl-propanol | 7.9 | 559 | — | AK |
| 240 | (6-methyl-3-methoxypyridin-2-yl)methyl | H | N-(2-hydroxyethyl)-N-(3,5-dimethylphenyl) | 7.9 | 573 | 85° C. | AL |
| 241 | 1-methylbenzimidazol-4-ylmethyl | H | 4-CF₃-2-(ethylamino)phenyl-propanol | 7.9 | 636 | 149° C. | AI |

TABLE 13-continued
| Comp. No. | G¹—R¹ | R²ᵃ | R³ᵃ | Activity | Mass (MH+) | Melting point/salt | Synthesis scheme |
|---|---|---|---|---|---|---|---|
| 242 | 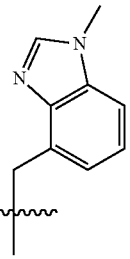 | H | 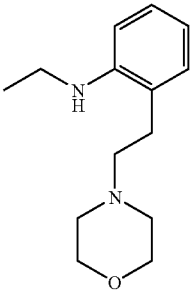 | 7.8 | 623 | — | AI |
| 243 | 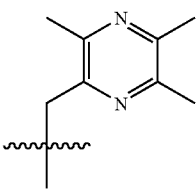 | H | 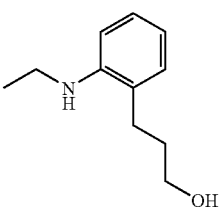 | 7.8 | 558 | — | AE |
| 244 | 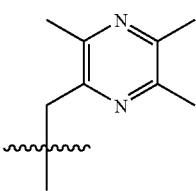 | H | 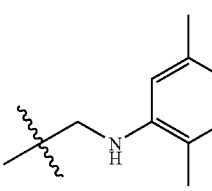 | 7.8 | 528 | — | AE |
| 245 | 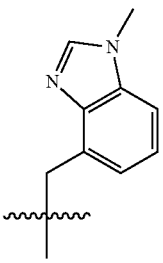 | H | 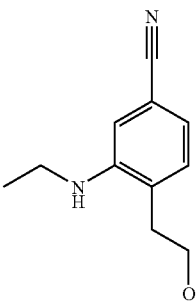 | 7.8 | 579 | 202° C. | AI |
| 246 | 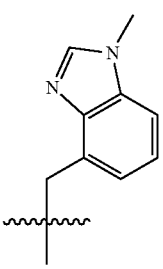 | H | 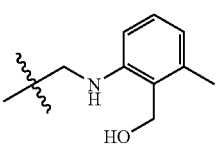 | 7.7 | 554 | — | AI |

TABLE 13-continued

| Comp. No. | G¹—R¹ | R²ª | R³ª | Activity | Mass (MH+) | Melting point/salt | Synthesis scheme |
|---|---|---|---|---|---|---|---|
| 247 | (1-methylbenzimidazol-4-ylmethyl) | H | (3-(2-hydroxyethyl)phenyl)ethylamino | 7.7 | 554 | — | AI |
| 248 | (3-methoxy-6-methylpyridin-2-ylmethyl) | H | (2-(2-hydroxyethyl)-3-methylphenyl)methylamino | 7.7 | 559 | — | AK |
| 249 | (6-methylpyridin-2-ylmethyl) | H | N-(3,5-dimethylphenyl)-3-carbamoylpropylamino | 7.7 | 584 | 77° C. | AG |
| 250 | (quinolin-8-ylethyl) | H | (2-(3-hydroxypropyl)-5-trifluoromethylphenyl)ethylamino | 7.7 | 633 | 200° C. | AW |
| 251 | (2,3-dimethyl-5,6,7,8-tetrahydroquinoxalin-5-ylmethyl) | (2-(2-carbamoylethyl)phenyl)ethylamino | H | 7.7 | 597 | — | AA |

TABLE 13-continued
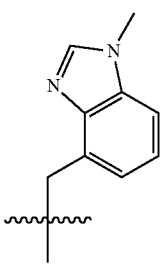
| Comp. No. | G¹—R¹ | R²ª | R³ª | Activity | Mass (MH+) | Melting point/salt | Synthesis scheme |
|---|---|---|---|---|---|---|---|
| 252 | 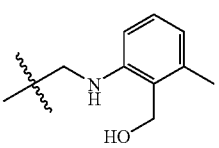 | H | 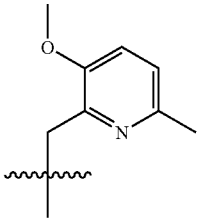 | 7.6 | 554 | — | AI |
| 253 | 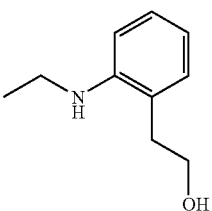 | H | 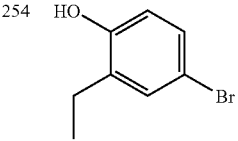 | 7.6 | 545 | — | AK |
| 254 | 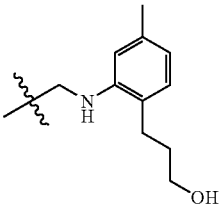 | 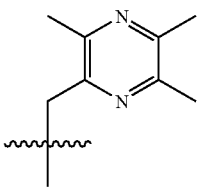 | H | 7.6 | 622 | 225° C. | AM |
| 255 | 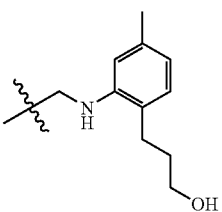 | H | 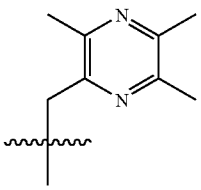 | 7.6 | 572 | 120° C. | AE |
| 256 | 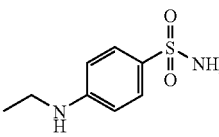 | H | 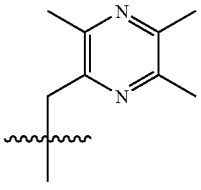 | 7.6 | 579 | — | AE |
| 257 | 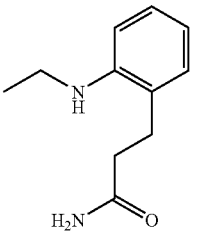 | H |  | 7.6 | 571 | — | AE |

TABLE 13-continued

| Comp. No. | G¹—R¹ | R²ᵃ | R³ᵃ | Activity | Mass (MH+) | Melting point/salt | Synthesis scheme |
|---|---|---|---|---|---|---|---|
| 258 | 1-methylbenzimidazol-4-ylmethyl | H | 2-(ethylamino)benzyl alcohol | 7.5 | 540 | — | AI |
| 259 | 1-methylbenzimidazol-4-ylmethyl | H | 4-(ethylamino)benzenesulfonamide | 7.5 | 589 | — | AI |
| 260 | 1-methylbenzimidazol-4-ylmethyl | H | (2,5-dimethylphenylamino)methyl | 7.5 | 538 | — | AI |
| 261 | 6-bromo-2-ethylpyridin-2-yl | H | N-(3,5-dimethylphenyl)-N-(carbamoylpropyl)aminomethyl | 7.5 | 648 | 82° C. | AH |
| 262 | 3-methoxy-6-methylpyridin-2-ylmethyl | H | (2,5-dimethylphenylamino)methyl | 7.5 | 529 | — | AK |

TABLE 13-continued

| Comp. No. | G¹—R¹ | R²ᵃ | R³ᵃ | Activity | Mass (MH+) | Melting point/salt | Synthesis scheme |
|---|---|---|---|---|---|---|---|
| 263 | trimethylpyrazinyl-CH₂- | H | 2-(ethylamino)phenyl-CH₂CH₂OH | 7.5 | 544 | — | AE |
| 264 | trimethylpyrazinyl-CH₂- | H | 2-(ethylamino)benzamide | 7.5 | 543 | — | AE |
| 265 | 3-methoxy-6-methylpyridin-2-yl-CH₂- | H | 2-(ethylamino)phenyl-CH₂CH₂C(O)NH₂ | 7.4 | 572 | — | AK |
| 266 | trimethylpyrazinyl-CH₂- | H | 3,5-dimethylphenyl-NH-CH₂- | 7.4 | 528 | — | AE |
| 267 | 6-bromo-2-ethylpyridin-2-yl | H | 4-methyl-2-(3-hydroxypropyl)phenyl-NH-CH₂- | 7.3 | 607 | 141° C. | AG |
| 268 | 3-methoxy-6-methylpyridin-2-yl-CH₂- | H | 2-(ethylamino)phenyl-CH₂CH₂-morpholinyl | 7.3 | 614 | — | AK |

TABLE 13-continued

| Comp. No. | G¹—R¹ | R²ª | R³ª | Activity | Mass (MH+) | Melting point/salt | Synthesis scheme |
|---|---|---|---|---|---|---|---|
| 269 | trimethylpyrazinyl-CH₂- | H | 3-bromophenyl-NH-CH₂- | 7.3 | 578 | — | AE |
| 270 | 1-methylbenzimidazol-4-yl-CH₂- | H | 3,5-dimethylphenyl-NH-CH₂- | 7.2 | 538 | — | AI |
| 271 | 3-methoxy-6-methylpyridin-2-yl-CH₂- | H | 3,5-dimethylphenyl-NH-CH₂- | 7.2 | 529 | — | AK |
| 272 | 3-methoxy-6-methylpyridin-2-yl-CH₂- | H | 4-sulfamoylphenyl-NH-CH₂- | 7.2 | 580 | — | AK |
| 273 | trimethylpyrazinyl-CH₂- | H | 2-(hydroxymethyl)phenyl-NH-CH₂- | 7.2 | 530 | — | AE |
| 274 | 6-methylpyridin-2-yl-CH₂- | H | 5-methyl-2-(3-hydroxypropyl)phenyl-NH-CH₂- | 7.2 | 543 | 143° C. | AG |

TABLE 13-continued

| Comp. No. | G¹—R¹ | R²ᵃ | R³ᵃ | Activity | Mass (MH+) | Melting point/salt | Synthesis scheme |
|---|---|---|---|---|---|---|---|
| 275 | 6-methylpyridin-2-ylmethyl | H | 2-(2-hydroxyethyl)-5-methylphenylaminomethyl | 7.2 | 529 | — | AG |
| 276 | 5,6,7,8-tetrahydroquinoxalin-5-yl | 2,5-dimethylphenylaminomethyl | H | 7.2 | 554 | — | AA |
| 277 | 1-methylbenzimidazol-4-ylmethyl | H | 2-(2-hydroxyethyl)-3-methylphenylaminomethyl | 7.1 | 568 | — | AI |
| 278 | (6-bromopyridin-2-yl)ethyl | H | N-(2-hydroxyethyl)-3,5-dimethylphenylaminomethyl | 7.1 | 607 | 161° C/ HCl | AG |
| 279 | (3-methoxy-6-methylpyridin-2-yl)methyl | H | 2-(hydroxymethyl)-N-ethylphenylamino | 7.1 | 531 | — | AK |
| 280 | (3-methoxy-6-methylpyridin-2-yl)methyl | H | 2-(hydroxymethyl)-5-methylphenylaminomethyl | 7.1 | 545 | — | AK |

TABLE 13-continued

| Comp. No. | G¹—R¹ | R²ª | R³ª | Activity | Mass (MH+) | Melting point/salt | Synthesis scheme |
|---|---|---|---|---|---|---|---|
| 281 | (6-methylpyridin-2-yl)methyl | H | N-(2-hydroxyethyl)-N-(3,5-dimethylphenyl)aminomethyl | 7.1 | 543 | 156° C. | AG |
| 282 | (5,6-dimethylpyrazin-2-yl)methyl | H | (2-(2-hydroxyethyl)-3-methylphenyl)aminomethyl | 7.1 | 558 | — | AE |
| 283 | (5,6-dimethylpyrazin-2-yl)methyl | H | (3-methylphenyl)aminomethyl | 7.1 | 514 | — | AE |
| 284 | (5,6-dimethylpyrazin-2-yl)methyl | H | (2-(hydroxymethyl)-5-methylphenyl)aminomethyl | 7.1 | 544 | — | AE |
| 285 | (5,6-dimethylpyrazin-2-yl)methyl | H | (2-(hydroxymethyl)-3-methylphenyl)aminomethyl | 7.1 | 544 | — | AE |
| 286 | (2,3-dimethyl-5,6,7,8-tetrahydroquinoxalin-5-yl)methyl | 2-(2-hydroxyethyl)phenyl(ethyl)amino | H | 7.1 | 570 | — | AA |

TABLE 13-continued

| Comp. No. | G¹—R¹ | R²ᵃ | R³ᵃ | Activity | Mass (MH+) | Melting point/salt | Synthesis scheme |
|---|---|---|---|---|---|---|---|
| 287 | tetrahydroquinoxaline-CH₂ | ethylamino-(hydroxymethyl)phenyl | H | 7.1 | 556 | — | AA |
| 288 | 1-methylbenzimidazol-4-yl-CH₂ | H | 2-(ethylamino)benzamide | 7 | 553 | — | AI |
| 289 | trimethylpyrazinyl-CH₂ | H | 3,5-dichlorophenyl-NH-ethyl | 7 | 568 | — | AE |
| 290 | trimethylpyrazinyl-CH₂ | H | 3-ethynylphenyl-NH-ethyl | 7 | 524 | — | AE |
| 291 | trimethylpyrazinyl-CH₂ | H | 4-carbamoylphenyl-NH-ethyl | 7 | 543 | — | AE |
| 292 | tetrahydroquinoxaline-CH₂ | methyl-(hydroxyethyl)phenyl-NH-CH₂ | H | 7 | 584 | — | AA |

TABLE 13-continued

| Comp. No. | G¹—R¹ | R²ᵃ | R³ᵃ | Activity | Mass (MH+) | Melting point/salt | Synthesis scheme |
|---|---|---|---|---|---|---|---|
| 293 | tetrahydroquinoxaline-dimethyl | CH₂-NH-(3-methyl-2-hydroxymethylphenyl) | H | 7 | 570 | — | AA |
| 294 | 6-bromo-2-ethylpyridine | CH₂OH | H | 6.9 | 460 | 70° C. | AG |
| 295 | 1-methylbenzimidazol-4-ylmethyl | H | CH₂-NH-(3-methylphenyl) | 6.9 | 524 | — | AI |
| 296 | 1-methylbenzimidazol-4-ylmethyl | H | CH₂-NH-(4-carbamoylphenyl) | 6.9 | 553 | — | AI |
| 297 | 6-methyl-3-oxy-2-methylpyridine | H | CH₂-NH-(3-bromophenyl) | 6.9 | 579 | — | AK |
| 298 | 6-methyl-3-oxy-2-methylpyridine | H | CH₂-NH-(3-methyl-2-hydroxymethylphenyl) | 6.9 | 545 | — | AK |

TABLE 13-continued

| Comp. No. | G¹—R¹ | R²ᵃ | R³ᵃ | Activity | Mass (MH+) | Melting point/salt | Synthesis scheme |
| --- | --- | --- | --- | --- | --- | --- | --- |
| 299 | 2,3,5-trimethylpyrazinyl-methyl | H | 2-(2-morpholinoethyl)-N-ethylanilinyl | 6.9 | 613 | — | AE |
| 300 | 2,3,5-trimethylpyrazinyl-methyl | H | 3-(2-hydroxyethyl)-N-ethylanilinyl | 6.9 | 544 | — | AE |
| 301 | (3-hydroxy-2-pyridyl)methyl | 4-methyl-2-(3-hydroxypropyl)-N-methylanilinyl | H | 6.8 | 545 | 218° C. | AC |
| 302 | (3-methoxy-6-methyl-2-pyridyl)methyl | H | 4-carbamoyl-N-ethylanilinyl | 6.8 | 544 | — | AK |
| 303 | (3-methoxy-6-methyl-2-pyridyl)methyl | H | 2-carbamoyl-N-ethylanilinyl | 6.8 | 544 | — | AK |

TABLE 13-continued
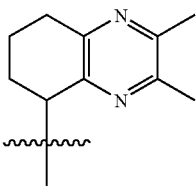
| Comp. No. | G¹—R¹ | R²ᵃ | R³ᵃ | Activity | Mass (MH+) | Melting point/salt | Synthesis scheme |
|---|---|---|---|---|---|---|---|
| 304 | 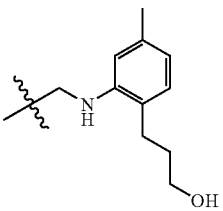 | 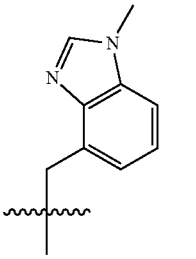 | H | 6.8 | 598 | 155° C. | AA |
| 305 | 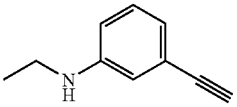 | H | 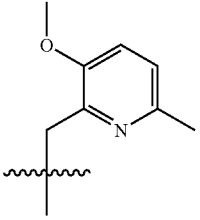 | 6.7 | 534 | — | AI |
| 306 | 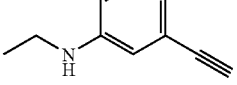 | H | 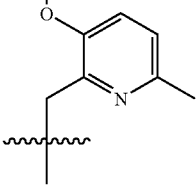 | 6.7 | 525 | — | AK |
| 307 | 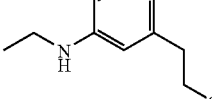 | H | 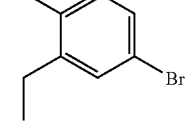 | 6.7 | 545 | — | AK |
| 308 | 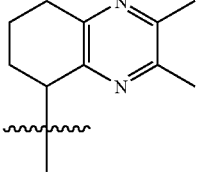 | H | CH₂OH | 6.7 | 475 | 230° C. | AM |
| 309 | 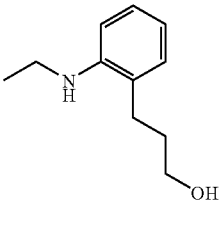 | H | 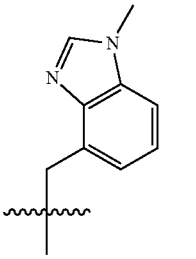 | 6.7 | 584 | — | AA |

TABLE 13-continued

| Comp. No. | G¹—R¹ | R²ª | R³ª | Activity | Mass (MH+) | Melting point/salt | Synthesis scheme |
|---|---|---|---|---|---|---|---|
| 310 | tetrahydroquinoxaline-dimethyl | CH₂-NH-(3,5-dimethylphenyl) | H | 6.7 | 554 | — | AA |
| 311 | tetrahydroquinoxaline-dimethyl | H | CH₂OH | 6.6 | 451 | 160° C. | AA |
| 312 | N-methylbenzimidazole-ethyl | H | CH₂CH₂-NH-(3,5-dichlorophenyl) | 6.6 | 578 | — | AI |
| 313 | N-methylbenzimidazole-ethyl | H | CH₂CH₂-NH-(3-bromophenyl) | 6.6 | 588 | — | AI |
| 314 | methoxy-methylpyridine-ethyl | H | CH₂-NH-(3-methylphenyl) | 6.6 | 515 | — | AK |

TABLE 13-continued

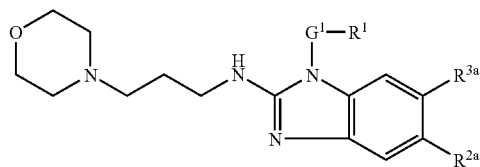

| Comp. No. | G¹—R¹ | R²ᵃ | R³ᵃ | Activity | Mass (MH+) | Melting point/salt | Synthesis scheme |
|---|---|---|---|---|---|---|---|
| 315 | 4-F-phenylethyl | H | N-(3,5-dimethylphenyl)-N-(propanamide) methyl | 6.5 | 587 | 75° C. | AH |
| 316 | 2,3-dimethyl-5,6,7,8-tetrahydroquinoxalin-5-yl | H | (3-methylphenyl)aminomethyl | 6.5 | 540 | — | AA |
| 317 | 2,3-dimethyl-5,6,7,8-tetrahydroquinoxalin-5-yl | H | [2-(hydroxymethyl)-4-methylphenyl]aminomethyl | 6.5 | 570 | — | AA |
| 318 | 2,3-dimethyl-5,6,7,8-tetrahydroquinoxalin-5-yl | H | {2-[2-(morpholin-4-yl)ethyl]phenyl}aminomethyl | 6.5 | 639 | — | AA |
| 319 | 4-F-phenylethyl | H | [2-(3-hydroxypropyl)-4-methylphenyl]aminomethyl | 6.4 | 546 | 114° C. | AG |

TABLE 13-continued

| Comp. No. | G¹—R¹ | R²ᵃ | R³ᵃ | Activity | Mass (MH+) | Melting point/salt | Synthesis scheme |
|---|---|---|---|---|---|---|---|
| 320 | (6-methyl-pyridin-2-yl with O-(CH₂)₂-O substituent) | H | CH₂OH | 6.3 | 484 | 102° C. | AK |
| 321 | (5,6,7,8-tetrahydro-2,3-dimethylquinoxalin-5-yl) | (3-(2-hydroxyethyl)phenyl)NH-CH₂- | H | 6.3 | 570 | — | AA |
| 322 | (2-hydroxy-5-bromo-3-ethyl-phenyl) | CH₂OH | H | 6.1 | 475 | 235° C. | AM |
| 323 | (6-methyl-pyridin-2-yl) | H | (2,5-dimethylphenyl)NH-CH₂- | 6 | 499 | — | AG |
| 324 | (5,6,7,8-tetrahydro-2,3-dimethylquinoxalin-5-yl) | (4-carbamoylphenyl)NH-CH₂- | H | 6 | 569 | — | AA |
| 325 | (1-methyl-1H-benzimidazol-4-yl) | H | CH₂OH | 5.9 | 435 | 167° C. | AI |

TABLE 13-continued

| Comp. No. | G¹—R¹ | R²ᵃ | R³ᵃ | Activity | Mass (MH+) | Melting point/salt | Synthesis scheme |
|---|---|---|---|---|---|---|---|
| 326 | tetrahydroquinoxaline-dimethyl | NH-ethyl-(3-bromophenyl) | H | 5.9 | 603 | — | AA |
| 327 | 3-hydroxy-2-ethylpyridine | H | CH₂OH | 5.8 | 398 | 254° C. | AC |
| 328 | 1-methylbenzimidazole-ethyl | CH₂-NH-(4-methyl-2-(3-hydroxypropyl)phenyl) | H | 5.8 | 582 | 90° C. | AI |
| 329 | tetrahydroquinoxaline-dimethyl | NH-ethyl-(3-ethynylphenyl) | H | 5.8 | 550 | — | AA |
| 330 | 4-fluorophenylethyl | H | CH₂-N(CH₂CH₂OH)-(3,5-dimethylphenyl) | 5.7 | 546 | 165° C. | AH |
| 331 | tetrahydroquinoxaline-dimethyl | NH-ethyl-(3,5-dichlorophenyl) | H | 5.7 | 594 | — | AA |

TABLE 13-continued
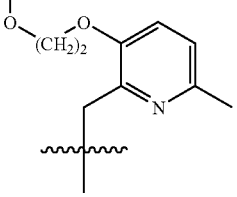
| Comp. No. | G¹—R¹ | R²ᵃ | R³ᵃ | Activity | Mass (MH+) | Melting point/salt | Synthesis scheme |
|---|---|---|---|---|---|---|---|
| 332 | 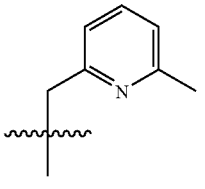 | CH₂OH | H | 5.5 | 484 | 138° C. | AK |
| 333 | 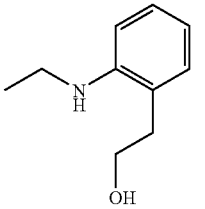 | H | 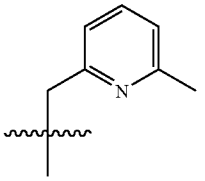 | 5.5 | 515 | — | AG |
| 334 | 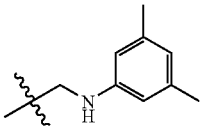 | H | 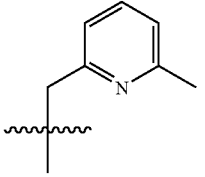 | 5.5 | 499 | — | AG |
| 335 | 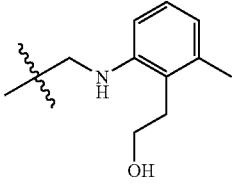 | H | 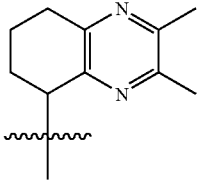 | 5.5 | 529 | — | AG |
| 336 | 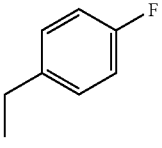 | CH₂OH | H | 5.4 | 451 | 202° C. | AA |
| 337 | 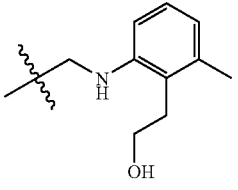 | H | 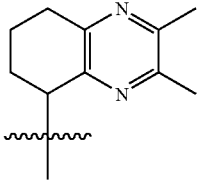 | 5.4 | 532 | — | AG |

TABLE 13-continued
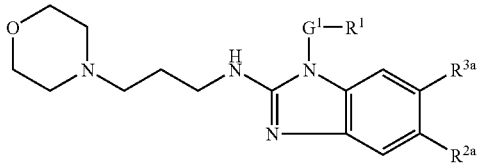
| Comp. No. | G¹—R¹ | R²ᵃ | R³ᵃ | Activity | Mass (MH+) | Melting point/salt | Synthesis scheme |
|---|---|---|---|---|---|---|---|
| 338 | 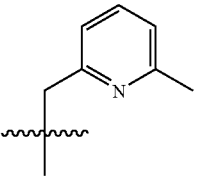 | H | 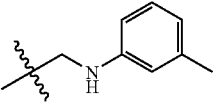 | 5.4 | 485 | — | AG |
| 339 | 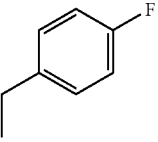 | H | 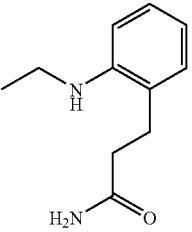 | 5.3 | 545 | — | AG |
| 340 | 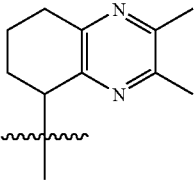 | 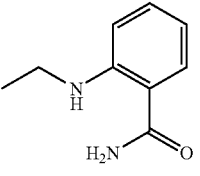 | H | 5.3 | 569 | — | AA |
| 341 | 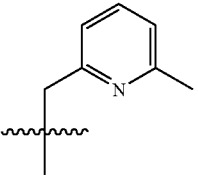 | H | 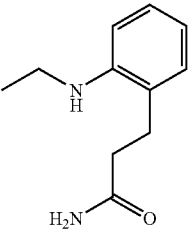 | 5.2 | 542 | — | AG |
| 342 | 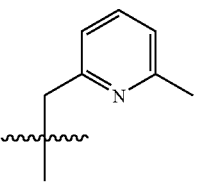 | H | 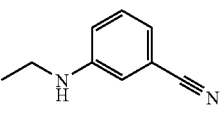 | 5.1 | 496 | — | AG |
| 343 | 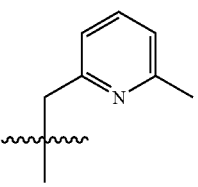 | H | 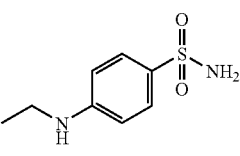 | 5.1 | 550 | — | AG |

TABLE 13-continued
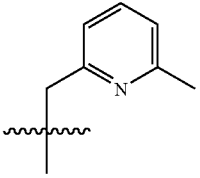
| Comp. No. | G¹—R¹ | R²ᵃ | R³ᵃ | Activity | Mass (MH+) | Melting point/salt | Synthesis scheme |
|---|---|---|---|---|---|---|---|
| 344 | 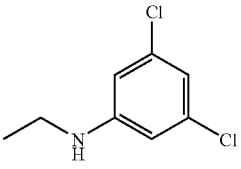 | H | 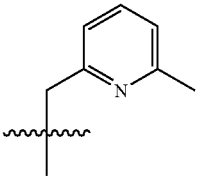 | 5 | 539 | — | AG |
| 345 | 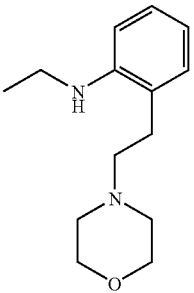 | H | 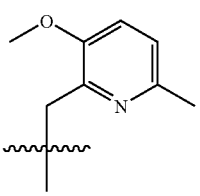 | 5 | 584 | — | AG |
| 346 | 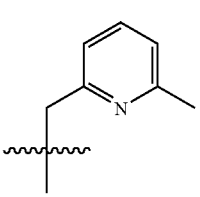 | H | $CH_2OH$ | 4.9 | 426 | 135° C. | AK |
| 347 | 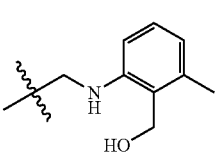 | H | 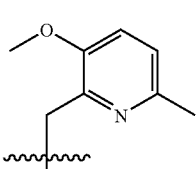 | 4.9 | 515 | — | AG |
| 348 | 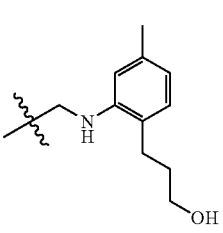 | H | 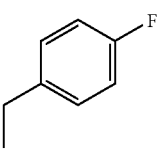 | 4.8 | 573 | 128° C. | AK |
| 349 | 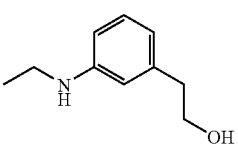 | H | (structure) | 4.8 | 518 | — | AG |

TABLE 13-continued
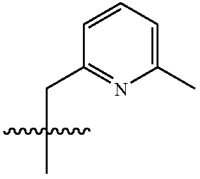
| Comp. No. | G¹—R¹ | R²ᵃ | R³ᵃ | Activity | Mass (MH+) | Melting point/salt | Synthesis scheme |
|---|---|---|---|---|---|---|---|
| 350 | 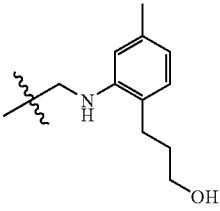 | 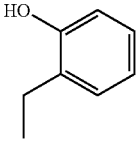 | H | 4.7 | 543 | 146° C. | AG |
| 351 | 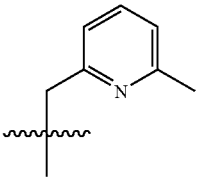 | H | $CH_2OH$ | 4.7 | 397 | 126° C. | AM |
| 352 | 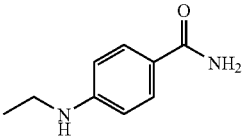 | H | 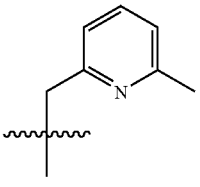 | 4.5 | 514 | — | AG |
| 353 | 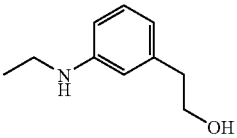 | H | 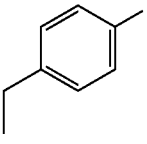 | 4.5 | 515 | — | AG |
| 354 | 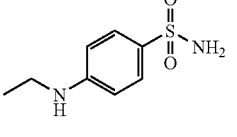 | H | 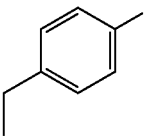 | 4.4 | 553 | — | AG |
| 355 | 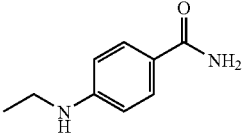 | H | 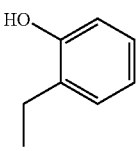 | 4.4 | 517 | — | AG |
| 356 | 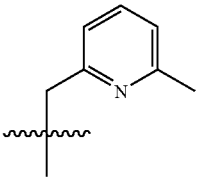 | $CH_2OH$ | H | 4.4 | 397 | 122° C. | AM |

TABLE 13-continued
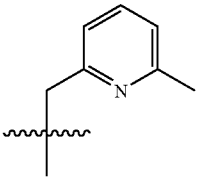
| Comp. No. | G¹—R¹ | R²ᵃ | R³ᵃ | Activity | Mass (MH+) | Melting point/salt | Synthesis scheme |
|---|---|---|---|---|---|---|---|
| 357 | 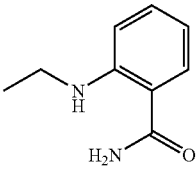 | H | 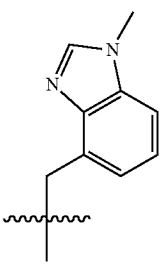 | 4.3 | 514 | — | AG |
| 358 | 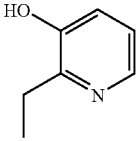 | $CH_2OH$ | H | 4.1 | 435 | 173° C. | AI |
| 359 | 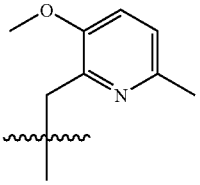 | $CH_2OH$ | H | <4 | 398 | 242° C. | AC |
| 360 | 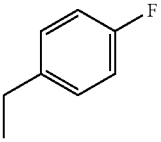 | $CH_2OH$ | H | <4 | 426 | 138° C. | AK |
| 361 | 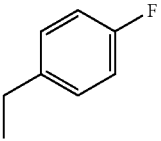 | H | $CH_2OH$ | <4 | 399 | — | AG |
| 362 | 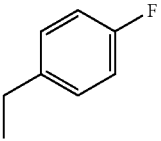 | $CH_2OH$ | H | <4 | 399 | — | AG |
| 363 | 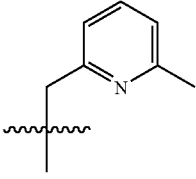 | H | $CH_2OH$ | <4 | 396 | — | AG |

TABLE 13-continued

| Comp. No. | G¹—R¹ | R²ᵃ | R³ᵃ | Activity | Mass (MH+) | Melting point/salt | Synthesis scheme |
|---|---|---|---|---|---|---|---|
| 364 | (6-methylpyridin-2-yl)methyl | CH₂OH | H | <4 | 396 | 124° C. | AG |
| 365 | 4-fluorobenzyl | 2-(3-hydroxypropyl)-4-methylphenyl-NH-CH₂- | H | <4 | 546 | 60° C. | AG |
| 366 | (6-bromopyridin-2-yl)methyl | 2-(3-hydroxypropyl)-4-methylphenyl-NH-CH₂- | H | <4 | 607 | 73° C. | AG |
| 367 | 4-fluorobenzyl | H | 2-(3-hydroxypropyl)phenyl-NH-CH₂- | <4 | 532 | — | AG |
| 368 | 4-fluorobenzyl | H | 2-(2-hydroxyethyl)phenyl-NH-CH₂- | <4 | 518 | — | AG |
| 369 | 4-fluorobenzyl | H | 3,5-dichlorophenyl-NH-CH₂- | <4 | 542 | — | AG |
| 370 | 4-fluorobenzyl | H | 3,5-dimethylphenyl-NH-CH₂- | <4 | 502 | — | AG |

TABLE 13-continued
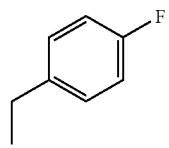
| Comp. No. | G¹—R¹ | R²ᵃ | R³ᵃ | Activity | Mass (MH+) | Melting point/salt | Synthesis scheme |
|---|---|---|---|---|---|---|---|
| 371 | 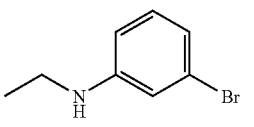 | H | 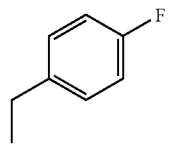 | <4 | 552 | — | AG |
| 372 | 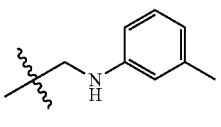 | H | 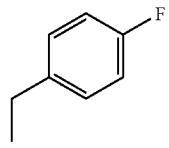 | <4 | 488 | — | AG |
| 373 | 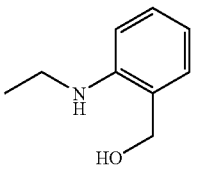 | H | 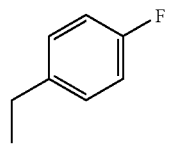 | <4 | 504 | — | AG |
| 374 | 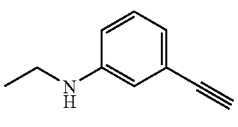 | H | 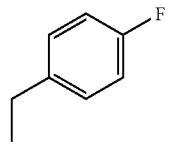 | <4 | 498 | — | AG |
| 375 | 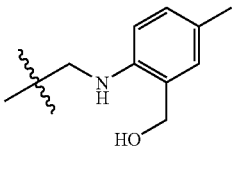 | H | 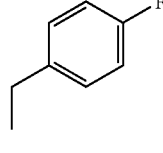 | <4 | 518 | — | AG |
| 376 | 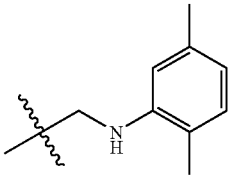 | H | 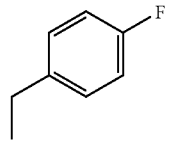 | <4 | 502 | — | AG |
| 377 | 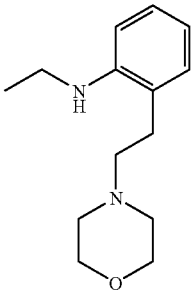 | H | | <4 | 587 | — | AG |

TABLE 13-continued

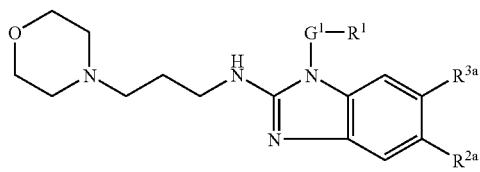

| Comp. No. | G¹—R¹ | R²ᵃ | R³ᵃ | Activity | Mass (MH+) | Melting point/salt | Synthesis scheme |
|---|---|---|---|---|---|---|---|
| 378 | 4-fluorobenzyl | H | -CH₂-NH-(2-methyl-6-hydroxymethyl)phenyl | <4 | 518 | — | AG |
| 379 | 4-fluorobenzyl | H | -CH₂-NH-(2-carbamoyl)phenyl | <4 | 517 | — | AG |
| 380 | (3,5,6-trimethylpyrazin-2-yl)methyl | -CH₂-NH-(4-methyl-2-(3-hydroxypropyl))phenyl | H | <4 | 572 | 145° C. | AE |
| 381 | (3,5,6-trimethylpyrazin-2-yl)methyl | CH₂OH | H | <4 | 425 | 100° C. | AE |
| 382 | (6-methylpyridin-2-yl)methyl | H | -CH₂-NH-(3-bromo)phenyl | <4 | 549 | — | AG |
| 383 | (6-methylpyridin-2-yl)methyl | H | -CH₂-NH-(2-hydroxymethyl)phenyl | <4 | 501 | — | AG |
| 384 | (6-methylpyridin-2-yl)methyl | H | -CH₂-NH-(4-methyl-2-hydroxymethyl)phenyl | <4 | 515 | — | AG |

Example 42

In vitro Screening for Activity against Respiratory Syncytial Virus.

The percent protection against cytopathology caused by viruses (antiviral activity or $EC_{50}$) achieved by tested compounds and their cytotoxicity ($CC_{50}$) are both calculated from dose-response curves. The selectivity of the antiviral effect is represented by the selectivity index (SI), calculated by dividing the $CC_{50}$ (cytotoxic dose for 50% of the cells) by the $EC_{50}$ (antiviral activity for 50% of the cells). The tables in the above experimental part list the category to which each of the prepared compounds belongs: Compounds belonging to activity category "A" have an $pEC_{50}$ (−log of $EC_{50}$ when expressed in molar units) equal to or more than 7. Compounds belonging to activity category "B" have a pEC50 value between 6 and 7. Compounds belonging to activity category "C" have a pEC50 value equal to or below 6.

Automated tetrazolium-based colorimetric assays were used for determination of $EC_{50}$ and $CC_{50}$ of test compounds. Flat-bottom, 96-well plastic microtiter trays were filled with 180 µl of Eagle's Basal Medium, supplemented with 5% FCS (0% for FLU) and 20 mM Hepes buffer. Subsequently, stock solutions (7.8× final test concentration) of compounds were added in 45 µl volumes to a series of triplicate wells so as to allow simultaneous evaluation of their effects on virus- and mock-infected cells. Five five-fold dilutions were made directly in the microtiter trays using a robot system. Untreated virus controls, and HeLa cell controls were included in each test. Approximately 100 $TCID_{50}$ of Respiratory Syncytial Virus was added to two of the three rows in a volume of 50 µl. The same volume of medium was added to the third row to measure the cytotoxicity of the compounds at the same concentrations as those used to measure the antiviral activity. After two hours of incubation, a suspension ($4 \times 10^5$ cells/ml) of HeLa cells was added to all wells in a volume of 50 µl. The cultures were incubated at 37° C. in a 5% $CO_2$ atmosphere. Seven days after infection the cytotoxicity and the antiviral activity was examined spectrophotometrically. To each well of the microtiter tray, 25 µl of a solution of MTT (3-(4,5-dimethylthiazol-2-yl)-2,5-diphenyltetrazolium bromide) was added. The trays were further incubated at 37° C. for 2 hours, after which the medium was removed from each cup. Solubilization of the formazan crystals was achieved by adding 100 µl 2-propanol. Complete dissolution of the formazan crystals were obtained after the trays have been placed on a plate shaker for 10 min. Finally, the absorbances were read in an eight-channel computer-controlled photometer (Multiskan MCC, Flow Laboratories) at two wavelengths (540 and 690 nm). The absorbance measured at 690 nm was automatically subtracted from the absorbance at 540 nm, so as to eliminate the effects of non-specific absorption.

The invention claimed is:

1. A compound which is 2-[6-{[2-(3-hydroxy-propyl)-5-methyl-phenylamino]-methyl}-2-(3-morpholin-4-yl-propylamino)-benzimidazol-1-ylmethyl]-6-methyl-pyridin-3-ol, or an, N-oxide, pharmaceutically acceptable salt, quaternary amine, or metal complex thereof.

2. A pharmaceutical composition comprising a pharmaceutically acceptable carrier, and a compound as described in claim 1.

3. A method for treating a respiratory syncytial viral infection comprising administering to a human subject in need thereof an anti-virally effective amount of the compound of claim 1.

4. A method for treating a respiratory syncytial viral infection comprising administering to a human subject in need thereof an anti-virally effective amount of the composition of claim 3.

5. A pharmaceutical composition made by mixing the compound of claim 1 and a pharmaceutically acceptable carrier.

6. A process for making a pharmaceutical composition comprising mixing the compound of claim 1 and a pharmaceutically acceptable carrier.

7. The pharmaceutical composition of claim 2, further comprising an additional antiviral agent.

8. The pharmaceutical composition of claim 2, further comprising an antiviral agent selected from the group consisting of interferon-beta and tumor necrosis factor-alpha.

9. A method of treating a warm-blooded animal infected by a respiratory syncytial virus, or being at risk of infection by a respiratory syncytial virus, comprising administering to the warm-blooded animal an anti-virally effective amount of the compound of claim 1.

10. A method for treating a respiratory synctial viral infection comprising administering to a human subject in need thereof an anti-virally effective amount of the compound of claim 1 and an additional antiviral agent.

11. The method of claim 10, wherein the additional antiviral agent is selected from the group consisting of interferon-beta and tumor necrosis factor-alpha.

12. A method of treating a warm-blooded animal infected by a respiratory syncytial virus, or being at risk of infection by a respiratory syncytial virus, comprising administering to the warm-blooded animal an anti-virally effective amount of the compound of claim 1 and an additional antiviral agent.

13. The method of claim 12, wherein the additional antiviral agent is selected from the group consisting of interferon-beta and tumor necrosis factor-alpha.

14. A compound which is 2-[6-{[2-(3-hydroxy-propyl)-5-methyl-phenylamino]-methyl}-2-(3-morpholin-4-yl-propylamino)-benzimidazol-1-ylmethyl]-6-methyl-pyridin-3-ol and pharmaceutically acceptable salts thereof.

15. A pharmaceutical composition comprising the compound of claim 14 and a pharmaceutically acceptable carrier.

16. A method for treating a respiratory syncytial viral infection comprising administering to a human subject in need thereof an anti-virally effective amount of the compound of claim 14.

17. A method for treating a respiratory syncytial viral infection comprising administering to a human subject in need thereof an anti-virally effective amount of the composition of claim 15.

18. A pharmaceutical composition made by mixing the compound of claim 14 and a pharmaceutically acceptable carrier.

19. A process for making a pharmaceutical composition comprising mixing the compound of claim 14 and a pharmaceutically acceptable carrier.

20. The pharmaceutical composition of claim 15, further comprising an additional antiviral agent.

21. The pharmaceutical composition of claim 15, further comprising an additional antiviral agent selected from the group consisting of interferon-beta and tumor necrosis factor-alpha.

22. A method of treating a warm-blooded animal infected by a respiratory syncytial virus, or being at risk of infection by a respiratory syncytial virus, comprising administering to the warm-blooded animal an anti-virally effective amount of the compound of claim 14.

23. A method for treating a respiratory synctial viral infection comprising administering to a human subject in need thereof an anti-virally effective amount of the compound of claim 14, and an additional antiviral agent.

24. The method of claim 23, wherein the additional antiviral agent is selected from the group consisting of interferon-beta and tumor necrosis factor-alpha.

25. A method of treating a warm-blooded animal infected by a respiratory syncytial virus, or being at risk of infection by a respiratory syncytial virus, comprising administering to the warm-blooded animal an anti-virally effective amount of the compound of claim 14 and an additional antiviral agent.

26. The method of claim 25, wherein the additional antiviral agent is selected from the group consisting of interferon-beta and tumor necrosis factor-alpha.

27. A compound which is 2-[6-{[2-(3-hydroxy-propyl)-5-methyl-phenylamino]-methyl}-2-(3-morpholin-4-yl-propylamino)-benzimidazol-1-ylmethyl]-6-methyl-pyridin-3-ol.

28. A pharmaceutical composition comprising the compound of claim 27 and a pharmaceutically acceptable carrier.

29. A method for treating a respiratory syncytial viral infection comprising administering to a human subject in need thereof an anti-virally effective amount of the compound of claim 27.

30. The pharmaceutical composition of claim 28, further comprising an additional antiviral agent.

31. The pharmaceutical composition of claim 28, further comprising an additional antiviral agent selected from the group consisting of interferon-beta and tumor necrosis factor-alpha.

32. A method of treating a warm-blooded animal infected by a respiratory syncytial virus, or being at risk of infection by a respiratory syncytial virus, comprising administering to the warm-blooded animal an anti-virally effective amount of the compound of claim 27.

33. A method for treating a respiratory synctial viral infection comprising administering to a human subject in need thereof an anti-virally effective amount of the compound of claim 27 and an additional antiviral agent.

34. The method of claim 33, wherein the additional antiviral agent is selected from the group consisting of interferon-beta and tumor necrosis factor-alpha.

35. A method of treating a warm-blooded animal infected by a respiratory syncytial virus, or being at risk of infection by a respiratory syncytial virus, comprising administering to the warm-blooded animal an anti-virally effective amount of the compound of claim 27 and an additional antiviral agent.

36. The method of claim 35, wherein the additional antiviral agent is selected from the group consisting of interferon-beta and tumor necrosis factor-alpha.

* * * * *